(12) United States Patent
Sun et al.

(10) Patent No.: US 11,845,751 B2
(45) Date of Patent: *Dec. 19, 2023

(54) TRIAZOLOTRIAZINE DERIVATIVES AS A2A RECEPTOR ANTAGONISTS

(71) Applicant: ZHEJIANG VIMGREEN PHARMACEUTICALS, LTD., Zhejiang (CN)

(72) Inventors: Sanxing Sun, Zhejiang (CN); Long Zhao, Zhejiang (CN); Chongbo Hu, Zhejiang (CN); Zhengshu Chen, Zhejiang (CN); Jinqi Ye, Zhejiang (CN)

(73) Assignee: ZHEJIANG VIMGREEN PHARMACEUTICALS, LTD., Zhejiang (CN)

(*) Notice: Subject to any disclaimer, the term of this patent is extended or adjusted under 35 U.S.C. 154(b) by 156 days.

This patent is subject to a terminal disclaimer.

(21) Appl. No.: 17/255,464

(22) PCT Filed: Jun. 26, 2018

(86) PCT No.: PCT/IB2018/054691
§ 371 (c)(1),
(2) Date: Dec. 23, 2020

(87) PCT Pub. No.: WO2020/002969
PCT Pub. Date: Jan. 2, 2020

(65) Prior Publication Data
US 2021/0332055 A1    Oct. 28, 2021

(51) Int. Cl.
*C07D 519/00*    (2006.01)
*A61P 35/00*    (2006.01)
*A61K 31/53*    (2006.01)
*C07D 487/04*    (2006.01)

(52) U.S. Cl.
CPC .................. *C07D 487/04* (2013.01)

(58) Field of Classification Search
CPC ..... C07D 487/04; C07D 519/00; A61P 35/00; A61K 31/53
USPC ......................................... 514/246
See application file for complete search history.

(56) References Cited

U.S. PATENT DOCUMENTS 5,270,311 A * 12/1993 Caulkett ................. A61P 43/00
544/212
5,356,894 A   10/1994 Caulkett et al.
5,380,714 A    1/1995 Jones et al.

FOREIGN PATENT DOCUMENTS

| CN | 1056879 A | 12/1991 |
| EP | 0515108 A2 | 11/1992 |
| WO | 2004092170 A2 | 10/2004 |

OTHER PUBLICATIONS

George A. Patani and Edmond J. LaVoie, Chemical Reviews, 1996, 96, 3147-3176, "Bioisosterism: A Rational Approach in Drug Design" (Year: 1996).*
Nicholas A. Meanwell , Top Med Chem (2015) 9: 283-382, "The Influence of Bioisosteres in Drug Design: Tactical Applications to Address Developability Problems", published online on Jan. 28, 2014. (Year: 2015).*
PCT/IB2018/054691 International Search Report dated Mar. 28, 2019.
Dong Guo, et al., Binding Kinetics of ZM241385 Derivatives at the human Adenosine A2A Receptor, ChemMedChem, vol. 9, No. 4, Dec. 31, 2014.
CN 2018800484059 Search Report dated Jul. 27, 2022.
Hsiao, Po-Yuan, et al., An Fc-Small Molecule Conjugate for Targeted Inhibition of the Adenosine 2A Receptor, ChemBioChem, vol. 17, No. 20, pp. 1951-1960, Wiley-VCH Verlag GmbH & Co., Aug. 26, 2016.
EP 18924617.6 Extended European Search Report dated May 11, 2022.
Hsiao, Po-Yuan, et al., An Fc-Small Molecule Conjugate for Targeted Inhibition of the Adenosine 2A Receptor, ChemBioChem, vol. 17, No. 20, pp. 1951-1960, Wiley-VCH Verlag GmbH & Co., Oct. 17, 2016.
Jorg, M., et al., Synthesis and Pharmacological Evaluation of Dual Acting Ligands Targeting the Adenosine A2A and Dopamine D2 Receptors for the Potential Treatment of Parkinson's Disease, J of Medicinal Chemistry, vol. 58, No. 2, pp. 718-738, Am Chemical Society, Dec. 9, 2014, Dec. 24, 2014.
Jorg, M., et al., Novel adenosine A2A receptor ligands: a synthetic, functional and computational investigation of selected literature adenosine A2A receptor antagonists for extending into extracellular space, Bioorganic & Medicinal Chemistry Letters, Elsevier, vol. 23, No. 11, pp. 3427-3433, Apr. 2, 2013.

(Continued)

*Primary Examiner* — Jared Barsky
*Assistant Examiner* — Liyuan Mou
(74) *Attorney, Agent, or Firm* — Honigman LLP; Thomas A. Wootton, Esq.; Jonathan P. O'Brien

(57) ABSTRACT

The present invention provides triazolotriazine derivatives of formula (1) as A2A receptor antagonists. Compounds of formula (1) and pharmaceutical compositions including the compounds can be used for the treatment of disorders related to A2A receptor hyperfunctioning, such as certain types cancers. Compounds of formula (1) and methods of preparing the compounds are disclosed in the invention.

(Formula 1)

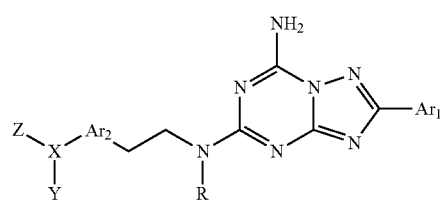

2 Claims, No Drawings

(56) References Cited

OTHER PUBLICATIONS

Rakers, C., et al., In Silico Prediction of Human Sulfotransferase 1E1 Activity Guided by Pharmacophores from Molecular Dynamics Simulations, J of Biological Chemistry, vol. 291, No. 1, pp. 58-71, Jan. 1, 2016.

* cited by examiner

TRIAZOLOTRIAZINE DERIVATIVES AS A2A RECEPTOR ANTAGONISTS

FIELD OF THE INVENTION

The present invention relates to compounds of triazolotriazine derivatives that can be used as A2A receptor antagonists. The present invention further relates to methods of preparing said compounds and pharmaceutical compositions comprising said compounds. The compounds and compositions thereof can be used for the treatment or prevention of disorders associated with hyperactive A2A receptors, such as A2A receptor-mediated immune tolerance to cancer and related abnormal cell proliferation.

BACKGROUND OF THE INVENTION

Adenosine is a naturally occurring purine nucleoside that modulates various physiological functions. Adenosine binds to purinergic receptors, which are members of the G protein-coupled receptor (GPCR) family that includes adenosine A1, A2A, A2B and A3 receptors (A1R, A2AR, A2BR and A3R). Among them, the Adenosine A2A receptor (A2AR) couples to adenylate cyclase in a stimulatory manner that induces classical second messenger pathways, including the production of cyclic adenosine monophosphate (cAMP) (Current Medicinal Chemistry. 2014, 21, 3918-3935). A2AR mediates multiple physiological effects of adenosine, both in the central nervous system and in peripheral tissues. The functional interactions between A2AR and dopamine D2 in the basal ganglia have triggered decades of investigation of A2AR antagonists as anti-Parkinson drugs. Other therapeutic applications of A2AR antagonism include cognition enhancement, neuroprotection, and painkilling. More recent studies have demonstrated that inhibition of A2AR may provide a powerful new treatment of cancer (Computational and Structural Biotechnology Journal. 2015, 15, 265-272).

Studies have shown that A2AR may protect tumors from the attack of anti-tumor T cells and other immune cells (PNAS. 2006, 103, No. 35, 13132-7). The immune system has evolved an array of regulatory mechanisms to protect against tissue damage from autoimmunity or during active response to pathogen. Both central mechanisms such as negative selection in the thymus and peripheral mechanisms such as deletion, anergy, and the deployment of regulatory T cells (Tregs) contribute to the establishment of self-tolerance. Included in these protective mechanisms are various inhibitory receptors that are upregulated on lymphocytes during an active immune response. These inhibitory receptors and their related signaling networks, known as "immune checkpoint pathways," provide a negative feedback mechanism that is crucial for the protection of tissues from immune attack. Yet, although the negative feedback loops created by the checkpoint pathways are critical in modulating excessive immune response, they are also subject to dysregulation in the presence of cancer and provide tumors with a means of immune evasion. The adenosine signaling is one of the various negative feedback mechanisms that serve to dampen immune response and protect tissues from the associated injury.

It is known that extracellular adenosine can signal through adenosine receptors including A1R, A2AR, A2BR, and A3R (Drug Dev. Res. 1996, 39, 243-52). Due to that A2AR and A2BR are expressed on a variety of immune cells and endothelial cells, adenosine signaling through A2AR (high affinity) and A2BR (low affinity) has an important role in protecting tissues during immune responses (Autoimmunity. 2007, 40, 425-32; Handb. Exp. Pharmacol. 2009, 193, 399-441; Cancer Discov. 2014, 4, 879-88). In particular, because of the higher affinity of adenosine binding on A2AR and the higher expression of A2AR on a much broader array of immune cells, most of this protective effect is carried through the A2A adenosine receptor (Nature. 2001, 414, 916-20).

Under normal physiologic conditions, the extracellular amount of adenosine is balanced by rapid cellular uptake that prevents a significant increase in extracellular levels (Clin. Invest. 2012, 122, 693-710; Gastroenterology. 2009, 136, 607-18). However, in the tumor microenvironment, increased cellular turnover, tissue breakdown and hypoxia trigger the release of a much larger amount of ATP and adenosine into the extracellular environment (Am. J. Physiol. 1993, 265, C577-606; Cancer Res. 1997, 57, 2602-5). Besides, while the build-up of extracellular adenosine is partly a result of direct liberation of intracellular adenosine that is formed from increased ATP metabolism during cellular stress, the adenosine level is also increased by the catabolism of extracellular ATP and ADP by the tandem activity of the ectonucleotidases CD39 and CD73, which are upregulated in a number of cell types within the tumor microenvironment, including endothelial cells, stromal cells, tumor cells, and, importantly, on several subsets of immune cells, including Tregs, CD8+ T cells, B cells, NK cells, dendritic cells (DC), myeloid derived suppressor cells (MDSCs), and tumor-associated macrophages (TAMs) (Cancer Immunol. Res. 2014, 2, 598-605; Cancer Discov. 2014, 4, 879-88; Clin. Cancer Res. 2013, 19, 5626-35; J. Biomed. Biotechnol. 2012, 2012, 485156). As a result, such high levels of extracellular adenosine can't be easily absorbed (Am. J. Physiol. 1993, 265, C577-606; Cancer Res. 1997, 57, 2602-5; Am. J. Physiol. 1987, 252, H886-93). In studies using a microdialysis probe, it is demonstrated that extracellular adenosine levels in solid tumors are 10-20 times higher than in adjacent tissues. Such high levels of adenosine are sufficient to disrupt the function of immune cells (Cancer Res. 1997, 57, 2602-5).

Indeed, the rise in extracellular adenosine level and activation of A2AR has a broad range of immunosuppressive effects (Cancer Res. 2007, 67, 5949-56), including increased production of immunosuppressive cytokines such as TGF-beta and IL-10 (Blood. 2008, 111, 251-9; Eur. J. Immunol. 2010, 40, 682-7), upregulation of alternate immune checkpoint pathway receptors such as PD-1 and LAG-3 (Blood. 2008, 111, 251-9; J. Immunol. 2007, 178, 4240-9), increased FOXP3 expression in CD4 T cells that drives a regulatory T cell phenotype, and induction of effector T cell anergy (Blood. 2008, 111, 251-9). Since Tregs express high levels of CD39 and CD73, as the CD4+ T cells are driven toward Treg phenotype by A2AR-mediated FOXP3 expression, an immunosuppressive amplification circuit that generates increasing amounts of adenosine is created and quickly dampens the immune response (J. Exp. Med. 2007, 204, 1257-65). In the end, the CD8+ effector cells become less cytotoxic and increasingly anergic under the influence of A2AR signaling (Blood 2008, 111, 251-9). What is more, in addition to dampening the effect of cytotoxic T cells, increased extracellular adenosine has been found to downmodulate the activity of a range of immune functions in the tumor microenvironment, including the activity of macrophages, NK cells, neutrophils, and dendritic cells (Blood. 2008, 112, 1822-31; Immunol Res. 2006, 36, 91-9; Blood. 2004, 103, 1391-7; Biochem. Pharmacol. 2000, 60, 993-9; Am. J. Respir. Cell Mol. Biol. 2009 40, 251-9).

Given the importance of adenosine signaling in mediating negative feedback loops of immune responses, pharmacologic blockade of A2A receptors on effector T cells, Tregs, NK cells, dendritic cells (DC), myeloid derived suppressor cells (MDSCs), and tumor-associated macrophages (TAMs) may counteract the immunosuppressive cloud of adenosine in the tumor microenvironment and enhance multiple phases of the immune response, including T cell activation, expansion, and effector function. Indeed, in vivo studies have shown that genetic or pharmacologic blockade of A2AR have profound effects on tissue inflammation, allowing for uncontrolled inflammatory response and tissue injury in mouse models of hepatitis and sepsis. The increased proliferative and destructive capacity of effector T cells against tumor in these studies clearly demonstrate the effectiveness of A2AR antagonism. In fact, even transient pharmacologic A2AR blockade is found to enhance immunologic memory, improving effector function several weeks after initial antigen challenge. Importantly, alternate inflammatory control mechanisms were unable to effectively compensate for the tissue damage resulting from the absence of A2AR signaling, thus establishing that A2AR signaling is a critical, non-redundant negative feedback control mechanism of immune responses (Computational and Structural Biotechnology Journal. 2015, 13, 265-272; Cancer Immunol. Immunother. 2012, 61, 917-26). This makes it conceivable that A2AR antagonists may provide a powerful treatment of cancer and other types of abnormal cell proliferation.

Accordingly, it is an object of the present invention to provide novel A2AR antagonists with desirable pharmaceutical properties. The goal is to achieve high efficacy for the treatment and prevention of cancer and other types of abnormal cell proliferation by restoring or enhancing immune responses.

DESCRIPTION OF THE INVENTION

The present invention relates to triazolotriazine compounds of general formula (1), including hydrates, solvates, pharmaceutically acceptable salts, prodrugs and complexes thereof,

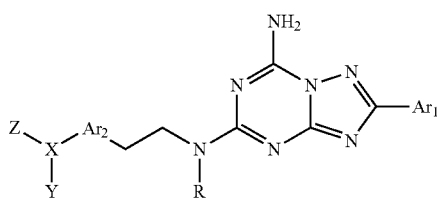

Formula 1 wherein:
R is hydrogen or optionally substituted $C_{1-5}$ alkyl; Any of said optionally substituted alkyls are substituted by halogen, cyano, hydroxyl, nitro, amino, alkylamino, cycloalkylamino, methyl, ethyl, methoxyl, ethoxyl, trifluoromethyl, trifluoroethyl, trifluoromethoxyl, or trifluoroethoxyl;
$Ar_1$ is an 5-6 membered aromatic ring that is optionally substituted with halogen, oxo, cyano, methyl, methoxyl, trifluoromethyl, or trifluoromethoxyl;
$Ar_2$ is a mono- or bicyclic aromatic ring that is optionally substituted with halogen, hydroxyl, cyano, methyl, methoxyl, trifluoromethyl, or trifluoromethoxyl;
X is selected from the group consisting of oxygen, sulfur, carbon, and nitrogen; and
Y and Z are each independently hydrogen, optionally substituted $C_{1-9}$ alkyl, optionally substituted mono- or bicyclic $C_{1-9}$ cycloalkyl, optionally substituted $C_{1-9}$ alkenyl, optionally substituted mono- or bicyclic $C_{1-9}$ cycloalkenyl, optionally substituted aryl, optionally substituted heteroaryl, optionally substituted aralkyl, optionally substituted heteroaralkyl, optionally substituted heterocycloalkyl, optionally substituted heterocycloalkenyl, optionally substituted heterocycloalkylalkyl, optionally substituted $C_{1-9}$ alkylcarbonyl, optionally substituted $C_{1-9}$ cycloalkylcarbonyl, optionally substituted heterocycloalkylcarbonyl, optionally substituted heterocycloalkylalkylcarbonyl, optionally substituted arylcarbonyl, or optionally substituted heteroarylcarbonyl; Any of said optionally substituted groups are substituted by halogen, cyano, hydroxyl, nitro, amino, alkylamino, cycloalkylamino, heterocyclyl, aminocarbonyl, sulfonyl, aminosulfonyl, carbonylamino, sulfonylamino, methyl, ethyl, aryl, methoxyl, ethoxyl, trifluoromethyl, trifluoroethyl, trifluoromethoxyl, trifluoroethoxyl, polyoxyethylene, polyoxypropylene, $C_{1-3}$ alkyl polyoxyethylene, or $C_{1-3}$ alkyl polyoxypropylene; Or Y and Z are joined to form an optionally substituted ring having from 3 to 10 ring atoms; Any of said optionally substituted ring is substituted by halogen, cyano, hydroxyl, oxo, nitro, amino, alkylamino, cycloalkylamino, aminocarbonyl, sulfonyl, aminosulfonyl, carbonylamino, sulfonylamino, methyl, ethyl, methoxyl, ethoxyl, trifluoromethyl, trifluoroethyl, trifluoromethoxyl, trifluoroethoxyl, polyoxyethylene, polyoxypropylene, $C_{1-3}$ alkyl polyoxyethylene, or $C_{1-3}$ alkyl polyoxypropylene; Or Y or Z is missing in the structure.

An embodiment of the present invention includes compounds wherein R in formula (1) is hydrogen, methyl, or trifluoromethyl.

A preferred embodiment of the present invention includes compounds wherein R in formula (1) is hydrogen or methyl.

A most preferred embodiment of the present invention includes compounds wherein R in formula (1) is hydrogen.

Another embodiment of the present invention includes compounds wherein $Ar_1$ in formula (1) is optionally substituted imidazolyl, triazolyl, tetrazolyl, furanyl, thiophenyl, oxazolyl, isoxazolyl, thiazolyl, isothiazolyl, oxadiazolyl, thiadiazolyl, phenyl, pyridyl, pyridazinyl, pyrimidyl, pyrazinyl, or triazinyl; Any of said optionally substituted aromatic rings are substituted by halogen, oxo, cyano, methyl, methoxyl, trifluoromethyl, or trifluoromethoxyl.

A preferred embodiment of the present invention includes compounds wherein $Ar_1$ in formula (1) is selected from the aromatic groups shown in Table (1).

TABLE 1

Preferred structures of $Ar_1$ in formula (1)

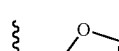

TABLE 1-continued

Preferred structures of Ar$_1$ in formula (1)

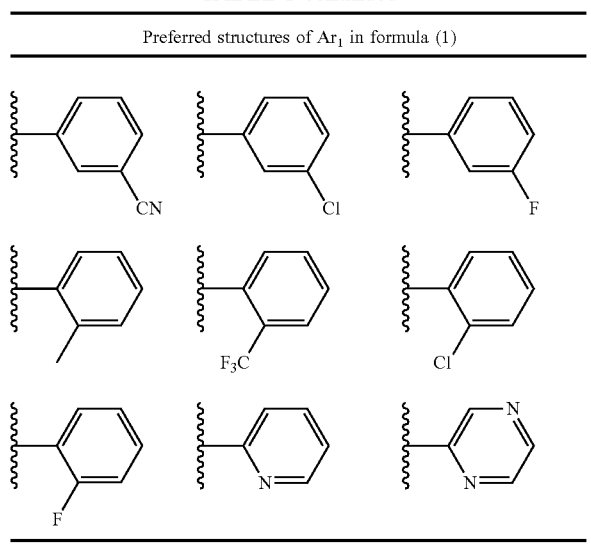

A most preferred embodiment of the present invention includes compounds wherein Ar$_1$ in formula (1) is 2-furanyl.

Another embodiment of the present invention includes compounds wherein Ar$_2$ in formula (1) is optionally substituted imidazolyl, triazolyl, tetrazolyl, furanyl, thiophenyl, oxazolyl, isoxazolyl, thiazolyl, isothiazolyl, oxadiazolyl, thiadiazolyl, phenyl, pyridyl, pyridazinyl, pyrimidyl, pyrazinyl, triazinyl, indolyl, isoindolyl, indazolyl, benzimidazolyl, azaindolyl, azaindazolyl, purinyl, benzofuranyl, isobenzofuranyl, benzothiophenyl, benzisoxazolyl, benzoisothiazolyl, benzoxazolyl, benzothiadiazolyl, quinolyl, isoquinolyl, quinoxalinyl, phthalazinyl, quinazolinyl, cinnolinyl, naphthyridinyl, pyridopyrimidinyl, pyridopyrazinyl, or pteridinyl; Any of said optionally substituted aromatic rings are substituted by halogen, hydroxyl, cyano, nitro, methyl, methoxyl, trifluoromethyl, or trifluoromethoxyl.

A preferred embodiment of the present invention includes compounds wherein Ar$_2$ in formula (1) is optionally substituted phenyl, pyridyl, pyridazinyl, or pyrimidyl; Any of said optionally substituted aromatic rings are substituted by halogen, hydroxyl, cyano, methyl, methoxyl, trifluoromethyl, or trifluoromethoxyl.

A most preferred embodiment of the present invention includes compounds wherein Ar$_2$ in formula (1) is phenyl or pyridyl that is optionally substituted with halogen or hydroxyl.

Another embodiment of the present invention includes compounds wherein X in formula (1) is oxygen, nitrogen, or sulfur.

A preferred embodiment of the present invention includes compounds wherein X in formula (1) is oxygen or nitrogen.

A most preferred embodiment of the present invention includes compounds wherein X in formula (1) is nitrogen.

Another embodiment of the present invention includes compounds wherein Y and Z in formula (1) are each independently hydrogen, optionally substituted C$_{2-5}$ alkyl, optionally substituted C$_{3-5}$ cycloalkyl, optionally substituted C$_{2-5}$ alkenyl, optionally substituted C$_{3-5}$ cycloalkenyl, optionally substituted aryl, optionally substituted heteroaryl, optionally substituted aralkyl, optionally substituted heteroaralkyl, optionally substituted heterocycloalkyl, or optionally substituted heterocycloalkylalkyl; Any of said optionally substituted groups are substituted by halogen, cyano, methoxyl, ethoxyl, trifluoromethoxyl, trifluoroethoxyl, or C$_{1-3}$ alkyl polyoxyethylene;

A preferred embodiment of the present invention includes compounds wherein Y and Z in formula (1) are each independently hydrogen, optionally substituted C$_{2-3}$ alkyl, or optionally substituted heterocycloalkyl; Any of said optionally substituted groups are substituted by methoxyl, ethoxyl, trifluoromethoxyl, or trifluoroethoxyl;

A most preferred embodiment of the present invention includes compounds wherein Y and Z in formula (1) are each independently hydrogen, optionally substituted ethyl, or optionally substituted oxetanyl; Any of said optionally substituted groups are substituted by methoxyl, ethoxyl, trifluoromethoxyl, or trifluoroethoxyl;

Another embodiment of the present invention includes compounds wherein Y and Z in formula (1) are joined to form an optionally substituted ring having from 4 to 8 ring atoms; Any of said optionally substituted rings are substituted by halogen, methyl, ethyl, methoxyl, ethoxyl, trifluoromethyl, trifluoroethyl, trifluoromethoxyl, or trifluoroethoxyl;

A preferred embodiment of the present invention includes compounds wherein Y and Z in formula (1) are joined to form an optionally substituted heterocycloalkyl ring having from 5 to 7 ring atoms; Any of said optionally substituted rings are substituted by halogen, oxo, methoxyl, ethoxyl, trifluoromethoxyl, or trifluoroethoxyl;

A most preferred embodiment of the present invention includes compounds wherein Y and Z in formula (1) are joined to form an optionally substituted morpholinyl ring; Any of said optionally substituted ring is substituted by halogen, methoxyl, ethoxyl, trifluoromethoxyl, or trifluoroethoxyl;

The term "alkyl" includes both straight- and branched-chain saturated aliphatic hydrocarbon groups having a certain number of carbon atoms. For example, C$_4$ alkyl includes n-butyl, isobutyl, sec-butyl and t-butyl. The term "cycloalkyl" includes both mono- and bicyclic saturated aliphatic hydrocarbon groups having a certain number of carbon atoms.

The term "alkenyl" includes both straight- and branched-chain aliphatic hydrocarbon groups containing at least one carbon-to-carbon double bond. Preferably, one carbon-to-carbon double bond is present.

The term "aryl" includes both monocyclic and bicyclic aromatic rings comprising 5 to 14 ring atoms, preferably 6 to 10 ring atoms, unless it is specified otherwise. The aryl group can be optionally substituted with one or more substituents. The term "aryl" also includes both monocyclic and bicyclic heteroaryl rings comprising 5 to 14 ring atoms, preferably 6 to 10 ring atoms, unless it is specified otherwise.

The term "heterocycloalkyl," also known as "heterocyclyl," includes saturated monocyclic and bicyclic ring systems comprising 3 to 14 ring atoms, preferably 4 to 10 ring atoms, in which one or more of the atoms is an element other than carbon, for example nitrogen, oxygen or sulfur, alone or in combination. Examples of heterocycloalkyl groups include, for example, azetidinyl, hexahydroazepinyl, piperazinyl, piperidinyl, pyrrolidinyl, morpholinyl, tetrahydrofuranyl, thiomorpholinyl, and tetrahydrothienyl, and N-oxides thereof.

The term "halogen" includes fluoro, chloro, bromo and iodo. The term "trifluoromethyl" refers to the group (—CF$_3$). The term "hydroxyl" or "hydroxy" means an "—OH" group.

The compounds of formula (1) of the present invention may exist in one or more geometrical, enantiomeric, diastereoisomeric or tautomeric forms. The compounds of formula (1) of the present invention include all such isomeric forms, including racemic and other mixtures thereof.

In another aspect, the compounds of formula (1) of the present invention may exist in either solvated or unsolvated form. The term "solvated" is used herein to describe a compound complex that comprises a compound of the present invention and a number of pharmaceutically acceptable solvent molecules, such as water and ethanol molecules. The compounds of formula (1) of the present invention include all solvated or unsolvated forms thereof.

In another aspect, the compounds of formula (1) of the present invention may exist in a form of pharmaceutically acceptable salts. The term "pharmaceutically acceptable salt" refers to a physiologically or toxicologically tolerable salt, and when appropriate, including pharmaceutically acceptable base addition salts and acid addition salts thereof. The compounds of formula (1) of the present invention include all pharmaceutically acceptable salts thereof.

In another aspect, the compounds of formula (1) of the present invention may exist in a form of pharmaceutically acceptable nanoparticles. Nanoparticles containing a compound of formula (1) of the present invention can be designed to improve the pharmacokinetics and biodistribution of the drug. For example, a compound of formula (1) may be encased in liposomes, which may extend the life of the drug that is being distributed. Nanoparticles of suitable size may also have a better safety profile because the nanoparticles will preferentially leak out of the porous blood vessels around the tumor cells. This may further provide the benefit of lower doses of the drug.

In another aspect, the compounds of formula (1) of the present invention may exist in the form of prodrugs. The term "prodrug" refers to a compound that is converted to a compound of the present invention by a metabolic process in vivo (for example, by hydrolysis, reduction or oxidation). The compounds of formula (1) of the present invention include all such prodrugs thereof.

In another aspect, the compounds of formula (1) of the present invention also include pharmaceutically acceptable isotopic variations in which one or more atoms is replaced by atoms having the same atomic number but different atomic mass. The atoms suitable for such isotope replacement include hydrogen, carbon, nitrogen, oxygen, phosphorus, sulfur, fluorine, iodine, and chlorine. Certain isotopic variations of the compounds of formula (1), such as deuterium replaced compounds, may afford certain therapeutic advantages resulting from greater metabolic stability, and hence may be preferred in some circumstances. The isotopic variations of the compounds of formula (1) can be prepared by conventional techniques known to those skilled in the art.

The Preparation of the Triazolotriazine Derivatives

Another aspect of the present invention is the preparation of the triazolotriazine compounds as A2A receptor antagonists. The triazolotriazine compounds of the invention can be prepared by various synthetic methods. As an illustrative example, two general synthetic routes to the target compound are shown in Scheme (1). In the first approach, after the intermediate (1A) is prepared in a suitable manner, the methylsulfonyl group of intermediate (1A) is replaced by an alkyl amino group to give the triazolotriazine compound (1C). In the second approach, after the intermediate (1B) is prepared in a suitable manner, the phenoxy group of intermediate (1B) is replaced by an alkyl amino group to give the triazolotriazine compound (1C).

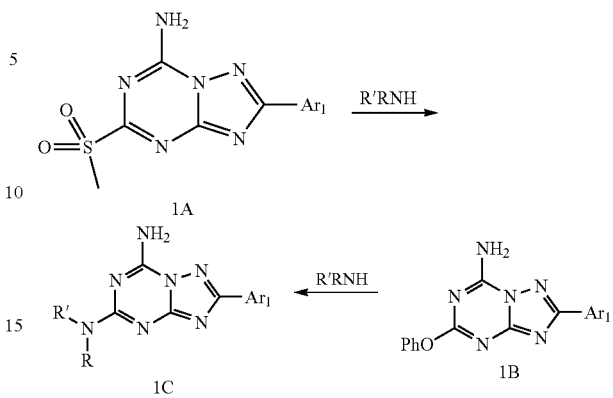

Scheme 1

The needed intermediates (1A) and (1B) in Scheme (1) can also be prepared by various synthetic methods. As an illustrative example, a general synthetic route to compound (1A) is shown in Scheme (2). In the first step, a suitable aryl hydrazide (2A) reacts with S-methylisothiourea (2B) in aqueous sodium hydroxide to give intermediate (2C). Vigorous heating of (2C) in aqueous medium in the following step provides intermediate (2D), which reacts with N-cyanodithioiminocarbonate (2E) to afford the sulfide intermediate (2F). Subsequent oxidation of intermediate (2F) with m-chloroperoxybenzoic acid provides the needed sulfone (1A). As is shown in Scheme (1), nucleophilic displacement of the methylsulfonyl group with a suitable alkyl amine gives the target compound (1C) (J. Chem. Soc., Perkin Trans. 1 1995, 801-808; Structural Chemistry. 2013, 24, 1241-1251).

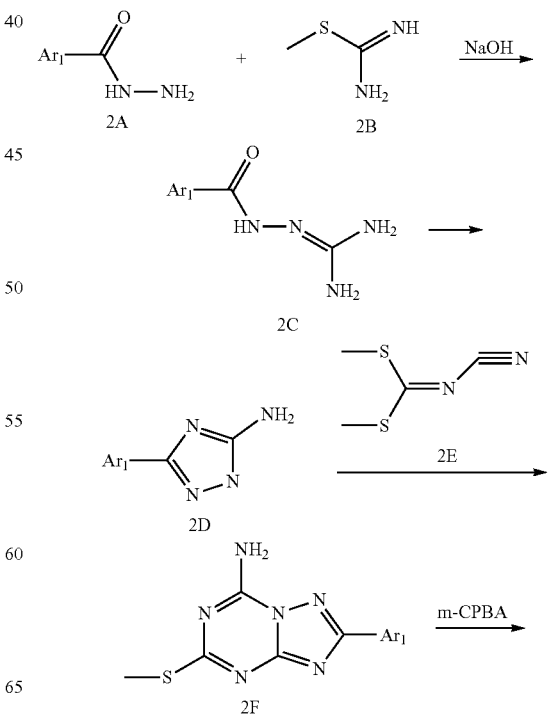

Scheme 2

-continued

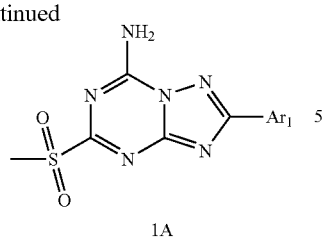
1A

The intermediate (2D) in Scheme (2) can also be prepared by various synthetic methods. As illustrative examples, three alternative synthetic routes to intermediate (2D) are shown in Scheme (3). It is worth emphasizing that among the three approaches, the one starting from a methyl ester or ethyl ester (3F) usually improves efficiency and gives higher yield.

The intermediate (1B) in Scheme (1) can be prepared as shown in Scheme (4). Starting from cyanuric chloride (4A), reflux in phenol provides 2,4,6-triphenoxy-1,3,5-triazine (4B). The following reaction with hydrazine hydrate gives 2-hydrazino-4,6-diphenoxy-1,3,5-triazine (4C), which upon reacting with suitable acid chloride gives the acyl hydrazides (4D). Cyclization of the hydrazide (4D) under dehydrative conditions provides the 2-substituted 5,7-diphenoxytriazolotriazine (4E), which can be converted into the key intermediate (1B) in refluxing methanolic ammonia (J. Chem. Soc., Perkin Trans. 1 1995, 801-808). The target compound (1C) is obtained by reacting compound (1B) with a suitable alkyl amine, as shown in Scheme (1).

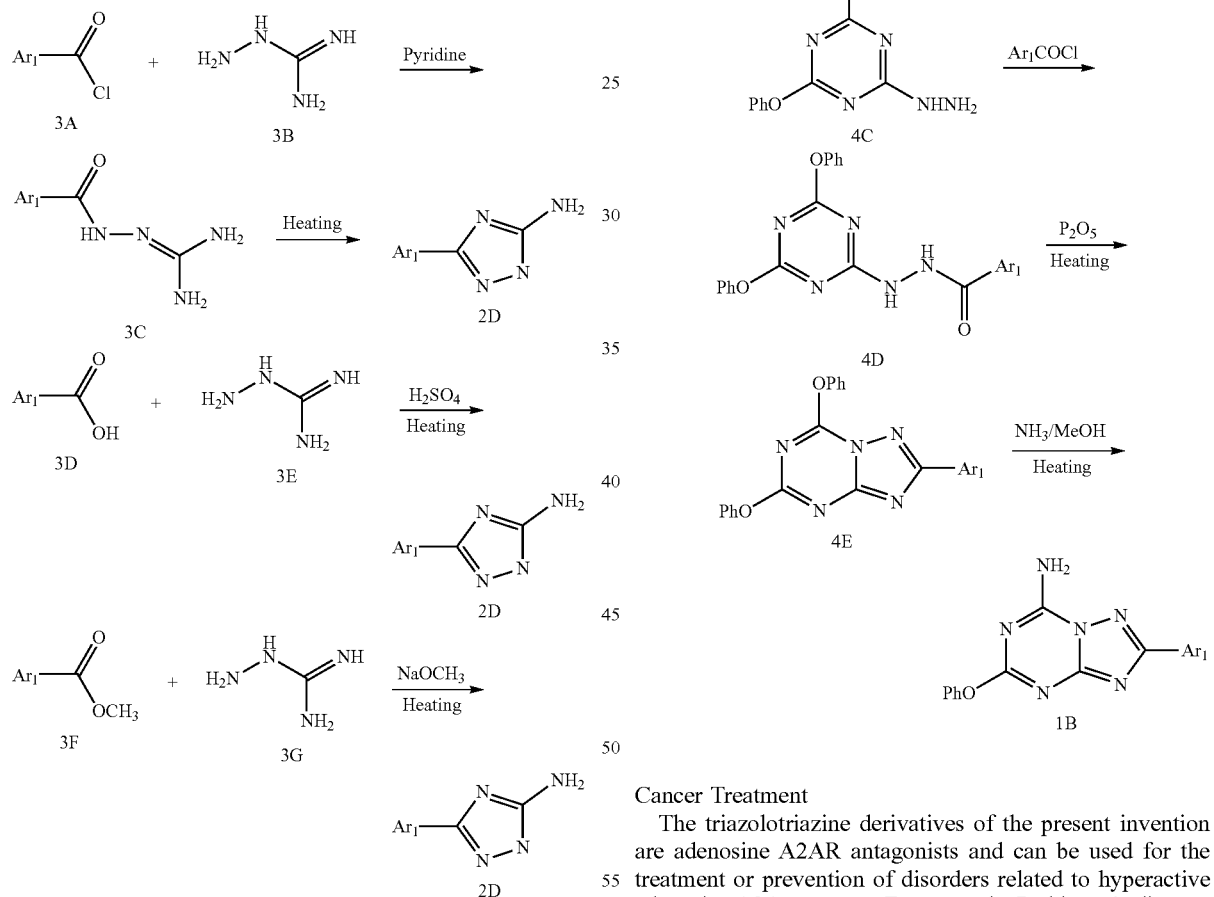

Cancer Treatment

The triazolotriazine derivatives of the present invention are adenosine A2AR antagonists and can be used for the treatment or prevention of disorders related to hyperactive adenosine A2A receptors. For example, Parkinson's disease, cognitive or memory impairment disorder, and Alzheimer's disease are some of the disorders that can be treated with the triazolotriazine derivatives of the present invention.

In particular, the A2AR antagonists of the present invention can be used for the treatment or prevention of cancer and related abnormal cell proliferations in a host, which is any multi-cellular vertebrate organism including both human and non-human mammals. The host is in particular human.

The importance of lymphoid cells in tumor immunity is well appreciated in recent years. The immune response to tumors includes immunologic surveillance, by which cellular mechanisms associated with cell-mediated immunity destroy newly transformed tumor cells after recognizing tumor-associated antigens. The cytotoxic immune cells, which are mainly T-cells, have been found within neuroblastoma, malignant melanomas, sarcomas, and carcinomas of the colon, breast, cervix, endometrium, ovary, testis, nasopharynx, and kidney. Antibody-mediated protection against tumor growth is also known, although it generally plays a less significant role than cell-mediated immunity against cancer.

The A2AR antagonists of the present invention can be used to increase the anti-tumor activity of immune cells in a host. The A2AR antagonists can reduce T cell anergy or the tolerance of T cells to cancer, can increase susceptibility of cancer cells to immune rejection, can inhibit the expansion of regulatory T cells, and can enhance the generation of memory T cells. The A2AR antagonists can improve both the natural immune response and various adaptive immunotherapy in a host.

In a typical embodiment of the present invention, a method of treating or preventing abnormal cell proliferation comprises administering to a patient an effective dose of an A2AR antagonist of formula (1), or a pharmaceutically acceptable salt or solvate thereof.

To be more effective, a synergistic effect may be achieved by combining the A2AR antagonists of the present invention with other modalities of cancer therapy, such as chemotherapy, tumor vaccines, and various immune checkpoint inhibitors. The term "combination therapy" refers to both concurrent and sequential administration of the active agents.

As an example of the combination therapy, a method of treating or preventing abnormal cell proliferation in a host comprises administering to a patient an A2AR antagonist of formula (1) in combination or alternation with an immune checkpoint inhibitor. The immune checkpoint inhibitor can be a PD-1 inhibitor, a PD-L1 inhibitor, a PD-L2 inhibitor, a CTLA-4 inhibitor, a BTLA inhibitor, a LAG3 inhibitor, a TIM-3 inhibitor, a B7-H3 inhibitor, a B7-H4 inhibitor, a KIR inhibitor, a TIGIT inhibitor, or a VISTA inhibitor.

In another example, a method of treating or preventing abnormal cell proliferation in a host comprises administering to a patient an A2AR antagonist of formula (1) in combination or alternation with a cell-based vaccine. The cell-based vaccine is based on cells that match the tumor to be prevented. For example, if a host is suffering from, or at risk of suffering from, a prostate cancer, the cell-based vaccine will be based on a prostate cancer tumor cell. In these instances, the cell is typically irradiated or otherwise prevented from replicating. Or, the cell is genetically modified to secrete a colony stimulating factor.

In another example, a method of treating or preventing abnormal cell proliferation in a host comprises administering to a patient an A2AR antagonist of formula (1) in combination or alternation with Chimeric Antigen Receptor (CAR) T-Cell Therapy.

In another example, a method of treating or preventing abnormal cell proliferation in a host comprises administering to a patient an A2AR antagonist of formula (1) in combination or alternation with an anti-cancer agent to treat abnormal cell proliferation. The anti-cancer agent can be an alkylating agent, an antimetabolite, an anthracycline derivative, a plant alkaloid, a topoisomerase inhibitor, an antitumor antibiotic, a kinase inhibitor, or a monoclonal antibody against tumor antigens.

In other examples, a synergistic effect may be achieved by combining the A2AR antagonists of the present invention with two or more other modalities of cancer therapy, such as chemotherapy, tumor vaccines, and immune checkpoint inhibitors. The term "combination therapy" refers to both concurrent and sequential administration of the active agents.

Pharmaceutical Compositions

The triazolotriazine derivatives of the present invention can be formulated as pharmaceutical compositions when administered to a host. The pharmaceutical compositions are determined by the chosen route of administration, such as orally, parenterally, intravenously, intramuscularly, nasally, buccally, topically, transdermally or subcutaneously. The triazolotriazine derivatives included in the pharmaceutical compositions should be sufficient to deliver a therapeutically effective amount to treat cancer or other disorders characterized by abnormal cell proliferation without causing serious toxic effects to the host. The treatment can involve daily or multi-daily administration of the triazolotriazine derivatives over a period of a few days to weeks, months, or even years.

A convenient mode of administration of the triazolotriazine derivatives of the present invention is oral. Oral compositions generally include an inert diluent or an edible carrier. The compositions may be enclosed in gelatin capsules or compressed into tablets. The tablets, pills, capsules, troches and the like can contain any of the following ingredients: a binder such as microcrystalline cellulose, gum tragacanth or gelatin; an excipient such as starch or lactose; a disintegrating agent such as alginic acid or corn starch; a lubricant such as magnesium stearate; a glidant such as colloidal silicon dioxide; a sweetening agent such as sucrose or saccharin; a flavoring agent such as peppermint, methyl salicylate, or orange flavoring; a wetting or emulsifying agent; preservatives; and pH buffering agents and the like, for example sodium acetate or sorbitan monolaurate. When the pharmaceutical compositions are in a capsule, a liquid carrier such as fatty oil may also be included. In addition, the pharmaceutical compositions can contain various other materials, such as coatings of sugar, shellac, or other enteric agents.

The triazolotriazine derivatives of the present invention can also be administered as a component of an elixir, suspension, syrup, wafer, chewing gum or the like. A syrup may contain, in addition to the triazolotriazine derivatives, sucrose as a sweetening agent, preservatives, coloring agents and flavoring agents. Solutions or suspensions used for parenteral, intradermal, subcutaneous, or topical application can include a sterile diluent such as water, saline solution, Ringer's solution, fixed oils, polyethylene glycols, glycerin, propylene glycol, fatty acids such as oleic acid and its glyceride derivatives, or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

The triazolotriazine derivatives of the present invention can also be placed in carriers that protect the derivatives against rapid elimination from the body. Various means to achieve controlled release, including implants and microencapsulated delivery systems, can also be used.

The triazolotriazine derivatives of the present invention can also be administered through the use of nebulizer, a dry powder inhaler or a metered dose inhaler inhaled through the nasal aerosols. The compositions may be prepared as solutions in saline, employing benzyl alcohol or other suitable preservatives, absorption promoters, fluorocarbons, and other conventional solubilizing or dispersing agents.

It is understandable that for any particular patient the specific dose and treatment regimen will depend upon a variety of factors including the activity of the specific compound employed, the age, body weight, general health, and sex of the patient, diet, time of administration, rate of excretion, the pathological condition to be treated, the goal of treatment, as well as the judgment of the physician. The amount of active ingredient may also depend on what is the co-administered therapeutic agent if it is a combination therapy.

EXAMPLES

The following examples, which are for detailed illustration only, are not intended to limit the scope of the present invention.

Example 1

2-(Furan-2-carboxamido) guanidine

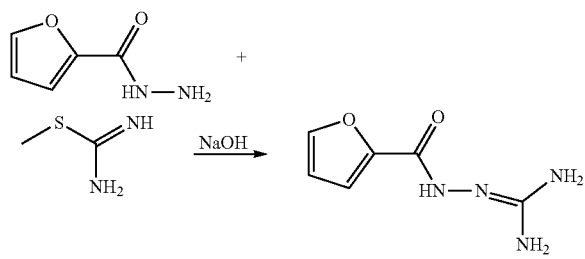

A mixture of furan-2-carbohydrazide (37.80 g, 300 mmol), S-methylisothiourea sulfate (41.70 g, 150 mmol) and an aqueous sodium hydroxide solution (2%, 1.2 L) was stirred at room temperature for 72 h. The precipitate was filtered, washed with ice-cold water, and used in the next step without further purification (25.25 g, 51.00% yield). $^1$H NMR (500 MHz, DMSO-d6) δ: 10.95 (s, 1H), 7.56 (s, 1H), 6.91 (d, J=91.9 Hz, 4H), 6.64 (s, 1H), 6.45 (s, 1H).

Example 2

3-(Furan-2-yl)-1H-1,2,4-triazol-5-amine

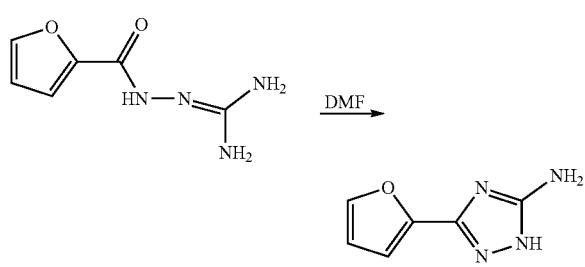

A stirred solution of 2-(furan-2-carboxamido) guanidine (23.20 g, 138 mmol) in DMF (464 mL) was heated at 125° C. overnight. After it was cooled to room temperature, the solvent was removed under reduced pressure. To the residue was added DCM (200 ml) and it was stirred for 30 min. The precipitate was filtered and washed with DCM (20 mL×2) to afford the title compound as yellow solid (17.37 g, 84.00% yield). $^1$H NMR (500 MHz, DMSO-d6) δ: 12.13 (s, 1H), 7.69 (s, 1H), 6.69 (d, J=1.8 Hz, 1H), 6.54 (dd, J=3.0, 1.7 Hz, 1H), 6.03 (s, 2H).

Example 2A 3-(Furan-2-yl)-1H-1,2,4-triazol-5-amine

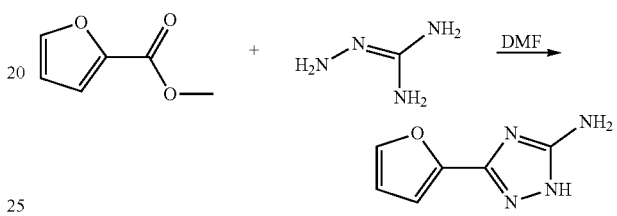

To a stirred solution of CH$_3$ONa (171.4 g, 3172 mol) and aminoguanidine hydrochloride (175.3 g, 1586 mmol) in methanol (1200 mL) at 0° C. was added slowly the solution of methyl furan-2-carboxylate (100 g, 793 mmol) in methanol (300 mL). The reaction mixture was then stirred at 75° C. overnight. The resulting mixture was filtered. The filtrate was concentrated in vacuo and the residue was dissolved in water (50 mL). 3N HCl was added to adjust pH to 4. The precipitated solid was collected by filtration and drying to afford the title compound as yellow solid (69.2 g, 58.1% yield). $^1$H NMR (500 MHz, DMSO-d6) δ: 12.44 (s, 1H), 7.69 (d, 1H), 6.70 (d, 1H), 6.54 (dd, 1H), 6.03 (s, 2H).

Example 3

2-(Furan-2-yl)-5-(methylthio)-[1,2,4]triazolo[1,5-α][1,3,5]triazin-7-amine

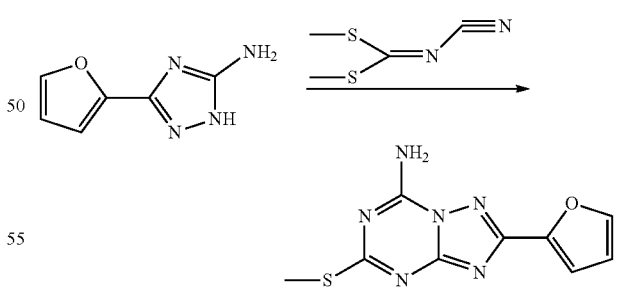

A mixture of 3-(furan-2-yl)-1H-1,2,4-triazol-5-amine (13.58 g, 90.46 mmol) and dimethyl cyanocarbonimidodithioate (13.23 g, 90.46 mmol) was stirred at 180° C. for 1.5 h. It was next cooled to room temperature. The residue was purified by column chromatography (PE:EA=1:1) to afford the title compound as white solid (7.00 g, 31.20% yield). $^1$H NMR (500 MHz, DMSO-d6) δ: 8.96 (s, 1H), 8.76 (s, 1H), 7.93 (d, J=0.9 Hz, 1H), 7.16 (d, J=3.3 Hz, 1H), 6.72 (dd, J=3.4, 1.7 Hz, 1H), 2.51 (s, 3H).

Example 4

2-(Furan-2-yl)-5-(methylsulfonyl)-[1,2,4]triazolo[1,5-α][1,3,5]triazin-7-amine

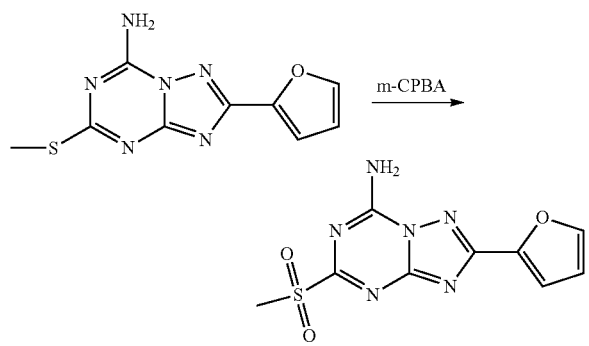

A solution of m-CPBA (85% strength, 26.20 g, 128.90 mmol) in DCM (240 mL) was added dropwise to a stirred, ice-cold suspension of 2-(furan-2-yl)-5-(methylthio)-[1,2,4]triazolo[1,5-α][1,3,5]triazin-7-amine (8.0 g, 32.2 mmol) in DCM (480 mL). The reaction was stirred at room temperature for 22 h before the solvent was removed under vacuum. The crude material was suspended in ethanol (120 mL) and stirred at room temperature for 30 min. The solid was filtered, washed with ethanol and dried to give the title compound as brown solid (7.82 g, 86.90% yield). $^1$H NMR (500 MHz, DMSO-d6) δ: 9.81 (s, 1H), 9.48 (s, 1H), 7.99 (d, J=1.0 Hz, 1H), 7.27 (d, J=3.4 Hz, 1H), 6.76 (dd, J=3.4, 1.8 Hz, 1H), 3.36 (s, 3H).

Example 5

2-(Furan-2-yl)-N5-(2-(pyridin-4-yl)ethyl)-[1,2,4]triazolo[1,5-α][1,3,5]triazine-5,7-diamine

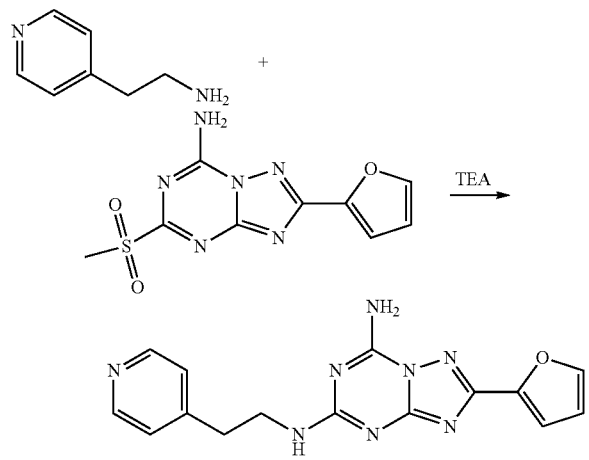

A solution of 2-(pyridin-4-yl)ethanamine (100 mg, 0.86 mmol), 2-(furan-2-yl)-5-(methylsulfonyl)-[1,2,4]triazolo[1,5-α][1,3,5]triazin-7-amine (230 mg, 0.82 mmol) and TEA (250 mg, 2.46 mmol) in MeCN (5 mL) was stirred overnight. The reaction mixture was quenched with water (30 mL) and extracted with DCM (15 mL×3). The organic layer was washed with water and brine, dried over sodium sulfate and concentrated in vacuo. The crude product was purified by column chromatography to afford the title compound as white solid (41.50 mg, 15.72% yield). $^1$H NMR (500 MHz, DMSO-d6) δ: 8.47 (d, J=4.5 Hz, 2H), 8.22 (s, 2H), 7.89 (d, J=14.3 Hz, 1H), 7.57 (d, J=46.0 Hz, 1H), 7.28 (s, 2H), 7.06 (s, 1H), 6.68 (s, 1H), 3.54 (d, J=5.6 Hz, 2H), 2.90 (s, 2H).

Example 6

3-(4-Methylpiperazin-1-yl)propyl methanesulfonate

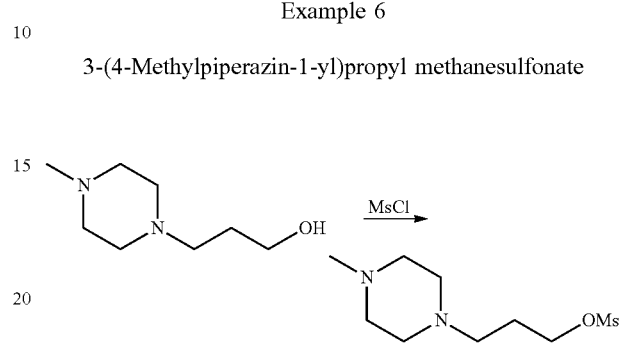

A solution of MsCl (0.80 g, 7.00 mmol) in DCM (10 mL) was added dropwise to a stirred, ice-cold suspension of 3-(4-methylpiperazin-1-yl)propan-1-ol (1.00 g, 6.32 mmol) in DCM (5 mL). The reaction was stirred at room temperature for 2 h before the solvent was removed under vacuum. The crude product (white solid) was used directly without purification (1.4 g, 94% yield). $^1$H NMR (500 MHz, CD$_3$OD_SPE) δ: 4.38 (t, J=5.9 Hz, 2H), 3.73 (dd, J=22.6, 16.8 Hz, 8H), 3.44-3.38 (m, 2H), 3.13 (s, 3H), 3.02 (s, 3H), 2.31-2.23 (m, 2H).

Example 7 tert-Butyl 4-(3-(4-methylpiperazin-1-yl)propoxy)phenethylcarbamate

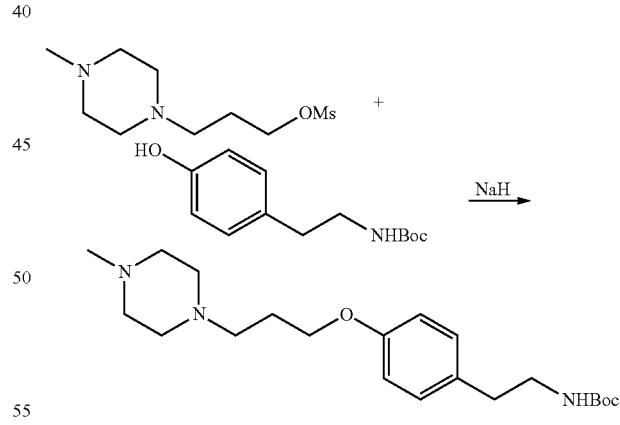

A mixture of 3-(4-methylpiperazin-1-yl)propyl methanesulfonate (580 mg, 2.12 mmol), tert-butyl 4-hydroxyphenethylcarbamate (550 mg, 2.33 mmol) and NaH (190 mg, 4.67 mmol) in dry DMF (20 mL) was stirred at 60° C. under N$_2$ overnight. The reaction mixture was quenched with water (80 mL) and extracted with ethyl acetate (20 mL×3). The organic layer was washed with water and brine, dried over sodium sulfate and concentrated in vacuo. The crude product was purified by column chromatography to afford the title compound as white solid (330 mg, 41.25% yield). $^1$H NMR (500 MHz, CD$_3$OD_SPE) δ: 7.09 (d, J=8.4 Hz, 2H), 6.83 (t, J=8.9 Hz, 2H), 3.99 (q, J=6.4 Hz, 2H), 3.19 (t, J=7.4 Hz, 2H), 2.61 (ddd, J=30.6, 19.0, 11.5 Hz, 10H), 2.32 (s, 3H), 1.99-1.89 (m, 2H), 1.39 (d, J=18.9 Hz, 9H).

Example 8

2-(4-(3-(4-Methylpiperazin-1-yl)propoxy)phenyl)ethanamine

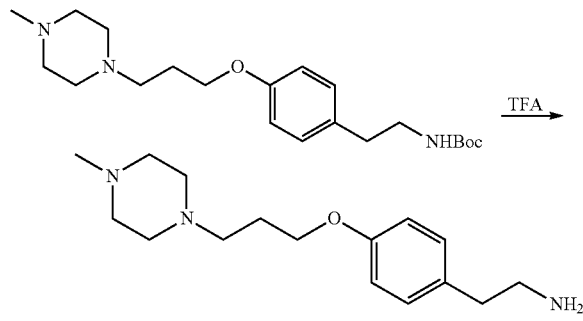

To a stirred solution of tert-butyl 4-(3-(4-methylpiperazin-1-yl) propoxy)phenethyl-carbamate (250 mg, 0.67 mmol) in DCM (5 mL) was slowly added TFA (1 mL) at room temperature. The reaction was stirred for 2 h. The reaction mixture was concentrated in vacuo to afford the crude product that was used directly without purification.

Example 9

2-(Furan-2-yl)-N5-(4-(3-(4-methylpiperazin-1-yl)propoxy)phenethyl)-[1,2,4]triazolo[1,5-α][1,3,5]triazine-5,7-diamine

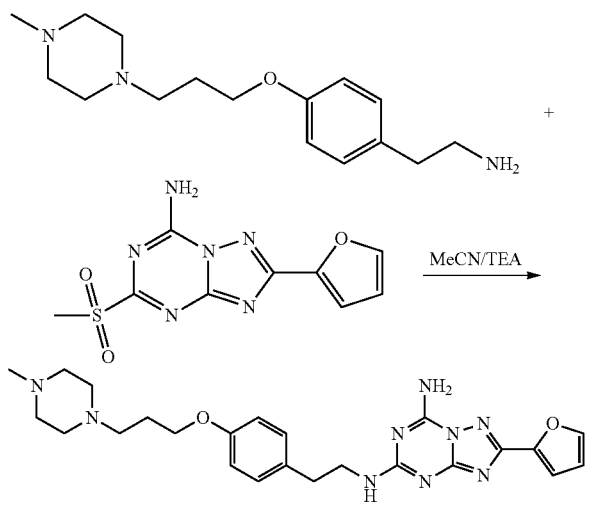

The reaction was carried out as in Example 5 to afford the title compound as brown solid (137 mg, 42.80% yield). ¹H NMR (500 MHz, CDCl₃) δ: 7.65-7.53 (m, 1H), 7.21 (s, 1H), 7.11 (d, J=8.0 Hz, 2H), 6.83 (d, J=8.1 Hz, 2H), 6.55 (dd, J=3.3, 1.7 Hz, 1H), 6.21 (d, J=123.0 Hz, 2H), 5.29 (d, J=6.9 Hz, 1H), 3.99 (t, J=5.9 Hz, 2H), 3.68 (t, J=25.9 Hz, 2H), 2.85 (dd, J=23.3, 16.8 Hz, 2H), 2.71-2.33 (m, 10H), 2.28 (s, 3H), 1.99-1.89 (m, 2H).

Example 10

2-(Dimethylamino)ethyl methanesulfonate

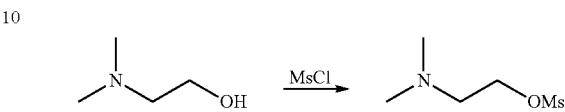

A solution of MsCl (4.30 g, 37.50 mmol) in DCM (30 mL) was added dropwise to a stirred, ice-cold suspension of 2-(dimethylamino)ethanol (2.68 g, 30 mmol) in DCM (20 mL). The reaction was stirred at room temperature for 2 h. The reaction mixture was filtered, washed with DCM (10 mL×3), and dried to afford the title compound as white solid (4.98 g, 81.60% yield). ¹H NMR (500 MHz, CD₃OD_SPE) δ: 4.64-4.58 (m, 2H), 3.63-3.56 (m, 2H), 3.22 (s, 3H), 2.98 (s, 6H).

Example 11 tert-Butyl 4-(2-(dimethylamino)ethoxy)phenethylcarbamate

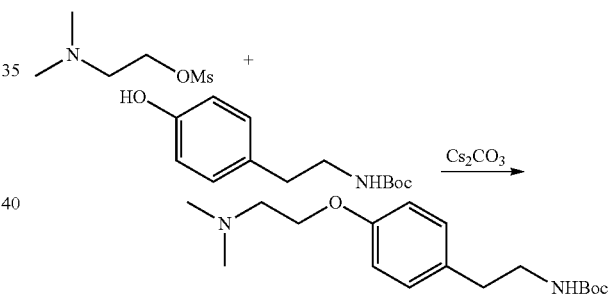

A mixture of 2-(dimethylamino)ethyl methanesulfonate (1.00 g, 4.91 mmol), tert-butyl 4-hydroxyphenethylcarbamate (1.17 g, 4.91 mmol) and cesium carbonate (4.80 g, 14.73 mmol) in acetone (20 mL) was stirred at room temperature overnight. The reaction mixture was filtered. The filtrate was concentrated and purified by column chromatography to afford the title compound as white solid (830 mg, 54.97% yield). ¹H NMR (500 MHz, CDCl₃) δ: 7.11 (d, J=8.4 Hz, 2H), 6.88 (d, J=8.4 Hz, 2H), 4.07 (t, J=5.8 Hz, 2H), 3.36 (d, J=5.9 Hz, 2H), 2.81-2.66 (m, 4H), 2.35 (s, 6H), 1.45 (s, 9H).

Example 12

2-(4-(2-Aminoethyl)phenoxy)-N,N-dimethylethanamine

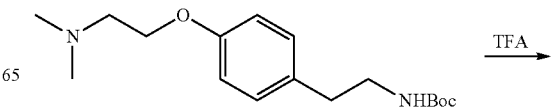

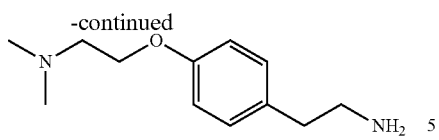

To a stirred solution of tert-butyl 4-(2-(dimethylamino)ethoxy)phenethylcarbamate (308 mg, 1.00 mmol) in DCM (5 mL) was added TFA (1 mL) at room temperature. The reaction was stirred for 1 h. The reaction mixture was concentrated in vacuo to afford the crude product that was used directly for the next step without purification.

Example 13

N5-(4-(2-(Dimethylamino)ethoxy)phenethyl)-2-(furan-2-yl)-[1,2,4]triazolo[1,5-α][1,3,5]-triazine-5,7-diamine

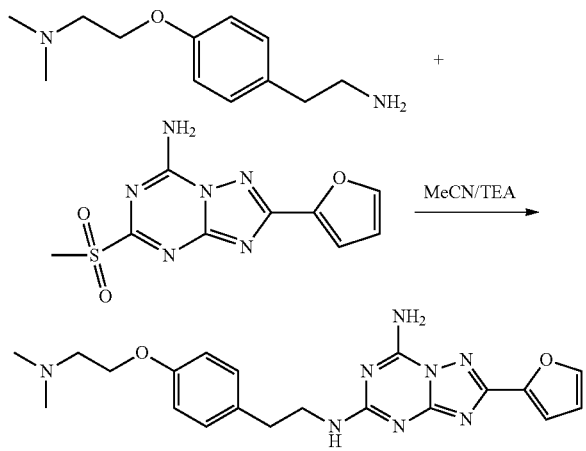

The reaction was carried out as in Example 5 to afford the title compound as white solid (75.80 mg, 18.58% yield). $^1$H NMR (500 MHz, DMSO-d6) δ: 8.31 (d, J=131.4 Hz, 2H), 7.87 (s, 1H), 7.47 (dd, J=25.9, 20.6 Hz, 1H), 7.16 (d, J=8.3 Hz, 2H), 7.06 (d, J=3.4 Hz, 1H), 6.87 (d, J=8.5 Hz, 2H), 6.68 (dd, J=3.1, 1.6 Hz, 1H), 4.02 (t, J=5.8 Hz, 2H), 3.45 (d, J=6.7 Hz, 2H), 2.78 (d, J=7.2 Hz, 2H), 2.64 (t, J=5.6 Hz, 2H), 2.24 (s, 6H).

Example 14 tert-Butyl 4-(2-(pyrrolidin-1-yl)ethoxy)phenethylcarbamate

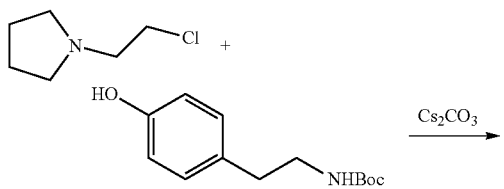

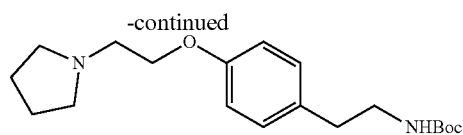

A mixture of 1-(2-chloroethyl)pyrrolidine hydrochloride (0.50 g, 2.94 mmol), tert-butyl 4-hydroxyphenethylcarbamate (0.70 g, 2.94 mmol), cesium carbonate (1.92 g, 5.88 mmol) and NaI (44 mg, 0.29 mmol) in acetone (10 mL) was stirred at room temperature overnight. The reaction mixture was filtered. The filtrate was concentrated and purified by column chromatography to afford the title compound as yellow oil (354 mg, 36.05% yield). $^1$H NMR (500 MHz, DMSO-d6) δ: 7.09 (d, J=8.5 Hz, 2H), 6.85 (d, J=8.5 Hz, 2H), 4.05 (t, J=5.8 Hz, 2H), 3.09 (dd, J=14.3, 6.4 Hz, 2H), 2.87 (s, 2H), 2.61 (t, J=7.4 Hz, 6H), 1.79-1.65 (m, 4H), 1.37 (s, 9H).

Example 15

2-(4-(2-(Pyrrolidin-1-yl)ethoxy)phenyl)ethanamine

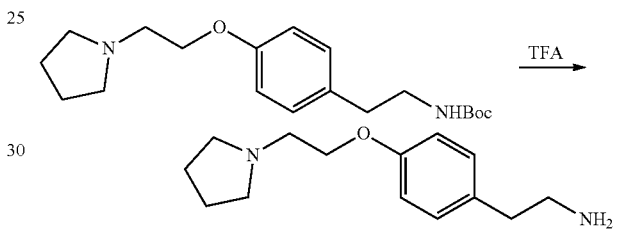

To a stirred solution of tert-butyl 4-(2-(pyrrolidin-1-yl)ethoxy)phenethylcarbamate (354 mg, 1.06 mmol) in DCM (10 mL) was added TFA (1 mL) at room temperature. The reaction was stirred overnight. The reaction mixture was concentrated in vacuo to afford the crude product that was used directly without purification.

Example 16

2-(Furan-2-yl)-N5-(4-(2-(pyrrolidin-1-yl)ethoxy)phenethyl)-[1,2,4]triazolo[1,5-α][1,3,5]-triazine-5,7-diamine

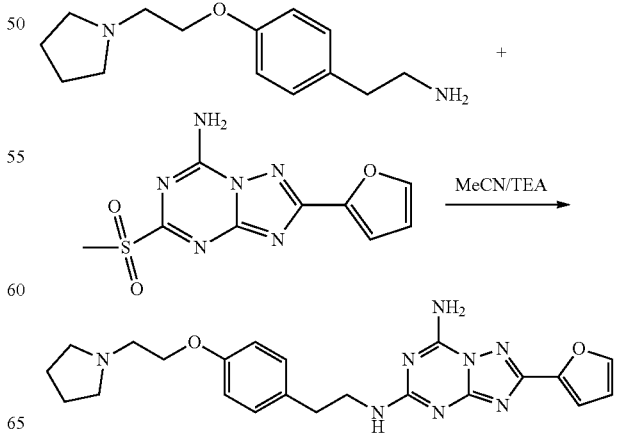

The reaction was carried out as in Example 5 to afford the title compound as white solid (87.7 mg, 21.24% yield). $^1$H NMR (500 MHz, DMSO-d6) δ: 8.30 (d, J=130.3 Hz, 2H), 7.87 (s, 1H), 7.45 (s, 1H), 7.16 (d, J=8.3 Hz, 2H), 7.06 (d, J=3.3 Hz, 1H), 6.87 (d, J=8.4 Hz, 2H), 6.71-6.64 (m, 1H), 4.05 (t, J=5.8 Hz, 2H), 3.49-3.42 (m, 2H), 2.80 (dd, J=21.4, 13.8 Hz, 4H), 2.59 (s, 4H), 1.70 (s, 4H).

Example 17 tert-Butyl 4-(3-(pyrrolidin-1-yl)propoxy)phenethylcarbamate

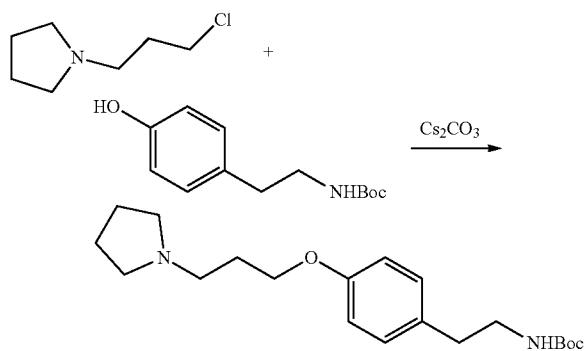

A mixture of 1-(3-chloropropyl)pyrrolidine hydrochloride (0.25 g, 1.36 mmol), tert-butyl 4-hydroxyphenethylcarbamate (0.32 g, 1.36 mmol), cesium carbonate (1.33 g, 4.08 mmol) and NaI (21 mg, 0.14 mmol) in acetone (10 mL) was stirred at 50° C. for 48 h. The reaction mixture was filtered. The filtrate was concentrated and purified by column chromatography to afford the title compound as yellow oil (200 mg, 42.19% yield).

Example 18

2-(4-(3-(Pyrrolidin-1-yl)propoxy)phenyl)ethanamine

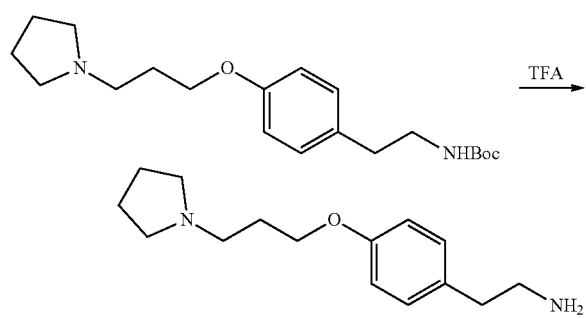

To a stirred solution of tert-butyl 4-(3-(pyrrolidin-1-yl)propoxy)phenethylcarbamate (200 mg, 0.57 mmol) in DCM (7 mL) was added TFA (1 mL) at room temperature. The reaction mixture was stirred for 1 h. The reaction mixture was concentrated in vacuo to afford the crude product that was used directly for the next reaction without purification.

Example 19

2-(Furan-2-yl)-N5-(4-(3-(pyrrolidin-1-yl)propoxy) phenethyl)-[1,2,4]triazolo[1,5-α][1,3,5]-triazine-5,7-diamine

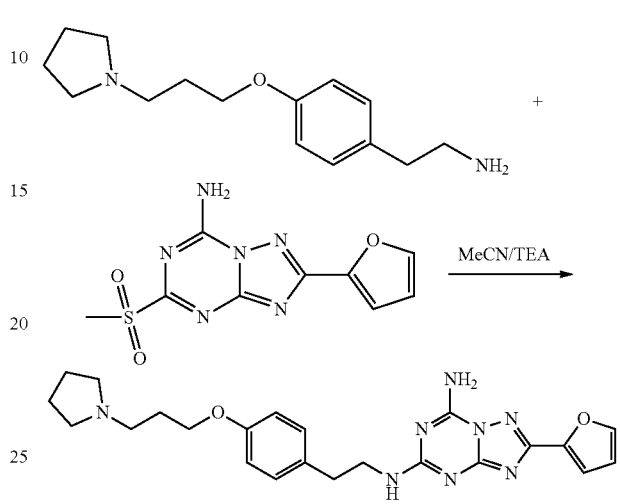

The reaction was carried out as in Example 5 to afford the title compound as white solid (25 mg, 9.8% yield). $^1$H NMR (500 MHz, DMSO-d6) δ: 8.17 (s, 2H), 7.87 (s, 1H), 7.47 (d, J=5.4 Hz, 1H), 7.18 (d, J=8.3 Hz, 2H), 7.05 (d, J=3.1 Hz, 1H), 6.88 (d, J=8.3 Hz, 2H), 6.68 (s, 1H), 4.02 (t, J=6.0 Hz, 2H), 3.49-3.43 (m, 2H), 3.15 (s, 6H), 2.79 (t, J=7.3 Hz, 2H), 2.07 (d, J=7.1 Hz, 2H), 1.90 (s, 4H).

Example 20 tert-Butyl 4-(2-(4-methylpiperazin-1-yl)ethoxy) phenethylcarbamate

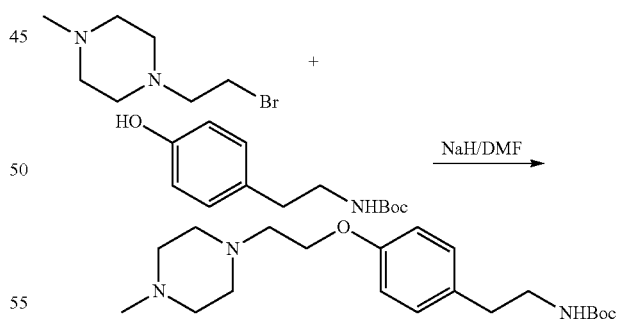

A mixture of 1-(2-bromoethyl)-4-methylpiperazine (200 mg, 0.54 mmol), tert-butyl 4-hydroxyphenethylcarbamate (128 mg, 0.54 mmol) and NaH (65 mg, 1.64 mmol) in dry DMF (12 mL) was stirred under N$_2$ at room temperature for 2 h. The reaction mixture was quenched with water (50 mL) and extracted with DCM (15 ml×3). The organic layer was washed with water and brine, dried over sodium sulfate and concentrated in vacuo. The crude product was purified by column chromatography to afford the title compound as white solid (88 mg, 44.90% yield).

Example 21

2-(4-(2-(4-Methylpiperazin-1-yl)ethoxy)phenyl)ethanamine

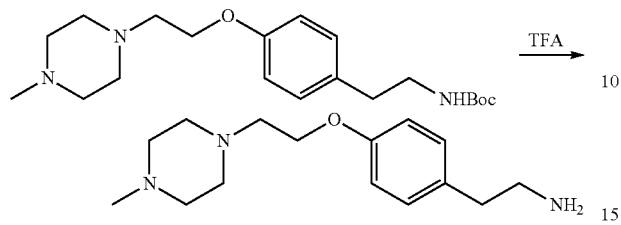

To a stirred solution of tert-butyl 4-(2-(4-methylpiperazin-1-yl)ethoxy) phenethyl-carbamate (88 mg, 0.24 mmol) in DCM (5 mL) was added TFA (1 mL) at room temperature. The reaction was stirred for 2 h. The reaction mixture was concentrated in vacuo to afford the crude product that was used directly without purification.

Example 22

2-(Furan-2-yl)-N5-(4-(2-(4-methylpiperazin-1-yl)ethoxy)phenethyl)-[1,2,4]triazolo[1,5-α][1,3,5]triazine-5,7-diamine

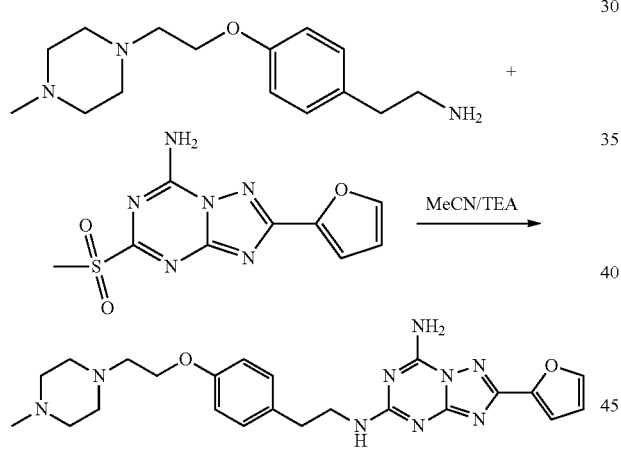

The reaction was carried out as in Example 5 to afford the title compound as brown solid (11 mg, 9.91% yield). $^1$H NMR (500 MHz, DMSO-d6) δ: 8.16 (s, 2H), 7.86 (s, 1H), 7.44 (s, 1H), 7.15 (d, J=8.2 Hz, 2H), 7.05 (d, J=3.3 Hz, 1H), 6.86 (d, J=8.4 Hz, 2H), 6.67 (s, 1H), 4.02 (t, J=5.8 Hz, 2H), 3.44 (dd, J=13.6, 6.7 Hz, 4H), 2.80-2.75 (m, 2H), 2.67 (t, J=5.7 Hz, 2H), 2.44 (d, J=34.3 Hz, 6H), 2.20 (s, 3H).

Example 23

2-(Furan-2-yl)-N5-(2-(pyridin-3-yl)ethyl)-[1,2,4]triazolo[1,5-α][1,3,5]triazine-5,7-diamine

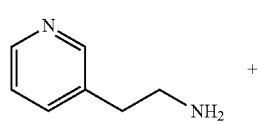

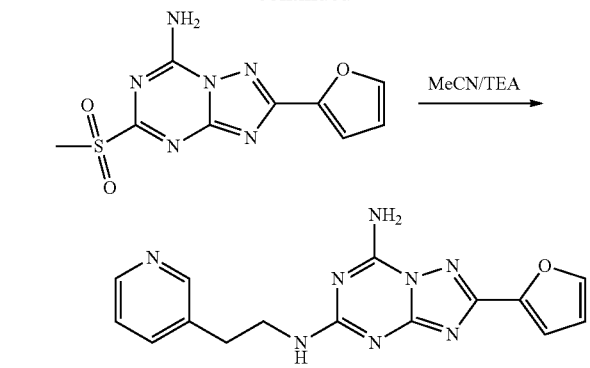

The reaction was carried out as in Example 5 to afford the title compound as white solid (64.8 mg, 20.12% yield). $^1$H NMR (500 MHz, CDCl$_3$) δ: 8.47 (d, J=9.3 Hz, 1H), 8.41 (dd, J=4.7, 1.3 Hz, 1H), 8.19 (s, 2H), 7.86 (s, 1H), 7.67 (t, J=8.7 Hz, 1H), 7.53 (dd, J=29.5, 24.0 Hz, 1H), 7.31 (dd, J=7.7, 4.8 Hz, 1H), 7.05 (d, J=3.3 Hz, 1H), 6.67 (d, J=1.5 Hz, 1H), 3.51 (dd, J=13.3, 6.7 Hz, 2H), 2.88 (t, J=7.1 Hz, 2H).

Example 24 tert-Butyl 4-(pyridin-2-ylmethoxy)phenethylcarbamate

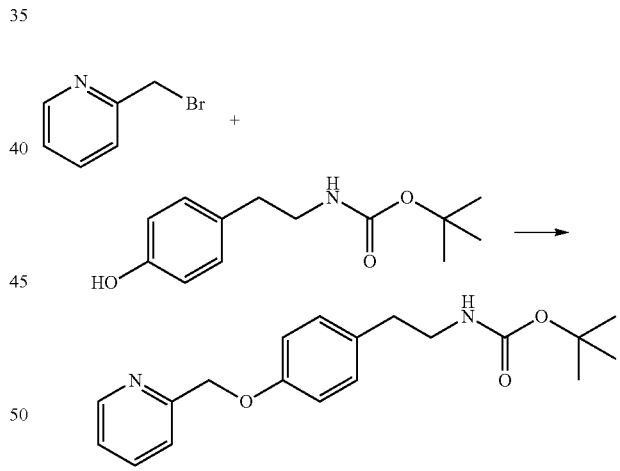

A mixture of tert-butyl 4-hydroxyphenethylcarbamate (1.03 g, 4.34 mol), cesium carbonate (3.88 g, 11.88 mmol) and 2-(bromomethyl)pyridine hydrobromide (1 g, 3.96 mmol) in acetone (20 mL) was stirred at room temperature for 4 h. The reaction mixture was filtrated. The filtrate was concentrated and purified by column chromatography (hexane:EtOAc=2:1) to afford the title compound as white solid (1.18 g, 61.8% yield). $^1$H NMR (500 MHz, DMSO-d6) δ: 8.58 (t, 1H), 7.82 (dt, 1H), 7.50 (d, 1H), 7.33 (t, 1H), 7.11 (d, 2H), 6.94 (d, 2H), 6.84 (t, 1H), 5.14 (s, 2H), 3.10 (q, 2H), 2.62 (t, 2H), 1.18 (s, 9H).

Example 25

2-(4-(Pyridin-2-ylmethoxy)phenyl)ethanamine

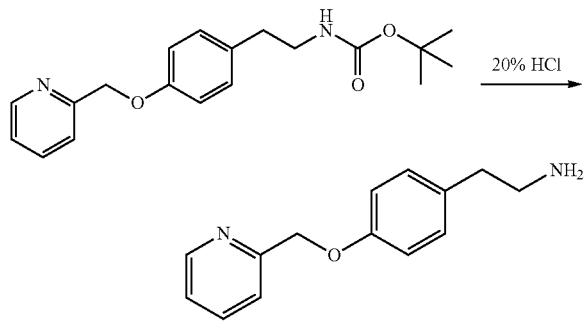

A mixture of tert-butyl 4-(pyridin-2-ylmethoxy)phenethylcarbamate (600 mg, 1.83 mmol) in 20% hydrochloric acid (2.3 mL) and methanol (5 mL) was stirred at room temperature for 40 hours. The reaction mixture was concentrated in vacuo to afford the crude product as yellow oil, which was used for the next step directly.

Example 26

2-(Furan-2-yl)-N5-(4-(pyridin-2-ylmethoxy)phenethyl)-[1,2,4]triazolo[1,5-α][1,3,5]triazine-5,7-diamine

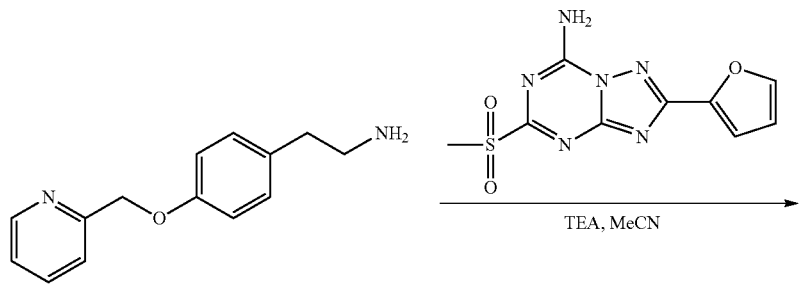

The reaction was carried out as in Example 5 to afford the title compound as white solid (109.2 mg, 14% yield). $^1$H NMR (500 MHz, DMSO-d6) δ: 8.57 (dd, 1H), 8.05-8.49 (d, 2H), 7.87 (s, 1H), 7.82 (dt, 1H), 7.49 (d, 1H), 7.45-7.54 (d, 1H), 7.34 (dt, 1H), 7.18 (t, 2H), 7.06 (dd, 1H), 6.95 (d, 2H), 5.15 (s, 2H), 3.45 (m, 2H), 2.79 (t, 2H).

Example 27 tert-Butyl 4-(pyridin-4-ylmethoxy)phenethylcarbamate

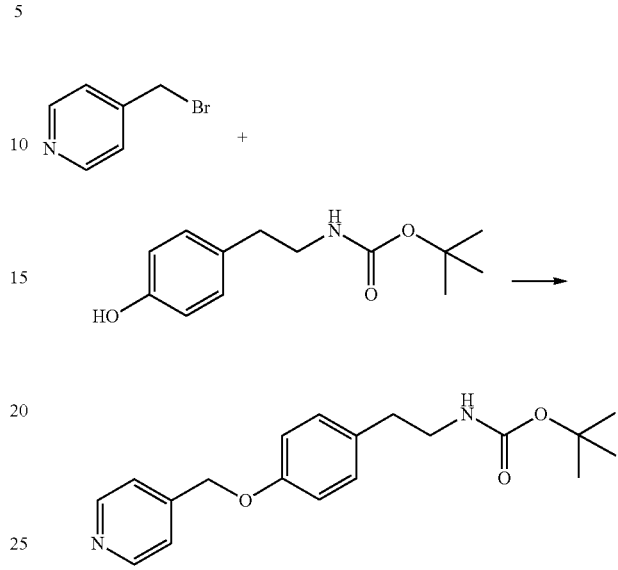

A mixture of tert-butyl 4-hydroxyphenethylcarbamate (516 mg, 2.17 mol), cesium carbonate (1.94 g, 5.94 mmol) and 4-(bromomethyl)pyridine hydrobromide (0.5 g, 1.98 mmol) in acetone (10 mL) was stirred at room temperature for 4 h. The reaction mixture was filtrated. The filtrate was concentrated and purified by column chromatography (hexane:EtOAc=2:1) to afford the title compound as white solid (0.63 g, 66% yield). $^1$H NMR (500 MHz, DMSO-d6) δ: 8.58 (dd, 1H), 7.42 (d, 2H), 7.10 (d, 2H), 6.94 (d, 2H), 6.84 (t, 1H), 5.15 (s, 2H), 3.10 (q, 2H), 2.62 (t, 2H), 1.18 (s, 9H).

Example 28

2-(4-(Pyridin-4-ylmethoxy)phenyl)ethanamine

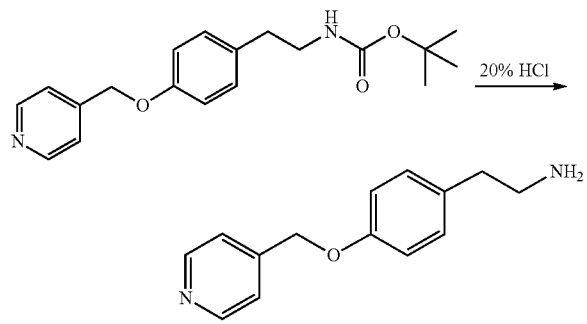

A mixture of tert-butyl 4-(pyridin-4-ylmethoxy)phenethylcarbamate (600 mg, 1.83 mmol) in 20% hydrochloric acid (2.3 mL) and methanol (5 mL) was stirred at room temperature for 15 hours. The reaction mixture was concentrated in vacuo to afford the crude product as yellow oil, which was used for the next step directly.

Example 29

2-(Furan-2-yl)-N5-(4-(pyridin-4-ylmethoxy)phenethyl)-[1,2,4]triazolo[1,5-α][1,3,5]triazine-5,7-diamine

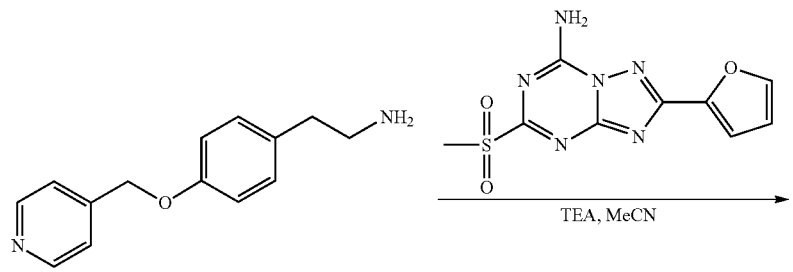

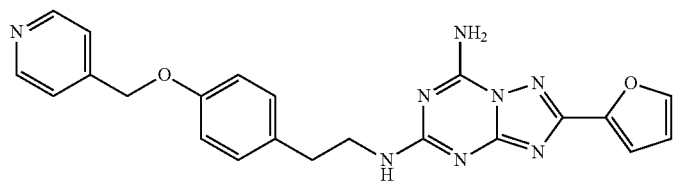

The reaction was carried out as in Example 5 to afford the title compound as white solid (101 mg, 12.9% yield). $^1$H NMR (500 MHz, DMSO-d6) δ: 8.57 (dd, 1H), 8.05-8.49 (d, 2H), 7.87 (s, 1H), 7.40-7.56 (m, 3H), 7.18 (d, 2H), 7.06 (d, 1H), 6.95 (d, 2H), 5.15 (s, 2H), 3.45 (m, 2H), 2.79 (t, 2H).

Example 30 tert-Butyl 4-(pyridin-3-ylmethoxy)phenethylcarbamate

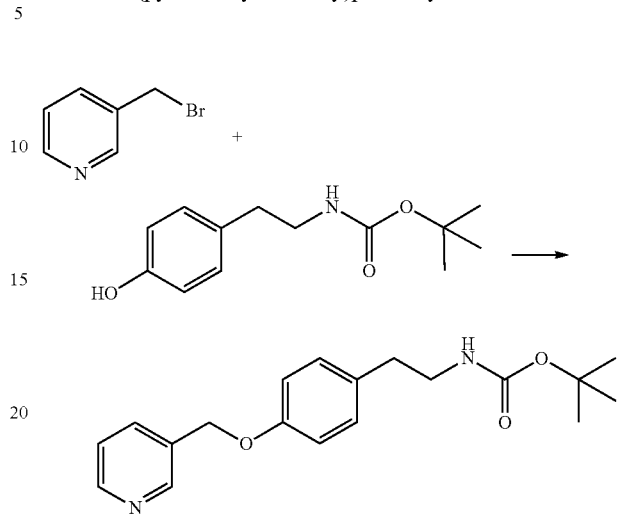

A mixture of tert-butyl 4-hydroxyphenethylcarbamate (310 mg, 1.31 mol), cesium carbonate (1.16 g, 3.57 mmol) and 3-(bromomethyl)pyridine hydrobromide (0.3 g, 1.19 mmol) in acetone (10 mL) was stirred at room temperature for 4 h. The reaction mixture was filtrated. The filtrate was concentrated and purified by column chromatography (hexane:EtOAc=2:1) to afford the title compound as white solid (0.36 g, 62.9% yield). $^1$H NMR (500 MHz, DMSO-d6) δ: 8.66 (d, 1H), 8.54 (dd, 1H), 7.85 (d, 1H), 7.42 (q, 1H), 7.11 (d, 2H), 6.94 (d, 2H), 6.84 (t, 1H), 5.12 (s, 2H), 3.10 (q, 2H), 2.62 (t, 2H), 1.18 (s, 9H).

Example 31

2-(4-(Pyridin-3-ylmethoxy)phenyl)ethanamine

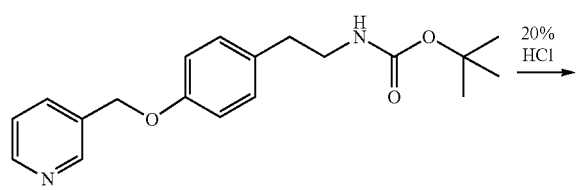

A mixture of tert-butyl 4-(pyridin-3-ylmethoxy)phenethylcarbamate (360 mg, 1.10 mmol) in 20% hydrochloric acid (2.0 mL) and methanol (5 mL) was stirred at room temperature for 2 hours. The reaction mixture was concentrated in vacuo to afford the crude product as yellow oil, which was used for the next step directly.

Example 32

2-(Furan-2-yl)-N5-(4-(pyridin-3-ylmethoxy)phenethyl)-[1,2,4]triazolo[1,5-α][1,3,5]triazine-5,7-diamine

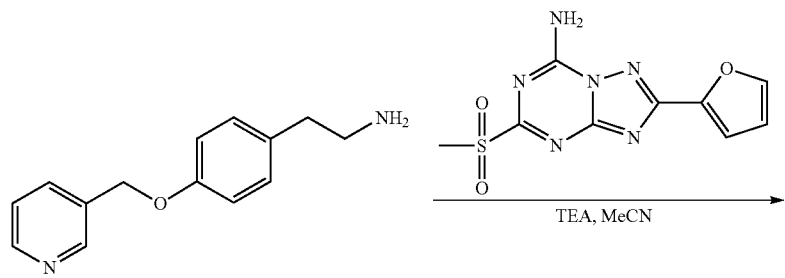

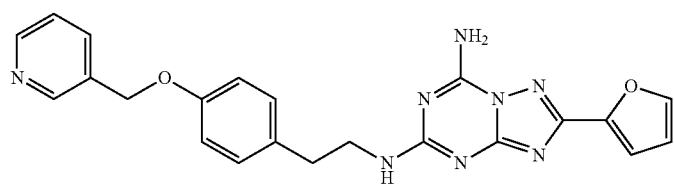

The reaction was carried out as in Example 5 to afford the title compound as white solid (130 mg, 36.5% yield). $^1$H NMR (500 MHz, DMSO-d6) δ: 8.66 (d, 1H), 8.55 (dd, 1H), 8.05-8.49 (d, 2H), 7.85 (t, 2H), 7.40-7.56 (m, 2H), 7.18 (d, 2H), 7.06 (d, 1H), 6.96 (d, 2H), 6.68 (q, 1H), 5.12 (s, 2H), 3.45 (q, 2H), 2.79 (t, 2H).

Example 33

3-(Pyridin-4-yl)propyl methanesulfonate

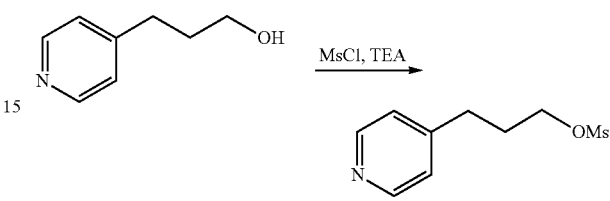

A mixture of 3-(pyridin-4-yl)propan-1-ol (500 mg, 3.64 mol), methanesulfonyl chloride (626 mg, 5.47 mmol) and triethylamine (736 mg, 7.28 mmol) in dichloromethane (10 mL) was stirred at room temperature for 2 h. The reaction mixture was quenched with water and extracted with dichloromethane. The organic layer was washed with water and brine, dried over sodium sulfate and concentrated in vacuo to afford the title compound as brown oil (680 mg, 86.7% yield). 114 NMR (500 MHz, DMSO-d6) δ: 8.48 (d, 2H), 7.45 (d, 2H), 4.26 (t, 2H), 3.06 (s, 3H), 2.84 (t, 2H), 2.11 (m, 2H).

Example 34 tert-Butyl 4-(3-(pyridin-4-yl)propoxy)phenethylcarbamate

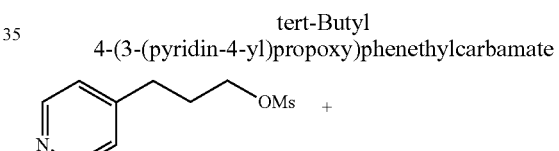

31

-continued

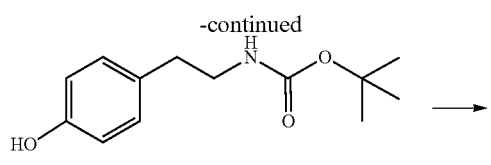

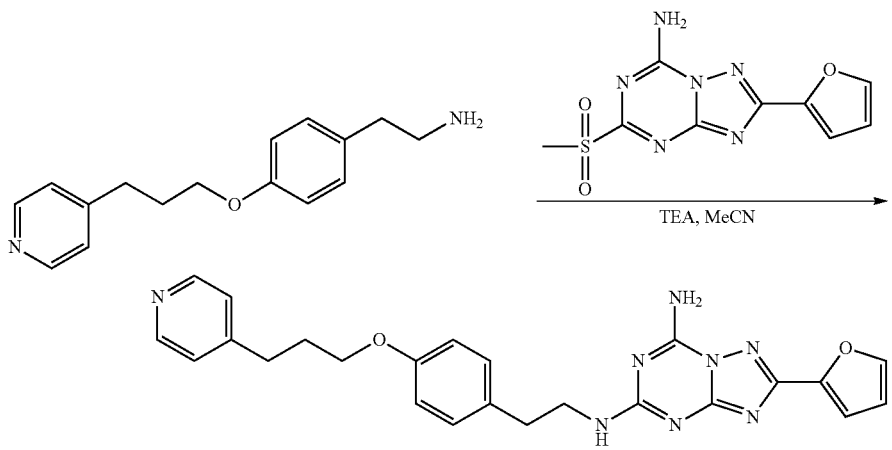

A mixture of tert-butyl 4-hydroxyphenethylcarbamate (364 mg, 1.53 mol), cesium carbonate (909 mg, 2.79 mmol) and 3-(pyridin-4-yl)propyl methanesulfonate (300 mg, 1.39 mmol) in acetone (10 mL) was stirred at room temperature overnight. The reaction mixture was filtrated. The filtrate was concentrated and purified by column chromatography (hexane:EtOAc=2:1) to afford the title compound as white solid (0.25 g, 50.3% yield). ¹H NMR (500 MHz, DMSO-d6) δ: 8.45 (d, 2H), 7.26 (d, 2H), 7.09 (d, 2H), 6.84 (d, 3H), 3.93 (t, 2H), 3.08 (q, 2H), 2.77 (t, 2H), 2.62 (t, 2H), 2.02 (m, 2H), 1.37 (s, 9H).

Example 35

2-(4-(3-(Pyridin-4-yl)propoxy)phenyl)ethanamine

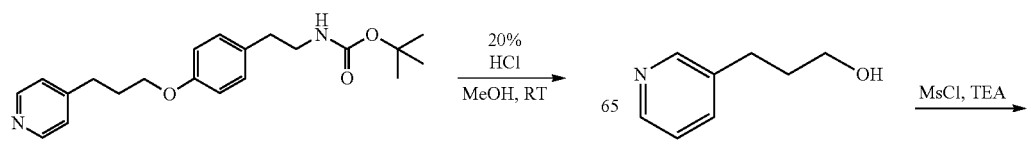

32

-continued

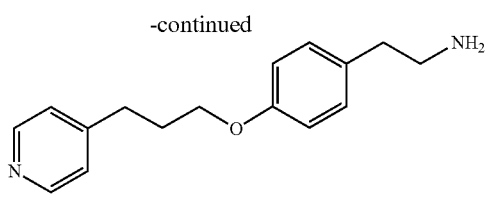

A mixture of tert-butyl 4-(3-(pyridin-4-yl)propoxy)phenethylcarbamate (250 mg, 0.70 mmol) in 20% hydrochloric acid (1 mL) and methanol (5 mL) was stirred at room temperature for 2 hours. The reaction mixture was concentrated in vacuo to afford the crude product as yellow oil, which was used for the next step directly.

Example 36

2-(Furan-2-yl)-N5-(4-(3-(pyridin-4-yl)propoxy)phenethyl)-[1,2,4]triazolo[1,5-α][1,3,5]-triazine-5,7-diamine The reaction was carried out as in Example 5 to afford the title compound as white solid (130 mg, 40.7% yield). ¹H NMR (500 MHz, DMSO-d6) δ: 8.45 (dd, 2H), 8.19 (s, 2H), 7.87 (s, 1H), 7.45-7.56 (m, 1H), 7.26 (d, 2H), 7.14 (d, 2H), 7.06 (d, 1H), 6.85 (d, 2H), 5.3.93 (t, 2H), 3.45 (q, 2H), 2.78 (m, 4H), 2.02 (m, 2H).

Example 37

3-(Pyridin-3-yl)propyl methanesulfonate

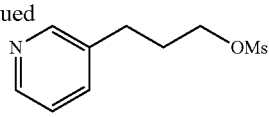

A mixture of 3-(pyridin-3-yl)propan-1-ol (500 mg, 3.64 mol), methanesulfonyl chloride (626 mg, 5.47 mmol) and triethylamine (736 mg, 7.28 mmol) in dichloromethane (10 mL) was stirred at room temperature for 2 h. The reaction mixture was quenched with water and extracted with dichloromethane. The organic layer was washed with water and brine, dried over sodium sulfate and concentrated in vacuo to afford the title compound as brown oil (710 mg, 90.5% yield).

Example 38 tert-Butyl 4-(3-(pyridin-3-yl)propoxy)phenethylcarbamate

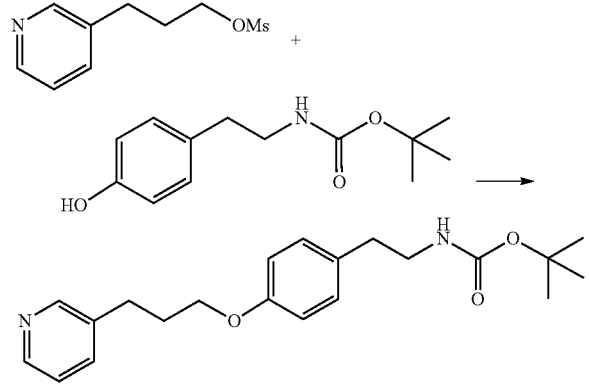

A mixture of tert-butyl 4-hydroxyphenethylcarbamate (364 mg, 1.53 mol), cesium carbonate (909 mg, 2.79 mmol) and 3-(pyridin-3-yl)propyl methanesulfonate (300 mg, 1.39 mmol) in acetone (10 mL) was stirred at room temperature overnight. The reaction mixture was filtrated. The filtrate was concentrated and purified by column chromatography (hexane:EtOAc=2:1) to afford the title compound as white solid (0.36 g, 72.4% yield). $^1$H NMR (500 MHz, DMSO-d6) δ: 8.45 (d, 1H), 8.40 (dd, 1H), 7.66 (dd, 1H), 7.31 (q, 1H), 7.09 (d, 2H), 6.84 (d, 3H), 3.93 (t, 2H), 3.08 (q, 2H), 2.77 (t, 2H), 2.62 (t, 2H), 2.02 (m, 2H), 1.37 (s, 9H).

Example 39

2-(4-(3-(Pyridin-3-yl)propoxy)phenyl)ethanamine

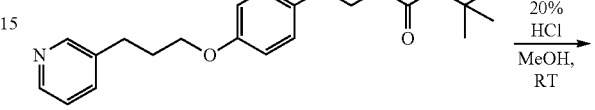

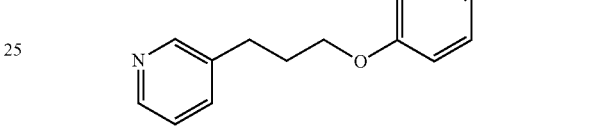

A mixture of tert-butyl 4-(pyridin-3-ylmethoxy)phenethylcarbamate (250 mg, 0.70 mmol) in 20% hydrochloric acid (1 mL) and methanol (5 mL) was stirred at room temperature for 2 hours. The reaction mixture was concentrated in vacuo to afford the crude product as yellow oil, which was used for the next step directly.

Example 40

2-(Furan-2-yl)-N5-(4-(3-(pyridin-3-yl)propoxy)phenethyl)-[1,2,4]triazolo[1,5-α][1,3,5]-triazine-5,7-diamine

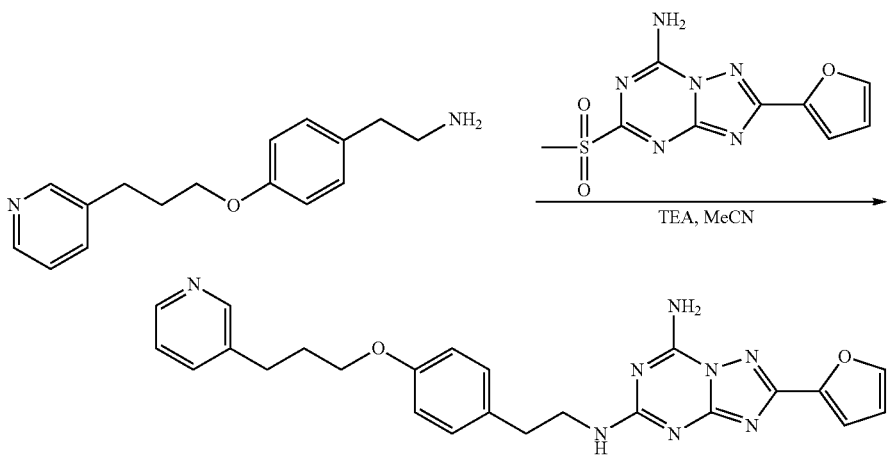

The reaction was carried out as in Example 5 to afford the title compound as white solid (145 mg, 45.4% yield). $^1$H NMR (500 MHz, DMSO-d6) δ: 8.45 (d, 1H), 8.40 (dd, 1H), 8.19 (s, 2H), 7.87 (s, 1H), 7.67 (dt, 1H), 7.44-7.54 (m, 1H), 7.31 (q, 1H), 7.14 (d, 2H), 7.06 (d, 1H), 6.85 (d, 2H), 6.66 (m, 1H), 3.93 (q, 2H), 3.45 (m, 2H), 2.78 (m, 4H), 2.02 (m, 2H).

Example 41

2-(Furan-2-yl)-N5-(2-(6-methoxypyridin-3-yl)ethyl)-[1,2,4]triazolo[1,5-α][1,3,5]triazine-5,7-diamine

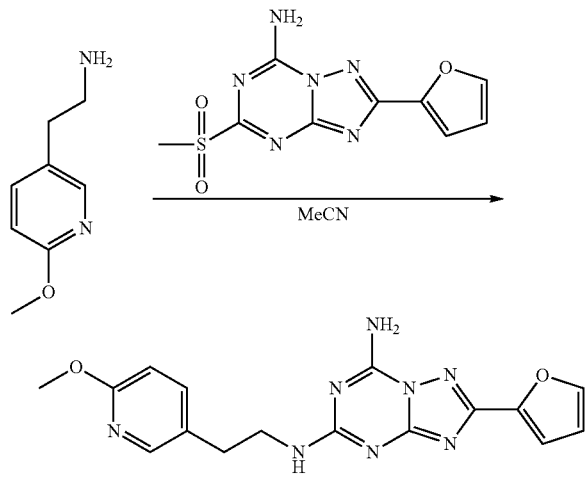

The reaction was carried out as in Example 5 to afford the title compound as white solid (135 mg, 38.4% yield). $^1$H NMR (500 MHz, DMSO-d6) δ: 8.50-8.05 (d, 2H), 8.02 (d, 1H), 7.87 (s, 1H), 7.63-7.46 (m, 2H), 7.06 (d, 1H), 6.75 (d, 1H), 6.67 (d, 1H), 3.81 (s, 3H), 3.46 (q, 2H), 2.81 (t, 2H).

Example 42

N5-(2-(1H-Imidazol-4-yl)ethyl)-2-(furan-2-yl)-[1,2,4]triazolo[1,5-α][1,3,5]triazine-5,7-diamine

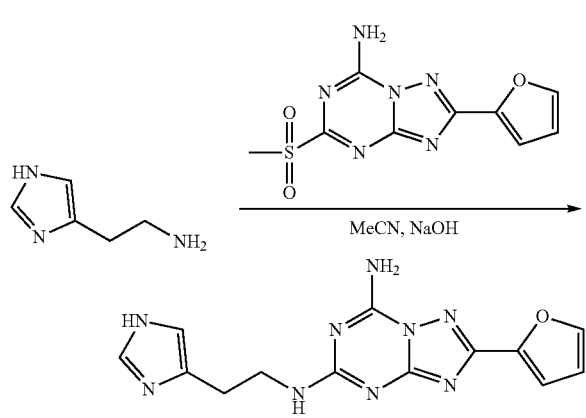

To a stirred solution of histamine dihydrochloride (184 mg, 1 mmol) and 2-(furan-3-yl)-5-(methylsulfonyl)-[1,2,4]triazolo[1,5-α][1,3,5]triazin-7-amine (280 mg, 1 mmol) in MeCN (10 mL) was added aqueous NaOH (4 mol/L) slowly to adjust pH to 8. After stirring at room temperature for 15 h, the reaction mixture was concentrated and purified by preparative TLC (dichloromethane/methanol=5:1) to afford the title compound as gray solid (30 mg, 9.6% yield). $^1$H NMR (500 MHz, DMSO-d6) δ: 8.50-8.05 (d, 2H), 7.87 (s, 1H), 7.74 (m, 1H), 7.51 (d, 1H), 7.04 (d, 1H), 6.91 (s, 1H), 6.67 (s, 1H), 3.51 (m, 2H), 2.79 (t, 2H).

Example 43

N5-(2-(1H-Imidazol-1-yl)ethyl)-2-(furan-2-yl)-[1,2,4]triazolo[1,5-α][1,3,5]triazine-5,7-diamine

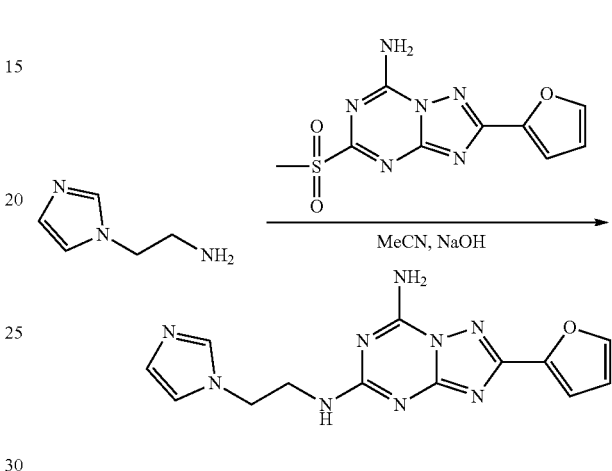

The reaction was carried out as in Example 42 to afford the title compound as white solid (32 mg, 10.3% yield). $^1$H NMR (500 MHz, DMSO-d6) δ: 8.50-8.05 (d, 2H), 7.87 (s, 1H), 7.61 (s, 1H), 7.51 (t, 1H), 7.17 (d, 1H), 7.06 (d, 1H), 6.88 (s, 1H), 6.67 (s, 1H), 4.18 (t, 2H), 3.57 (q, 2H).

Example 44

2-(Furan-2-yl)-N5-(2-(pyrimidin-4-yl)ethyl)-[1,2,4]triazolo[1,5-α][1,3,5]triazine-5,7-diamine

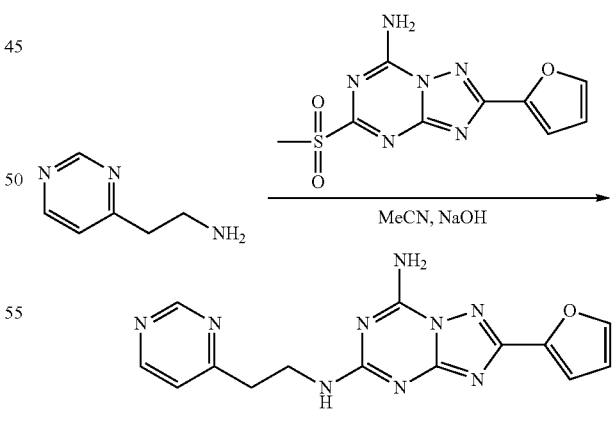

The reaction was carried out as in Example 42. The precipitated solid was filtered, washed with MeCN and water, and dried to afford the title compound as yellow solid (135 mg, 41.8% yield). $^1$H NMR (500 MHz, DMSO-d6) δ: 9.09 (s, 1H), 8.68 (d, 1H), 8.50-8.05 (d, 2H), 7.87 (s, 1H), 7.50-7.43 (m, 2H), 7.06 (d, 1H), 6.67 (s, 1H), 3.66 (m, 2H), 3.03 (t, 2H).

Example 45

2-(Furan-2-yl)-N5-(2-(2-methoxypyridin-4-yl)ethyl)-[1,2,4]triazolo[1,5-α][1,3,5]triazine-5,7-diamine

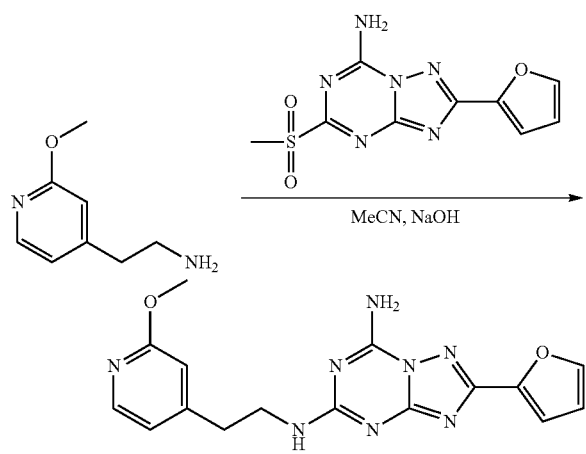

The reaction was carried out as in Example 42. The precipitated solid was filtered, washed with MeCN and water, and dried to afford the title compound as yellow solid (143 mg, 40.6% yield). $^1$H NMR (500 MHz, DMSO-d6) δ: 8.55-8.15 (d, 2H), 8.05 (d, 1H), 7.87 (s, 1H), 7.49 (m, 1H), 7.06 (d, 1H), 6.88 (d, 1H), 6.67 (m, 2H), 3.82 (s, 3H), 3.51 (q, 2H), 2.83 (t, 2H).

Example 46 tert-Butyl 4-(2-(piperidin-1-yl)ethoxy)phenethylcarbamate

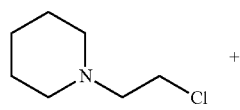

+

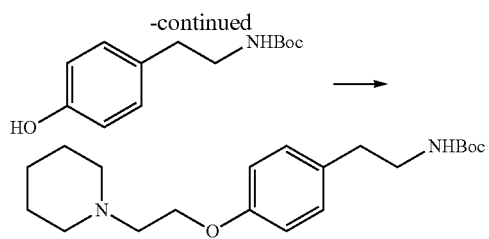

A mixture of tert-butyl 4-hydroxyphenethylcarbamate (474 mg, 2 mol), cesium carbonate (1.95 g, 6 mmol), NaI (4.8 mg, 0.2 mmol) and 1-(2-chloroethyl)piperidine hydrochloride (368 mg, 2 mmol) in acetone (10 mL) was stirred at 50° C. for 15 h. The reaction mixture was filtrated. The filtrate was concentrated and purified by column chromatography to afford the title compound as yellow oil (0.12 g, 17.2% yield). $^1$H NMR (500 MHz, DMSO-d6) δ: 7.10 (d, 2H), 6.85 (d, 3H), 4.06 (s, 2H), 3.09 (q, 2H), 2.77 (s, 2H), 2.61 (t, 5H), 1.54 (t, 4H), 1.40 (m, 3H), 1.36 (s, 9H).

Example 47

2-(4-(2-(Piperidin-1-yl)ethoxy)phenyl)ethanamine

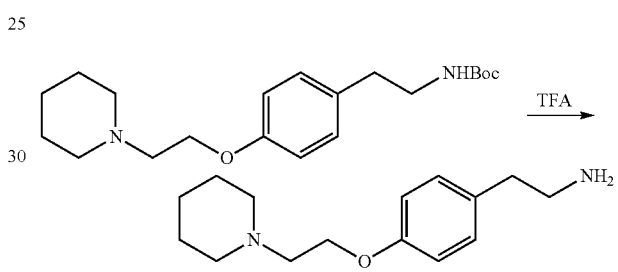

A mixture of tert-butyl 4-(2-(piperidin-1-yl)ethoxy)phenethylcarbamate (120 mg, 0.34 mmol) and trifluoroacetic acid (0.5 mL) in methanol (5 mL) was stirred at room temperature for 15 h. The reaction mixture was concentrated in vacuo to afford the crude product as yellow oil, which was used for the next step directly.

Example 48

2-(Furan-2-yl)-N5-(4-(2-(piperidin-1-yl)ethoxy)phenethyl)-[1,2,4]triazolo[1,5-α][1,3,5]-triazine-5,7-diamine

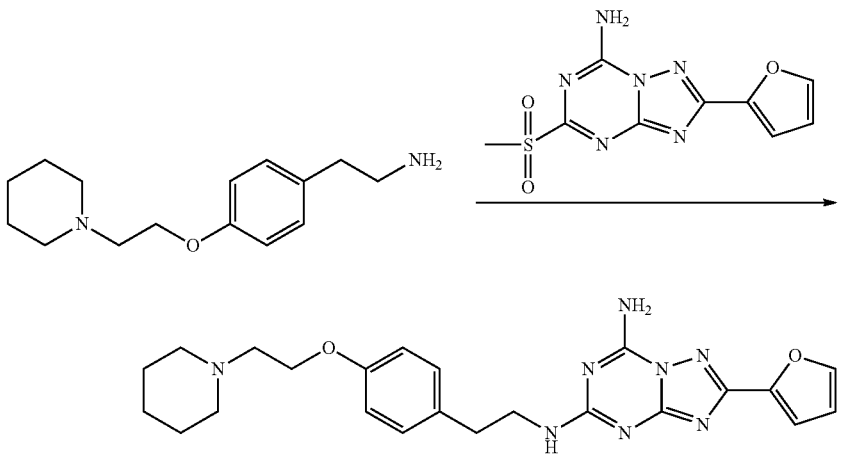

The reaction was carried out as in Example 42 to afford the title compound as yellow solid (20 mg, 13.1% yield). $^1$H NMR (500 MHz, DMSO-d6) δ: 8.05-8.49 (d, 2H), 7.87 (s, 1H), 7.46 (d, 1H), 7.19 (d, 2H), 7.06 (s, 1H), 6.92 (d, 2H), 6.68 (s, 1H), 4.29 (s, 2H), 3.45 (m, 5H), 2.80 (t, 3H), 1.72 (s, 5H), 1.48 (s, 3H).

Example 49 tert-Butyl 4-(2-(azepan-1-yl)ethoxy)phenethylcarbamate

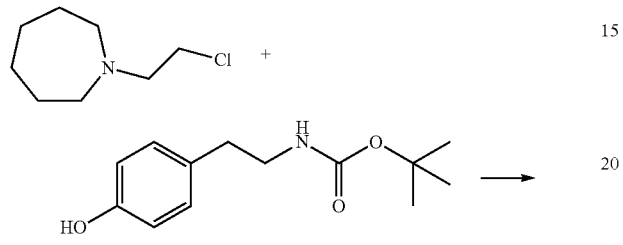

-continued

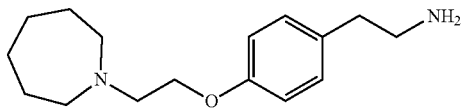

A mixture of tert-butyl 4-hydroxyphenethylcarbamate (474 mg, 2 mol), cesium carbonate (1.95 g, 6 mmol), NaI (4.8 mg, 0.2 mmol) and 1-(2-chloroethyl)azepane hydrochloride (396 mg, 2 mmol) in acetone (10 mL) was stirred at 50° C. for 15 h. The reaction mixture was filtrated. The filtrate was concentrated and purified by column chromatography to afford the title compound as yellow oil (90 mg, 12.4% yield). LCMS m/z [M+H]$^+$: 363.3.

Example 50

2-(4-(2-(Azepan-1-yl)ethoxy)phenyl)ethanamine

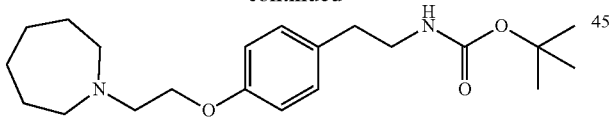

A mixture of tert-butyl 4-(2-(azepan-1-yl)ethoxy)phenethylcarbamate (90 mg, 0.25 mmol) and trifluoroacetic acid (0.5 mL) in methanol (5 mL) was stirred at room temperature for 15 h. The reaction mixture was concentrated in vacuo to afford the crude product as yellow oil, which was used for the next step directly.

Example 51

N5-(4-(2-(Azepan-1-yl)ethoxy)phenethyl)-2-(furan-2-yl)-[1,2,4]triazolo[1,5-α][1,3,5]triazine-5,7-diamine

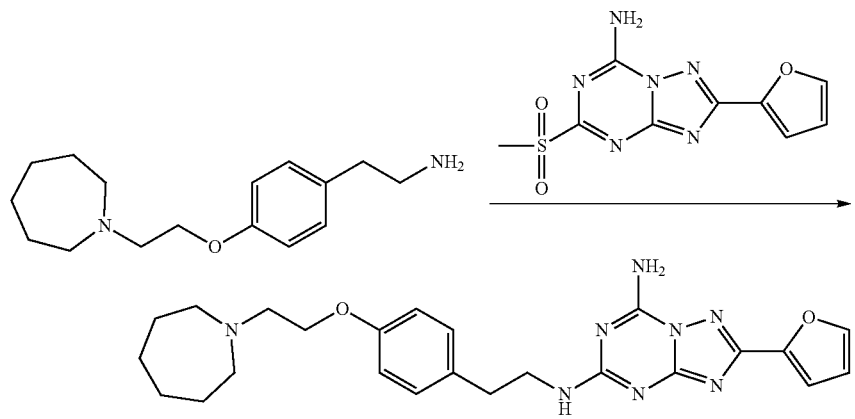

The reaction was carried out as in Example 42 to afford the title compound as yellow solid (10 mg, 8.7% yield). $^1$H NMR (500 MHz, DMSO-d6) δ: 8.05-8.49 (d, 2H), 7.87 (s, 1H), 7.47 (d, 1H), 7.21 (s, 2H), 7.06 (s, 1H), 6.93 (dd, 2H), 6.68 (s, 1H), 4.29 (s, 2H), 3.45 (m, 8H), 2.80 (t, 2H), 1.79 (s, 4H), 1.60 (s, 4H).

Example 52 tert-Butyl 4-(3-(piperidin-1-yl)propoxy)phenethylcarbamate

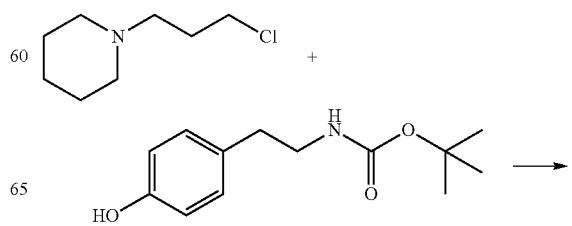

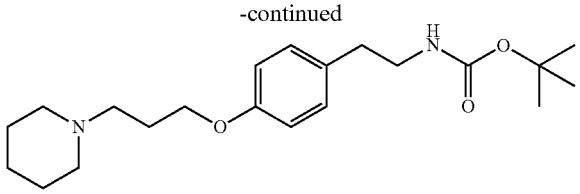

A mixture of tert-butyl 4-hydroxyphenethylcarbamate (474 mg, 2 mol), cesium carbonate (1.95 g, 6 mmol), NaI (4.8 mg, 0.2 mmol) and 1-(3-chloropropyl)piperidine hydrochloride (396 mg, 2 mmol) in acetone (10 mL) was stirred at 50° C. for 8 h. The reaction mixture was filtrated. The filtrate was concentrated and purified by column chromatography to afford the title compound as gray solid (443 mg, 61.2% yield). $^1$H NMR (500 MHz, DMSO-d6) δ: 7.07 (d, 2H), 6.82 (d, 3H), 3.94 (t, 2H), 3.09 (q, 2H), 2.62 (t, 2H), 2.50 (m, 6H), 1.50 (t, 6H), 1.36 (s, 9H).

Example 53

2-(4-(3-(Piperidin-1-yl)propoxy)phenyl)ethanamine

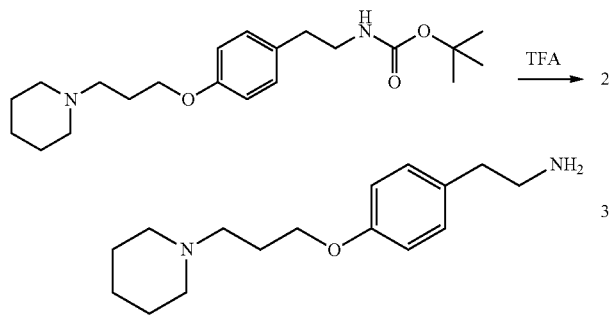

A mixture of tert-butyl 4-(3-(piperidin-1-yl)propoxy) phenethylcarbamate (438 mg, 1.0 mmol) and trifluoroacetic acid (1.5 mL) in methanol (5 mL) was stirred at room temperature for 3 hours. The reaction mixture was concentrated in vacuo to afford the crude product as yellow oil, which was used for the next step directly.

Example 54

2-(Furan-2-yl)-N5-(4-(3-(piperidin-1-yl)propoxy) phenethyl)-[1,2,4]triazolo[1,5-α][1,3,5]-triazine-5,7-diamine The reaction was carried out as in Example 42 to afford the title compound as yellow solid (350 mg, 63.1% yield). $^1$H NMR (500 MHz, DMSO-d6) δ: 8.05-8.49 (d, 2H), 7.87 (s, 1H), 7.46 (d, 1H), 7.19 (d, 2H), 7.06 (d, 1H), 6.88 (d, 2H), 6.68 (s, 1H), 4.01 (t, 2H), 3.45 (m, 4H), 3.12 (t, 2H), 2.78 (m, 4H), 2.16 (m, 2H), 1.78 (t, 4H), 1.39 (m, 2H).

Example 55 tert-Butyl 4-(2-methoxyethoxy)phenethylcarbamate

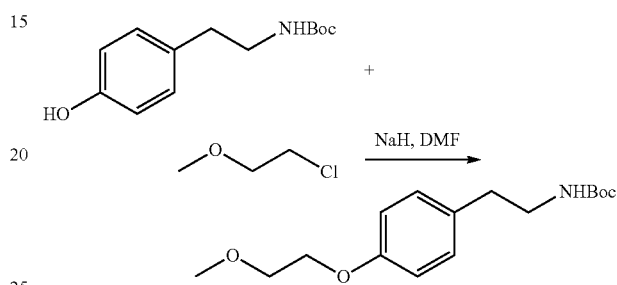

1-Chloro-2-methoxyethane (0.96 g, 10 mmol, diluted in 10 mL of DMF) was added dropwise to a stirred mixture of tert-butyl 4-hydroxyphenethylcarbamate (2.37 g, 10 mmol) and NaH (0.44 g, 11 mmol, 60% dispersion in mineral oil) in dry DMF (40 mL) under N$_2$ at 0° C. The reaction was stirred at room temperature for 23 h. After this time, the reaction mixture was stirred at 60° C. for 26 h. The reaction mixture was quenched with ice-water and extracted with ethyl acetate. The organic layer was washed with water and brine, dried over sodium sulfate and concentrated in vacuo. The crude product was purified by column chromatography to afford the title compound as white solid (1.636 g, 55% yield). $^1$H NMR (500 MHz, CDCl$_3$) δ: 7.11 (d, J=8.4 Hz, 2H), 6.96-6.86 (m, 2H), 4.54 (s, 1H), 4.18-4.09 (m, 2H), 3.76 (dd, J=5.4, 4.1 Hz, 2H), 3.47 (s, 3H), 3.36 (d, J=6.3 Hz, 2H), 2.75 (t, J=6.9 Hz, 2H), 1.45 (s, 9H).

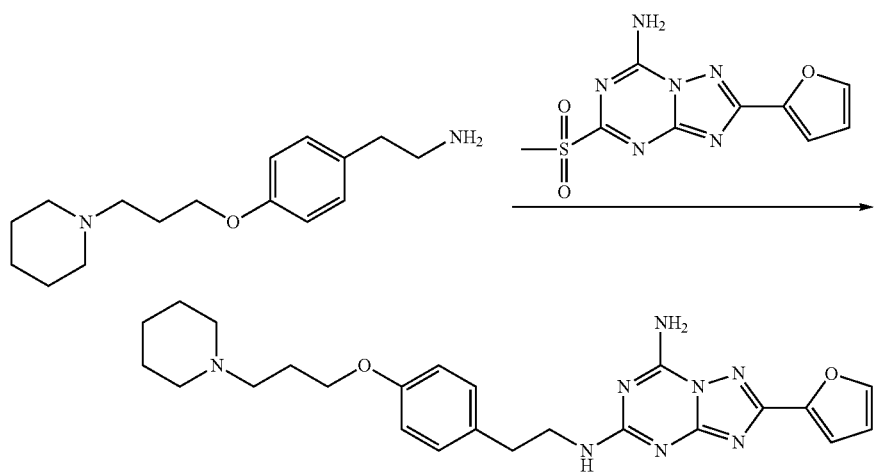

Example 56

2-(4-(2-Methoxyethoxy)phenyl)ethanamine

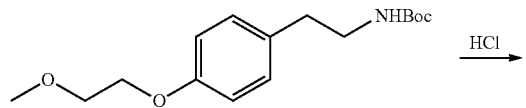

10% Hydrochloric acid (12.2 mL) was added to a stirred solution of tert-butyl 4-(2-methoxyethoxy)phenethylcarbamate (1.48 g, 5 mmol) in methanol (30 mL) at room temperature. After stirring for 24 h, the solvent was removed under reduced pressure. To the mixture was added 20% NaOH aqueous solution and it was extracted with ethyl acetate. The organic layer was washed with water and brine, dried over sodium sulfate and concentrated in vacuo. The crude product was purified by column chromatography to afford the title compound (0.547 g, 56% yield). $^1$H NMR (500 MHz, DMSO-d6) δ: 7.09 (d, J=8.5 Hz, 2H), 6.84 (d, J=8.5 Hz, 2H), 4.04 (dd, J=5.4, 3.9 Hz, 2H), 3.64 (dd, J=5.3, 3.9 Hz, 2H), 3.30 (s, 3H), 2.72 (t, J=7.2 Hz, 2H), 2.56 (t, J=7.2 Hz, 2H).

Example 57

2-(Furan-2-yl)-N5-(4-(2-methoxyethoxy)phenethyl)-[1,2,4]triazolo[1,5-α][1,3,5]triazine-5,7-diamine

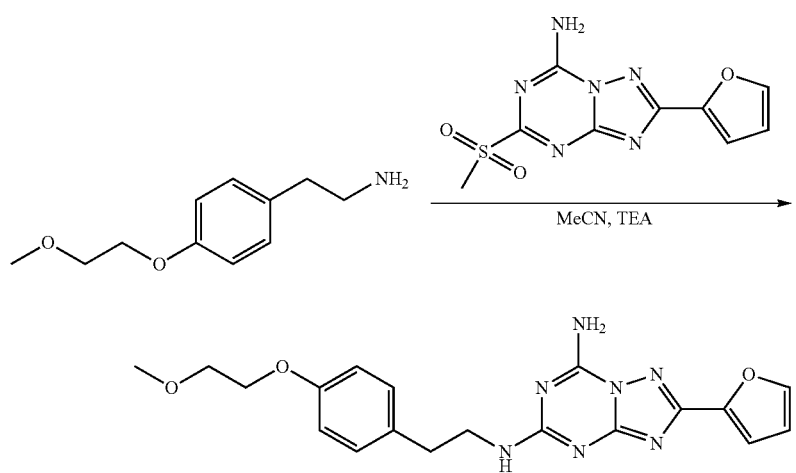

The reaction was carried out as in Example 5 to afford the title compound as yellow solid (0.151 g, 72% yield). $^1$H NMR (500 MHz, DMSO-d6) δ: 8.17 (br, 2H), 7.86 (d, J=8.2 Hz, 1H), 7.58-7.39 (m, 1H), 7.15 (t, J=7.7 Hz, 2H), 7.06 (d, J=3.4 Hz, 1H), 6.87 (d, J=8.4 Hz, 2H), 6.67 (d, J=1.5 Hz, 1H), 4.12-4.00 (m, 2H), 3.73-3.62 (m, 2H), 3.51-3.42 (m, 2H), 3.30 (s, 3H), 2.79 (t, J=7.3 Hz, 2H).

Example 58 tert-Butyl 4-(2-(2-methoxyethoxy)ethoxy)phenethylcarbamate

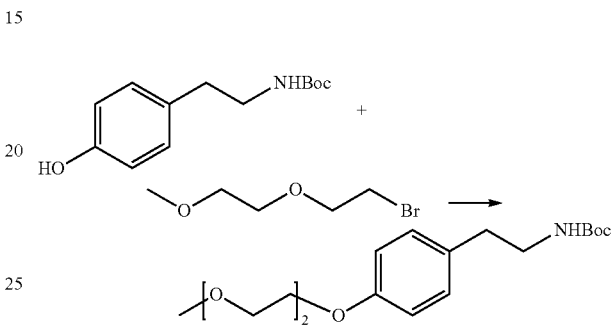

1-Bromo-2-(2-methoxyethoxy)ethane (1.83 g, 10 mmol, diluted in 10 mL of dried DMF) was added dropwise to a stirred mixture of tert-butyl 4-hydroxyphenethylcarbamate (2.61 g, 11 mmol) and NaH (0.44 g, 11 mmol, 60% dispersion in mineral oil) in dry DMF (40 mL) under N$_2$ at 0° C. The reaction was stirred at room temperature for 14 h. After this time, the reaction mixture was stirred at 60° C. for 8 h. The reaction was quenched with ice-water and extracted with ethyl acetate. The organic layer was washed with water and brine, dried over sodium sulfate and concentrated in vacuo. The crude product was purified by column chromatography to afford the title compound as colorless oil (2.311 g, 68% yield). $^1$H NMR (500 MHz, CDCl$_3$) δ: 7.19-7.01 (m, 2H), 6.93-6.81 (m, 2H), 4.58 (s, 1H), 4.13 (dd, J=9.8, 4.9 Hz, 2H), 3.86 (dd, J=9.5, 5.1 Hz, 2H), 3.79-3.67 (m, 2H), 3.65-3.53 (m, 2H), 3.40 (dd, J=4.0, 1.8 Hz, 3H), 3.34 (s, 2H), 2.73 (s, 2H), 1.44 (s, 9H).

Example 59

2-(4-(2-(2-Methoxyethoxy)ethoxy)phenyl)ethanamine

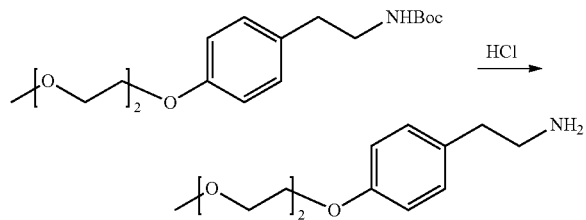

10% Hydrochloric acid (15.1 mL) was added to a stirred solution of tert-butyl 4-(2-(2-methoxyethoxy)ethoxy)phenethylcarbamate (2.1 g, 6.19 mmol) in methanol (30 mL) at room temperature. After stirring for 24 h, the solvent was removed under reduced pressure. To the reaction mixture was added 20% NaOH aqueous solution and it was extracted with ethyl acetate. The organic layer was washed with water and brine, dried over sodium sulfate and concentrated in vacuo. The crude product was purified by column chromatography to afford the title compound (1.04 g, 70% yield). $^1$H NMR (500 MHz, DMSO-d6) δ: 7.09 (d, J=8.0 Hz, 2H), 6.85 (dd, J=8.5, 1.6 Hz, 2H), 4.13-3.93 (m, 2H), 3.79-3.70 (m, 2H), 3.58 (dd, J=5.6, 3.9 Hz, 2H), 3.46 (dd, J=5.6, 3.9 Hz, 2H), 3.25 (d, J=0.9 Hz, 3H), 2.72 (d, J=4.1 Hz, 2H), 2.57 (dd, J=7.3, 2.1 Hz, 2H).

Example 60

2-(Furan-2-yl)-N5-(4-(2-(2-methoxyethoxy)ethoxy)phenethyl)-[1,2,4]triazolo[1,5-α][1,3,5]triazine-5,7-diamine

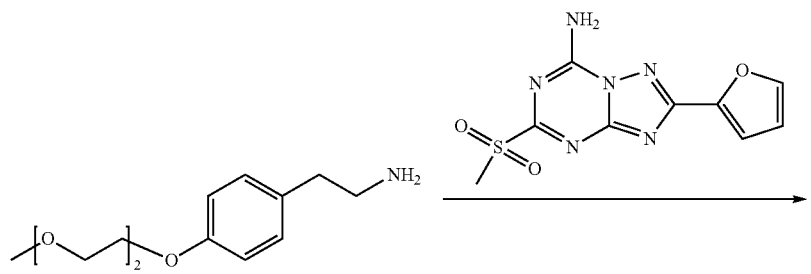

The reaction was carried out as in Example 5 to afford the title compound (0.14 g, 82% yield). $^1$H NMR (500 MHz, CDCl$_3$) δ: 7.60 (s, 1H), 7.23 (s, 1H), 7.12 (d, J=7.9 Hz, 2H), 6.85 (d, J=7.7 Hz, 2H), 6.58 (dd, J=3.2, 1.7 Hz, 1H), 6.15 (s, 2H), 5.47 (s, 1H), 4.13 (s, 2H), 3.97-3.84 (m, 2H), 3.80-3.58 (m, 6H), 3.42 (s, 3H), 2.87 (t, J=21.5 Hz, 2H).

Example 61

2-(2-(2-Methoxyethoxy)ethoxy)ethyl methanesulfonate

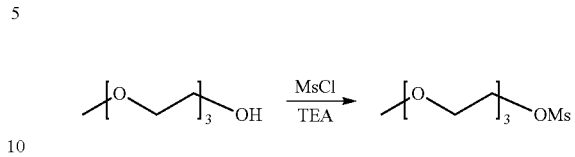

To a stirred solution of 2-(2-(2-methoxyethoxy)ethanol (2.00 g, 12.1 mmol) in DCM (20 mL) was added TEA (2.46 g, 24.3 mmol) and MsCl (2.09 g, 18.2 mmol) at 0° C. The reaction mixture was stirred at room temperature for 3 h. The reaction was neutralized with 10% HCl and water, and extracted with DCM. The organic layer was washed with water and brine, dried over sodium sulfate and concentrated in vacuo to afford the title compound as yellow oil (2.68 g, 91% yield). $^1$H NMR (500 MHz, CDCl$_3$) δ: 4.36-4.38 (m, 2H), 3.75-3.76 (m, 2H), 3.61-3.67 (m, 6H), 3.52-3.54 (m, 2H), 3.36 (s, 3H), 3.06 (s, 3H).

Example 62

1-Bromo-2-(2-(2-methoxyethoxy)ethoxy)ethane

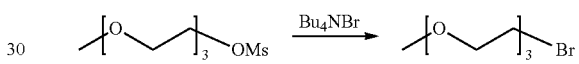

To a stirred solution of 2-(2-(2-Methoxyethoxy)ethoxy)ethyl methanesulfonate (1.5 g, 6.19 mmol) in MeCN (20 mL) was added Bu$_4$NBr (4.0 g, 12.4 mmol). The reaction mixture was stirred at 50° C. for 3 h. The reaction was quenched with water and extracted with EtOAc. The organic layer was washed with water and brine, dried over sodium sulfate and concentrated in vacuo. The crude product was purified by column chromatography to afford the title compound as colorless oil (0.5 g, 35% yield). $^1$H NMR (500 MHz, CDCl$_3$) δ: 3.83 (t, 2H), 3.66-3.70 (m, 6H), 3.56-3.58 (m, 2H), 3.79 (t, 2H), 3.40 (s, 3H).

Example 63 tert-Butyl 4-(2-(2-(2-methoxyethoxy)ethoxy)ethoxy)phenethylcarbamate

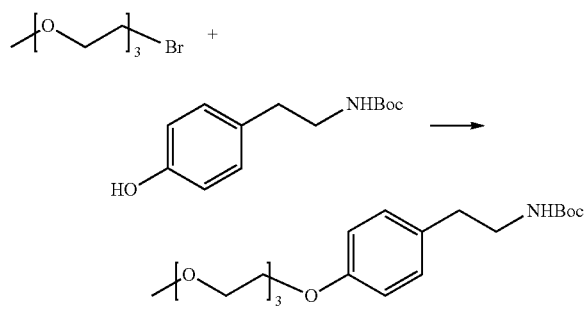

1-Bromo-2-(2-(2-methoxyethoxy)ethoxy)ethane (2.3 g, 10 mmol, diluted in 10 mL of dried DMF) was added dropwise to a stirred mixture of tert-butyl 4-hydroxyphenethylcarbamate (2.61 g, 11 mmol) and NaH (0.44 g, 11 mmol, 60% dispersion in mineral oil) in dry DMF (40 mL) under N₂ at 0° C. The reaction mixture was stirred at room temperature for 1 h. After this time, the reaction mixture was stirred at 60° C. for 24 h. The reaction mixture was quenched with ice-water and extracted with ethyl acetate. The organic layer was washed with water and brine, and dried over sodium sulfate. It was next concentrated in vacuo and purified by column chromatography to afford the title compound (2.76 g, 72% yield). $^1$H NMR (500 MHz, DMSO-d6) δ: 7.09 (d, J=8.4 Hz, 2H), 6.85 (d, J=8.5 Hz, 2H), 4.12-3.97 (m, 2H), 3.73 (d, J=4.8 Hz, 2H), 3.61-3.49 (m, 6H), 3.43 (dd, J=5.7, 3.8 Hz, 2H), 3.33-3.38 (m, 1H), 3.24 (s, 3H), 3.10 (d, J=6.2 Hz, 2H), 2.63 (t, J=7.4 Hz, 2H), 1.37 (s, 9H).

Example 64

2-(4-(2-(2-(2-Methoxyethoxy)ethoxy)ethoxy)phenyl)ethanamine

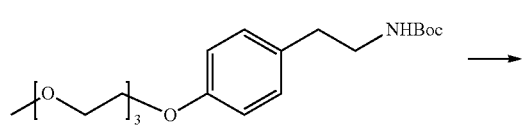

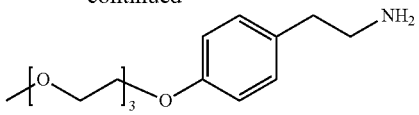

20% Hydrochloric acid (8.3 mL) was added to a stirred solution of tert-butyl 4-(2-(2-(2-methoxyethoxy)ethoxy)ethoxy)phenethylcarbamate (2.58 g, 6.73 mmol) in methanol (30 mL) at room temperature. After stirring for 24 h, the solvent was removed under reduced pressure, and the reaction mixture was neutralized with 20% NaOH aqueous solution and extracted with dichloromethane. The organic layer was washed with water, dried over sodium sulfate and concentrated in vacuo to afford the title compound (1.79 g, 94% yield). $^1$H NMR (500 MHz, DMSO-d6) δ: 7.09 (d, J=8.5 Hz, 2H), 6.84 (d, J=8.5 Hz, 2H), 4.08-4.01 (m, 2H), 3.75-3.69 (m, 2H), 3.58 (dd, J=6.0, 3.5 Hz, 2H), 3.56-3.49 (m, 4H), 3.42 (dd, J=5.7, 3.8 Hz, 2H), 3.23 (s, 3H), 2.71 (dd, J=7.7, 6.7 Hz, 2H), 2.56 (t, J=7.2 Hz, 2H).

Example 65

2-(Furan-2-yl)-N5-(4-(2-(2-(2-methoxyethoxy)ethoxy)ethoxy)phenethyl)-[1,2,4]triazolo[1,5-α][1,3,5]triazine-5,7-diamine

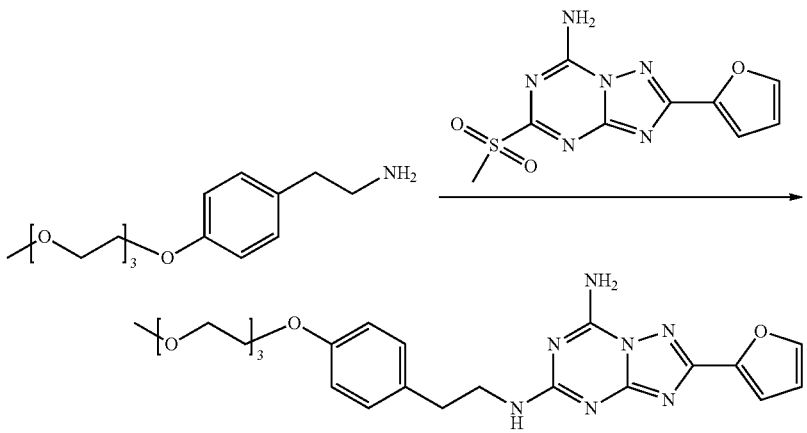

The reaction was carried out as in Example 5 to afford the title compound as White solid (0.147 g, 76% yield). $^1$H NMR (500 MHz, DMSO-d6) δ: 8.43-8.00 (br, 2H), 7.95-7.84 (m, 1H), 7.57-7.39 (m, 1H), 7.16 (d, J=8.1 Hz, 2H), 7.06 (d, J=3.3 Hz, 1H), 6.87 (d, J=8.3 Hz, 2H), 6.68 (s, 1H), 4.11-4.01 (m, 2H), 3.77-3.69 (m, 2H), 3.63-3.41 (m, 10H), 3.24 (s, 3H), 2.79 (t, J=7.2 Hz, 2H).

Example 66

2,5,8,11-Tetraoxatridecan-13-yl methanesulfonate

To a stirred solution of triethyl amine (4.368 g, 40 mmol) and 2,5,8,11-tetraoxatridecan-13-ol (4.165 g, 20 mmol) in dichloromethane (30 mL) was added methanesulfonyl chloride (4.165 g, 20 mmol, diluted in 20 ml of dichloromethane) dropwise over 30 minutes at 0° C. The reaction was then stirred at room temperature overnight. Water (40 mL) was next added to the reaction. It was extracted with dichloromethane (3×150 mL), and the organic phase was washed with 0.3 N HCl (2×80 mL) and water (3×100 mL). After drying with $Na_2SO_4$, removal of the solvent provided the title compound (5.507 g, 96% yield). $^1$H NMR (500 MHz, DMSO-d6) δ: 4.33-4.29 (m, 2H), 3.70-3.64 (m, 2H), 3.59-3.49 (m, 10H), 3.45-3.42 (m, 2H), 3.24 (s, 3H), 3.17 (s, 3H).

Example 67

13-Bromo-2,5,8,11-tetraoxatridecane

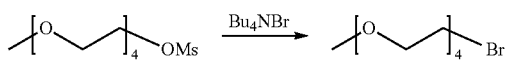

To a stirred solution of 2,5,8,11-tetraoxatridecan-13-yl methanesulfonate (4.295 g, 15 mmol) in acetonitrile (50 mL) was added $Bu_4NBr$ (9.671 g, 30 mmol) under $N_2$. The reaction was heated at 55° C. for 15 h. After cooling to room temperature and removal of solvent, water (150 mL) was added to the reaction mixture and it was extracted with dichloromethane (2×150 mL). The organic phase was washed with water (2×50 mL) and brine (3×50 mL). After drying with $Na_2SO_4$, removal of solvent provided the title compound as yellow oil (3.23 g, yield=79%). $^1$H NMR (500 MHz, DMSO-d6) δ: 3.74 (t, J=5.8 Hz, 2H), 3.59-3.56 (m, 4H), 3.54-3.50 (m, 8H), 3.44-3.42 (m, 2H), 3.25 (s, 3H).

Example 68 tert-Butyl 4-(2,5,8,11-tetraoxatridecan-13-yloxy)phenethylcarbamate

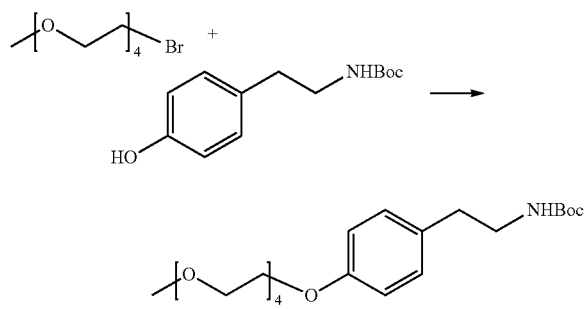

To a stirred solution of tert-butyl 4-hydroxyphenethylcarbamate (2.09 g, 8.8 mmol) and NaH (0.35 g, 8.8 mmol, 60% dispersion in mineral oil) in dry DMF (40 mL) was added dropwise 13-Bromo-2,5,8,11-tetraoxatridecane (2.17 g, 8 mmol) at room temperature under $N_2$. After stirring for 1 h, the reaction mixture was heated at 60° C. overnight. The reaction mixture was quenched with ice-water and extracted with ethyl acetate. The organic layer was washed with water and brine, dried over sodium sulfate and concentrated in vacuo. The crude product was purified by column chromatography to afford the title compound (2.73 g, 80% yield). $^1$H NMR (500 MHz, DMSO-d6) δ: 7.09 (d, J=8.4 Hz, 2H), 6.85 (d, J=8.5 Hz, 2H), 4.09-4.01 (m, 2H), 3.73 (d, J=4.8 Hz, 2H), 3.60-3.48 (m, 10H), 3.42 (dd, J=5.8, 3.7 Hz, 2H), 3.23 (s, 3H), 3.09 (d, J=7.0 Hz, 2H), 2.61 (t, J=7.5 Hz, 2H), 1.37 (s, 9H).

Example 69

2-(4-(2,5,8,11-Tetraoxatridecan-13-yloxy)phenyl)ethanamine

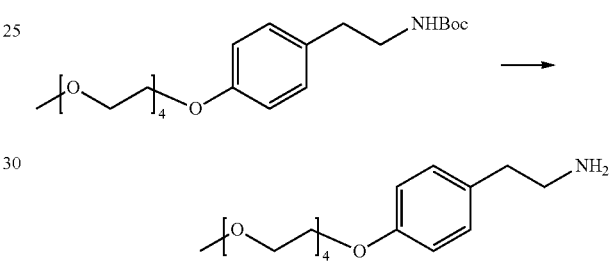

20% Hydrochloric acid (7.4 mL) was added to a stirred solution of tert-butyl 4-(2,5,8,11-tetraoxatridecan-13-yloxy)phenethylcarbamate (2.56 g, 6 mmol) in methanol (30 mL) at room temperature. After stirring for 24 h, the solvent was removed under reduced pressure. 20% NaOH aqueous solution was added and it was extracted with dichloromethane. The organic layer was washed with water, dried over sodium sulfate and concentrated to afford the title compound (1.84 g, 94% yield). $^1$H NMR (500 MHz, DMSO-d6) δ: 7.10 (d, J=8.5 Hz, 2H), 6.85 (d, J=8.6 Hz, 2H), 4.08-4.02 (m, 2H), 3.77-3.71 (m, 2H), 3.62-3.49 (m, 10H), 3.43 (dd, J=5.8, 3.8 Hz, 2H), 3.24 (s, 3H), 2.73 (t, J=7.2 Hz, 2H), 2.57 (t, J=7.2 Hz, 2H), 2.43-2.10 (m, 2H).

Example 70

N5-(4-(2,5,8,11-Tetraoxatridecan-13-yloxy)phenethyl)-2-(furan-2-yl)-[1,2,4]triazolo[1,5-α][1,3,5]triazine-5,7-diamine

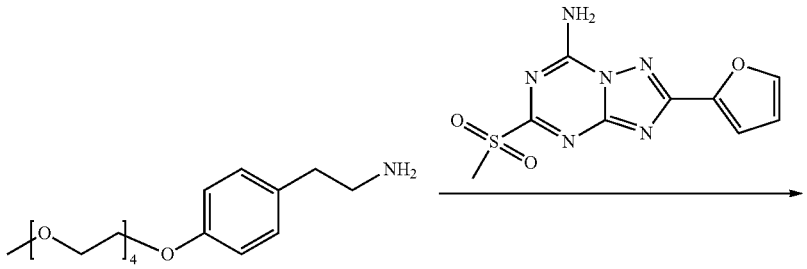

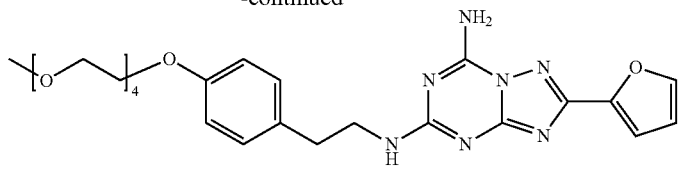

The reaction was carried out as in Example 5 to afford the title compound as yellow solid (0.181 g, 86% yield). $^1$H NMR (500 MHz, DMSO-d6) δ: 8.47-8.00 (br, 2H), 7.90-7.84 (m, 1H), 7.56-7.40 (m, 1H), 7.16 (d, J=8.1 Hz, 2H), 7.06 (d, J=3.3 Hz, 1H), 6.87 (d, J=8.4 Hz, 2H), 6.68 (s, 1H), 4.08-4.02 (m, 2H), 3.76-3.71 (m, 2H), 3.58 (dd, J=6.1, 3.5 Hz, 2H), 3.52 (ddd, J=9.3, 6.8, 4.9 Hz, 8H), 3.48-3.40 (m, 4H), 3.23 (s, 3H), 2.79 (t, J=7.3 Hz, 2H).

Example 71

2,5,8,11,14-Pentaoxahexadecan-16-yl methanesulfonate

To a stirred solution of triethyl amine (0.401 g, 3.96 mmol) and 2,5,8,11,14-pentaoxahexadecan-16-ol 0.500 g, 1.98 mmol) in dichloromethane (20 mL) was added methanesulfonyl chloride (0.341 g, 5.06 mmol, diluted in 10 mL dichloromethane) dropwise over 20 minutes at 0° C. The solution was then stirred at room temperature overnight. More dichloromethane (80 mL) was added and it washed with 1N HCl (2×30 mL) and water (30 mL). After drying with Na$_2$SO$_4$, removal of solvent provided the crude product. Purification by column chromatography afforded the title compound as colorless oil (0.38 g, 58% yield). $^1$H NMR (500 MHz, CDCl$_3$) δ: 4.41-4.38 (m, 2H), 3.79-3.77 (m, 2H), 3.68-3.64 (m, 14H), 3.56 (dd, J=5.7, 3.7 Hz, 2H), 3.39 (s, 3H), 3.09 (s, 3H).

Example 72 tert-Butyl 4-(2,5,8,11,14-pentaoxahexadecan-16-yloxy)phenethylcarbamate

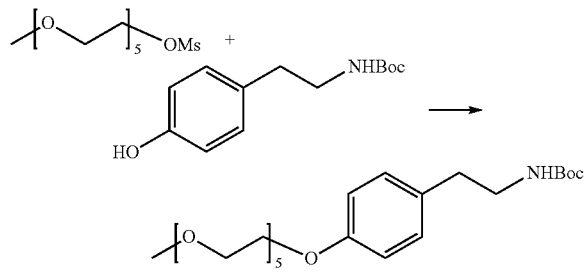

To a stirred mixture of tert-butyl 4-hydroxyphenethylcarbamate (0.283 g, 1.19 mmol) and NaH (0.048 g, 1.19 mmol, 60% dispersion in mineral oil) in dry DMF (10 mL) was added 2,5,8,11,14-pentaoxahexadecan-16-yl methanesulfonate (0.357 g, 1.08 mmol, diluted in dry DMF) at 0° C. under N$_2$. The reaction was stirred at room temperature for 1 h. After this time, the reaction mixture was heated at 60° C. overnight. The reaction mixture was quenched with ice-water and extracted with ethyl acetate. The organic layer was washed with water and brine, dried over sodium sulfate and concentrated in vacuo. The crude product was purified by column chromatography to afford the title compound as yellow oil (0.461 g, 90% yield). $^1$H NMR (500 MHz, CDCl$_3$) δ: 7.02 (d, J=8.4 Hz, 2H), 6.78 (d, J=8.5 Hz, 2H), 4.45 (s, 1H), 4.08-4.00 (m, 2H), 3.79-3.75 (m, 2H), 3.65 (dd, J=5.9, 3.5 Hz, 2H), 3.64-3.55 (m, 12H), 3.47 (dd, J=5.7, 3.7 Hz, 2H), 3.30 (s, 3H), 3.30-3.22 (m, 2H), 2.66 (s, 2H), 1.36 (s, 9H).

Example 73

2-(4-(2,5,8,11,14-Pentaoxahexadecan-16-yloxy)phenyl)ethanaminium chloride

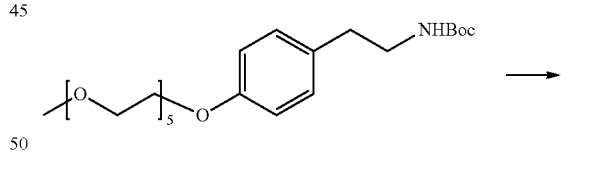

20% Hydrochloric acid (2 mL) was added to a stirred solution of tert-butyl 4-(2,5,8,11,14,17-hexaoxanonadecan-19-yloxy)phenethylcarbamate (0.450 g, 0.95 mmol) in methanol (20 mL) at room temperature. After stirring for 17 h, the excess solvent was removed under reduced pressure to afford the crude product, which was used for the next step directly.

Example 74

N5-(4-(2,5,8,11,14-Pentaoxahexadecan-16-yloxy)phenethyl)-2-(furan-2-yl)-[1,2,4]triazolo[1,5-α][1,3,5]triazine-5,7-diamine

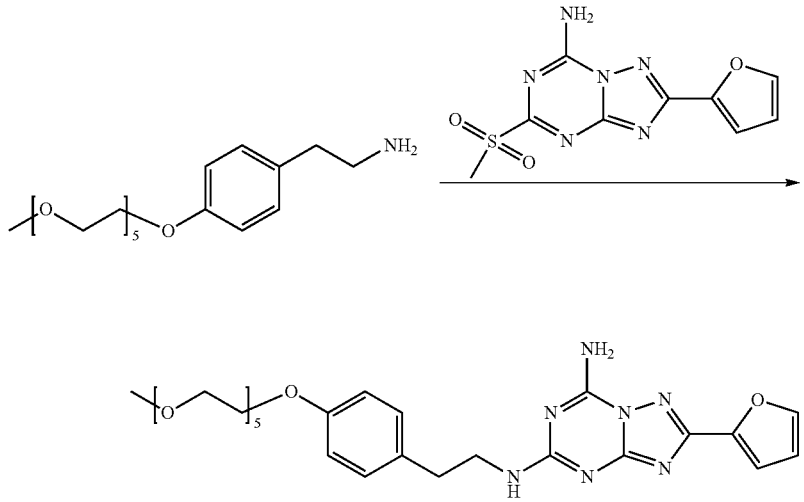

The reaction was carried out as in Example 5 to afford the title compound as yellow oil (0.133 g, 35% yield). $^1$H NMR (500 MHz, DMSO-d6) δ: 8.33 (br, 2H), 7.87 (br, 1H), 7.48 (dd, J=30.4, 24.9 Hz, 1H), 7.16 (d, J=8.3 Hz, 2H), 7.06 (d, J=3.3 Hz, 1H), 6.87 (d, J=8.5 Hz, 2H), 6.68 (dd, J=3.1, 1.7 Hz, 1H), 4.07-4.04 (m, 2H), 3.73 (dd, J=5.3, 4.0 Hz, 2H), 3.59-3.57 (m, 2H), 3.55-3.53 (m, 2H), 3.53-3.49 (m, 10H), 3.45 (d, J=7.2 Hz, 2H), 3.43-3.41 (m, 2H), 3.23 (s, 3H), 2.82-2.75 (m, 2H).

Example 75

2,5,8,11,14,17-Hexaoxanonadecan-19-yl methanesulfonate

To a stirred solution of triethyl amine (0.683 g, 6.75 mmol) and 2,5,8,11,14,17-hexaoxanonadecan-19-ol (1.00 g, 3.37 mmol) in dichloromethane (30 mL) was added methanesulfonyl chloride (0.58 g, 5.06 mmol, diluted in 20 ml of dichloromethane) dropwise over 30 minutes at 0° C. under N$_2$. The reaction was then stirred at room temperature overnight. More dichloromethane (150 mL) was added and it washed with 1N HCl (2×40 mL) and water (2×40 mL). After drying with Na$_2$SO$_4$, removal of the solvent provided the title compound as colorless oil (1.14 g, 90% yield). $^1$H NMR (500 MHz, DMSO-d6) δ: 4.35-4.29 (m, 2H), 3.71-3.65 (m, 2H), 3.59-3.56 (m, 2H), 3.56-3.47 (m, 16H), 3.43 (dd, J=5.7, 3.7 Hz, 2H), 3.25 (s, 3H), 3.18 (s, 3H).

Example 76 tert-Butyl 4-(2,5,8,11,14,17-hexaoxanonadecan-19-yloxy)phenethylcarbamate

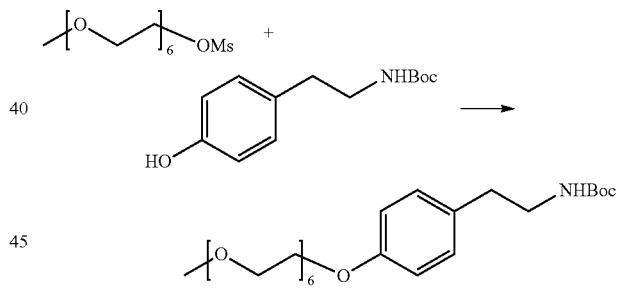

To a stirred mixture of tert-butyl 4-hydroxyphenethylcarbamate (0.38 g, 1.6 mmol) and NaH (0.065 g, 1.6 mmol, 60% dispersion in mineral oil) in dried DMF (20 mL) was added 2,5,8,11,14,17-hexaoxanonadecan-19-yl methanesulfonate (0.6 g, 1.6 mmol, diluted in 20 ml of dry DMF) dropwise at 0° C. under N$_2$. The reaction mixture was stirred at room temperature for 1 h. After this time, the reaction mixture was heated at 60° C. overnight. The reaction was quenched with ice-water and extracted with ethyl acetate. The organic layer was washed with water and brine, dried over sodium sulfate and concentrated in vacuo. The crude product was purified by column chromatography to afford the title compound (0.565 g, 68% yield). $^1$H NMR (500 MHz, CDCl$_3$) δ: 7.10 (d, J=8.2 Hz, 2H), 6.86 (d, J=8.5 Hz, 2H), 4.56 (s, 1H), 4.12 (t, J=4.9 Hz, 2H), 3.90-3.84 (m, 2H), 3.73 (dd, J=6.1, 3.5 Hz, 2H), 3.71-3.62 (m, 16H), 3.58-3.55 (m, 2H), 3.39 (s, 3H), 3.34 (d, J=5.8 Hz, 2H), 2.74 (t, J=6.7 Hz, 2H), 1.44 (s, 9H).

Example 77

2-(4-(2,5,8,11,14,17-Hexaoxanonadecan-19-yloxy)phenyl)ethanaminium chloride

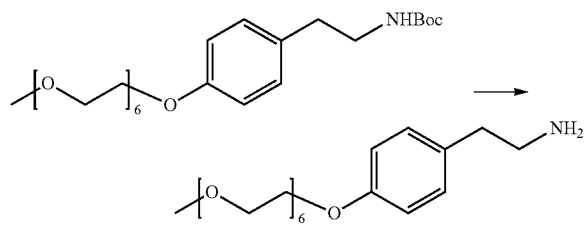

20% Hydrochloric acid (2 mL) was added to a stirred solution of tert-butyl 4-(2,5,8,11,14,17-hexaoxanonadecan-19-yloxy)phenethylcarbamate (0.539 g, 1.045 mmol) in methanol (20 mL) at room temperature. After stirring for 17 h, the solvent was removed under reduced pressure to afford the crude product, which was used for the next step directly.

Example 78

N5-(4-(2,5,8,11,14,17-Hexaoxanonadecan-19-yloxy)phenethyl)-2-(furan-2-yl)-[1,2,4]triazolo[1,5-α][1,3,5]triazine-5,7-diamine

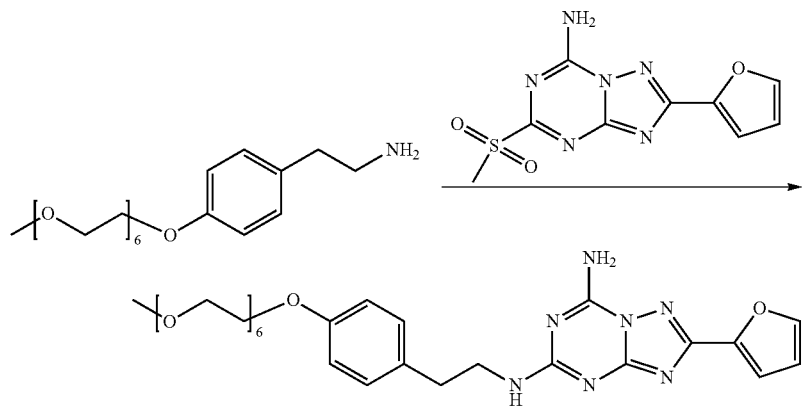

The reaction was carried out as in Example 5 to afford the title compound as yellow oil (0.026 g, 7% yield). $^1$H NMR (500 MHz, DMSO-d6) δ: 8.31 (br, 2H), 7.86 (br, 1H), 7.47 (br, 1H), 7.15 (d, J=8.3 Hz, 2H), 7.05 (d, J=3.2 Hz, 1H), 6.87 (d, J=8.4 Hz, 2H), 6.67 (d, J=1.6 Hz, 1H), 4.07-4.03 (m, 2H), 3.75-3.70 (m, 2H), 3.57 (dd, J=5.9, 3.2 Hz, 2H), 3.55-3.46 (m, 16H), 3.46-3.40 (m, 4H), 3.22 (s, 3H), 2.82-2.75 (m, 2H).

Example 79

4-(2-Bromoethyl)morpholine

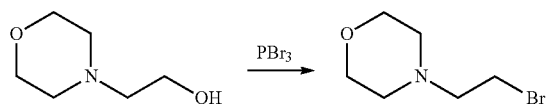 [SMILES: OCCN1CCOCC1 ; "PBr3" ; BrCCN1CCOCC1]

To a stirred solution of 2-morpholinoethanol (5 g, 37.74 mol) in dichloromethane (80 mL) was added dropwise the solution of tribromophosphine (4.26 mL, 45.29 mmol) in dichloromethane (30 mL) at 0° C. The reaction mixture was then stirred at 45° C. overnight. The resulting mixture was quenched with saturated sodium bicarbonate and extracted with dichloromethane. The organic layer was washed with brine and concentrated. The crude product was purified by column chromatography (DCM:MeOH=100:1) to afford the title product as yellow oil (1.88 g, 23.7% yield). $^1$H NMR (500 MHz, CD$_3$OD_SPE) δ: 3.73-3.65 (m, 4H), 3.49 (t, J=7.2 Hz, 2H), 2.79 (t, J=7.2 Hz, 2H), 2.54 (s, 4H); $^1$H NMR (500 MHz, DMSO-d6) δ: 3.69 (t, 4H), 3.49 (t, 2H), 2.79 (t, 2H), 2.54 (t, 4H).

Example 80 tert-Butyl 4-(2-morpholinoethoxy)phenethylcarbamate

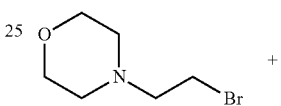

+

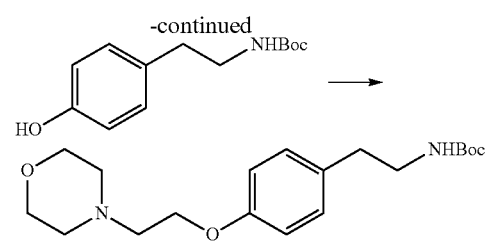

To a stirred mixture of tert-butyl 4-hydroxyphenethylcarbamate (0.612 g, 2.58 mmol) and potassium carbonate (0.356 g, 2.58 mmol) was added 4-(2-Bromoethyl)morpholine (0.640 g, 3.30 mmol, in 40 ml of acetone) at room temperature. After stirring for 2 h, the reaction mixture was heated at 55° C. overnight. The solvent was removed under reduced pressure. Column chromatography afforded the title compound as white solid (0.588 g, 65% yield). $^1$H NMR (500 MHz, DMSO-d6) δ: 7.09 (d, J=8.5 Hz, 2H), 6.85 (d, J=8.6 Hz, 2H), 4.04 (t, J=5.8 Hz, 2H), 3.65-3.54 (m, 4H), 3.09 (dd, J=13.9, 6.5 Hz, 2H), 2.64 (dt, J=15.0, 6.5 Hz, 4H), 2.47 (d, J=4.2 Hz, 4H), 1.37 (s, 9H).

Example 81

4-(2-(4-(2-Ammonioethyl)phenoxy)ethyl)morpholin-4-ium 2,2,2-trifluoroacetate

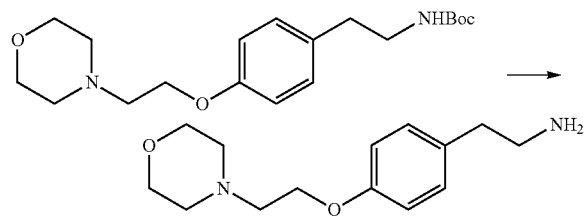

Trifluoroacetic acid (2 mL) was added dropwise to a stirred solution of tert-Butyl 4-(2-morpholinoethoxy)phenethylcarbamate (0.3 g, 0.77 mmol) in methanol (15 mL) at room temperature. After stirring for 1.5 h, the solvent was removed under reduced pressure to afford the crude product, which was used for the next step directly.

Example 82

2-(Furan-2-yl)-N5-(4-(2-morpholinoethoxy)phenethyl)-[1,2,4]triazolo[1,5-α][1,3,5]triazine-5,7-diamine

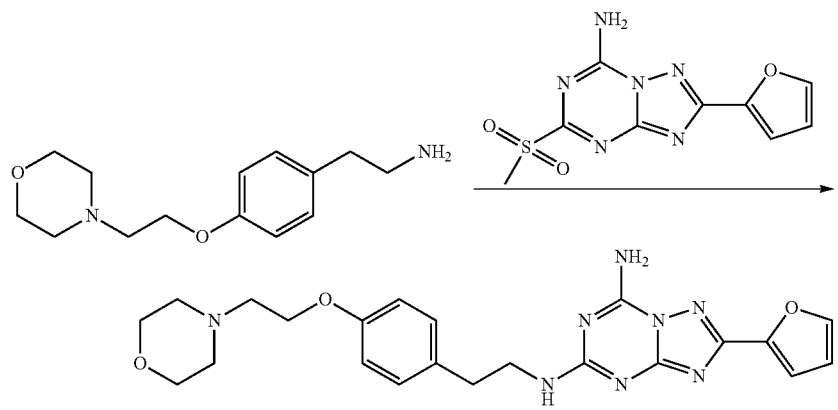

The reaction was carried out as in Example 5 to afford the title compound as white solid (0.080 g, 33% yield). ¹H NMR (500 MHz, DMSO-d6) δ: 8.29 (br, 2H), 7.87 (s, 1H), 7.46 (dd, J=25.9, 20.6 Hz, 1H), 7.16 (d, J=8.1 Hz, 2H), 7.06 (d, J=3.2 Hz, 1H), 6.87 (d, J=8.3 Hz, 2H), 6.68 (s, 1H), 4.05 (t, J=5.7 Hz, 2H), 3.61-3.53 (m, 4H), 3.49-3.43 (m, 2H), 2.79 (t, J=7.2 Hz, 2H), 2.67 (t, J=5.7 Hz, 2H), 2.46 (s, 4H).

Example 83

4-(3-((Methylsulfonyl)oxy)propyl)morpholin-4-ium chloride

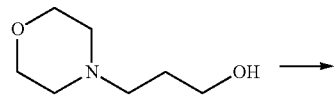

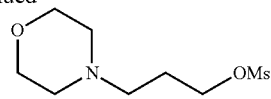

To a stirred solution of 3-morpholinopropan-1-ol (1.162 g, 8 mmol) in dichloromethane (15 mL) was added methane sulfonyl chloride (1.146 g, 10 mmol diluted in 20 ml of dichloromethane) dropwise over 30 min at 0° C. Then the reaction was stirred at room temperature overnight. The reaction mixture was filtered, washed with dichloromethane (5 mL×3) and dried to afford the title compound as white solid (1.7 g, 82% yield). ¹H NMR (500 MHz, CD₃OD_SPE) δ: 4.36 (t, J=5.8 Hz, 2H), 4.18-3.37 (m, 8H), 3.16 (br, 2H), 3.12 (s, 3H), 2.27-2.16 (m, 2H).

Example 84 tert-Butyl 4-(3-morpholinopropoxy)phenethylcarbamate

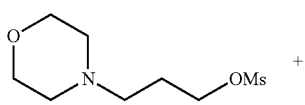

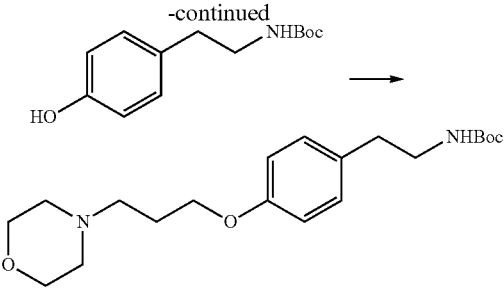

A mixture of tert-butyl 4-hydroxyphenethylcarbamate (0.548 g, 2.31 mmol), potassium carbonate (0.319 g, 2.31 mmol) and 4-(3-((methylsulfonyl)oxy)propyl)morpholin-4-ium chloride (0.512 g, 2.10 mmol) in acetone (30 mL) was stirred at room temperature for 1 h. Then the reaction mixture was stirred at 55° C. for 6 h. After adding more cesium carbonate (0.323 g, 1 mmol) to the reaction mixture and stirring at 55° C. overnight, the reaction mixture was filtered and washed with ethyl acetate (5 mL×3). The organic layer was concentrated in vacuo, and purified by column chromatography to afford the title compound as white solid (0.421 g, 55% yield). $^1$H NMR (500 MHz, DMSO-d6) δ: 7.08 (d, J=8.5 Hz, 2H), 6.83 (d, J=8.5 Hz, 2H), 3.96 (t, J=6.4 Hz, 2H), 3.57 (t, J=4.5 Hz, 4H), 3.08 (dd, J=14.2, 6.4 Hz, 2H), 2.65-2.58 (m, 2H), 2.43-2.31 (m, 7H), 1.88-1.83 (m, 2H), 1.37 (s, 9H).

Example 85

4-(3-(4-(2-Ammonioethyl)phenoxy)propyl)morpholin-4-ium 2,2,2-trifluoroacetate

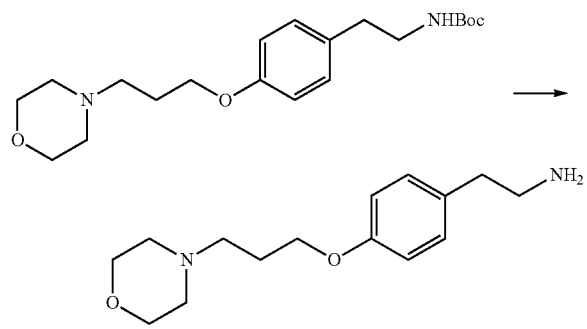

Trifluoroacetic acid (0.5 mL) was added dropwise to a stirred solution of tert-butyl 4-(3-morpholinopropoxy)phenethylcarbamate (0.200 g, 0.52 mmol) in dichloromethane (10 mL) at room temperature. The reaction was stirred overnight. Then the excess solvent was removed under reduced pressure to afford the crude product, which was used for the next step directly.

Example 86

2-(Furan-2-yl)-N5-(4-(3-morpholinopropoxy)phenethyl)-[1,2,4]triazolo[1,5-α][1,3,5]triazine-5,7-diamine

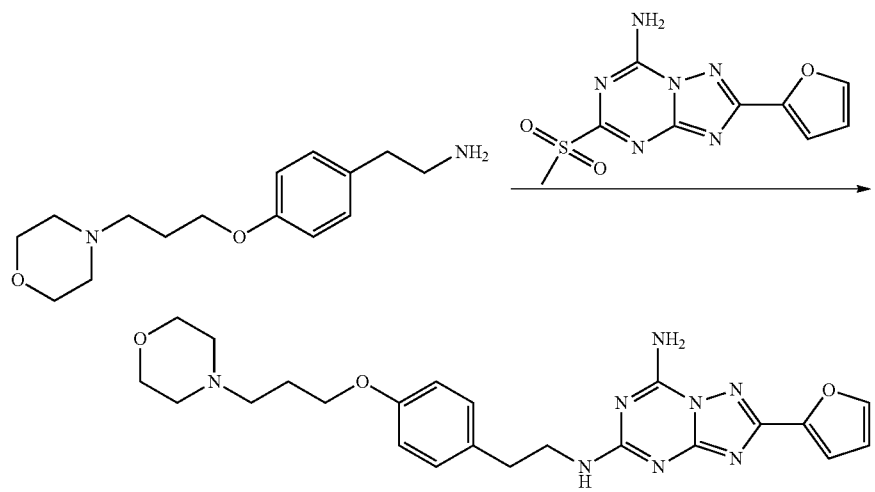

The reaction was carried out as in Example 5 to afford the title compound as gray solid (0.049 g, 29% yield). $^1$H NMR (500 MHz, DMSO-d6) δ: 8.28 (br, 2H), 7.87 (s, 1H), 7.47 (dd, J=25.5, 20.3 Hz, 1H), 7.15 (d, J=7.9 Hz, 2H), 7.06 (d, J=3.1 Hz, 1H), 6.85 (d, J=8.1 Hz, 2H), 6.68 (s, 1H), 3.96 (t, J=6.3 Hz, 2H), 3.64-3.53 (m, 4H), 3.44 (d, J=6.3 Hz, 2H), 2.83-2.74 (m, 2H), 2.42-2.35 (m, 6H), 1.90-1.81 (m, 2H).

Example 87

2-(Pyridin-2-yl)ethyl methanesulfonate

To a stirred solution of triethyl amine (1.21 g, 12 mmol) and 2-(pyridin-2-yl)ethanol (1.23 g, 10 mmol) in dichloromethane (20 mL) was added methanesulfonyl chloride (1.37 g, 12 mmol, diluted in 20 ml of dichloromethane) dropwise over 20 minutes at 0° C. The reaction was stirred at 0° C. for 2 h. More dichloromethane (50 mL) was added. The reaction mixture was washed with water (3×30 mL). After drying with Na$_2$SO$_4$, removal of the solvent provided the crude product as yellow oil (1.895 g, 94% yield), which was used for next reaction without further purification.

Example 88 tert-Butyl 4-(2-(pyridin-2-yl)ethoxy)phenethylcarbamate

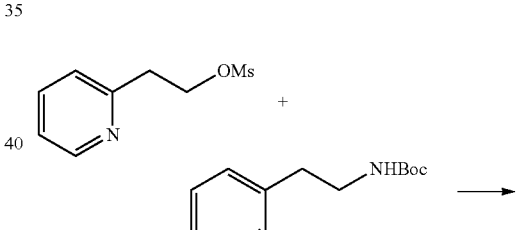

-continued

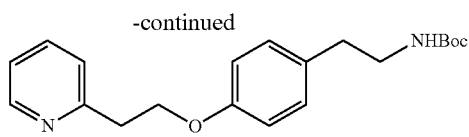

A mixture of tert-butyl 4-hydroxyphenethylcarbamate (0.653 g, 2.75 mmol), cesium carbonate (0.896 g, 2.75 mmol) and 2-(pyridin-2-yl)ethyl methanesulfonate (0.503 g, 2.5 mmol) in acetone (40 mL) was stirred at room temperature for 0.5 h. Then the reaction was heated at 55° C. for 48 h. The reaction mixture was filtered and washed with ethyl acetate (5 mL×3). The organic layer was concentrated in vacuo and purified by column chromatography to afford the title compound as white solid (0.074 g, 8.6% yield). $^1$H NMR (500 MHz, DMSO-d6) δ: 8.51 (d, J=4.2 Hz, 1H), 7.73 (td, J=7.6, 1.8 Hz, 1H), 7.36 (d, J=7.8 Hz, 1H), 7.24 (dd, J=6.8, 5.0 Hz, 1H), 7.08 (d, J=8.5 Hz, 2H), 6.84 (d, J=8.5 Hz, 3H), 4.31 (t, J=6.7 Hz, 2H), 3.17 (t, J=6.6 Hz, 2H), 3.08 (dd, J=14.1, 6.4 Hz, 2H), 2.61 (d, J=7.8 Hz, 2H), 1.37 (s, 9H).

Example 89

2-(2-(4-(2-Ammonioethyl)phenoxy)ethyl)pyridin-1-ium chloride

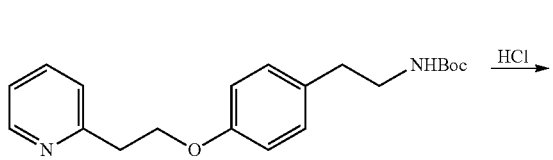

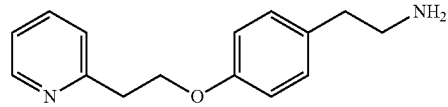

20% Hydrochloric acid (1 mL) was added dropwise to a stirred solution of tert-Butyl 4-(2-(pyridin-2-yl)ethoxy) phenethylcarbamate (0.068 g, 0.193 mmol) in methanol (15 mL) at room temperature. After stirring for 48 h, the excess solvent was removed under reduced pressure to afford the crude product, which was used for the next step directly.

Example 90

2-(Furan-2-yl)-N5-(4-(2-(pyridin-2-yl)ethoxy)phenethyl)-[1,2,4]triazolo[1,5-α][1,3,5]triazine-5,7-diamine

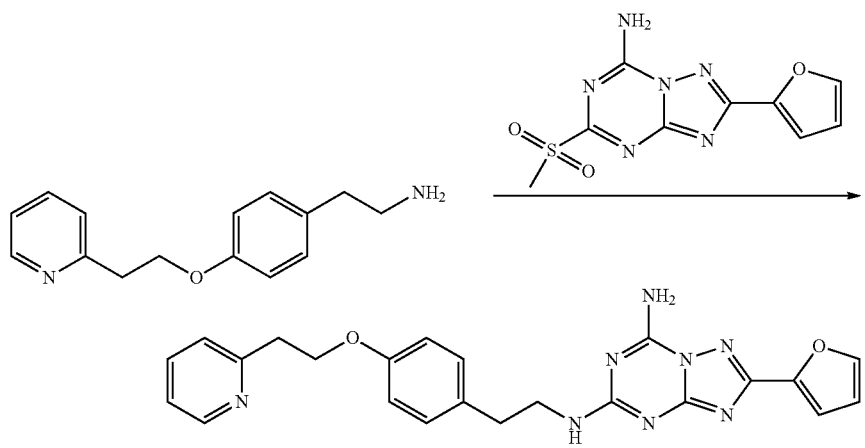

The reaction was carried out as in Example 5 to afford the title compound as yellow solid (0.045 g, 66% yield). $^1$H NMR (500 MHz, DMSO-d6) δ: 8.51 (d, J=4.2 Hz, 1H), 8.31 (br, 2H), 7.87 (s, 1H), 7.72 (td, J=7.7, 1.7 Hz, 1H), 7.45 (t, J=5.4 Hz, 1H), 7.36 (d, J=7.8 Hz, 1H), 7.26-7.22 (m, 1H), 7.15 (d, J=8.1 Hz, 2H), 7.06 (d, J=3.2 Hz, 1H), 6.86 (d, J=8.3 Hz, 2H), 6.68 (s, 1H), 4.32 (t, J=6.6 Hz, 2H), 3.44 (d, J=6.7 Hz, 2H), 3.17 (t, J=6.6 Hz, 2H), 2.83-2.74 (m, 2H).

Example 91

2-(2-Morpholinoethoxy)ethyl methanesulfonate

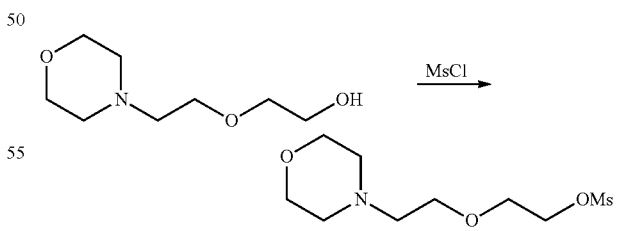

To a stirred solution of 2-(2-morpholinoethoxy)ethanol (0.440 g, 2.511 mmol) and triethyl amine (0.318 g, 3.139 mmol) in dichloromethane (30 mL) at 0° C. was added methanesulfonyl chloride (0.380 g, 3.139 mmol, diluted in 20 ml of dichloromethane) dropwise over 30 min. Then the reaction mixture was stirred at room temperature for 2 h. After more dichloromethane (40 mL) was added to the reaction, it was washed with 10% potassium carbonate (30 mL) and water (30 mL). After drying with Na₂SO₄, removal of the solvent provided the crude product (0.51 g), which was used for next step directly.

Example 92 tert-Butyl 4-(2-(2-morpholinoethoxy)ethoxy)phenethylcarbamate

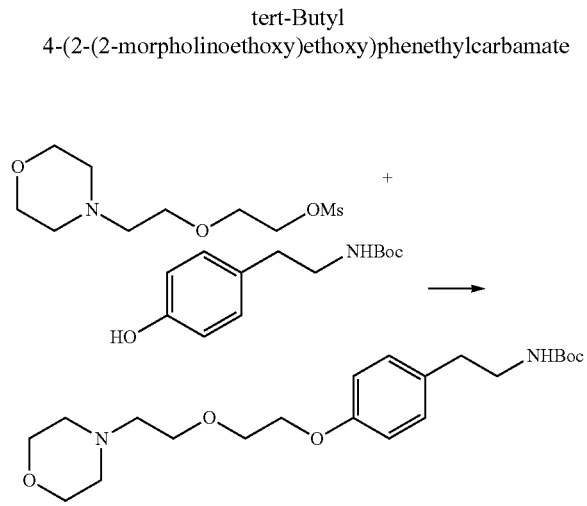

To a stirred mixture of tert-butyl 4-hydroxyphenethylcarbamate (0.309 g, 1.302 mmol) and NaH (0.052 g, 1.302 mmol, 60% dispersion in mineral oil) in dry THF (30 mL) at 0° C. under N₂ was added 2-(2-morpholinoethoxy)ethyl methanesulfonate (0.510 g, 2.013 mmol, dissolved in 5 ml of dry DMF) dropwise. After it was stirred at room temperature for 1 h, the reaction mixture was heated at 55° C. overnight. After the solvent was removed under reduced pressure, water (25 mL) was added to the reaction mixture and it was extracted with ethyl acetate (4×40 mL). The organic layer was washed with brine (2×30 mL), dried over sodium sulfate and concentrated in vacuo. The crude product was purified by column chromatography to afford the title compound as red solid (0.183 g, 36% yield). ¹H NMR (500 MHz, DMSO-d6) δ: 7.09 (d, J=8.5 Hz, 2H), 6.85 (d, J=8.5 Hz, 2H), 4.08-4.02 (m, 2H), 3.73-3.68 (m, 2H), 3.56 (dt, J=9.2, 5.3 Hz, 6H), 3.13-3.03 (m, 2H), 2.65-2.59 (m, 2H), 2.47 (t, J=5.8 Hz, 2H), 2.40 (s, 4H), 1.37 (s, 9H).

Example 93

4-(2-(2-(4-(2-Ammonioethyl)phenoxy)ethoxy)ethyl)morpholin-4-ium chloride

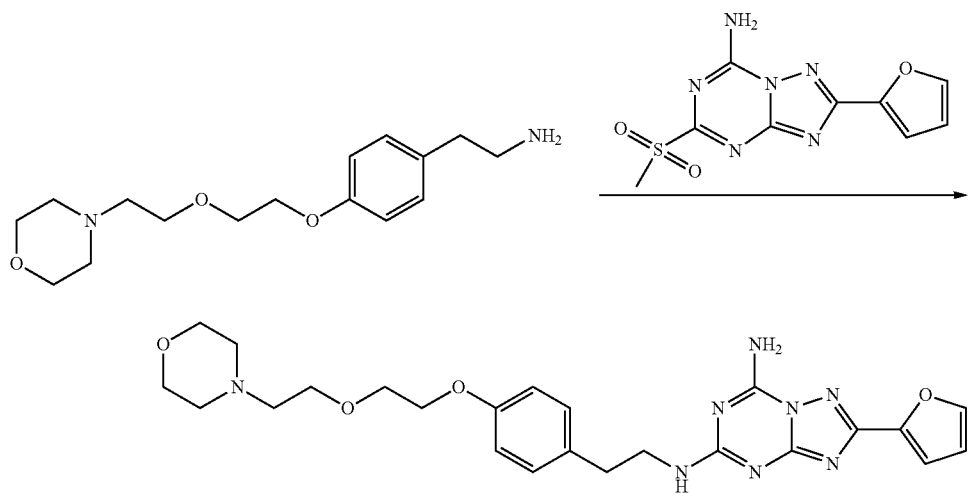

20% Hydrochloric acid (1 mL) was added dropwise to a stirred solution of tert-butyl 4-(2-(2-morpholinoethoxy)ethoxy)phenethylcarbamate (0.100 g, 0.254 mmol) in methanol (10 mL) at room temperature. After stirring for 4 h, the excess solvent was removed under reduced pressure to afford the crude product, which was used for next reaction without further purification.

Example 94

2-(Furan-2-yl)-N5-(4-(2-(2-morpholinoethoxy)ethoxy)phenethyl)-[1,2,4]triazolo[1,5-α][1,3,5]triazine-5,7-diamine The reaction was carried out as in Example 5 to afford the title compound as yellow solid (0.012 g, 12% yield). ¹H NMR (500 MHz, DMSO-d6) δ: 8.28 (br, 2H), 7.87 (s, 1H), 7.46 (dd, J=26.9, 21.3 Hz, 1H), 7.16 (d, J=8.3 Hz, 2H), 7.09-7.04 (m, 1H), 6.87 (d, J=8.4 Hz, 2H), 6.68 (d, J=1.6 Hz, 1H), 4.09-4.03 (m, 2H), 3.76-3.67 (m, 2H), 3.63-3.40 (m, 8H), 2.78 (d, J=7.1 Hz, 2H), 2.47 (t, J=5.9 Hz, 2H), 2.39 (s, 4H).

Example 95

Benzyl 4-hydroxyphenethylcarbamate

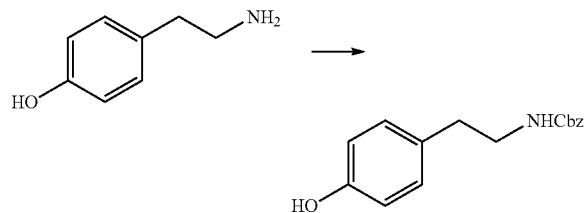

To a stirred mixture of 4-(2-aminoethyl)phenol (2 g, 14.57 mmol) and Na$_2$CO$_3$ (3.09 g, 29.15 mmol) in 1,4-dioxane (28 mL) and water (7 mL) at 0° C. was added benzyl carbonochloridate (2.7 g, 3.139 mmol, diluted in 2 ml of 1,4-dioxane) dropwise over 30 min. Then the reaction mixture was stirred at room temperature overnight. The reaction mixture was diluted with water (50 mL) and extracted with ethyl acetate (3×60 mL). The organic layer was washed with brine (2×30 mL) and dried with Na$_2$SO$_4$. After removal of the solvent, purification by column chromatography afforded the title compound as white solid (2.922 g, 74% yield). $^1$H NMR (500 MHz, DMSO-d6) δ: 9.17 (s, 1H), 7.43-7.28 (m, 6H), 6.97 (d, J=8.4 Hz, 2H), 6.67 (d, J=8.4 Hz, 2H), 5.00 (s, 2H), 3.22-3.12 (m, 2H), 2.60 (d, J=7.7 Hz, 2H).

Example 96

Benzyl 4-(2-(azetidin-1-yl)ethoxy)phenethylcarbamate

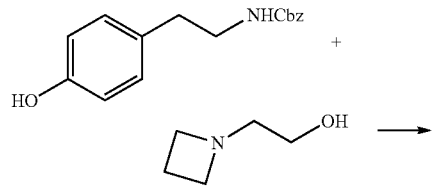

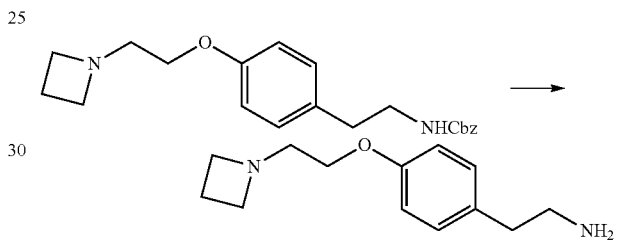

To a stirred solution of 2-(azetidin-1-yl)ethanol (0.280 g, 2.76 mmol), benzyl 4-hydroxyphenethylcarbamate (0.25 g, 0.92 mmol) and PPh$_3$ (0.725 g, 2.76 mmol) in dry THF (30 mL) at 0° C. under N$_2$ was added DIAD (0.559 g, 2.76 mmol, diluted in 2 ml of dry THF) dropwise over 30 min. The reaction mixture was stirred at room temperature overnight. After the excess solvent was removed under reduced pressure, Purification by column chromatography (EtOAc/MeOH) afforded the title compound as yellow solid (0.153 g, 47% yield). $^1$H NMR (500 MHz, DMSO-d6) δ: 7.55-7.22 (m, 6H), 7.08 (d, J=8.4 Hz, 2H), 6.80 (d, J=8.5 Hz, 2H), 5.00 (s, 2H), 3.85 (t, J=5.7 Hz, 2H), 3.17 (dd, J=15.1, 8.2 Hz, 6H), 2.74-2.61 (m, 4H), 2.01-1.90 (m, 2H).

Example 97

2-(4-(2-(Azetidin-1-yl)ethoxy)phenyl)ethanamine

A mixture of benzyl 4-(2-(azetidin-1-yl)ethoxy)phenethylcarbamate (0.110 g, 0.337 mmol) and Pd/C (10%, 30 mg) in MeOH (10 mL) was stirred under H2 balloon at room temperature for 5 h. The reaction mixture was filtered through diatomite. The filtrate was concentrated in vacuo to afford the crude product (0.059 g, 79%), which was used for the next reaction without further purification.

Example 98

N5-(4-(2-(Azetidin-1-yl)ethoxy)phenethyl)-2-(furan-2-yl)-[1,2,4]triazolo[1,5-α][1,3,5]triazine-5,7-diamine

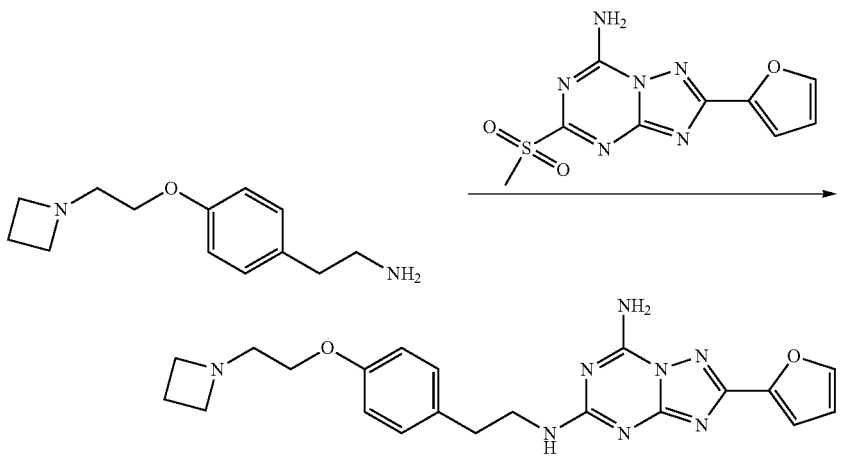

To a stirred solution of 2-(4-(2-(azetidin-1-yl)ethoxy) phenyl)ethanamine (0.267 mmol), 2-(furan-2-yl)-5-(methyl-sulfonyl)-[1,2,4]triazolo[1,5-α][1,3,5]triazin-7-amine (0.081 g, 0.290 mmol), triethylamine (0.099 g, 0.957 mmol) in acetonitrile (20 mL) at room temperature overnight. The solvent was removed under reduced pressure, the crude product was purified by column chromatography (EtOAc/MeOH) to afford the title compound as white solid (0.031 g, 28%). $^1$H NMR (500 MHz, DMSO-d6) δ: 8.30 (br, 2H), 7.87 (s, 1H), 7.47 (dd, J=26.5, 21.0 Hz, 1H), 7.14 (d, J=8.0 Hz, 2H), 7.05 (d, J=3.3 Hz, 1H), 6.83 (d, J=8.2 Hz, 2H), 6.67 (s, 1H), 3.86 (t, J=5.6 Hz, 2H), 3.44 (d, J=6.9 Hz, 2H), 3.17 (t, J=6.9 Hz, 4H), 2.81-2.74 (m, 2H), 2.68 (t, J=5.6 Hz, 2H), 1.98-1.92 (m, 2H).

Example 99

2-(2-(2-(2-(2-(2-(2-Methoxyethoxy)ethoxy)ethoxy)ethoxy)ethoxy)ethoxy)ethyl methanesulfonate

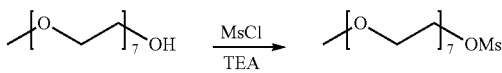

To a stirred solution of 2-(2-(2-(2-(2-(2-(2-methoxy-ethoxy)ethoxy)ethoxy)-ethoxy)ethoxy)ethoxy)ethanol (540 mg, 1.58 mmol) in DCM (20 mL) was added TEA (481.5 mg, 4.75 mmol) and MsCl (272 mg, 2.38 mmol) at 0° C. The reaction mixture was stirred at room temperature for 3 h. The reaction mixture was neutralized with 10% HCl and water, and extracted with DCM. The organic layer was washed with water and brine, dried over sodium sulfate and concentrated in vacuo to afford the title compound as colorless oil (663 mg, 100% yield). $^1$H NMR (500 MHz, CDCl$_3$) δ: 4.38-4.40 (m, 2H), 3.77-3.79 (m, 2H), 3.65-3.67 (m, 22H), 3.55-3.57 (m, 2H), 3.39 (s, 3H), 3.09 (s, 3H).

Example 100 tert-Butyl 4-(2-(2-(2-(2-(2-(2-(2-methoxyethoxy) ethoxy)ethoxy)ethoxy)-ethoxy)ethoxy)phen-ethylcarbamate

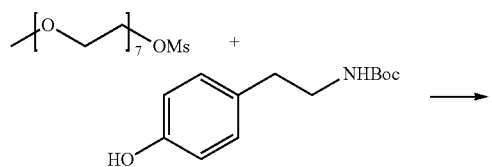

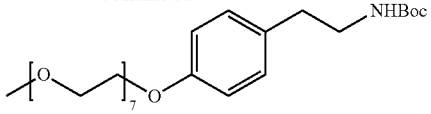

To a stirred solution of tert-butyl 4-hydroxyphenethylcarbamate (340 mg, 1.43 mmol) in dry THF (15 mL) was added NaH (58 mg, 1.45 mmol) at 0° C. under N$_2$. The reaction mixture was stirred at room temperature for 1 h. 2-(2-(2-(2-(2-(2-(2-methoxyethoxy)ethoxy)ethoxy)-ethoxy)ethoxy) ethoxy)ethyl methanesulfonate (300 mg, 0.71 mmol) was added next. The reaction mixture was stirred at 55° C. overnight. The reaction mixture was quenched with water and extracted with EtOAc. The organic layer was washed with water and brine, dried over sodium sulfate and concentrated in vacuo. The crude product was purified by column chromatography (EtOAc:MeOH=15:1) to afford the title compound as colorless oil (268 mg, 62% yield). $^1$H NMR (500 MHz, CDCl$_3$) δ: 7.10 (d, 2H), 6.87 (d, 2H), 4.55 (br, 1H), 4.12 (t, 2H), 3.86 (t, 2H), 3.73-3.75 (m, 2H), 3.64-3.70 (m, 20H), 3.55-3.57 (m, 2H), 3.39 (s, 3H), 3.34-3.35 (m, 2H), 2.74 (t, 2H), 1.45 (s, 9H).

Example 101

2-(4-(2-(2-(2-(2-(2-(2-(2-Methoxyethoxy)ethoxy) ethoxy)ethoxy)ethoxy)ethoxy)-ethoxy)phenyl) ethanamine

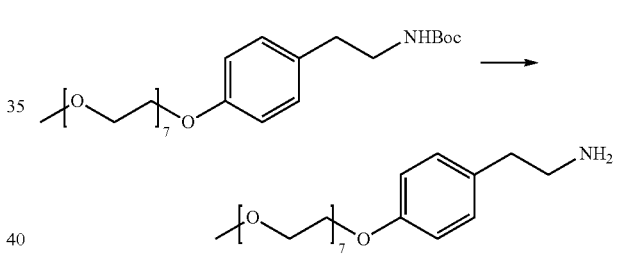

To a stirred solution of tert-butyl 4-(2-(2-(2-(2-(2-(2-(2-methoxyethoxy)ethoxy)ethoxy)-ethoxy)ethoxy)ethoxy) ethoxy)phenethylcarbamate (260 mg, 0.43 mmol) in methanol (5 mL) was added 20% aqueous HCl (2 mL). The reaction mixture was stirred at room temperature overnight. The excess HCl and methanol were removed in vacuo. The crude product was used for the next step directly.

Example 102

N5-(4-(2-(2-(2-(2-(2-(2-(2-Methoxyethoxy)ethoxy) ethoxy)ethoxy)ethoxy)ethoxy)ethoxy)-phenethyl)-2-(furan-2-yl)-[1,2,4]triazolo[1,5-a][1,3,5]triazine-5,7-diamine

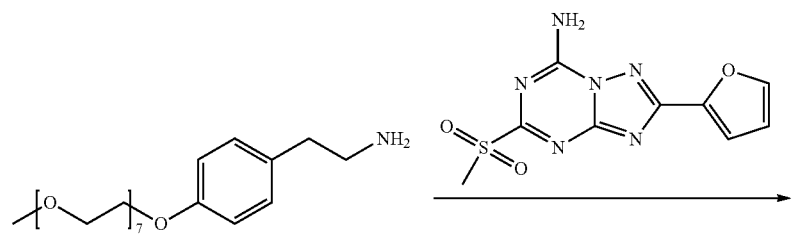

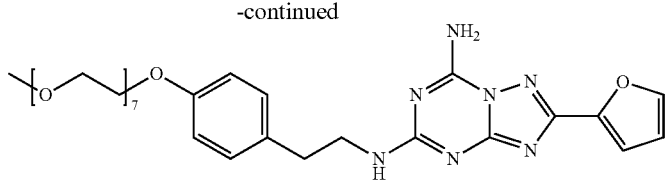

The reaction was carried out as in Example 5 to afford the title compound as colorless oil (155 mg, 54% yield). $^1$H NMR (500 MHz, DMSO-d6) δ: 8.09-8.20 (m, 2H), 7.87 (s, 1H), 7.43-7.52 (m, 1H), 7.15-7.17 (m, 2H), 7.06 (dd, 1H), 6.87 (d, 2H), 6.67-6.68 (m, 1d), 4.05 (t, 2H), 3.71-3.73 (m, 2H), 3.57-3.59 (m, 2H), 3.41-3.55 (m, 24H), 3.41-3.45 (m, 4H), 3.23 (s, 3H), 2.79 (t, 2H).

Example 103 tert-Butyl 4-hydroxyphenethylcarbamate

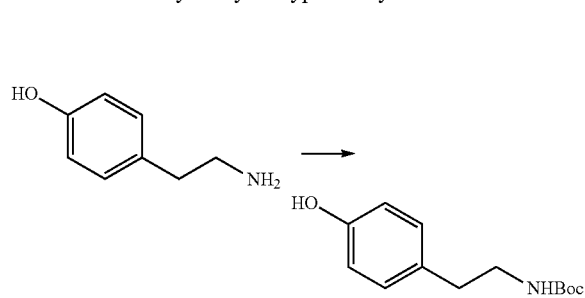

To a stirred solution of 4-(2-aminoethyl)phenol (13.8 g, 0.1 mol) in DCM was added TEA (10.1 g, 0.1 mol) and di-tert-butyl dicarbonate (21.8 g, 0.1 mol). The reaction mixture was stirred at room temperature overnight. The reaction mixture was neutralized with 10% HCl and extracted with DCM. The organic layer was washed with water and brine, dried over sodium sulfate and concentrated in vacuo. The crude product was purified by column chromatography to afford the title compound as yellow solid (20 g, 84% yield). $^1$H NMR (500 MHz, DMSO-d6) δ: 9.14 (s, 1H), 9.96 (d, 2H), 6.81 (t, 1H), 6.66 (d, 2H), 3.04-3.08 (m, 2H), 2.56 (t, 2H), 1.36 (s, 9H).

Example 104

1-Bromo-2-(2-(2-(2-methoxyethoxy)ethoxy)ethoxy) ethane

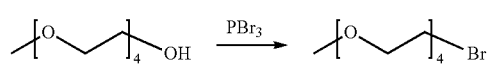

To a stirred solution of 2-(2-(2-(2-methoxyethoxy) ethoxy)ethoxy)ethanol (2.0 g, 9.6 mmol) in DCM (30 mL) was slowly added PBr$_3$ (3.9 g, 14.4 mmol) at 0° C. The reaction mixture was stirred at room temperature for 4 h. The reaction mixture was neutralized with NaHCO$_3$ (aq.) and extracted with EtOAc. The organic layer was washed with water and brine, dried over sodium sulfate and concentrated in vacuo. The crude product was purified by column chromatography (DCM:MeOH=15:1) to afford the title compound as colorless oil (700 mg, 27% yield). $^1$H NMR (500 MHz, CDCl$_3$) δ: 3.83 (t, 2H), 3.65-3.71 (m, 10H), 3.56-3.58 (m, 2H), 3.49 (t, 2H), 3.40 (s, 3H).

Example 105

2-(2-(3-(2-(2-(2-(2-Methoxyethoxy)ethoxy) ethoxy)ethoxy)ethoxy)propoxy)ethoxy)-ethanol

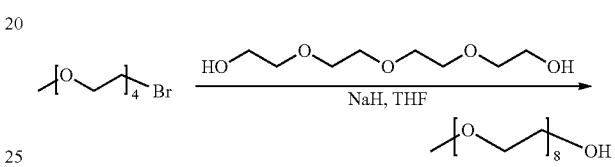

To a stirred solution of tetraethylene glycol (500 mg, 2.57 mmol) in dry THF (30 mL) was added NaH (130 mg, 3.25 mmol) at 0° C. under N$_2$. The reaction mixture was stirred at room temperature for 1 h. 1-Bromo-2-(2-(2-(2-methoxy-ethoxy)ethoxy)ethoxy)ethane (700 mg, 2.57 mmol, in 5 mL of THF) was next added dropwise at 0° C. The reaction mixture was stirred at room temperature overnight. The reaction mixture was quenched with water and extracted with EtOAc. The organic layer was washed with water and brine, dried over sodium sulfate and concentrated in vacuo. The crude product was purified by column chromatography (DCM:MeOH=60:1) to afford the title compound as colorless oil (230 mg, 25% yield), which was used for the next step directly.

Example 106

2-(2-(3-(2-(2-(2-(2-Methoxyethoxy)ethoxy) ethoxy)ethoxy)ethoxy)propoxy)ethoxy)ethyl methanesulfonate

To a stirred solution of crude 2-(2-(3-(2-(2-(2-(2-(2-methoxyethoxy)ethoxy)ethoxy)-ethoxy)ethoxy)propoxy) ethoxy)ethanol (2.65 g) in DCM (20 mL) was added TEA (2.1 g, 20.6 mmol) and MsCl (1.18 g, 10.3 mmol) at 0° C. The reaction mixture was stirred at room temperature for 1 h. The reaction mixture was neutralized with 10% HCl and extracted with EtOAc. The organic layer was washed with water and brine, dried over sodium sulfate and concentrated in vacuo. The crude product was purified by column chromatography (EtOAc:MeOH=15:1) to afford the title compound as colorless oil (300 mg). $^1$H NMR (500 MHz, CDCl$_3$) δ: 4.38-4.40 (m, 2H), 3.77-3.79 (m, 2H), 3.65-3.69 (m, 26H), 3.55-3.57 (m, 2H), 3.39 (s, 3H), 3.10 (s, 3H).

Example 107 tert-Butyl 4-(2-(2-(2-(2-(2-(2-(2-(2-methoxyethoxy)ethoxy)ethoxy)ethoxy)ethoxy)ethoxy)-ethoxy)ethoxy)phenethylcarbamate

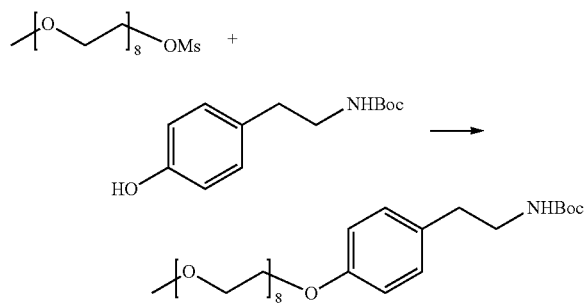

To a stirred solution of tert-butyl 4-hydroxyphenethylcarbamate (307 mg, 1.29 mmol) in dry THF (10 mL) was added NaH (51.7 mg, 1.29 mmol) at 0° C. under N₂. The reaction mixture was stirred at room temperature for 1 h. 2-(2-(3-(2-(2-(2-(2-(2-Methoxyethoxy)ethoxy)ethoxy)-ethoxy)ethoxy)propoxy)ethoxy)ethyl methanesulfonate (300 mg, 0.65 mmol) was added next. The reaction mixture was stirred at 50° C. overnight. The reaction mixture was quenched with water and extracted with EtOAc. The organic layer was washed with water and brine, dried over sodium sulfate and concentrated in vacuo. The crude product was purified by column chromatography (EtOAc:MeOH=15:1) to afford the title compound as colorless oil (180 mg, 46% yield). ¹H NMR (500 MHz, CDCl₃) δ: 7.10 (d, 2H), 6.87 (d, 2H), 4.55 (br, 1H), 4.12 (t, 2H), 3.86 (t, 2H), 3.69-3.76 (m, 6H), 3.65-3.67 (m, 20H), 3.55-3.57 (m, 2H), 3.39 (s, 3H), 3.34-3.35 (m, 2H), 2.74 (t, 2H), 1.45 (s, 9H).

Example 108

2-(4-(2-(2-(2-(2-(2-(2-(2-(2-Methoxyethoxy)ethoxy)ethoxy)ethoxy)ethoxy)ethoxy)ethoxy)-ethoxy)phenyl)ethanamine

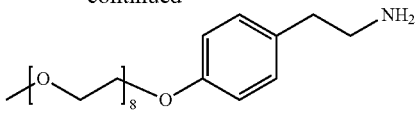

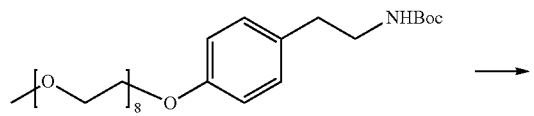

To a stirred solution of tert-butyl 4-(2-(2-(2-(2-(2-(2-(2-(2-methoxyethoxy)ethoxy)ethoxy)ethoxy)ethoxy)ethoxy)ethoxy)ethoxy)phenethylcarbamate (96 mg, 0.16 mmol) in methanol (5 mL) was added 20% aqueous HCl (1 mL). The reaction mixture was stirred at room temperature overnight. The excess HCl and methanol were removed. The crude product was used for the next step directly.

Example 109

N5-(4-(2-(2-(2-(2-(2-(2-(2-(2-Methoxyethoxy)ethoxy)ethoxy)ethoxy)ethoxy)ethoxy)ethoxy)ethoxy)phenethyl)-2-(furan-2-yl)-[1,2,4]triazolo[1,5-a][1,3,5]triazine-5,7-diamine

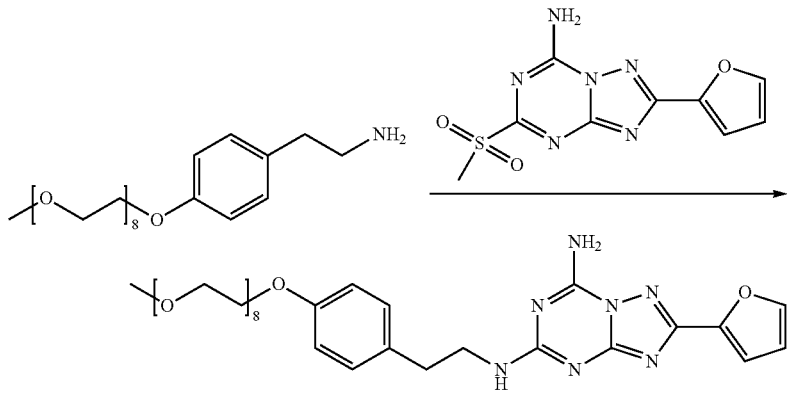

The reaction was carried out as in Example 5 to afford the title compound as colorless oil (41 mg, 24% yield). ¹H NMR (500 MHz, DMSO-d6) δ: 8.09-8.20 (m, 2H), 7.87 (s, 1H), 7.43-7.53 (m, 1H), 7.15-7.16 (m, 2H), 7.06 (dd, 1H), 6.87 (d, 2H), 6.67-6.68 (m, 1d), 4.05 (t, 2H), 3.71-3.73 (m, 2H), 3.57-3.58 (m, 2H), 3.49-3.50 (m, 24H), 3.41-3.45 (m, 4H), 3.23 (s, 3H), 2.79 (t, 2H).

Example 110

3-(Dimethylamino)propyl 4-methylbenzenesulfonate

To a stirred solution of 3-(dimethylamino)propan-1-ol (1 g, 9.7 mmol) in DCM (20 mL) was added TEA (1.96 g, 19.38 mmol) and 4-methylbenzene-1-sulfonyl chloride (2.77 g, 14.5 mmol) at 0° C. The reaction mixture was stirred at room temperature for 1 h. The reaction mixture was quenched with water and extracted with EtOAc. The organic layer was washed with water and brine, dried over sodium sulfate and concentrated in vacuo. The crude product was purified by column chromatography (EtOAc:MeOH=15:1)

to afford the title compound as white solid (1.0 g, 40% yield). $^1$H NMR (500 MHz, CDCl$_3$) δ: 7.78 (d, 2H), 7.33 (d, 2H), 4.08 (t, 2H), 2.44 (s, 3H), 2.28 (t, 2H), 2.14 (s, 6H), 1.76-1.82 (m, 2H).

Example 111 tert-Butyl 4-(3-(dimethylamino)propoxy)phenethylcarbamate

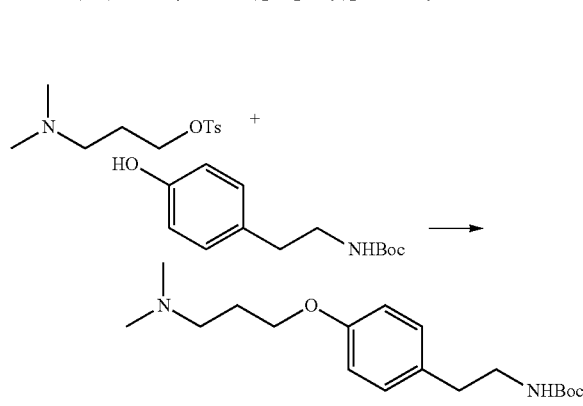

To a stirred solution of 3-(dimethylamino)propyl 4-methylbenzenesulfonate (500 mg, 1.94 mmol) in DMF (20 mL) was added cesium carbonate (1.26 g, 3.88 mmol) and tert-butyl 4-hydroxyphenethylcarbamate (460 mg, 1.94 mmol). The reaction mixture was stirred at 80° C. overnight. The reaction mixture was quenched with water and extracted with EtOAc. The organic layer was washed with water and brine, dried over sodium sulfate and concentrated in vacuo. The crude product was purified by column chromatography (EtOAc:MeOH=15:1) to afford the title compound as yellow oil (257 mg, 41% yield). $^1$H NMR (500 MHz, CDCl$_3$) 7.10 (d, 2H), 6.86 (d, 2H), 4.54 (br, 1H), 4.01 (t, 2H), 3.35-3.36 (m, 2H), 2.74 (t, 2H), 2.47 (t, 2H), 2.27 (s, 6H), 1.94-2.00 (m, 2H), 1.45 (s, 9H).

Example 112

2-(2-(3-(2-(2-(2-(2-Methoxyethoxy)ethoxy) ethoxy)ethoxy)ethoxy)propoxy)ethoxy)ethyl methanesulfonate

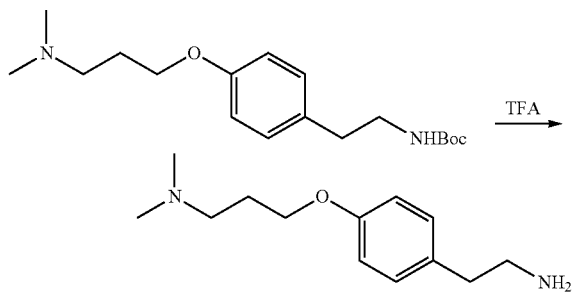

To a stirred solution of tert-butyl 4-(3-(dimethylamino) propoxy)phenethylcarbamate (257 mg) in DCM (3 mL) was added TFA (1 mL). The reaction mixture was stirred at room temperature for 1 h. The excessed DCM and TFA were removed. The crude product was used for the next step directly.

Example 113

N$^7$-(4-(3-(Dimethylamino)propoxy)phenethyl)-2-(furan-2-yl)-[1,2,4]triazolo[1,5-a]pyridine-5,7-diamine

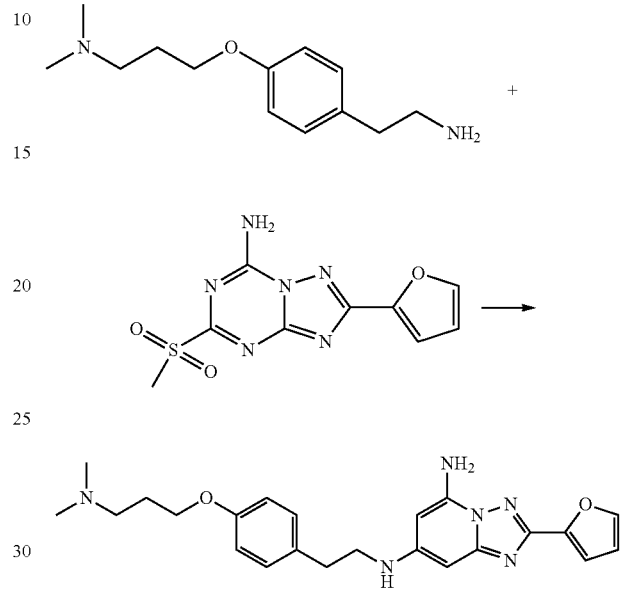

The reaction was carried out as in Example 5 to afford the title compound as white solid (100 mg, 30% yield). $^1$H NMR (500 MHz, DMSO-d6) δ: 8.15-8.18 (m, 2H), 7.86 (s, 1H), 7.44-7.51 (m, 1H), 7.15-7.16 (m, 2H), 7.05 (d, 1H), 6.85 (d, 2H), 6.66-6.67 (m, 1H), 3.97 (t, 2H), 3.41-3.47 (m, 2H), 2.76-2.79 (m, 4H), 2.46-2.48 (m, 6H), 1.92-1.95 (m, 2H).

Example 114

2-(2-(2-(2-(2-(2-(2-(2-(2-Methoxyethoxy)ethoxy) ethoxy)ethoxy)ethoxy)ethoxy)ethoxy)-ethoxy)ethyl methanesulfonate

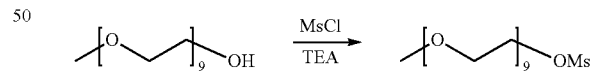

To a stirred solution of 2-(2-(2-(2-(2-(2-(2-(2-(2-methoxyethoxy)ethoxy)ethoxy)-ethoxy)ethoxy)ethoxy) ethoxy)ethoxy)ethanol (500 mg, 1.16 mmol) in DCM (10 mL) was added TEA (354 mg, 3.5 mmol) and MsCl (200 mg, 1.74 mmol) at 0° C. The reaction mixture was stirred at room temperature for 3 h. The reaction mixture was neutralized with 10% HCl and extracted with DCM. The organic layer was washed with water and brine, dried over sodium sulfate and concentrated in vacuo to afford the title compound as colorless oil (585 mg, 99% yield). $^1$H NMR (500 MHz, CDCl$_3$) δ: 4.36-4.38 (m, 2H), 3.75-3.76 (m, 2H), 3.62-3.66 (m, 30H), 3.53-3.55 (m, 2H), 3.37 (s, 3H), 3.07 (s, 3H).

Example 115 tert-Butyl 4-(2-(2-(2-(2-(2-(2-(2-(2-(2-methoxy-ethoxy)ethoxy)ethoxy)ethoxy)ethoxy)ethoxy)-ethoxy)ethoxy)ethoxy)phenethylcarbamate

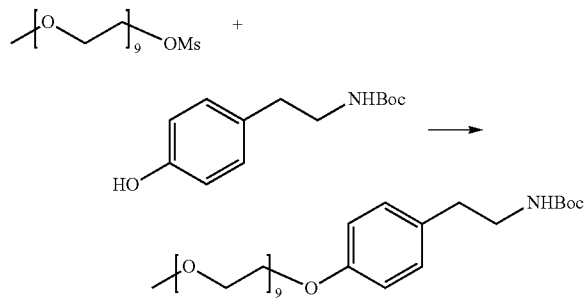

To a stirred solution of tert-butyl 4-hydroxyphenethylcarbamate (280 mg, 1.18 mmol) in dry THF (15 mL) was added NaH (48 mg, 1.18 mmol) at 0° C. under N₂. The reaction mixture was stirred at room temperature for 1 h. 2-(2-(2-(2-(2-(2-(2-(2-Methoxyethoxy)ethoxy)-ethoxy)ethoxy)ethoxy)ethoxy)ethoxy)ethyl methanesulfonate (300 mg, 0.59 mmol) was added next. The reaction mixture was stirred at 50° C. overnight. The reaction mixture was quenched with water and extracted with EtOAc. The organic layer was washed with water and brine, dried over sodium sulfate and concentrated in vacuo. The crude product was purified by column chromatography (EtOAc:MeOH=15:1) to afford the title compound as colorless oil (280 mg, 71% yield). ¹H NMR (500 MHz, CDCl₃) δ: 7.10 (d, 2H), 6.87 (d, 2H), 4.55 (br, 1H), 4.12 (t, 2H), 3.86 (t, 2H), 3.73-3.75 (m, 2H), 3.65-3.71 (m, 30H), 3.55-3.57 (m, 2H), 3.39 (s, 3H), 2.74 (t, 2H), 1.45 (s, 9H).

Example 116

2-(4-(2-(2-(2-(2-(2-(2-(2-(2-(2-Methoxyethoxy)ethoxy)ethoxy)ethoxy)ethoxy)ethoxy)-ethoxy)ethoxy)phenyl)ethanamine

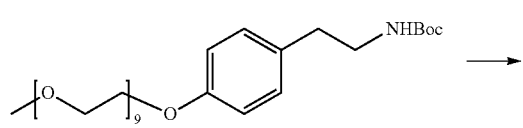

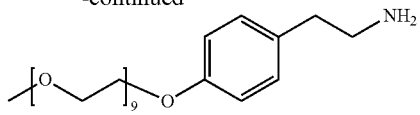

To a stirred solution of tert-butyl 4-(2-(2-(2-(2-(2-(2-(2-(2-(2-methoxyethoxy)ethoxy)-ethoxy)ethoxy)ethoxy)ethoxy)ethoxy)ethoxy)phenethylcarbamate (170 mg, 0.26 mmol) in methanol (5 mL) was added 20% aqueous HCl (3 mL). The reaction mixture was stirred at room temperature overnight. The excess HCl and methanol were removed in vacuo. The crude product was used for the next step directly.

Example 117

N5-(4-(2-(2-(2-(2-(2-(2-(2-(2-(2-Methoxyethoxy)ethoxy)ethoxy)ethoxy)ethoxy)-ethoxy)ethoxy)ethoxy)phenethyl)-2-(furan-2-yl)-[1,2,4]triazolo[1,5-a][1,3,5]triazine-5,7-diamine

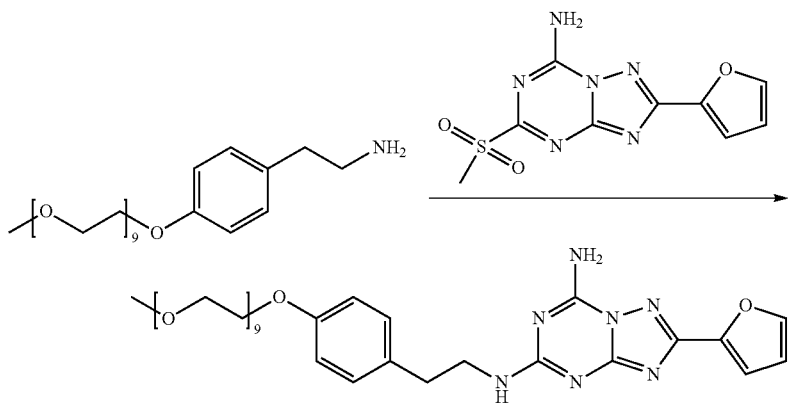

The reaction was carried out as in Example 5 to afford the title compound as colorless oil (140 mg, 72% yield). ¹H NMR (500 MHz, DMSO-d6) δ: 8.09-8.20 (m, 2H), 7.87 (s, 1H), 7.44-7.53 (m, 1H), 7.15-7.16 (m, 2H), 7.06 (dd, 1H), 6.87 (d, 2H), 6.67-6.68 (m, 1d), 4.05 (t, 2H), 3.71-3.73 (m, 2H), 3.57-3.59 (m, 2H), 3.41-3.54 (m, 32H), 3.41-3.45 (m, 4H), 3.23 (s, 3H), 2.78 (t, 2H).

Example 118

(1-Methylpiperidin-4-yl)methyl methanesulfonate

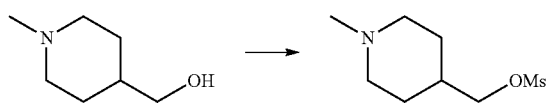

To a stirred solution of (1-methylpiperidin-4-yl)methanol (500 mg, 3.86 mmol) in DCM (20 mL) was added methanesulfonyl chloride (665 mg, 5.8 mmol) at 0° C. The reaction mixture was stirred at room temperature for 3 h. The reaction mixture was neutralized with NaHCO₃ (aq.) and extracted with DCM. The organic layer was washed with water and brine, dried over sodium sulfate and concentrated in vacuo to afford the title compound as white solid (570 mg, 71% yield). $^1$H NMR (500 MHz, CDCl$_3$) δ: 3.66-3.77 (m, 4H), 3.63 (s, 2H), 3.49 (s, 3H), 2.94 (t, 1H), 2.73 (s, 3H), 2.32-2.39 (m, 2H), 1.80-1.84 (m, 2H).

Example 119 tert-Butyl 4-((1-methylpiperidin-4-yl)methoxy)phenethylcarbamate

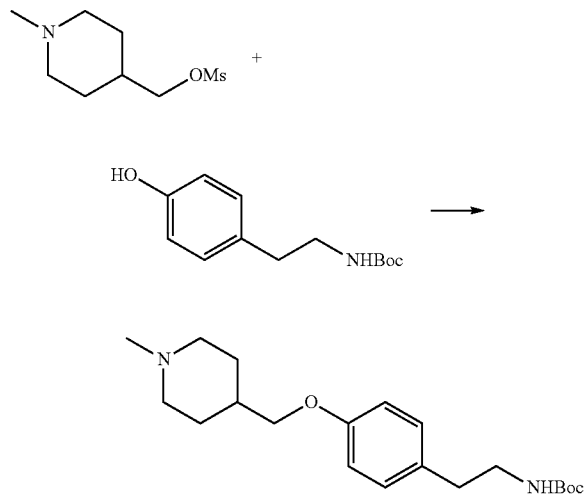

To a stirred solution of (1-methylpiperidin-4-yl)methyl methanesulfonate (300 mg, 1.45 mmol) in MeCN (20 mL) was added cesium carbonate (940 mg, 2.89 mmol) and tert-butyl 4-hydroxyphenethylcarbamate (500 mg, 2.11 mmol). The reaction mixture was stirred at 70° C. under N$_2$ overnight. The reaction mixture was quenched with water and extracted with EtOAc. The organic layer was washed with water and brine, dried over sodium sulfate and concentrated in vacuo. The crude product was purified by column chromatography to afford the title compound as yellow oil (159 mg), which was used for the next step directly.

Example 120

2-(4-((1-Methylpiperidin-4-yl)methoxy)phenyl)ethanamine

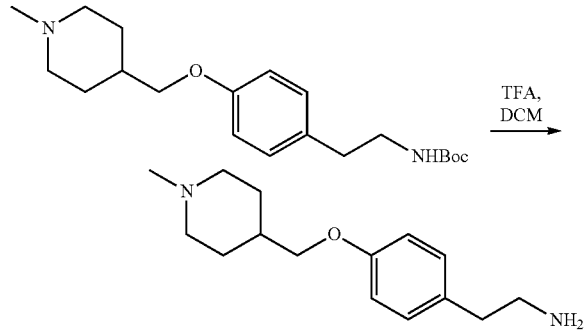

To a stirred solution of tert-butyl 4-((1-methylpiperidin-4-yl)methoxy)phenethyl-carbamate (157 mg) in DCM (3 mL) was added TFA (2 mL). The reaction mixture was stirred at room temperature for 1 h. The excess DCM and TFA were removed. The crude product was used for the next step directly.

Example 121

N5-(4-((1-Methylpiperidin-4-yl)methoxy)phenethyl)-2-(furan-2-yl)-[1,2,4]triazolo[1,5-a][1,3,5]triazine-5,7-diamine

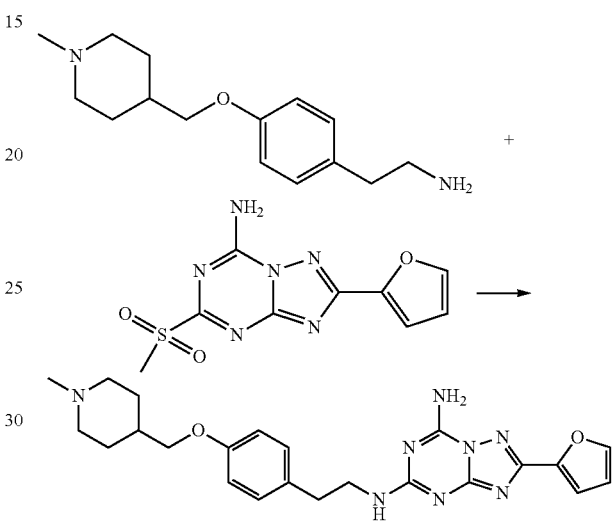

The reaction was carried out as in Example 5 to afford the title compound as white solid (15 mg, 7.5% yield). $^1$H NMR (500 MHz, DMSO-d6) δ: 8.15-8.18 (m, 2H), 7.86 (s, 1H), 7.44-7.51 (m, 1H), 7.15 (d, 2H), 7.05 (d, 1H), 6.85 (d, 2H), 6.67 (s, 1d), 3.92 (t, 2H), 2.90 (t, 1H), 2.77 (t, 2H), 2.64-2.72 (m, 2H), 2.40 (s, 3H), 2.29-2.36 (m, 2H), 1.97-2.02 (m, 2H), 1.75-1.78 (m, 2H), 1.46-1.49 (m, 2H).

Example 122

Benzyl 4-(2-(aziridin-1-yl)ethoxy)phenethylcarbamate

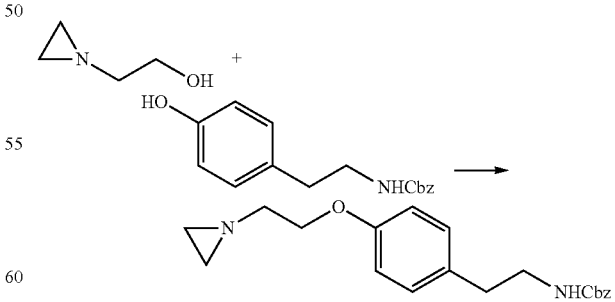

To a stirred solution of benzyl 4-hydroxyphenethylcarbamate (250 mg, 0.92 mmol) in dry THF (20 mL) was added PPh$_3$ (1.2 g, 4.60 mmol) and (2-(aziridin-1-yl)ethanol (400 mg, 4.60 mmol) at −5° C. under N$_2$. DIAD (931 mg, 4.60 mmol) was next added dropwise at the same temperature.

The reaction mixture was stirred at room temperature overnight. The solvent was removed. The crude product was purified by column chromatography to afford the title compound as white solid (280 mg, 89% yield). $^1$H NMR (500 MHz, DMSO-d6) δ: 7.34-3.37 (m, 2H), 7.29-7.32 (m, 4H), 7.09 (d, 2H), 6.84 (d, 2H), 5.00 (s, 2H), 4.73-4.79 (m, 2H), 3.15-3.19 (m, 2H), 2.64 (t, 2H), 2.24 (t, 2H), 1.58-1.59 (m, 2H), 1.53 (br, 2H).

Example 123

2-(4-(2-(Aziridin-1-yl)ethoxy)phenyl)ethanamine

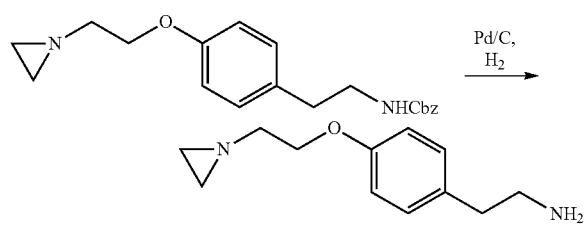

A mixture of benzyl 4-(2-(aziridin-1-yl)ethoxy)phenethylcarbamate (280 mg, 0.82 mmol) and Pd/C (10%, 20 mg) in MeOH (10 mL) was stirred under H2 at room temperature overnight. The reaction mixture was filtered through diatomite. The filtrate was concentrated in vacuo to afford the title compound as colorless oil (200 mg, 85% yield), which was used for the next step directly.

Example 124

N5-(4-(2-(Aziridin-1-yl)ethoxy)phenethyl)-2-(furan-2-yl)-[1,2,4]triazolo[1,5-a][1,3,5]triazine-5,7-diamine

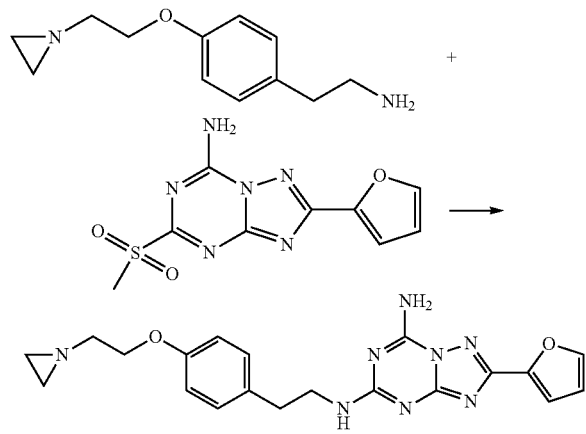

The reaction was carried out as in Example 5 to afford the title compound as yellow solid (24 mg, 13% yield). $^1$H NMR (500 MHz, DMSO-d6) δ: 8.09-8.20 (m, 2H), 7.87 (s, 1H), 7.45-7.53 (m, 1H), 7.16 (br, 2H), 7.05 (t, 1H), 6.87 (d, 2H), 6.68 (br, 1d), 3.97-3.98 (m, 2H), 3.44 (br, 2H), 2.86-2.87 (m, 2H), 2.78 (t, 2H), 2.60-2.61 (m, 2H), 1.20-1.23 (m, 2H).

Example 125

Benzyl 4-(3-(azetidin-1-yl)propoxy)phenethylcarbamate

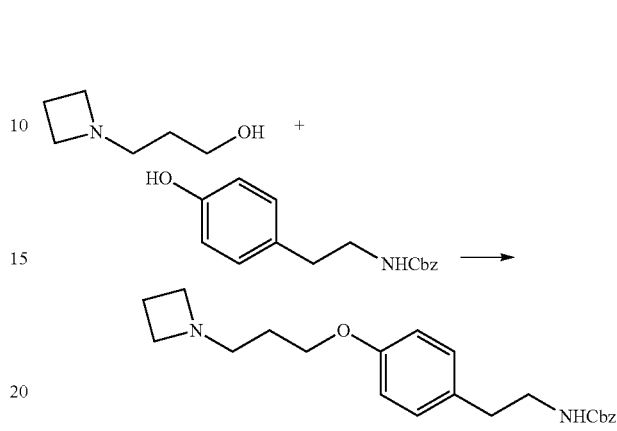

To a stirred solution of benzyl 4-hydroxyphenethylcarbamate (250 mg, 0.92 mmol) in dry THF (20 mL) was added PPh$_3$ (725 mg, 2.76 mmol) and 3-(azetidin-1-yl)propan-1-ol (318 mg, 2.76 mmol) at −5° C. under N$_2$. DIAD (559 mg, 2.76 mmol) was next added at the same temperature. The reaction mixture was stirred at room temperature overnight. The solvent was removed. The crude product was purified by column chromatography to afford the title compound as white solid (200 mg, 59% yield). $^1$H NMR (500 MHz, DMSO-d6) δ: 7.34-3.36 (m, 2H), 7.29-7.31 (m, 4H), 7.08 (d, 2H), 6.81 (d, 2H), 5.00 (s, 2H), 3.91 (t, 2H), 3.15-3.19 (m, 2H), 3.05 (t, 4H), 2.63 (t, 2H), 2.42 (t, 2H), 1.90-1.95 (m, 2H), 1.62-1.68 (m, 2H).

Example 126

2-(4-(3-(Azetidin-1-yl)propoxy)phenyl)ethanamine

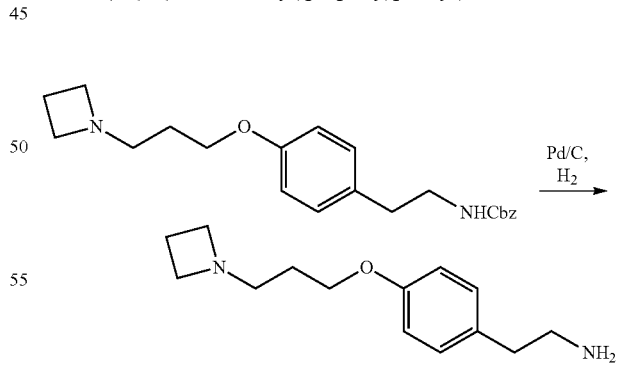

A mixture of benzyl 4-(3-(azetidin-1-yl)propoxy)phenethylcarbamate (200 mg, 0.82 mmol) and Pd/C (10%, 20 mg) in MeOH (10 mL) was stirred under H2 at room temperature overnight. The reaction mixture was filtered through diatomite. The filtrate was concentrated in vacuo to afford the title compound as colorless oil (160 mg, 100% yield), which was used directly for the next step.

Example 127

N5-(4-(3-(Azetidin-1-yl)propoxy)phenethyl)-2-(furan-2-yl)-[1,2,4]triazolo[1,5-a][1,3,5]triazine-5,7-diamine

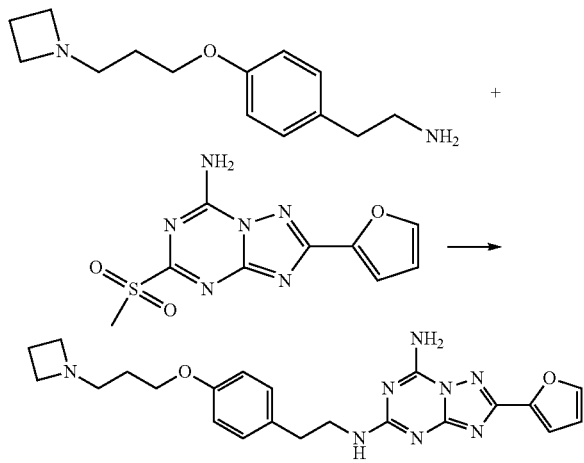

The reaction was carried out as in Example 5 to afford the title compound as white solid (36 mg, 21% yield). ¹H NMR (500 MHz, DMSO-d6) δ: 8.09-8.20 (m, 2H), 7.87 (s, 1H), 7.45-7.53 (m, 1H), 7.14 (d, 2H), 7.05 (d, 1H), 6.83 (d, 2H), 6.67 (br, 1d), 3.92 (t, 2H), 3.43-3.44 (m, 2H), 3.08 (t, 4H), 2.77 (t, 2H), 2.44 (t, 2H), 1.90-1.96 (m, 2H), 1.63-1.68 (m, 2H).

Example 128

Benzyl 4-(2-(2-(dimethylamino)ethoxy)ethoxy)phenethylcarbamate

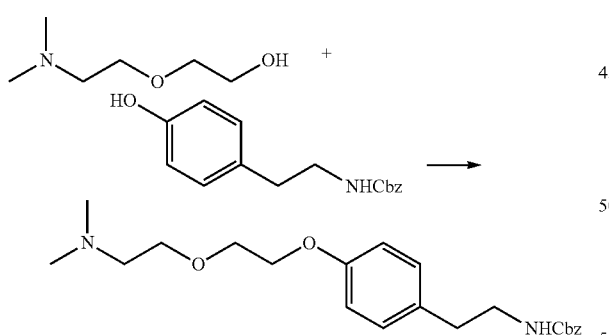

To a stirred solution of benzyl 4-hydroxyphenethylcarbamate (250 mg, 0.92 mmol) in dry THF (20 mL) was added PPh₃ (1.21 g, 4.60 mmol) and 2-(2-(dimethylamino)ethoxy)ethanol (613 mg, 4.60 mmol) at −5° C. under N₂. DIAD (931 mg, 4.60 mmol) was next added at the same temperature. The reaction mixture was stirred at room temperature overnight. The solvent was removed. The crude product was purified by column chromatography (EtOAc:MeOH=15:1) to afford the title compound as yellow oil (180 mg, 51% yield). ¹H NMR (500 MHz, DMSO-d6) δ: 7.34-3.39 (m, 2H), 7.29-7.31 (m, 4H), 7.09 (d, 2H), 6.84 (d, 2H), 5.00 (s, 2H), 4.03 (t, 2H), 3.68-3.70 (m, 2H), 3.52 (t, 2H), 3.15-3.19 (m, 2H), 2.64 (t, 2H), 2.39 (t, 2H), 1.19 (s, 6H).

Example 129

2-(4-(2-(2-(Dimethylamino)ethoxy)ethoxy)phenyl)ethanamine

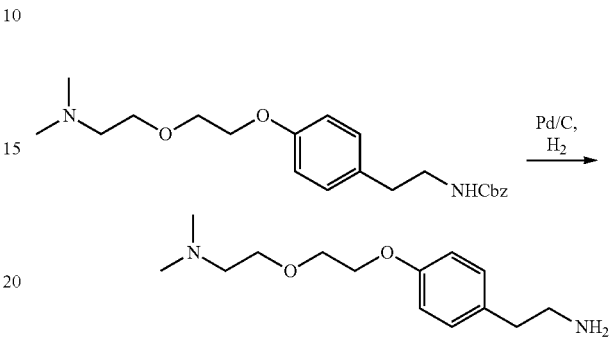

A mixture of benzyl 4-(2-(2-(dimethylamino)ethoxy)ethoxy)phenethylcarbamate (180 mg, 0.82 mmol) and Pd/C (10%, 20 mg) in MeOH (15 mL) was stirred under H2 at room temperature for 4 h. The reaction mixture was filtered through diatomite. The filtrate was concentrated in vacuo to afford the title compound as colorless oil (148 mg, 100% yield), which was used for the next reaction directly.

Example 130

N5-(4-(2-(2-(Dimethylamino)ethoxy)ethoxy)phenethyl)-2-(furan-2-yl)-[1,2,4]triazolo[1,5-a][1,3,5]triazine-5,7-diamine

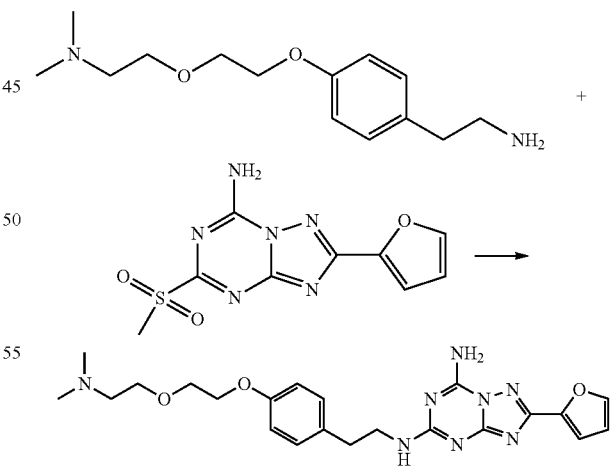

The reaction was carried out as in Example 5 to afford the title compound as white solid (25 mg, 20% yield). ¹H NMR (500 MHz, DMSO-d6) δ: 8.09-8.20 (m, 2H), 7.87 (s, 1H), 7.45-7.53 (m, 1H), 7.14 (d, 2H), 7.05 (d, 1H), 6.83 (d, 2H), 6.67 (br, 1d), 4.04 (t, 2H), 3.70 (t, 2H), 3.54 (t, 2H), 3.45 (t, 2H), 2.44 (t, 2H), 2.78 (t, 2H), 2.17 (s, 6H).

Example 131

3-(Diethylamino)propyl methanesulfonate

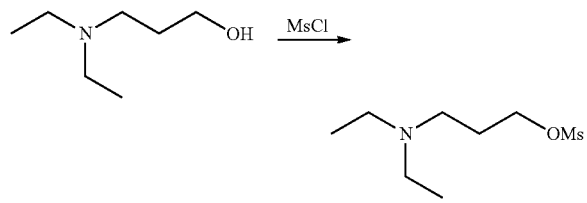

To a stirred solution of triethyl amine (1.86 g, 18.4 mmol) and 3-(diethylamino)propan-1-ol (1.05 g, 8.00 mmol) in dichloromethane (20 mL) at 0° C. was added methanesulfonyl chloride (0.58 g, 5.06 mmol, diluted in 3 mL of dichloromethane) dropwise over 20 minutes. The reaction was then stirred at room temperature for 2 h. After more dichloromethane (80 mL) was added, the reaction mixture washed with water (3×20 mL). After drying with $Na_2SO_4$, removal of solvent provided the crude compound. The crude product was purified by column chromatography (ethyl acetate/methanol) to afford the title compound as colorless oil (0.622 g, 37.1% yield).

Example 132 tert-Butyl 4-(3-(diethylamino)propoxy)phenethylcarbamate

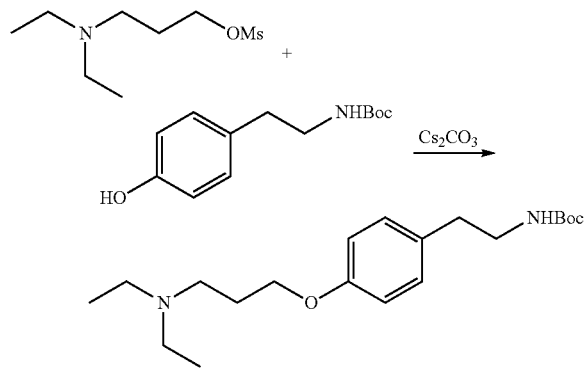

A stirred mixture of tert-butyl 4-hydroxyphenethylcarbamate (0.475 g, 2 mmol), 3-(diethylamino)propyl methanesulfonate (0.419 g, 2 mmol) and cesium carbonate (1.303 g) in acetone (20 mL) was heated at 50° C. overnight. The reaction mixture was filtered and washed with dichloromethane. The filtrate was concentrated in vacuo and purified by column chromatography to afford the title compound as light-yellow oil (0.527 g, 75.2% yield). $^1$H NMR (500 MHz, DMSO-d6) δ: 7.07 (d, J=8.5 Hz, 2H), 6.82 (d, J=8.6 Hz, 3H), 3.95 (t, J=6.3 Hz, 2H), 3.09 (dd, J=14.2, 6.4 Hz, 2H), 2.64-2.57 (m, 2H), 2.50 (dd, J=4.5, 2.6 Hz, 2H), 2.44 (q, J=7.1 Hz, 4H), 1.84-1.73 (m, 2H), 1.37 (s, 9H), 0.94 (t, J=7.1 Hz, 6H).

Example 133

3-(4-(2-Aminoethyl)phenoxy)-N,N-diethylpropan-1-amine

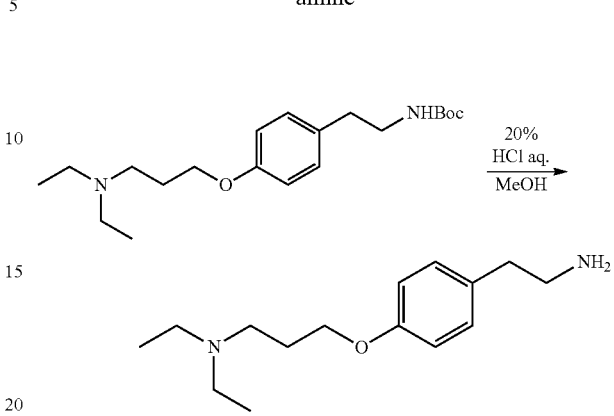

Hydrochloric acid (20%, 2 mL) was added to a stirred solution of tert-butyl 4-(3-(diethylamino)propoxy)phenethylcarbamate (0.35 g, 1 mmol) in methanol (5 mL) at room temperature. The reaction was stirred for 17 h. The excess solvent was removed under reduced pressure to afford the crude product, which was used for the next step directly.

Example 134

N5-(4-(3-(Diethylamino)propoxy)phenethyl)-2-(furan-2-yl)-[1,2,4]triazolo[1,5-a][1,3,5]triazine-5,7-diamine

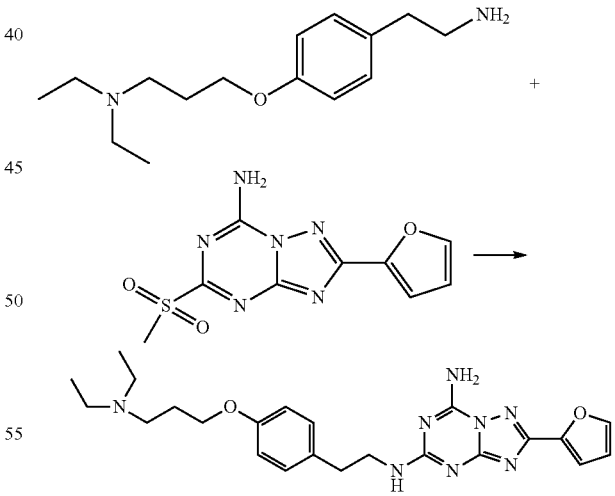

The reaction was carried out as in Example 5 to afford the title compound as white solid (0.0489 g, 10.9% yield). $^1$H NMR (500 MHz, DMSO-d6) δ: 8.29 (d, J=136.8 Hz, 2H), 7.87 (s, 1H), 7.48 (d, J=42.8 Hz, 1H), 7.15 (d, J=7.0 Hz, 2H), 7.06 (d, J=2.5 Hz, 1H), 6.84 (d, J=7.7 Hz, 2H), 6.67 (s, 1H), 3.95 (t, J=6.0 Hz, 2H), 3.45 (s, 2H), 2.77 (d, J=6.4 Hz, 2H), 2.50-2.39 (m, 6H), 1.83-1.69 (m, 2H), 0.93 (t, J=7.0 Hz, 6H); LC-MS m/z [M+H]$^+$: 451.

Example 135

2-(3,3-Difluoropiperidin-1-yl)ethanol

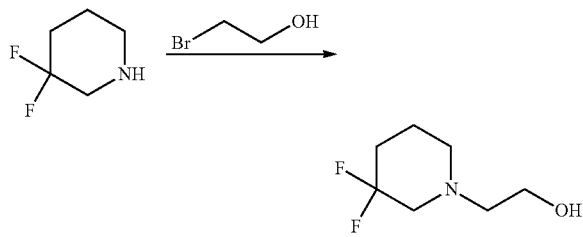

A stirred mixture of 3,3-difluoropiperidine hydrochloride (1 g, 6.34 mmol), 2-bromoethanol (2.38 g, 19 mmol), potassium carbonate (1.752 g, 12.68 mmol), and cesium carbonate (2.065 g, 6.34 mmol) in MeCN (50 mL) was heated at 70° C. for 2 days. The reaction mixture was filtrated, and the filtrate was concentrated to give the crude product. Purification by column chromatography afforded the title compound as colorless oil (0.8 g, 76.4% yield). $^1$H NMR (500 MHz, DMSO-d6) δ: 4.44 (t, J=5.2 Hz, 1H), 3.50 (dd, J=11.3, 6.0 Hz, 2H), 2.67 (t, J=11.8 Hz, 2H), 2.46 (t, J=6.1 Hz, 2H), 2.45-2.40 (m, 2H), 1.88-1.79 (m, 2H), 1.62 (td, J=11.0, 6.1 Hz, 2H).

Example 136

2-(3,3-Difluoropiperidin-1-yl)ethyl methanesulfonate

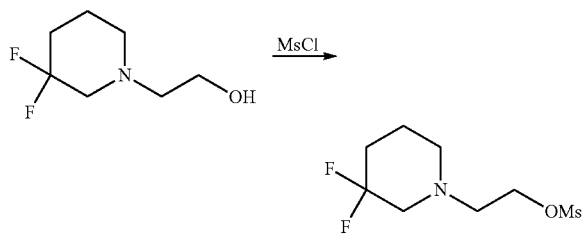

To a stirred solution of triethyl amine (0.735 g, 7.26 mmol) and 2-(3,3-difluoropiperidin-1-yl)ethanol (0.6 g, 3.63 mmol) in dichloromethane (35 mL) at 0° C. was added methanesulfonyl chloride (0.541 g, 4.72 mmol, diluted in 5 ml of dichloromethane) dropwise over 10 min. The reaction was stirred at room temperature for 20 min. After more dichloromethane (80 mL) was added, the reaction mixture washed with water (2×20 mL). After drying with Na$_2$SO$_4$, removal of the solvent afforded the crude product (0.771 g, 87.3% yield), which was used for the next step directly.

Example 137 tert-Butyl 4-(2-(3,3-difluoropiperidin-1-yl)ethoxy)phenethylcarbamate

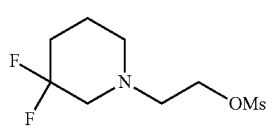

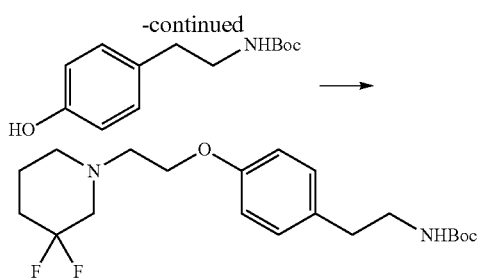

A stirred mixture of 2-(3,3-difluoropiperidin-1-yl)ethyl methanesulfonate (0.76 g, 3.124 mmol), tert-butyl 4-hydroxyphenethylcarbamate (0.593 g, 2.499 mmol) and cesium carbonate (2.035 g, 6.248 mmol) in MeCN (40 mL) was heated at 50° C. overnight. The reaction mixture was filtrated and the filtrate was concentrated. Purified by column chromatography afforded the title compound as colorless oil (0.29 g, 30.2% yield). $^1$H NMR (500 MHz, DMSO-d6) δ: 7.08 (d, J=8.5 Hz, 2H), 6.84 (dd, J=12.6, 7.0 Hz, 3H), 4.04 (t, J=5.8 Hz, 2H), 3.13-3.02 (m, 2H), 2.82-2.70 (m, 4H), 2.66-2.57 (m, 2H), 2.52 (d, J=8.3 Hz, 2H), 1.85 (dt, J=20.8, 7.0 Hz, 2H), 1.64 (td, J=11.1, 6.1 Hz, 2H), 1.36 (s, 9H).

Example 138

2-(4-(2-(3,3-Difluoropiperidin-1-yl)ethoxy)phenyl)ethanamine

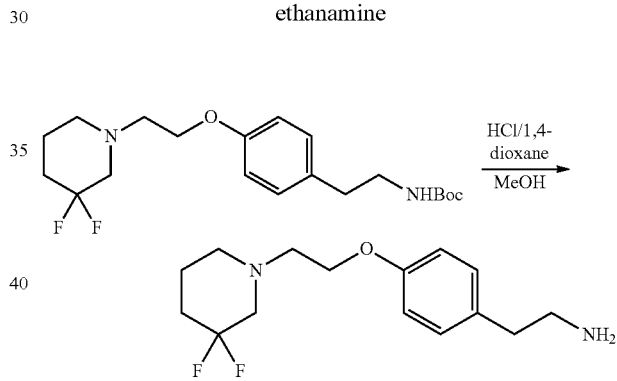

HCl (2.5 mL, 4N solution in 1,4-dioxane) was added to a stirred solution of tert-butyl 4-(2-(3,3-difluoropiperidin-1-yl)ethoxy)phenethylcarbamate (0.28 g, 0.73 mmol) in 1,4-dioxane (4 mL) at room temperature. After stirring for 4 h, the excess solvent was removed under reduced pressure to afford the crude product, which was used for the next step directly.

Example 139

N5-(4-(2-(3,3-Difluoropiperidin-1-yl)ethoxy)phenethyl)-2-(furan-2-yl)-[1,2,4]triazolo[1,5-a][1,3,5]triazine-5,7-diamine

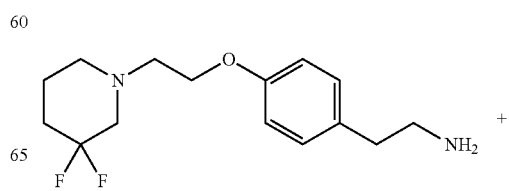

-continued

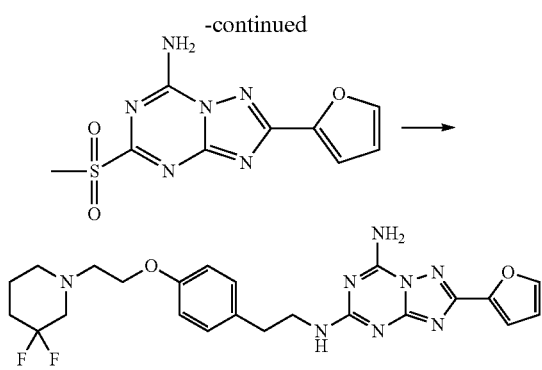

The reaction was carried out as in Example 5 to afford the title compound as white solid (0.140 g, 49.5% yield). LC-MS m/z [M+H]$^+$: 485; $^1$H NMR (500 MHz, DMSO-d6) δ: 8.33 (d, J=125.8 Hz, 2H), 7.87 (s, 1H), 7.49 (dd, J=27.5, 22.0 Hz, 1H), 7.17 (dd, J=15.3, 8.5 Hz, 2H), 7.06 (d, J=3.3 Hz, 1H), 6.87 (d, J=8.5 Hz, 2H), 6.68 (dd, J=3.2, 1.7 Hz, 1H), 4.05 (t, J=5.3 Hz, 2H), 3.44 (dd, J=13.5, 6.8 Hz, 2H), 2.87-2.69 (m, 6H), 2.52 (d, J=5.6 Hz, 2H), 1.85 (td, J=14.0, 7.0 Hz, 2H), 1.71-1.59 (m, 2H).

Example 140 tert-Butyl 4-(2-fluoroethoxy)phenethylcarbamate

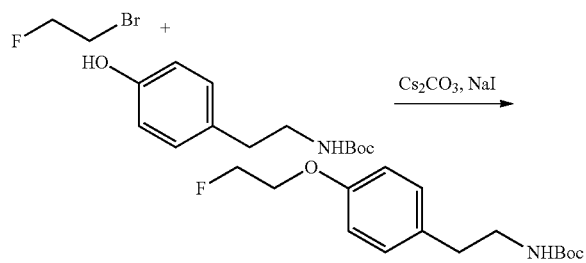

A stirred mixture of tert-butyl 4-hydroxyphenethylcarbamate (0.475 g, 2 mmol), 1-bromo-2-fluoroethane (0.305 g, 2.4 mmol), cesium carbonate (1.303 g, 4 mmol) and NaI (3 mg, 0.02 mmol) in MeCN (40 mL) was heated at 60° C. overnight. The reaction mixture was filtered and washed with dichloromethane. The filtrate was concentrated in vacuo and purified by column chromatography to afford the title compound as white solid (0.46 g, 81.2% yield). $^1$H NMR (500 MHz, DMSO-d6) δ: $^1$H NMR (500 MHz, DMSO-d6) δ: 7.10 (d, J=8.5 Hz, 2H), 6.87 (d, J=8.5 Hz, 2H), 6.82 (d, J=5.1 Hz, 1H), 4.84-4.60 (m, 2H), 4.30-4.04 (m, 2H), 3.09 (dd, J=14.2, 6.4 Hz, 2H), 2.73-2.56 (m, 2H), 1.36 (s, 9H).

Example 141

2-(4-(2-Fluoroethoxy)phenyl)ethanamine

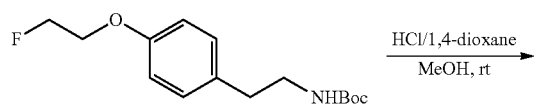

-continued

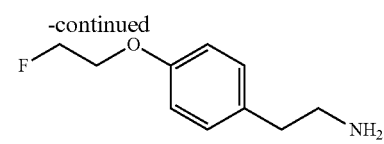

HCl (2 mL, 4N solution in 1,4-dioxane) was added to a stirred solution of tert-butyl 4-(2-fluoroethoxy)phenethylcarbamate (0.208 g, 0.734 mmol) in MeOH (4 mL) at room temperature. After stirring overnight, the excess solvent was removed under reduced pressure to afford the crude product, which was used for the next step directly.

Example 142

N5-(4-(2-Fluoroethoxy)phenethyl)-2-(furan-2-yl)-[1,2,4]triazolo[1,5-a][1,3,5]triazine-5,7-diamine

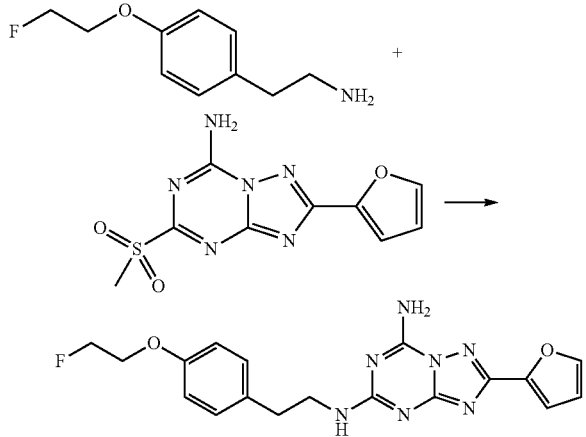

The reaction was carried out as in Example 5 to afford the title compound as white solid (0.103 g, 52.3% yield). $^1$H NMR (500 MHz, DMSO-d6) δ: 8.28 (d, J=141.4 Hz, 2H), 7.86 (s, 1H), 7.46 (dd, J=27.5, 22.1 Hz, 1H), 7.18 (d, J=8.2 Hz, 2H), 7.06 (d, J=3.1 Hz, 1H), 6.90 (d, J=8.3 Hz, 2H), 6.67 (d, J=1.3 Hz, 1H), 4.79-4.63 (m, 2H), 4.33-4.13 (m, 2H), 3.51-3.39 (m, 2H), 2.80 (t, J=7.3 Hz, 2H).

Example 143

(3-Fluoro-4-methoxyphenyl)ethanamine

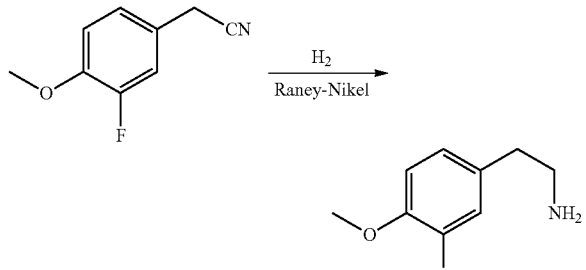

A mixture of 2-(3-fluoro-4-methoxyphenyl)acetonitrile (1 g, 6.05 mmol), NH$_3$/MeOH (7N, 5 mL) and Raney-Nickel (0.1 g) in MeOH (10 mL) was stirred under H2 at 55° C. overnight. The reaction mixture was filtered through Celite. The filtrate was concentrated in vacuo to afford the title compound as greenish oil (0.95 g, 92.7% yield). $^1$H NMR (500 MHz, DMSO-d6) δ: 7.13-7.00 (m, 2H), 6.95 (d, J=8.4 Hz, 1H), 3.80 (s, 3H), 3.01-2.63 (m, 2H), 2.60 (d, J=18.7 Hz, 2H), 1.27 (br, 2H).

Example 144

4-(Aminoethyl)-2-fluorophenol hydrobromide

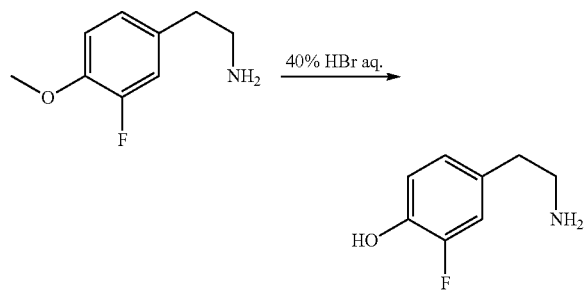

A stirred mixture of (3-fluoro-4-methoxyphenyl) ethanamine (0.95 g, 5.61 mmol) in hydrobromic acid (20 mL, 40% aqueous solution) was heated at 90° C. overnight. The solvent was removed under reduce pressure. To the residue was added ethyl ether (15 mL) and ethanol (3 mL), and it was stirred at room temperature for 1 h. The residue was then filtered and dried to afford the crude product (1.2 g, 96.3% yield), which was used for the next reaction directly.

Example 145

4-(2-((7-Amino-2-(furan-2-yl)-[1,2,4]triazolo[1,5-a][1,3,5]triazin-5-yl)amino)ethyl)-2-fluorophenol

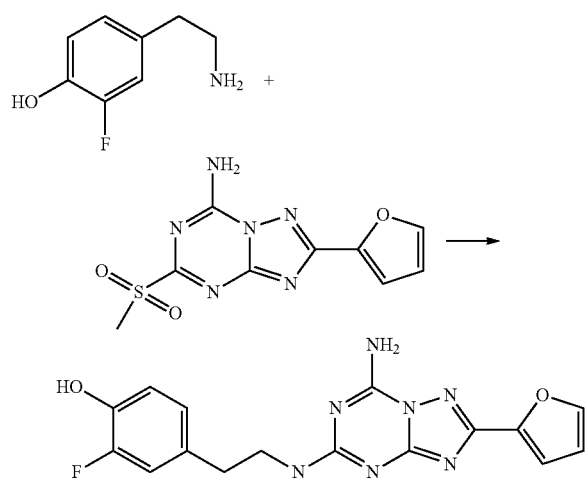

The reaction was carried out as in Example 5 to afford the title compound as white solid (0.016 g, 9.2% yield). $^1$H NMR (500 MHz, DMSO-d6) δ: 9.55 (s, 1H), 8.12 (br, 2H), 7.86 (s, 1H), 7.47 (d, J=43.7 Hz, 1H), 7.11-6.98 (m, 2H), 6.85 (s, 2H), 6.67 (s, 1H), 3.44 (d, J=4.6 Hz, 2H), 2.75 (s, 2H).

Example 146

Benzyl 3-fluoro-4-hydroxyphenethylcarbamate

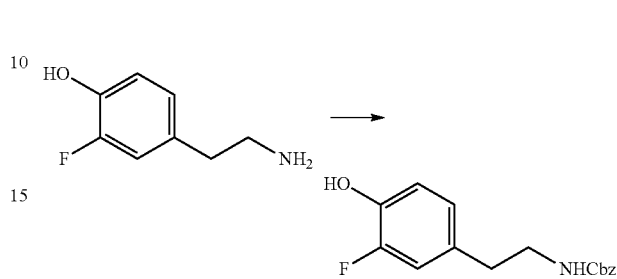

To a stirred mixture of 4-(2-aminoethyl)-2-fluorophenol hydrobromide (1.89 g, 8 mmol) and Na$_2$CO$_3$ (1.7 g, 16 mmol) in THF (28 mL) and H$_2$O (7 mL) was added CbzCl (1.364 g, 8 mmol) dropwise over 20 min. The reaction was stirred at room temperature overnight. The resulting mixture was concentrated and purified by column chromatography (n-hexane/EtOAc) to afford the title compound as colorless oil (1.438 g, 66.1% yield). $^1$H NMR (500 MHz, DMSO-d6) δ: 9.55 (s, 1H), 7.42-7.27 (m, 7H), 6.99-6.76 (m, 3H), 5.00 (s, 2H), 3.18 (dd, J=13.3, 6.9 Hz, 2H), 2.61 (t, J=7.2 Hz, 2H).

Example 147

2-(Pyrrolidin-1-yl)ethyl methanesulfonate

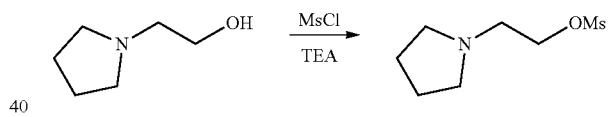

To a stirred solution of triethyl amine (0.878 g, 8.68 mmol) and 2-(pyrrolidin-1-yl)ethanol (0.5 g, 4.34 mmol) in dichloromethane (20 mL) at 0° C. was added methanesulfonyl chloride (0.596 g, 5.21 mmol, diluted in 3 mL of dichloromethane) dropwise over 20 minutes. The solution was then stirred at room temperature for 0.5 h. After more dichloromethane (80 mL) was added, the reaction mixture washed with water (3×20 mL), dried with Na$_2$SO$_4$ and concentrated in vacuo to provide the crude compound (0.364 g, 43.3% yield), which was used for the next step directly.

Example 148

Benzyl 3-fluoro-4-(2-(pyrrolidin-1-yl)ethoxy)phenethylcarbamate

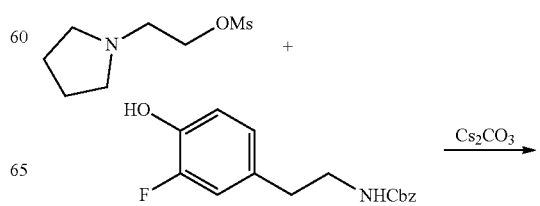

-continued

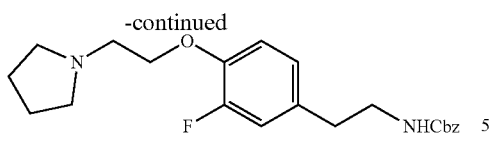

A mixture of benzyl 3-fluoro-4-hydroxyphenethylcarbamate (0.323 g, 1.175 mmol), 2-(pyrrolidin-1-yl)ethyl methanesulfonate (0.364 g, 1.88 mmol), cesium carbonate (0.764 g, 2.35 mmol) and NaI (0.02 g, 0.13 mmol) in acetonitrile (30 mL) was stirred at 60° C. overnight. The reaction mixture was filtered and washed with ethyl acetate. The filtrate was concentrated in vacuo and purified by column chromatography to afford the title compound as light-yellow oil (0.144 g, 31.7% yield). $^1$H NMR (500 MHz, DMSO-d6) δ: 7.44-7.23 (m, 6H), 7.14-7.02 (m, 2H), 6.93 (d, J=8.3 Hz, 1H), 5.00 (s, 2H), 4.09 (t, J=5.9 Hz, 2H), 3.41 (d, J=64.9 Hz, 2H), 3.20 (dd, J=13.1, 6.9 Hz, 2H), 2.78 (t, J=5.9 Hz, 2H), 2.67 (s, 2H), 2.52 (d, J=6.6 Hz, 2H), 1.73-1.59 (m, 4H).

Example 149

2-(3-Fluoro-4-(2-(pyrrolidin-1-yl)ethoxy)phenyl)ethanamine

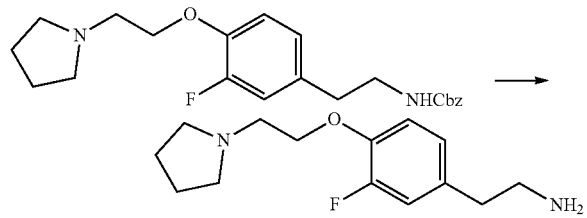

A mixture of benzyl 3-fluoro-4-(2-(pyrrolidin-1-yl)ethoxy)phenethylcarbamate (0.14 g, 0.362 mmol) and Pd/C (10%, 100 mg) in MeOH (10 mL) was stirred under H2 at 50° C. for 7 h. TLC showed the reaction completed. The reaction mixture was filtered through Celite. The filtrate was concentrated in vacuo to afford the crude product, which was used for the next step directly.

Example 150

N5-(3-Fluoro-4-(2-(pyrrolidin-1-yl)ethoxy)phenethyl)-2-(furan-2-yl)-[1,2,4]triazolo[1,5-a][1,3,5]triazine-5,7-diamine

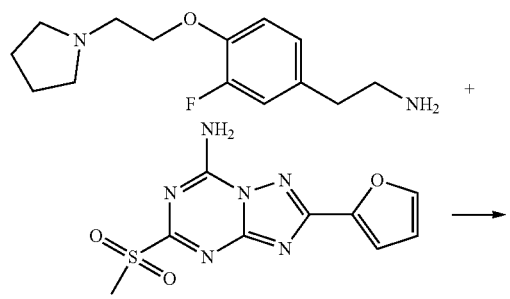

-continued

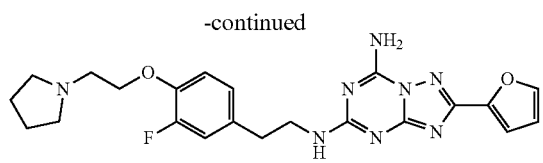

The reaction was carried out as in Example 5 to afford the title compound as white solid (0.0497 g, 33.7% yield). LC-MS m/z [M+H]$^+$: 453; $^1$H NMR (500 MHz, DMSO-d6) δ: 8.29 (br, 2H), 7.87 (s, 1H), 7.47 (dd, J=28.2, 22.7 Hz, 1H), 7.16-7.04 (m, 3H), 6.98 (d, J=8.0 Hz, 1H), 6.67 (d, J=1.3 Hz, 1H), 4.09 (t, J=5.9 Hz, 2H), 3.47 (dd, J=13.4, 6.7 Hz, 2H), 2.84-2.75 (m, 4H), 2.51 (d, J=1.8 Hz, 4H), 1.67 (dt, J=6.5, 3.1 Hz, 4H).

Example 151

Benzyl 4-(2-bromoethoxy)phenethylcarbamate

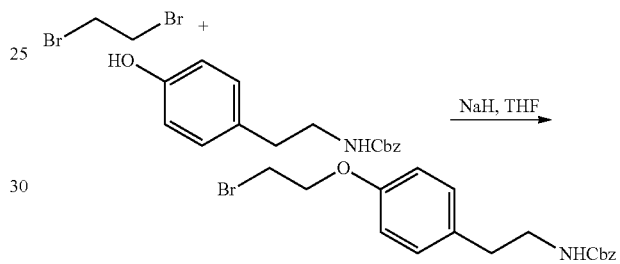

1,2-Dibromoethane (1.717 g, 9.14 mmol) was added dropwise to a stirred mixture of benzyl 4-hydroxyphenethylcarbamate (1.24 g, 4.57 mmol) and NaH (0.237 g, 5.94 mmol, 60% dispersion in mineral oil) in dry THF (20 mL) under N$_2$ at room temperature over 0.5 h. After this time, the reaction mixture was stirred at 55° C. overnight. The reaction mixture was quenched with ice-water and extracted with ethyl acetate. The organic layer was washed with water and brine, dried over sodium sulfate and concentrated in vacuo. The crude product was purified by column chromatography to afford the title compound (0.252 g, 14.6% yield). $^1$H NMR (500 MHz, DMSO-d6) δ: 7.43-7.23 (m, 6H), 7.11 (d, J=8.4 Hz, 2H), 6.87 (d, J=8.5 Hz, 2H), 5.00 (s, 2H), 4.32-4.24 (m, 2H), 3.84-3.71 (m, 2H), 3.18 (dd, J=13.6, 6.7 Hz, 2H), 2.65 (t, J=7.3 Hz, 2H).

Example 152

(S)-Benzyl 4-(2-(3-(dimethylamino)pyrrolidin-1-yl)ethoxy)phenethylcarbamate

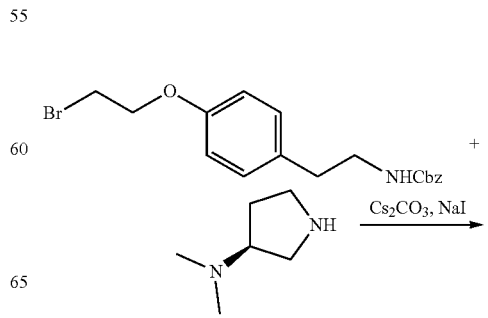

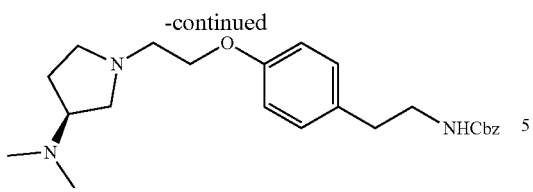

A stirred mixture of benzyl 4-(2-bromoethoxy)phenethylcarbamate (0.24 g, 0.634 mmol), (S)-N,N-dimethylpyrrolidin-3-amine dihydrochloride (0.119 g, 0.634 mmol), cesium carbonate (0.62 g, 1.902 mmol) and NaI (0.02 g, 0.13 mmol) in acetonitrile (20 mL) was heated at 70° C. overnight. The reaction mixture was filtered and washed with ethyl acetate. The filtrate was concentrated in vacuo and purified by column chromatography to afford the title compound as yellow solid (0.167 g, 64% yield). $^1$H NMR (500 MHz, DMSO-d6) δ: 7.45-7.23 (m, 6H), 7.09 (d, J=8.5 Hz, 2H), 6.84 (d, J=8.5 Hz, 2H), 5.00 (s, 2H), 4.00 (t, J=5.9 Hz, 2H), 3.17 (dd, J=13.6, 6.8 Hz, 2H), 2.78 (dt, J=15.7, 6.3 Hz, 2H), 2.67 (ddd, J=25.7, 13.4, 6.5 Hz, 5H), 2.49-2.44 (m, 1H), 2.36-2.29 (m, 1H), 2.10 (s, 6H), 1.87-1.75 (m, 1H), 1.58 (ddt, J=12.4, 8.5, 6.1 Hz, 1H).

Example 153

(S)-1-(2-(4-(2-Aminoethyl)phenoxy)ethyl)-N,N-dimethylpyrrolidin-3-amine

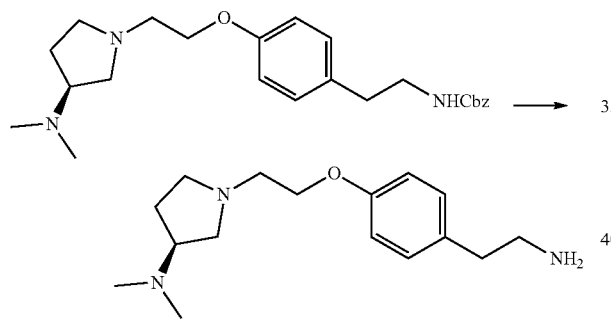

A mixture of (S)-benzyl 4-(2-(3-(dimethylamino)pyrrolidin-1-yl)ethoxy)phenethylcarbamate (0.165 g, 0.4 mmol) and Pd/C (10%, 60 mg) in MeOH (10 mL) was stirred under H2 at 50° C. for 20 h. TLC showed the reaction completed. The reaction mixture was filtered through Celite. The filtrate was concentrated in vacuo to afford the crude product, which was used for the next step directly.

Example 154

(S)-N5-(4-(2-(3-(Dimethylamino)pyrrolidin-1-yl)ethoxy)phenethyl)-2-(furan-2-yl)-[1,2,4]triazolo[1,5-a][1,3,5]triazine-5,7-diamine

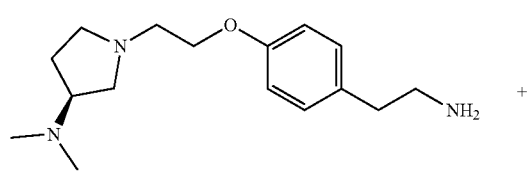

+

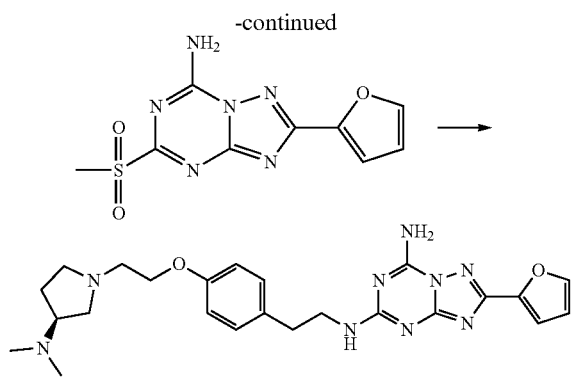

The reaction was carried out as in Example 5 to afford the title compound as white solid (0.0674 g, 35.3% yield). LC-MS m/z [M+H]$^+$: 478; $^1$H NMR (500 MHz, DMSO-d6) δ: 8.33 (br, 2H), 7.87 (s, 1H), 7.49 (dd, J=27.3, 21.7 Hz, 1H), 7.15 (d, J=8.1 Hz, 2H), 7.06 (d, J=3.2 Hz, 1H), 6.86 (d, J=8.3 Hz, 2H), 6.68 (d, J=1.5 Hz, 1H), 4.00 (t, J=5.8 Hz, 2H), 3.44 (dd, J=13.4, 6.7 Hz, 2H), 2.77 (dd, J=11.1, 5.1 Hz, 4H), 2.72-2.61 (m, 3H), 2.48-2.43 (m, 1H), 2.35-2.28 (m, 1H), 2.09 (s, 6H), 1.82 (dt, J=13.9, 7.8 Hz, 1H), 1.57 (ddd, J=14.4, 12.5, 6.1 Hz, 1H).

Example 155

2-(4-Methylpiperazin-1-yl)ethyl methanesulfonate

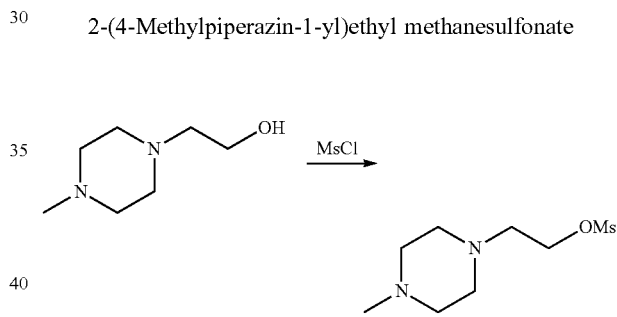

To a stirred solution of triethyl amine (0.702 g, 6.94 mmol) and 2-(4-methylpiperazin-1-yl)ethanol (0.5 g, 3.47 mmol) in dichloromethane (20 mL) at 0° C. was added methanesulfonyl chloride (0.477 g, 4.16 mmol, diluted in 3 mL of dichloromethane) dropwise over 20 minutes. The solution was stirred at room temperature for 1 h. After more Dichloromethane (40 mL) was added, the reaction mixture washed with water (3×20 mL), dried with Na$_2$SO$_4$ and concentrated in vacuo to provide the crude compound as light-yellow oil (0.43 g, 55.7% yield), which was used for the next step directly.

Example 156

Benzyl 3-fluoro-4-(2-(4-methylpiperazin-1-yl)ethoxy)phenethylcarbamate

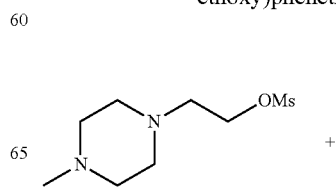

+

-continued

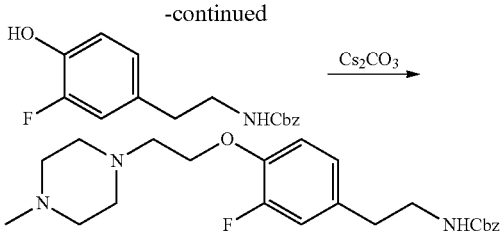

A stirred mixture of 2-(4-methylpiperazin-1-yl)ethyl methanesulfonate (0.4 g, 1.8 mmol), benzyl 3-fluoro-4-hydroxyphenethylcarbamate (0.26 g, 0.9 mmol), cesium carbonate (0.88 g, 2.7), and NaI (0.02 g, 0.13 mmol) in acetonitrile (20 mL) was heated at 60° C. overnight. The reaction mixture was filtered and washed with ethyl acetate. The filtrate was concentrated in vacuo and purified by column chromatography to afford the title compound as yellow solid (0.08 g, 21.1% yield). $^{1}$H NMR (500 MHz, DMSO-d6) δ: 7.46-7.22 (m, 6H), 7.14-7.00 (m, 2H), 6.92 (d, J=8.2 Hz, 1H), 4.99 (s, 2H), 4.09 (t, J=5.8 Hz, 2H), 3.32 (s, 2H), 3.19 (dt, J=6.3, 5.6 Hz, 2H), 2.73-2.60 (m, 4H), 2.49-2.43 (m, 2H), 2.32 (br, 4H), 2.15 (s, 3H).

Example 157

2-(3-Fluoro-4-(2-(4-methylpiperazin-1-yl)ethoxy)phenyl)ethanamine

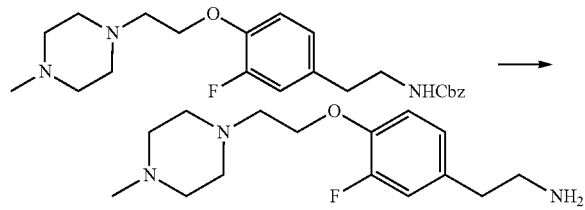

A stirred mixture of benzyl 3-fluoro-4-(2-(4-methylpiperazin-1-yl)ethoxy)phenethyl-carbamate (0.08 g, 0.19 mmol) and Pd/C (10%, 60 mg) in MeOH (5 mL) was heated under H2 at 50° C. for 6 h. TLC showed the reaction completed. The reaction mixture was filtered through Celite. The filtrate was concentrated in vacuo to afford the crude product, which was used for the next step directly.

Example 158

N5-(3-Fluoro-4-(2-(4-methylpiperazin-1-yl)ethoxy)phenethyl)-2-(furan-2-yl)-[1,2,4]triazolo[1,5-a][1,3,5]triazine-5,7-diamine

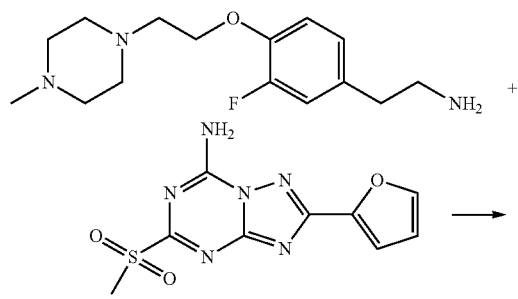

-continued

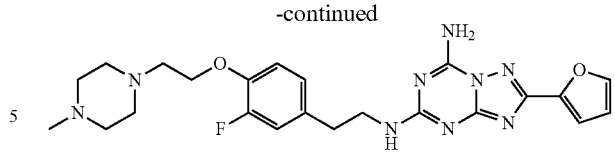

The reaction was carried out as in Example 5 to afford the title compound as white solid (0.0284 g, 31% yield). LC-MS m/z [M+H]$^{+}$: 482; $^{1}$H NMR (500 MHz, DMSO-d6) δ: 8.32 (br, 2H), 7.87 (s, 1H), 7.48 (dd, J=28.3, 23.0 Hz, 1H), 7.20-7.04 (m, 3H), 6.98 (d, J=7.5 Hz, 1H), 6.67 (s, 1H), 4.09 (t, J=5.8 Hz, 2H), 3.46 (dd, J=13.1, 6.6 Hz, 2H), 2.79 (t, J=7.3 Hz, 2H), 2.67 (t, J=5.7 Hz, 2H), 2.31 (br, 8H), 2.14 (s, 3H).

Example 159 tert-Butyl 4-(2-bromoethoxy)phenethylcarbamate

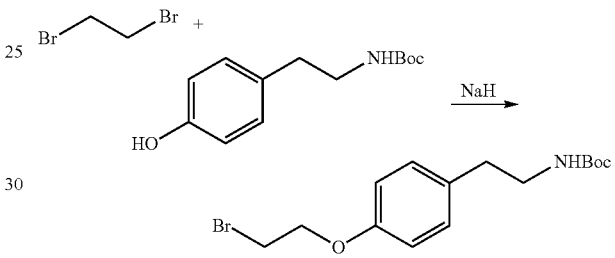

1,2-Dibromoethane (4.74 g, 25.28 mmol) was added dropwise to a stirred mixture of tert-butyl 4-hydroxyphenethylcarbamate (3 g, 12.64 mmol) and NaH (0.657 g, 16.43 mmol, 60% dispersion in mineral oil) in dry THF (40 mL) under N$_2$ at room temperature. After stirring for 0.5 h, the reaction mixture was stirred at 55° C. for 20 h. The reaction mixture was quenched with ice-water and extracted with ethyl acetate. The organic layer was washed with water and brine, dried over sodium sulfate and concentrated in vacuo. The crude product was purified by column chromatography to afford the title compound as white solid (0.64 g, 14.7% yield). $^{1}$H NMR (500 MHz, DMSO-d6) δ: 7.10 (d, J=8.5 Hz, 2H), 6.87 (d, J=8.5 Hz, 2H), 6.83 (t, J=5.3 Hz, 1H), 4.34-4.22 (m, 2H), 3.83-3.68 (m, 2H), 3.08 (dd, J=14.0, 6.5 Hz, 2H), 2.62 (t, J=7.5 Hz, 2H), 1.36 (s, 9H).

Example 160 tert-Butyl 4-(2-(3-(dimethylamino)azetidin-1-yl)ethoxy)phenethylcarbamate

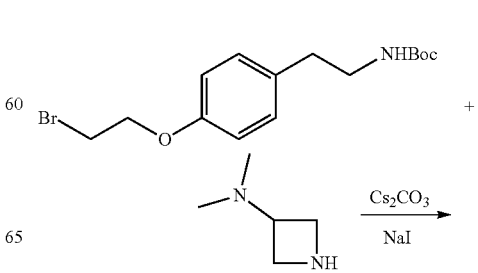

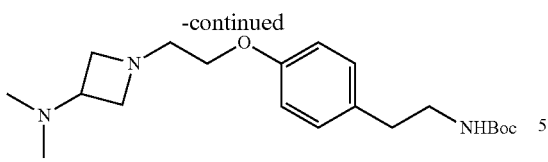
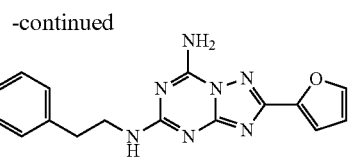

A stirred mixture of tert-butyl 4-(2-bromoethoxy)phenethylcarbamate (0.32 g, 0.93 mmol), N,N-dimethylazetidin-3-amine hydrochloride (0.161 g, 0.93 mmol), cesium carbonate (0.909 g, 2.79 mmol) and NaI (0.02 g, 0.13 mmol) in acetonitrile (20 mL) was heated at 70° C. overnight. The reaction mixture was filtered and washed with ethyl acetate. The filtrate was concentrated in vacuo and purified by column chromatography to afford the title compound as light-yellow oil (0.247 g, 73.1% yield). $^1$H NMR (500 MHz, DMSO-d6) δ: 7.07 (d, J=8.5 Hz, 2H), 6.91-6.76 (m, 3H), 3.87 (t, J=5.6 Hz, 2H), 3.41 (t, J=6.7 Hz, 2H), 3.07 (dd, J=14.3, 6.4 Hz, 2H), 2.81 (t, J=7.0 Hz, 2H), 2.70 (t, J=5.6 Hz, 2H), 2.64-2.56 (m, 2H), 1.99 (s, 6H), 1.36 (s, 9H).

Example 161

1-(2-(4-(2-Aminoethyl)phenoxy)ethyl)-N,N-dimethylazetidin-3-amine

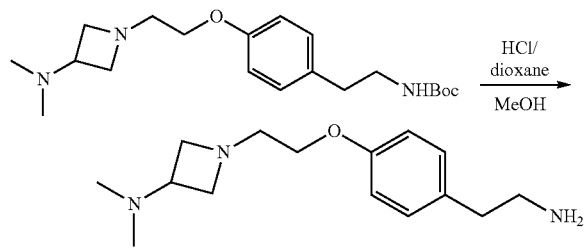

HCl (4 mL, 4N solution in 1,4-dioxane) was added to a stirred solution of tert-butyl 4-(2-(3-(dimethylamino)azetidin-1-yl)ethoxy)phenethylcarbamate (0.316 g, 0.94 mmol) in 1,4-dioxane (2 mL) and MeOH (1 mL) at room temperature. After stirring for 2 h, the excess solvent was removed under reduced pressure to afford the crude product, which was used for the next step directly.

Example 162

N5-(4-(2-(3-(Dimethylamino)azetidin-1-yl)ethoxy)phenethyl)-2-(furan-2-yl)-[1,2,4]triazolo[1,5-a][1,3,5]triazine-5,7-diamine

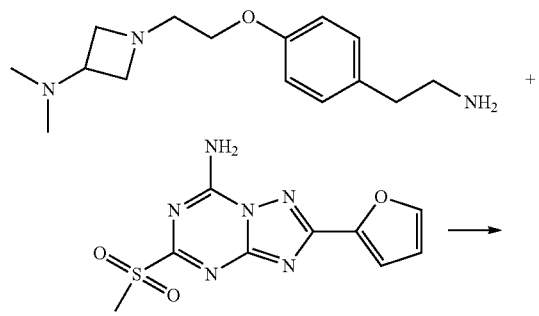

The reaction was carried out as in Example 5 to afford the title compound as white solid (0.0854 g, 33.9% yield). LC-MS m/z [M+H]$^+$: 464; $^1$H NMR (500 MHz, DMSO-d6) δ: 8.15 (br, 2H), 7.88 (s, 1H), 7.50 (dd, J=27.7, 22.1 Hz, 1H), 7.15 (t, J=7.4 Hz, 2H), 7.06 (d, J=3.3 Hz, 1H), 6.84 (d, J=8.4 Hz, 2H), 6.68 (dd, J=3.2, 1.7 Hz, 1H), 3.88 (t, J=5.6 Hz, 2H), 3.42 (dd, J=14.7, 8.7 Hz, 4H), 2.86-2.68 (m, 7H), 1.99 (s, 6H).

Example 163 tert-Butyl 4-((2-(2-methoxyethoxy)ethyl)amino)phenethylcarbamate

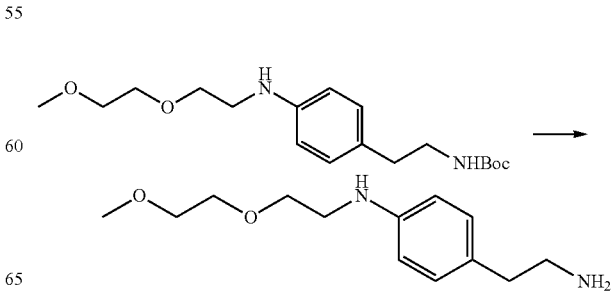

A stirred mixture of 1-bromo-2-(2-methoxyethoxy)ethane (0.366 g, 2 mmol), tert-butyl 4-aminophenethylcarbamate (0.614 g, 2.6 mmol), cesium carbonate (0.847 g, 2.6 mmol) and NaI (0.03 g, 0.2 mmol) in DMF (15 mL) was heated at 110° C. for 2 h. The reaction mixture was diluted with water (40 mL) and extracted with ethyl acetate (2×60 mL). The organic layer was washed with water (30 mL) and brine (30 mL), concentrated in vacuo, and purified by column chromatography to afford the title compound as light-yellow oil (0.17 g, 25% yield). $^1$H NMR (500 MHz, DMSO-d6) δ: 6.88 (d, J=8.3 Hz, 2H), 6.80 (d, J=6.1 Hz, 1H), 6.50 (t, J=7.0 Hz, 2H), 5.34 (t, J=5.5 Hz, 1H), 3.53 (t, J=5.0 Hz, 4H), 3.45 (dd, J=5.7, 3.7 Hz, 2H), 3.24 (s, 3H), 3.14 (q, J=5.7 Hz, 2H), 3.03 (dd, J=14.3, 6.1 Hz, 3H), 2.52 (s, 2H), 1.37 (s, 9H).

Example 164

4-(2-Aminoethyl)-N-(2-(2-methoxyethoxy)ethyl)aniline

HCl (5 mL, 4N solution in 1,4-dioxane) was added to a stirred solution of tert-butyl 4-((2-(2-methoxyethoxy)ethyl)amino)phenethylcarbamate (0.17 g, 0.5 mmol) in MeOH (2 mL) at room temperature. After stirring overnight, the excess solvent was removed under reduced pressure to afford the crude product, which was used for the next step directly.

Example 165

2-(Furan-2-yl)-N5-(4-((2-(2-methoxyethoxy)ethyl)amino)phenethyl)-[1,2,4]triazolo[1,5-a][1,3,5]triazine-5,7-diamine

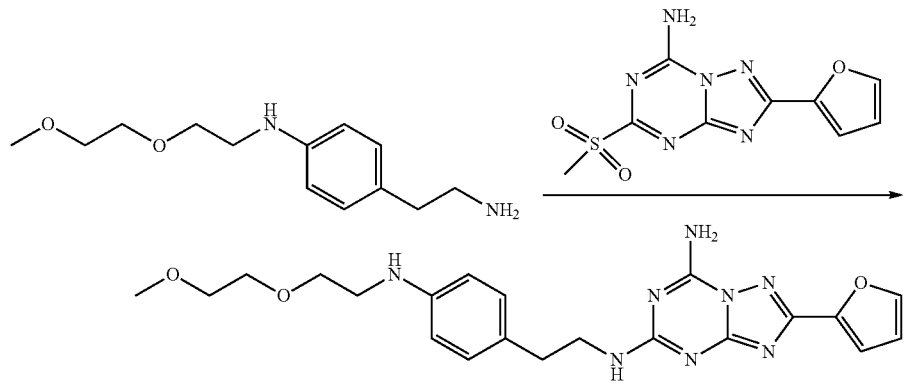
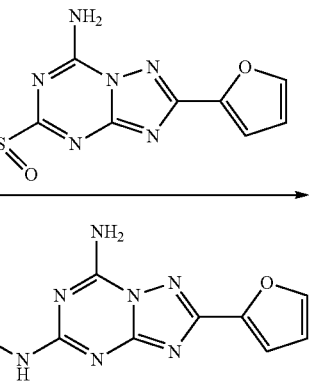

The reaction was carried out as in Example 5 to afford the title compound as white solid (0.0269 g, 15.3% yield). LC-MS m/z [M+H]$^+$: 439; $^1$H NMR (500 MHz, DMSO-d6) δ: 8.18 (br, 2H), 7.87 (s, 1H), 7.45 (dd, J=26.9, 21.4 Hz, 1H), 7.06 (d, J=3.3 Hz, 1H), 6.96 (d, J=8.0 Hz, 2H), 6.67 (s, 1H), 6.54 (d, J=8.1 Hz, 2H), 5.36 (s, 1H), 3.54 (dd, J=7.6, 4.5 Hz, 4H), 3.47-3.37 (m, 4H), 3.24 (s, 3H), 3.15 (s, 2H), 2.73-2.63 (m, 2H).

Example 166 tert-Butyl 4-((2-methoxyethyl)(methyl)amino)phenethylcarbamate and tert-Butyl 4-((2-methoxyethyl)(methyl)amino)phenethyl(methyl)carbamate

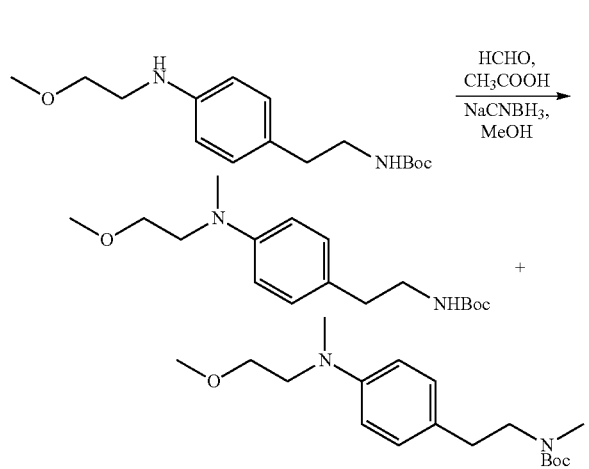

A solution of tert-butyl 4-(2-methoxyethylamino)phenethylcarbamate (0.654 g, 4.1 mmol) and formaldehyde (3 mL, 36-38% in water) in AcOH (5 mL) was stirred at room temperature for 20 min. Then NaBH$_3$CN (1.71 g, diluted in 5 mL of methanol) was added slowly to the reaction mixture. The reaction was stirred at room temperature overnight. After the excess solvent was removed under reduced pressure, the residue was taken up in 10% Na$_2$CO$_3$ aqueous solution (30 mL). It was extracted with ethyl acetate (2×40 mL), dried with Na$_2$SO$_4$ and concentrated. Purification by column chromatography (n-hexane/EtOAc) afforded the two products as a mixture (0.184 g).

Example 167

4-(2-Aminoethyl)-N-(2-methoxyethyl)-N-methylbenzenamine and N-(2-Methoxyethyl)-N-methyl-4-(2-(methylamino)ethyl)benzenamine

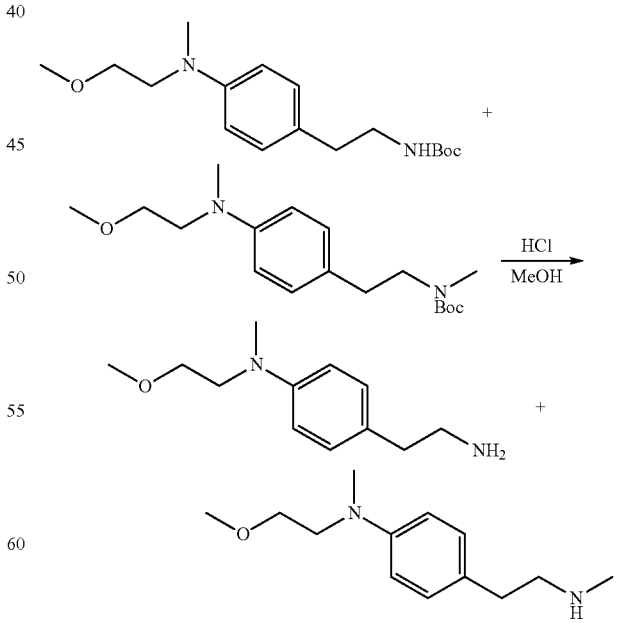

HCl (5 mL, 4N solution in 1,4-dioxane) was added to a stirred solution of the products of the previous example (Example 166) (0.184 g, 0.596 mmol) in MeOH (2 mL) at room temperature. After stirring overnight, the excess solvent was removed under reduced pressure to afford the two crude products as a mixture, which was used for the next step directly.

Example 168

2-(Furan-2-yl)-N5-(4-((2-methoxyethyl)(methyl)amino)phenethyl)-N5-methyl-[1,2,4]triazolo[1,5-a][1,3,5]triazine-5,7-diamine and 2-(Furan-2-yl)-N5-(4-((2-methoxyethyl)(methyl)amino)phenethyl)-[1,2,4]triazolo[1,5-a][1,3,5]triazine-5,7-diamine

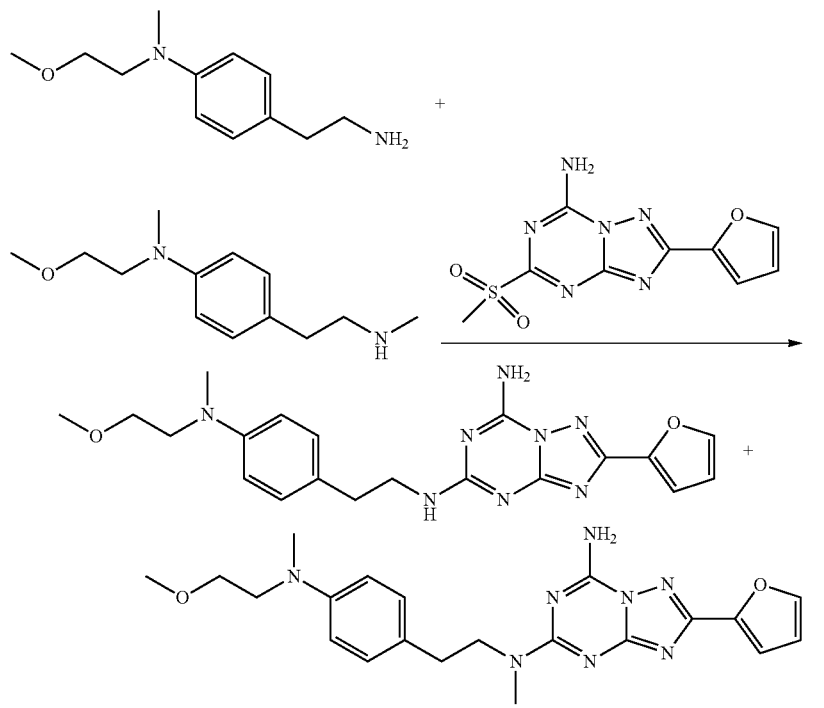

The reaction was carried out as in Example 5 to afford 2-(furan-2-yl)-N5-(4-((2-methoxyethyl)(methyl)amino)phenethyl)-N5-methyl-[1,2,4]triazolo[1,5-a][1,3,5]triazine-5,7-diamine (0.0225 g, 11.2% yield, white solid) and 2-(furan-2-yl)-N5-(4-((2-methoxyethyl)(methyl)amino)phenethyl)-[1,2,4]triazolo[1,5-a][1,3,5]triazine-5,7-diamine (0.071 g, 36.4% yield, white solid).

2-(Furan-2-yl)-N5-(4-((2-methoxyethyl)(methyl)amino)phenethyl)-N5-methyl-[1,2,4]triazolo[1,5-a][1,3,5]triazine-5,7-diamine. LC-MS m/z [M+H]$^+$: 423; $^1$H NMR (500 MHz, DMSO-d6) δ: 8.27 (br, 2H), 7.88 (s, 1H), 7.08 (s, 3H), 6.67 (d, J=18.4 Hz, 3H), 3.71 (d, J=5.2 Hz, 2H), 3.45 (s, 4H), 3.24 (s, 3H), 3.06 (d, J=14.3 Hz, 3H), 2.88 (s, 3H), 2.74 (s, 2H).

2-(Furan-2-yl)-N5-(4-((2-methoxyethyl)(methyl)amino)phenethyl)-[1,2,4]triazolo[1,5-a][1,3,5]triazine-5,7-diamine. LC-MS m/z [M+H]$^+$: 409; $^1$H NMR (500 MHz, DMSO-d6) 8.16 (br, 2H), 7.87 (s, 1H), 7.53-7.38 (m, 1H), 7.05 (t, J=5.8 Hz, 3H), 6.72-6.59 (m, 3H), 3.43 (dt, J=14.2, 5.4 Hz, 6H), 3.24 (s, 3H), 2.87 (s, 3H), 2.77-2.66 (m, 2H).

Example 169 tert-Butyl 4-(2-(1H-pyrrolo[3,4-c]pyridin-2(3H)-yl)ethoxy)phenethylcarbamate

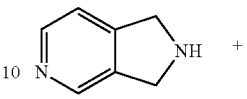

-continued

A stirred mixture of tert-butyl 4-(2-bromoethoxy)phenethylcarbamate (0.2 g, 0.58 mmol), 2,3-dihydro-1H-pyrrolo[3,4-c]pyridine dihydrochloride (0.112 g, 0.58 mmol), cesium carbonate (0.567 g, 1.74 mmol) and NaI (0.009 g, 0.06 mmol) in acetonitrile (10 mL) was heated at 70° C. overnight. The reaction mixture was filtered and washed with ethyl acetate. The filtrate was concentrated in vacuo and purified by column chromatography to afford the title compound as yellow solid (0.058 g, 26% yield). $^1$H NMR (500 MHz, DMSO-d6) δ: 8.51-8.37 (m, 2H), 7.32 (d, J=4.8 Hz, 1H), 7.10 (d, J=8.5 Hz, 2H), 6.87 (dd, J=15.2, 7.1 Hz, 3H), 4.12 (t, J=5.7 Hz, 2H), 4.01 (d, J=8.4 Hz, 4H), 3.16-3.00 (m, 4H), 2.68-2.56 (m, 2H), 1.36 (d, J=7.5 Hz, 9H).

Example 170

2-(4-(2-(1H-Pyrrolo[3,4-c]pyridin-2(3H)-yl)ethoxy)phenyl)ethanamine

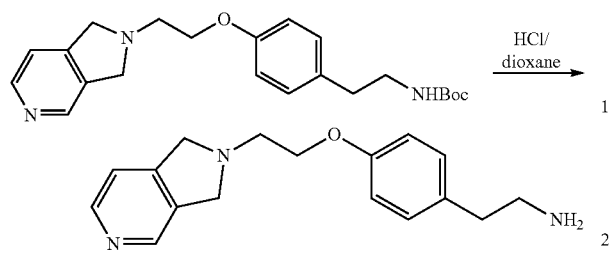

HCl (2 mL, 4N solution in 1,4-dioxane) was added to a stirred solution of tert-butyl 4-(2-(1H-pyrrolo[3,4-c]pyridin-2(3H)-yl)ethoxy)phenethylcarbamate (0.05 g, 0.13 mmol) in MeOH (2 mL) at room temperature. After stirring overnight, the excess solvent was removed under reduced pressure to afford the crude product, which was used for the next step directly.

Example 171

N5-(4-(2-(1H-Pyrrolo[3,4-c]pyridin-2(3H)-yl)ethoxy)phenethyl)-2-(furan-2-yl)-[1,2,4]triazolo[1,5-a][1,3,5]triazine-5,7-diamine

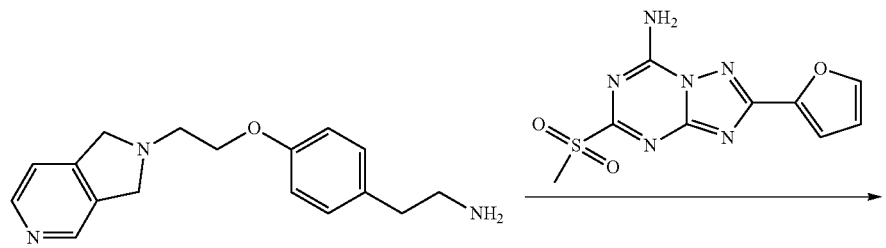

The reaction was carried out as in Example 5 to afford the title compound as yellow solid (0.013 g, 14.2% yield). $^1$H NMR (500 MHz, DMSO-d6) δ: 8.50 (s, 1H), 8.42 (d, J=4.6 Hz, 1H), 8.20 (br, 2H), 7.87 (s, 1H), 7.51 (d, J=39.3 Hz, 1H), 7.34 (d, J=4.3 Hz, 1H), 7.05 (d, J=3.0 Hz, 1H), 6.92 (d, J=8.0 Hz, 2H), 6.68 (s, 1H), 4.13 (d, J=22.7 Hz, 6H), 3.53-3.40 (m, 2H), 3.26-3.12 (m, 2H), 2.87-2.72 (m, 2H).

Example 172 tert-Butyl 4-((tetrahydro-2H-pyran-4-yl)amino)phenethylcarbamate

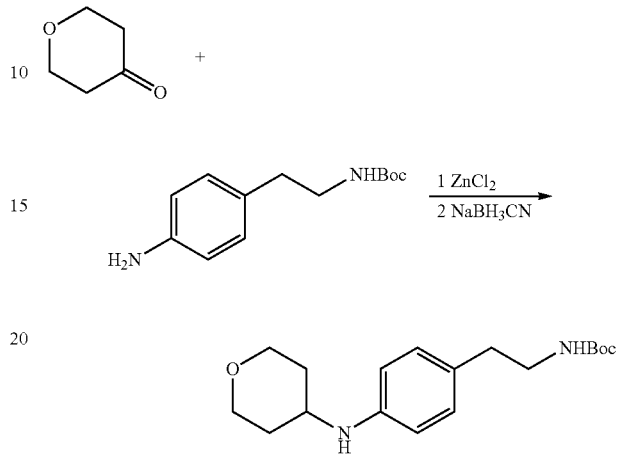

A mixture of dihydro-2H-pyran-4(3H)-one (0.21 g, 2.1 mmol), tert-butyl 4-aminophenethylcarbamate (0.25 g, 1.05 mmol) and ZnCl$_2$ (0.43 g, 3.15 mmol) in methanol (10 mL) was stirred at room temperature overnight. After this time NaBH$_3$CN (0.33 g, 5.25 mmol) was added to the stirred mixture and the reaction was heated at 40° C. for 4 h. After it was cooled to room temperature, the reaction mixture was filtered and washed with ethyl acetate. The filtrate was concentrated in vacuo and purified by column chromatography to afford the title compound as light-yellow oil (0.217 g, 64.5% yield). $^1$H NMR (500 MHz, DMSO-d6) δ: 6.87 (d, J=8.3 Hz, 2H), 6.77 (t, J=5.4 Hz, 1H), 6.52 (d, J=8.4 Hz, 2H), 5.27 (d, J=8.2 Hz, 1H), 3.85 (dt, J=11.5, 3.4 Hz, 2H), 3.42-3.35 (m, 3H), 3.03 (dd, J=14.7, 6.2 Hz, 2H), 2.51 (d, J=6.2 Hz, 2H), 1.88-1.81 (m, 2H), 1.37 (s, 9H), 1.35-1.30 (m, 2H).

Example 173

N-(4-(2-Aminoethyl)phenyl)tetrahydro-2H-pyran-4-amine

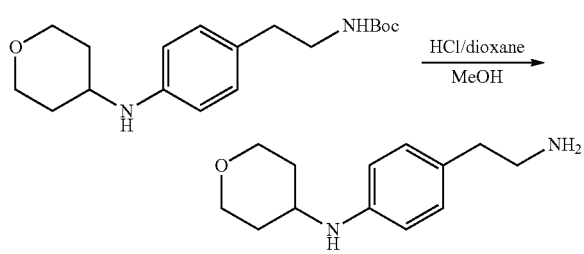

HCl (5 mL, 4N solution in 1,4-dioxane) was added to a stirred solution of tert-butyl 4-((tetrahydro-2H-pyran-4-yl)amino)phenethylcarbamate (0.217 g, 0.68 mmol) in MeOH (2 mL) at room temperature. After stirring for 1.5 h, the excess solvent was removed under reduced pressure to afford the crude product, which was used for the next step directly.

Example 174

2-(Furan-2-yl)-N5-(4-((tetrahydro-2H-pyran-4-yl)amino)phenethyl)-[1,2,4]triazolo[1,5-a][1,3,5]triazine-5,7-diamine

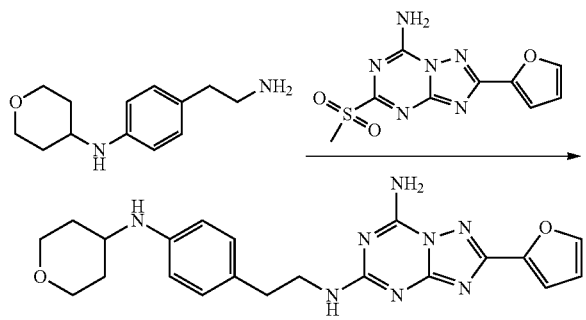

The reaction was carried out as in Example 5 to afford the title compound as white solid (0.072 g, 31.7% yield). ¹H NMR (500 MHz, DMSO-d6) δ: 8.29 (br, 2H), 7.87 (s, 1H), 7.44 (dd, J=24.7, 19.4 Hz, 1H), 7.05 (d, J=3.1 Hz, 1H), 6.95 (d, J=7.8 Hz, 2H), 6.67 (s, 1H), 6.54 (d, J=8.0 Hz, 2H), 5.30 (d, J=8.0 Hz, 1H), 3.85 (d, J=11.4 Hz, 2H), 3.39 (t, J=10.6 Hz, 5H), 2.75-2.58 (m, 2H), 1.85 (d, J=12.2 Hz, 2H), 1.33 (td, J=14.6, 4.1 Hz, 2H).

Example 175 tert-Butyl 4-((tetrahydrofuran-3-yl)amino)phenethylcarbamate

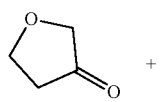

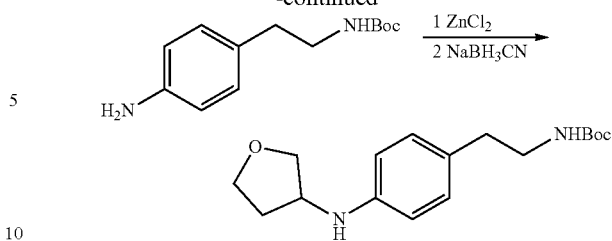

A mixture of dihydrofuran-3(2H)-one (0.361 g, 4.2 mmol), tert-butyl 4-aminophenethylcarbamate (0.5 g, 2.1 mmol) and ZnCl₂ (0.859 g, 6.3 mmol) in methanol (10 mL) was stirred at room temperature overnight. After this time NaBH₃CN (0.66 g, 10.5 mmol) was added to the stirred mixture and the reaction was heated at 40° C. for 4 h. The reaction mixture was diluted with water (30 mL) and extracted with ethyl acetate (30 mL×3). The organic layer was washed with water (20 mL) and brine (20 mL×2), dried with Na₂SO₄ and concentrated. The residue was purified by column chromatography to afford the title compound as colorless oil (0.22 g, 34.2% yield). ¹H NMR (500 MHz, DMSO-d6) δ: 6.89 (d, J=8.3 Hz, 2H), 6.79 (t, J=5.1 Hz, 1H), 6.49 (d, J=8.4 Hz, 2H), 5.61 (d, J=6.3 Hz, 1H), 3.92 (td, J=6.2, 3.1 Hz, 1H), 3.83 (ddd, J=22.8, 11.9, 6.6 Hz, 2H), 3.74-3.67 (m, 1H), 3.48 (dd, J=8.6, 3.6 Hz, 1H), 3.03 (dd, J=14.3, 6.5 Hz, 2H), 2.52 (d, J=8.8 Hz, 2H), 2.14 (dq, J=12.6, 7.4 Hz, 1H), 1.77-1.68 (m, 1H), 1.37 (s, 9H).

Example 176

N-(4-(2-Aminoethyl)phenyl)tetrahydrofuran-3-amine

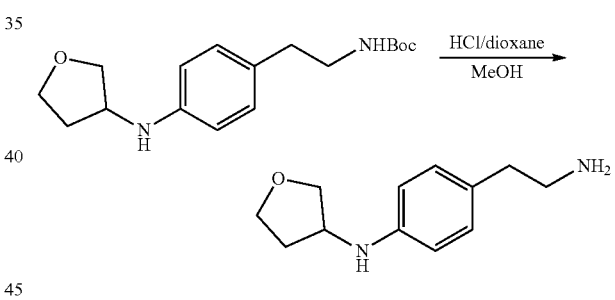

HCl (4 mL, 4N solution in 1,4-dioxane) was added to a stirred solution of tert-butyl 4-((tetrahydrofuran-3-yl)amino)phenethylcarbamate (0.22 g, 0.718 mmol) in MeOH (2 mL) at room temperature. After stirring for 1.5 h, the excess solvent was removed under reduced pressure to afford the crude product, which was used for the next step directly.

Example 177

2-(Furan-2-yl)-N5-(4-((tetrahydrofuran-3-yl)amino)phenethyl)-[1,2,4]triazolo[1,5-a][1,3,5]triazine-5,7-diamine

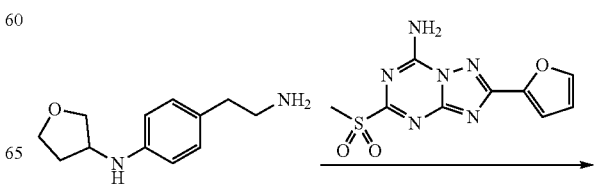

107

-continued

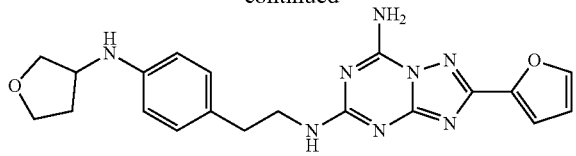

The reaction was carried out as in Example 5 to afford the title compound as white solid (0.1419 g, 54.0% yield). LC-MS m/z [M+H]+: 407; $^1$H NMR (500 MHz, DMSO-d6) δ: 8.30 (br, 2H), 7.87 (s, 1H), 7.44 (dd, J=25.7, 20.6 Hz, 1H), 7.06 (d, J=2.5 Hz, 1H), 6.97 (d, J=7.3 Hz, 2H), 6.67 (s, 1H), 6.52 (d, J=7.4 Hz, 2H), 5.63 (d, J=6.0 Hz, 1H), 3.92 (s, 1H), 3.90-3.84 (m, 1H), 3.80 (q, J=7.6 Hz, 1H), 3.70 (dd, J=13.9, 6.9 Hz, 1H), 3.49 (dd, J=8.5, 2.7 Hz, 1H), 3.45-3.37 (m, 2H), 2.76-2.63 (m, 2H), 2.14 (dq, J=14.0, 7.2 Hz, 1H), 1.73 (dt, J=16.4, 8.4 Hz, 1H).

Example 178 tert-Butyl 4-(ethylamino)phenethylcarbamate

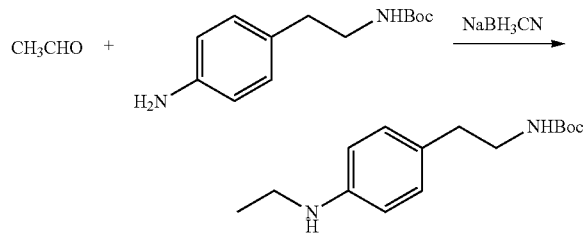

A mixture of acetaldehyde (0.08 g, 1.82 mmol), tert-butyl 4-aminophenethylcarbamate (0.6 g, 2.54 mmol) and NaBH$_3$CN (0.66 g, 10.5 mmol) in methanol (10 mL) was stirred at room temperature overnight. Water (30 mL) was afterward added to the reaction mixture and the mixture was extracted with ethyl acetate (30 mL×3). The organic layer was washed with water (20 mL) and brine (20 mL×2), dried with Na$_2$SO$_4$ and concentrated. The residue was purified by column chromatography to afford the title compound as light-yellow oil (0.327 g, 68.0% yield). $^1$H NMR (500 MHz, DMSO-d6) δ: 6.89 (d, J=8.3 Hz, 2H), 6.79 (t, J=5.4 Hz, 1H), 6.48 (d, J=8.4 Hz, 2H), 5.29 (t, J=5.4 Hz, 1H), 3.09-2.90 (m, 4H), 2.54-2.50 (m, 2H), 1.38 (s, 9H), 1.14 (t, J=7.1 Hz, 3H).

Example 179

4-(2-Aminoethyl)-N-ethylaniline

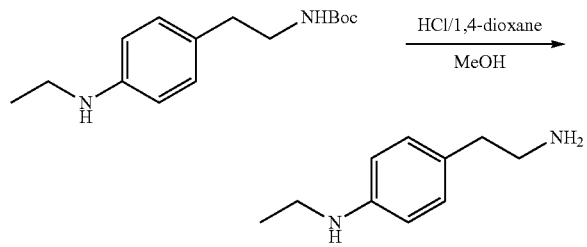

108

HCl (4 mL, 4N solution in 1,4-dioxane) was added to a stirred solution of tert-butyl 4-(ethylamino)phenethylcarbamate (0.327 g, 1.237 mmol) in MeOH (2 mL) at room temperature. After stirring for 1.5 h, the excess solvent was removed under reduced pressure to afford the crude product, which was used for the next step directly.

Example 180

2-(Furan-2-yl)-N5-(4-(methylamino)phenethyl)-[1,2,4]triazolo[1,5-a][1,3,5]triazine-5,7-diamine

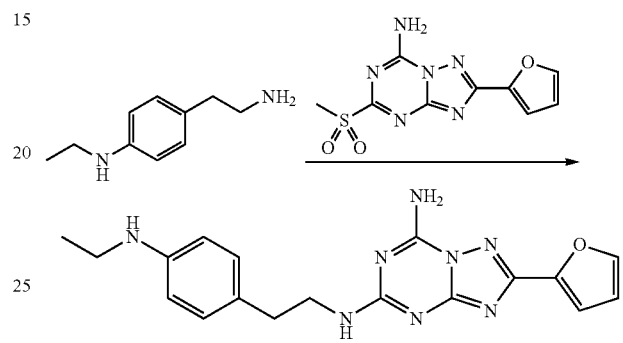

The reaction was carried out as in Example 5 to afford the title compound as white solid (0.1378 g, 52.0% yield). $^1$H NMR (500 MHz, DMSO-d6) δ: 8.29 (br, 2H), 7.87 (s, 1H), 7.45 (dt, J=41.9, 5.4 Hz, 1H), 7.06 (d, J=3.4 Hz, 1H), 6.96 (d, J=8.2 Hz, 2H), 6.74-6.62 (m, 1H), 6.50 (d, J=8.2 Hz, 2H), 5.31 (t, J=4.9 Hz, 1H), 3.39 (dd, J=14.4, 6.2 Hz, 2H), 3.06-2.94 (m, 2H), 2.73-2.63 (m, 2H), 1.14 (t, J=7.1 Hz, 3H).

Example 181 tert-Butyl 4-((tetrahydro-2H-thiopyran-4-yl)amino)phenethylcarbamate

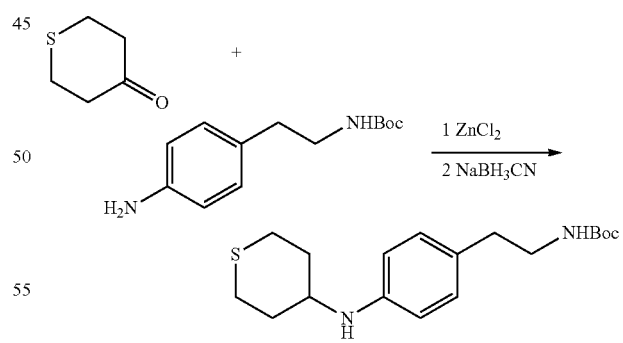

A mixture of dihydro-2H-thiopyran-4(3H)-one (0.488 g, 4.2 mmol), tert-butyl 4-aminophenethylcarbamate (0.5 g, 2.1 mmol) and ZnCl$_2$ (0.859 g, 6.3 mmol) in methanol (10 mL) was stirred at room temperature overnight. After this time NaBH$_3$CN (0.66 g, 10.5 mmol) was added and the mixture was heated at 40° C. for 4 h. After it was cooled to room temperature, the reaction mixture was filtered and washed with ethyl acetate. The filtrate was concentrated in vacuo and purified by column chromatography to afford the title compound as light-yellow solid (0.401 g, 56.7% yield). $^1$H NMR (500 MHz, DMSO-d6) δ: 6.87 (d, J=8.3 Hz, 2H), 6.79 (t, J=5.3 Hz, 1H), 6.50 (d, J=8.4 Hz, 2H), 5.31 (d, J=8.6 Hz, 1H), 3.26-3.19 (m, 1H), 3.03 (dd, J=14.6, 6.3 Hz, 2H), 2.68 (dd, J=9.6, 3.4 Hz, 4H), 2.52 (d, J=9.6 Hz, 2H), 2.20-2.09 (m, 2H), 1.47 (ddd, J=13.4, 9.7, 4.7 Hz, 2H), 1.37 (s, 9H).

Example 182

N-(4-(2-Aminoethyl)phenyl)tetrahydro-2H-thiopyran-4-amine

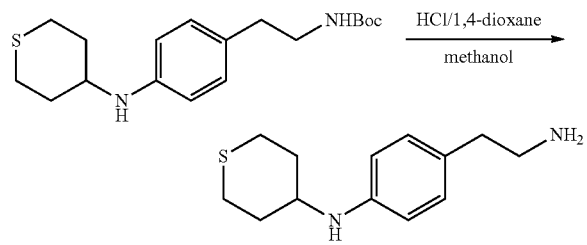

HCl (4 mL, 4N solution in 1,4-dioxane) was added to a stirred solution of tert-butyl 4-((tetrahydro-2H-thiopyran-4-yl)amino)phenethylcarbamate (0.3 g, 0.89 mmol) in MeOH (2 mL) at room temperature. After stirring for 1.5 h, the excess solvent was removed under reduced pressure to afford the crude product, which was used for the next step directly.

Example 183

2-(Furan-2-yl)-N5-(4-((tetrahydro-2H-thiopyran-4-yl)amino)phenethyl)-[1,2,4]triazolo[1,5-a][1,3,5]triazine-5,7-diamine

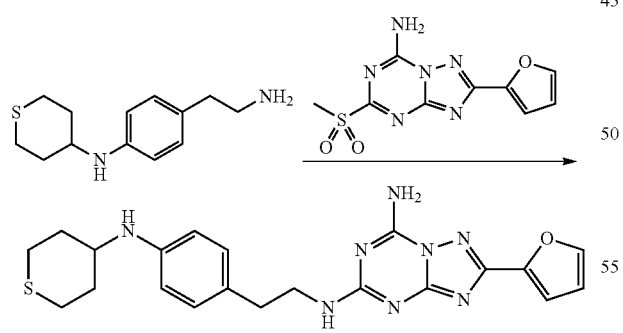

The reaction was carried out as in Example 5 to afford the title compound as white solid (0.0966 g, 31.2% yield). $^1$H NMR (500 MHz, DMSO-d6) δ: 8.29 (br, 2H), 7.87 (s, 1H), 7.43 (dd, J=25.2, 19.6 Hz, 1H), 7.06 (d, J=3.3 Hz, 1H), 6.95 (d, J=8.1 Hz, 2H), 6.68 (d, J=1.5 Hz, 1H), 6.52 (d, J=8.2 Hz, 2H), 5.32 (d, J=7.7 Hz, 1H), 3.39 (dd, J=14.0, 6.5 Hz, 2H), 3.23 (d, J=8.6 Hz, 1H), 2.74-2.60 (m, 6H), 2.15 (dd, J=12.9, 3.1 Hz, 2H), 1.54-1.42 (m, 2H).

Example 184 tert-Butyl 4-(ethyl(2-methoxyethyl)amino)phenethylcarbamate

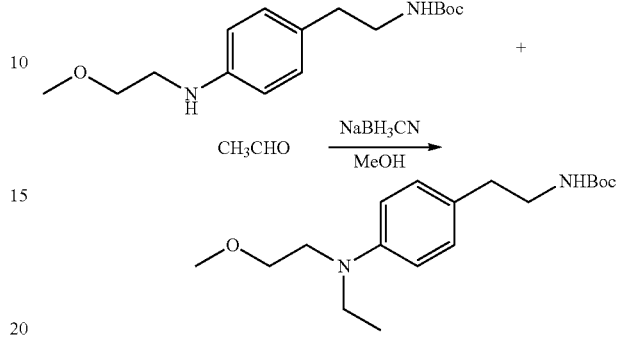

A solution of 4-(2-aminoethyl)-N-(2-methoxyethyl)aniline (0.7 g, 2.38 mmol) and acetaldehyde (0.157 g, 3.57 mmol) in methanol (10 mL) was stirred at room temperature for 10 min. After this time NaBH$_3$CN (0.748 g, 11.9 mmol) was added to the mixture and the reaction was stirred at room temperature overnight. Water (20 mL) was next added to the reaction mixture and the mixture was extracted with ethyl acetate (40 mL×2). The organic layer was washed with water (20 mL) and brine (20 mL), dried with Na$_2$SO$_4$ and concentrated. The residue was purified by column chromatography to afford the title compound as colorless oil (0.233 g, 30.4% yield). $^1$H NMR (500 MHz, DMSO-d6) δ: 6.96 (d, J=8.6 Hz, 2H), 6.82 (t, J=5.4 Hz, 1H), 6.59 (d, J=8.7 Hz, 2H), 3.45 (dd, J=9.1, 3.2 Hz, 2H), 3.39 (dd, J=9.0, 3.4 Hz, 2H), 3.33 (s, 2H), 3.26 (s, 3H), 3.05 (dd, J=14.7, 6.2 Hz, 2H), 2.54 (d, J=8.0 Hz, 2H), 1.37 (s, 9H), 1.04 (t, J=7.0 Hz, 3H).

Example 185

4-(2-Aminoethyl)-N-ethyl-N-(2-methoxyethyl)aniline

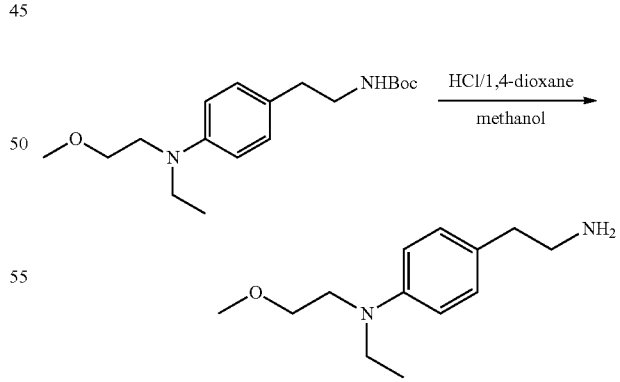

HCl (4 mL, 4N solution in 1,4-dioxane) was added to a stirred solution of tert-butyl 4-(ethyl(2-methoxyethyl)amino)phenethylcarbamate (0.209 g, 0.648 mmol) in MeOH (2 mL) at room temperature. After stirring for 1.5 h, the excess solvent was removed under reduced pressure to afford the crude product, which was used for the next step directly.

Example 186

N5-(4-(Ethyl(2-methoxyethyl)amino)phenethyl)-2-(furan-2-yl)-[1,2,4]triazolo[1,5-a][1,3,5]triazine-5,7-diamine

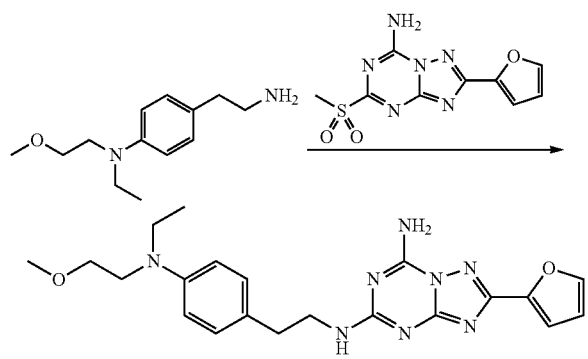

The reaction was carried out as in Example 5 to afford the title compound as white solid (0.0841 g, 38.3% yield). $^1$H NMR (500 MHz, DMSO-d6) δ: 8.24 (br, 2H), 7.88 (s, 1H), 7.49 (dt, J=41.0, 5.5 Hz, 1H), 7.04 (dd, J=15.8, 5.9 Hz, 3H), 6.68 (dd, J=3.3, 1.7 Hz, 1H), 6.61 (d, J=8.6 Hz, 2H), 3.42 (tt, J=7.3, 3.8 Hz, 6H), 3.32 (d, J=7.0 Hz, 2H), 3.26 (s, 3H), 2.70 (dd, J=14.9, 7.6 Hz, 2H), 1.05 (t, J=7.0 Hz, 3H).

Example 187 tert-Butyl 4-((1,1-dioxidotetrahydro-2H-thiopyran-4-yl)amino)phenethylcarbamate

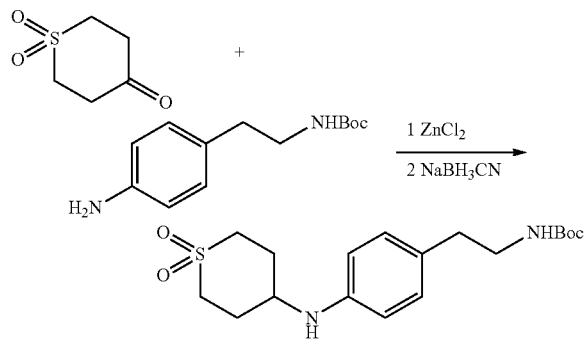

A mixture of dihydro-2H-thiopyran-4(3H)-one 1,1-dioxide (0.466 g, 3.15 mmol), tert-butyl 4-aminophenethylcarbamate (0.5 g, 2.1 mmol) and ZnCl$_2$ (0.859 g, 6.3 mmol) in methanol (10 mL) was stirred at room temperature overnight. After this time NaBH$_3$CN (0.66 g, 10.5 mmol) was added to the stirred mixture and the reaction was heated at 40° C. for 4 h. After it was cooled to room temperature, the reaction mixture was filtered and washed with ethyl acetate. The filtrate was concentrated in vacuo and purified by column chromatography to afford the title compound as light white solid (0.329 g, 42.5% yield). $^1$H NMR (500 MHz, DMSO-d6) δ: 6.91 (d, J=8.3 Hz, 2H), 6.81 (s, 1H), 6.54 (d, J=8.4 Hz, 2H), 5.51 (d, J=8.8 Hz, 1H), 3.61 (qd, J=9.0, 5.8 Hz, 1H), 3.28-3.09 (m, 4H), 3.04 (dd, J=14.7, 6.2 Hz, 2H), 2.53 (s, 2H), 2.19-2.08 (m, 2H), 1.97-1.79 (m, 2H), 1.37 (s, 9H).

Example 188

4-((4-(2-Aminoethyl)phenyl)amino)tetrahydro-2H-thiopyran 1,1-dioxide

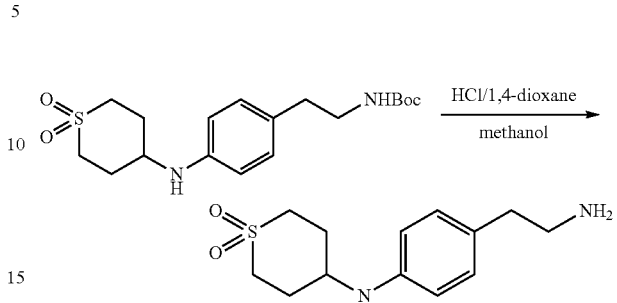

HCl (4 mL, 4N solution in 1,4-dioxane) was added to a stirred solution of tert-butyl 4-((1,1-dioxidotetrahydro-2H-thiopyran-4-yl)amino)phenethylcarbamate (0.329 g, 0.893 mmol) in MeOH (3 mL) at room temperature. After stirring for 2 h, the excess solvent was removed under reduced pressure to afford the crude product, which was used for the next step directly.

Example 189

4-((4-(2-((7-Amino-2-(furan-2-yl)-[1,2,4]triazolo[1,5-a][1,3,5]triazin-5-yl)amino)ethyl)-phenyl)amino)tetrahydro-2H-thiopyran 1,1-dioxide

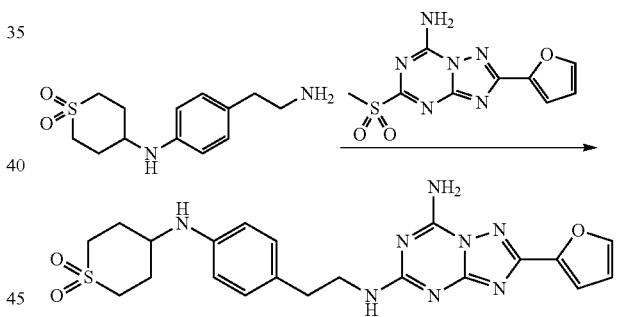

The reaction was carried out as in Example 5 to afford the title compound as white solid (0.1208 g, 36.3% yield). $^1$H NMR (500 MHz, DMSO-d6) δ: 8.30 (br, 2H), 7.87 (s, 1H), 7.47 (d, J=37.2 Hz, 1H), 7.02 (dd, J=38.2, 4.7 Hz, 3H), 6.68 (s, 1H), 6.56 (d, J=7.3 Hz, 2H), 5.53 (d, J=8.0 Hz, 1H), 3.62 (d, J=7.9 Hz, 1H), 3.41 (s, 2H), 3.27-3.05 (m, 4H), 2.68 (d, J=6.8 Hz, 2H), 2.15 (d, J=11.4 Hz, 2H), 1.88 (d, J=10.4 Hz, 2H).

Example 190 tert-Butyl 4-(methylamino)phenethylcarbamate

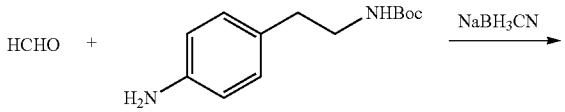

-continued

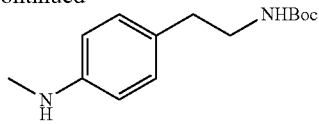

A solution of formaldehyde (0.303 g, 4 mmol, 40% in water), tert-butyl 4-aminophenethylcarbamate (1.135 g, 4.8 mmol) and NaBH$_3$CN (1.257 g, 20 mmol) in methanol (14 mL) was stirred at room temperature for 4 h. Water (30 mL) was added to the reaction mixture afterward and the mixture was extracted with ethyl acetate (30 mL×3). The organic layer was washed with water (20 mL) and brine (20 mL), dried with Na$_2$SO$_4$ and concentrated. The residue was purified by column chromatography to afford the title compound as colorless oil (0.337 g, 33.7% yield). $^1$H NMR (500 MHz, DMSO-d6) (d, J=8.3 Hz, 2H), 6.79 (t, J=5.3 Hz, 1H), 6.46 (d, J=8.4 Hz, 2H), 5.41 (q, J=5.0 Hz, 1H), 3.03 (dd, J=14.9, 6.1 Hz, 2H), 2.64 (d, J=5.2 Hz, 3H), 2.54-2.51 (m, 2H), 1.38 (s, 9H).

Example 191

4-(2-Aminoethyl)-N-methylaniline

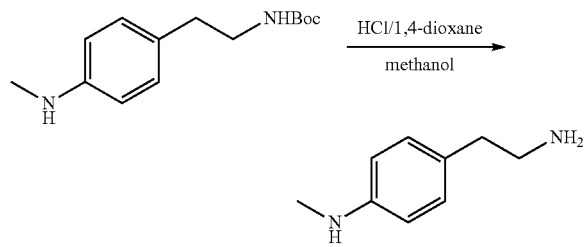

HCl (4 mL, 4N solution in 1,4-dioxane) was added to a stirred solution of tert-butyl 4-(methylamino)phenethylcarbamate (0.25 g, 1 mmol) in MeOH (3 mL) at room temperature. After stirring for 2 h, the excess solvent was removed under reduced pressure to afford the crude product, which was used for the next step directly.

Example 192

2-(Furan-2-yl)-N5-(4-(methylamino)phenethyl)-[1,2,4]triazolo[1,5-a][1,3,5]triazine-5,7-diamine

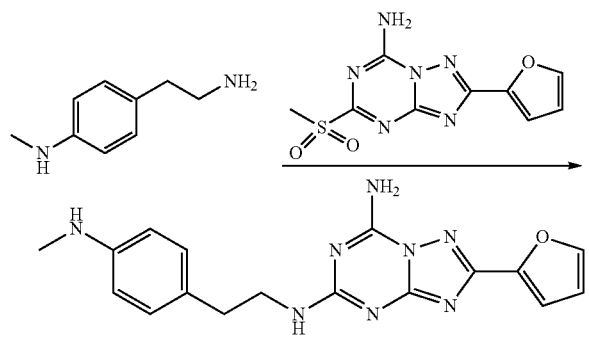

The reaction was carried out as in Example 5 to afford the title compound as white solid (0.0609 g, 24.8% yield). $^1$H NMR (500 MHz, DMSO-d6) δ: 8.29 (br, 2H), 7.87 (s, 1H), 7.43 (dd, J=26.2, 20.7 Hz, 1H), 7.06 (d, J=3.3 Hz, 1H), 6.98 (d, J=8.2 Hz, 2H), 6.68 (d, J=1.6 Hz, 1H), 6.48 (d, J=8.2 Hz, 2H), 5.44 (s, 1H), 3.40 (dd, J=14.2, 6.4 Hz, 2H), 2.72-2.66 (m, 2H), 2.64 (s, 3H).

Example 193

Benzyl 4-aminophenethylcarbamate

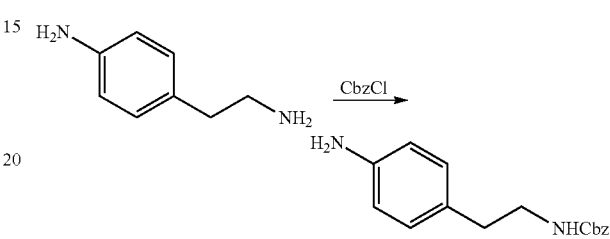

To a stirred solution of benzyl 4-aminophenethylcarbamate (3 g, 22 mmol) and TEA (4.45 g, 44 mmol) in DCM (30 mL) was added CbzCl (3.4 g, 20 mmol) dropwise over 20 minutes. The mixture was stirred at room temperature overnight. The reaction mixture was filtered and washed with ethyl acetate. The filtrate was concentrated in vacuo and purified by column chromatography (n-hexane/EtOAc) to afford the title compound as light-yellow solid (1.46 g, 21.4% yield). $^1$H NMR (500 MHz, DMSO-d6) δ: 7.43-7.25 (m, 6H), 6.84 (d, J=8.1 Hz, 2H), 6.49 (d, J=8.2 Hz, 2H), 5.01 (s, 2H), 4.85 (s, 2H), 3.17-3.05 (m, 2H), 2.57-2.51 (m, 2H).

Example 194

Benzyl 4-((oxetan-3-ylmethyl)amino)phenethylcarbamate

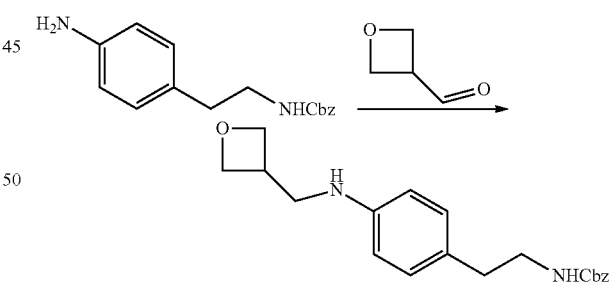

A solution of oxetane-3-carbaldehyde (0.35 g, 4.07 mmol), tert-butyl 4-aminophenethylcarbamate (1 g, 3.7 mmol) and NaBH$_3$CN (1.16 g, 20 mmol) in methanol (10 mL) was stirred at room temperature for 4 h. Water (30 mL) was added to the reaction mixture afterward and the mixture was extracted with ethyl acetate (50 mL×2). The organic layer was washed with water (20 mL) and brine (20 mL), dried with Na$_2$SO$_4$ and concentrated. The residue was purified by column chromatography to afford the title compound as white solid (0.527 g, 41.8% yield). $^1$H NMR (500 MHz, DMSO-d6) δ: 7.44-7.19 (m, 6H), 6.91 (d, J=8.3 Hz, 2H), 6.50 (d, J=8.4 Hz, 2H), 5.51 (t, J=5.6 Hz, 1H), 5.01 (s, 2H), 4.66 (dd, J=7.6, 6.0 Hz, 2H), 4.30 (t, J=5.9 Hz, 2H), 3.31-3.25 (m, 2H), 3.15 (ddd, J=18.5, 13.7, 6.0 Hz, 3H), 2.61-2.52 (m, 2H).

Example 195

4-(2-Aminoethyl)-N-(oxetan-3-ylmethyl)aniline

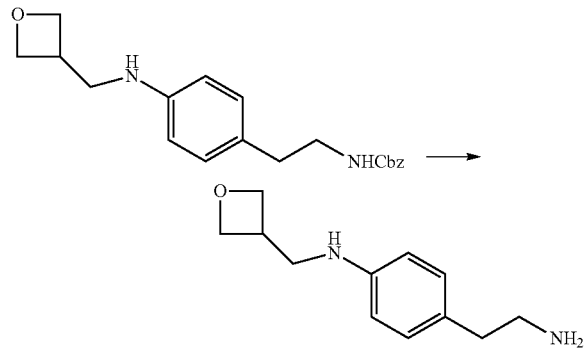

A mixture of benzyl 4-((oxetan-3-ylmethyl)amino)phenethylcarbamate (0.3 g, 0.88 mmol) and Pd/C (10%, 100 mg) in MeOH (7 mL) was stirred under H2 at room temperature for 17 h. TLC showed the reaction completed. The reaction mixture was filtered through Celite and concentrated in vacuo to afford the crude product, which was used for the next step directly.

Example 196

2-(Furan-2-yl)-N5-(4-(oxetan-3-ylmethyl)phenethyl)-[1,2,4]triazolo[1,5-a][1,3,5]triazine-5,7-diamine

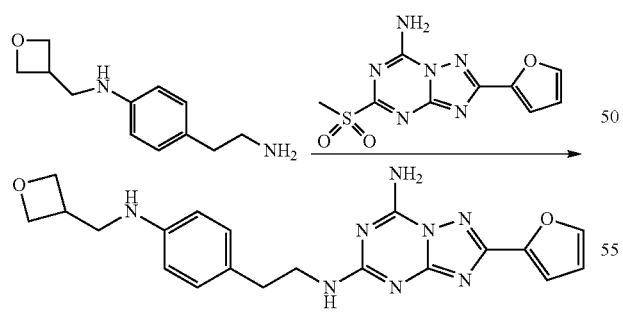

The reaction was carried out as in Example 5 to afford the title compound as white solid (0.1809 g, 65.6% yield). $^1$H NMR (500 MHz, DMSO-d6) δ: 8.28 (br, 2H), 7.87 (s, 1H), 7.42 (dd, J=25.3, 19.7 Hz, 1H), 7.06 (d, J=3.2 Hz, 1H), 6.97 (d, J=8.2 Hz, 2H), 6.68 (d, J=1.6 Hz, 1H), 6.52 (d, J=8.2 Hz, 2H), 5.50 (s, 1H), 4.66 (dd, J=7.6, 6.0 Hz, 2H), 4.30 (t, J=5.9 Hz, 2H), 3.40 (dd, J=14.1, 6.5 Hz, 2H), 3.28 (dd, J=13.3, 6.5 Hz, 2H), 3.22-3.08 (m, 1H), 2.72-2.63 (m, 2H).

Example 197

2-(3,3-Difluoropyrrolidin-1-yl)ethanol

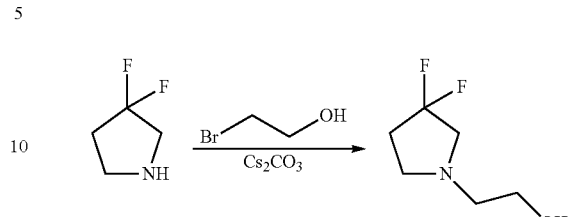

To a solution of 3,3-difluoropyrrolidine hydrochloride (600 mg, 4.17 mmol) in MeCN (15 mL) was added cesium carbonate (2.7 g, 8.34 mmol) and 2-bromoethanol (626 mg, 1.47 mmol). The reaction mixture was stirred at 70° C. overnight. TLC showed the reaction completed. The reaction mixture was quenched with water and extracted with EtOAc. The organic layer was washed with water and brine, dried over sodium sulfate and concentrated in vacuo. The crude product was purified by column chromatography (EtOAc:MeOH=5:1) to afford the title compound as colorless oil (630 mg, 100% yield).

Example 198

2-(3,3-Difluoropyrrolidin-1-yl)ethyl methanesulfonate

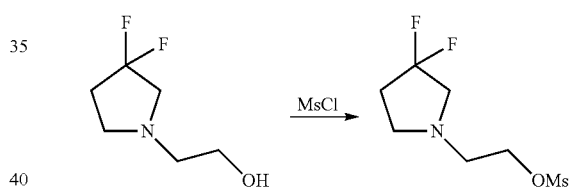

To a solution of 2-(3,3-difluoropyrrolidin-1-yl)ethanol (627 mg, 4.14 mmol) in DCM (20 mL) was added TEA (1.2 g, 11.8 mmol) and methanesulfonyl chloride (711 mg, 6.2 mmol) at 0° C. The reaction mixture was stirred at room temperature for 1.5 h. TLC showed the reaction completed. The reaction mixture was neutralized with 2N HCl (aq.) and extracted with DCM. The organic layer was washed with water and brine, dried over sodium sulfate and concentrated in vacuo to afford the title compound as yellow oil (600 mg, 63% yield).

Example 199 tert-Butyl 4-(2-(3,3-difluoropyrrolidin-1-yl)ethoxy)phenethylcarbamate

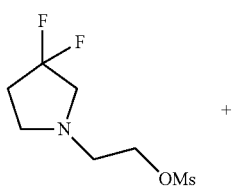 +

117

-continued

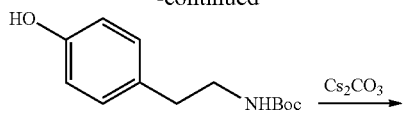

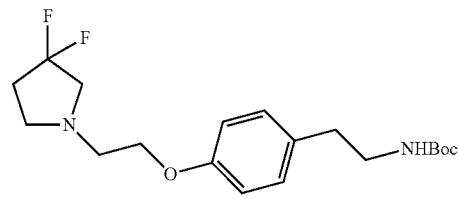

To a solution of 2-(3,3-difluoropyrrolidin-1-yl)ethyl methanesulfonate (600 mg, 2.61 mmol) in MeCN (15 mL) was added cesium carbonate (1.7 g, 5.2 mmol) and tert-butyl 4-hydroxyphenethylcarbamate 350 mg, 1.28 mmol). The reaction mixture was stirred at 70° C. overnight. TLC showed the reaction completed. The reaction mixture was quenched with water and extracted with EtOAc. The organic layer was washed with water and brine, dried over sodium sulfate and concentrated in vacuo. The crude product was purified by column chromatography (EtOAc:Hexane=1:2) to afford the crude product as colorless oil (500 mg, 52% yield).

Example 200

2-(4-(2-(3,3-Difluoropyrrolidin-1-yl)ethoxy)phenyl)ethanamine

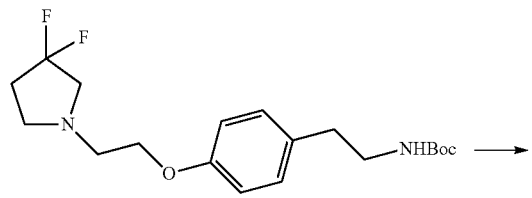

118

-continued

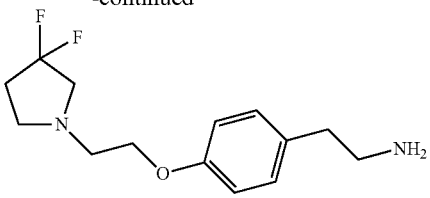

To a solution of tert-butyl 4-(2-(3,3-difluoropyrrolidin-1-yl)ethoxy)phenethylcarbamate (280 mg, 0.87 mmol) in 1,4-dioxane (4 mL) was added 4N HCL/dioxane (4 mL). The reaction mixture was stirred at room temperature for 2 h. TLC showed the reaction completed. The excess HCl and 1,4-dioxane were removed. The crude product was used for the next step directly.

Example 201

N5-(4-(2-(3,3-Difluoropyrrolidin-1-yl)ethoxy)phenethyl)-2-(furan-2-yl)-[1,2,4]triazolo[1,5-a][1,3,5]triazine-5,7-diamine

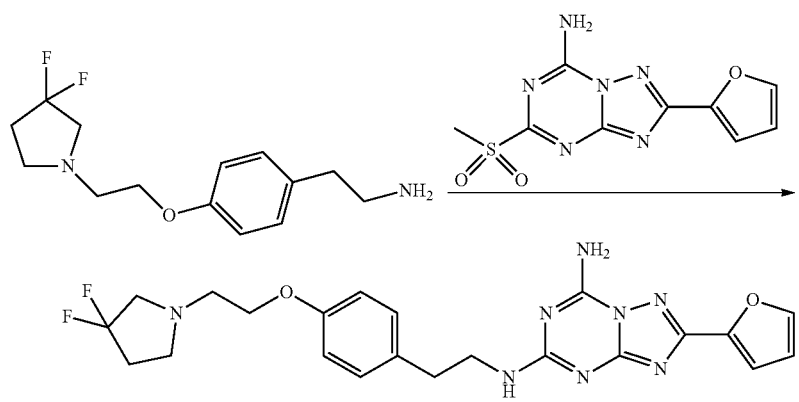

The reaction was carried out as in Example 5 to afford the title compound as white solid (70.4 mg, 23% yield). LCMS [M+1]$^+$: 471.20; $^1$H NMR (500 MHz, DMSO-d6): 8.05-8.22 (m, 2H), 7.87 (s, 1H), 7.45-7.55 (m, 1H), 7.15 (d, 2H), 7.06 (d, 1H), 6.87 (d, 2H), 6.67 (s, 1H), 4.03 (t, 2H), 3.43-3.44 (m, 2H), 2.97 (t, 2H), 2.76-2.80 (m, 6H), 2.19-2.24 (m, 2H).

Example 202 tert-Butyl 4-(2-(3-fluoroazetidin-1-yl)ethoxy)phenethylcarbamate

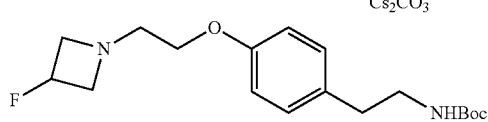

To a solution of tert-butyl 4-(2-(3-fluoroazetidin-1-yl)ethoxy)phenethylcarbamate (400 mg, 3.58 mmol) in MeCN (15 mL) was added cesium carbonate (2.3 g, 7.0 mmol) and 3-fluoroazetidine hydrochloride (300 mg, 0.87 mmol). The reaction mixture was stirred at 70° C. overnight. TLC showed the reaction completed. The reaction mixture quenched with water and extracted with EtOAc. The organic layer was washed with water and brine, dried over sodium sulfate and concentrated in vacuo. The crude product was purified by column chromatography to afford the title compound as white solid (140 mg, 47% yield). $^1$H NMR (500 MHz, DMSO-d6) δ: 7.07 (d, 2H), 6.80-6.85 (m, 3H), 5.17-5.21 (m, 0.5H), 5.06-5.10 (m, 0.5H), 3.90 (t, 2H), 3.57-3.63 (m, 2H), 3.12-3.20 (m, 2H), 3.05-3.09 (m, 2H), 2.78 (t, 2H), 2.60 (t, 2H), 1.36 (s, 9H).

Example 203

2-(4-(2-(3-Fluoroazetidin-1-yl)ethoxy)phenyl)ethanamine

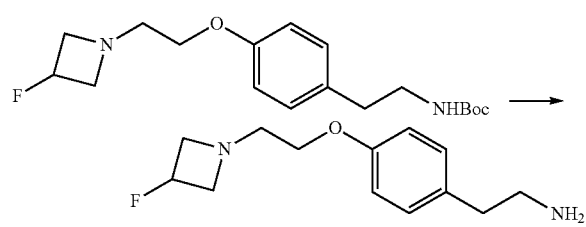

To a solution of tert-butyl 4-(2-(3-fluoroazetidin-1-yl)ethoxy)phenethylcarbamate (140 mg, 1.41 mmol) in 1,4-dioxane (4 mL) was added 4N HCL/dioxane (4 mL). The reaction mixture was stirred at room temperature for 2 h. TLC showed the reaction completed. The excess HCl and 1,4-dioxane were removed. The crude product was used for the next step directly.

Example 204

N5-(4-(2-(3-Fluoroazetidin-1-yl)ethoxy)phenethyl)-2-(furan-2-yl)-[1,2,4]triazolo[1,5-a][1,3,5]triazine-5,7-diamine

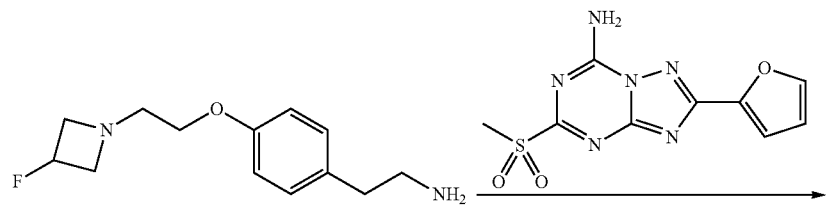

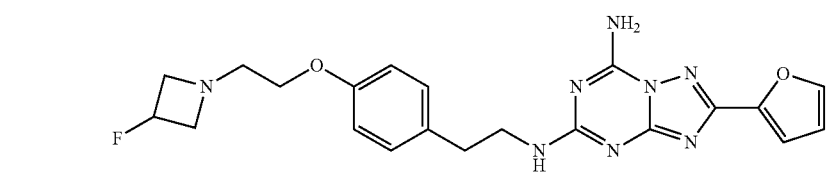

The reaction was carried out as in Example 5 to afford the title compound as white solid (53.3 mg, 35% yield). $^1$H NMR (500 MHz, DMSO-d6): 8.09-8.21 (m, 2H), 7.87 (s, 1H), 7.45-7.55 (m, 1H), 714-7.16 (m, 2H), 7.05 (d, 1H), 6.83 (d, 2H), 6.67 (dr, 1H), 5.17-5.21 (m, 0.5H), 5.06-5.10 (m, 0.5H), 3.90 (t, 2H), 3.58-3.63 (m, 2H), 3.41-3.45 (m, 2H), 3.13-3.21 (m, 2H), 2.76-2.79 (m, 4H).

Example 205 tert-Butyl 4-(2,2,2-trifluoroethoxy)phenethylcarbamate

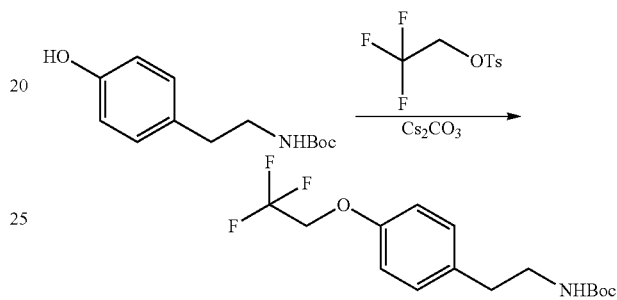

To a solution of tert-butyl 4-hydroxyphenethylcarbamate (1.0 g, 4.2 mmol) in DMF (30 mL) was added cesium carbonate (2.7 g, 8.4 mmol) and 2,2,2-trifluoroethyl 4-methylbenzenesulfonate (1.6 g, 6.3 mmol). The reaction mixture was stirred at 110° C. overnight. TLC showed the reaction completed. The reaction mixture was quenched with water and extracted with EtOAc. The organic layer was washed with water and brine, dried over sodium sulfate and concentrated in vacuo. The crude product was purified by column chromatography (EtOAc:Hexane=1:5) to afford the title compound as white solid (425 mg, 32% yield). $^1$H NMR (500 MHz, DMSO-d6): 7.14 (d, 2H), 6.96 (d, 2H), 6.83 (t, 1H), 4.67-4.72 (m, 2H), 3.07-3.11 (m, 2H), 2.63 (t, 2H), 1.36 (s, 9H).

Example 206

2-(4-(2,2,2-Trifluoroethoxy)phenyl)ethanamine

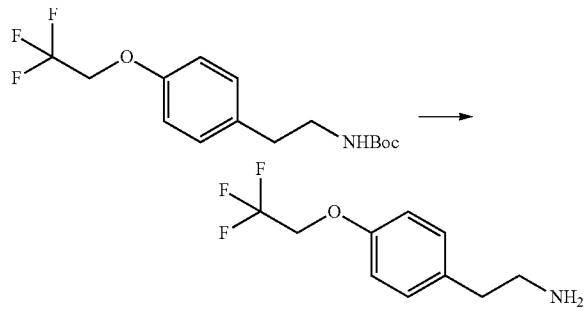

To a solution of tert-butyl 4-(2,2,2-trifluoroethoxy)phenethylcarbamate (276 mg, 0.86 mmol) in 1,4-dioxane (4 mL) was added 4N HCL/dioxane (4 mL). The reaction mixture was stirred at room temperature for 5 h. TLC showed the reaction completed. The excess HCl and 1,4-dioxane were removed. The crude product was used for the next step directly.

Example 207

N5-(4-(2,2,2-Trifluoroethoxy)phenethyl)-2-(furan-2-yl)-[1,2,4]triazolo[1,5-a][1,3,5]triazine-5,7-diamine

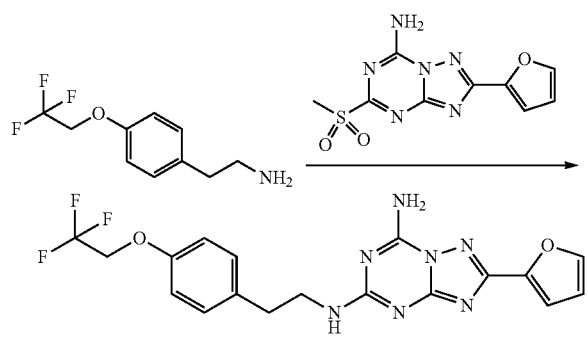

To a solution of 2-(4-(2,2,2-trifluoroethoxy)phenyl)ethanamine (0.86 mmol) in MeCN (10 mL) was added TEA (194 mg, 1.91 mmol) and 2-(furan-2-yl)-5-(methylsulfonyl)-[1,2,4]triazolo[1,5-a][1,3,5]triazin-7-amine (200 mg, 0.71 mmol). The reaction mixture was stirred at room temperature overnight. TLC showed the reaction completed. The reaction mixture was concentrated in vacuo. The crude product was purified by column chromatography to afford the title compound as white solid (105.9 mg, 35% yield). $^1$H NMR (500 MHz, DMSO-d6): 8.05-8.08 (m, 2H), 7.87 (s, 1H), 7.44-7.54 (m, 1H), 7.21 (d, 2H), 7.06 (d, 1H), 6.98 (d, 2H), 6.67 (s, 1H), 4.68-4.74 (m, 2H), 3.45-3.46 (m, 2H), 2.80-2.83 (m, 2H).

Example 208

Benzyl 4-hydroxyphenethyl(methyl)carbamate

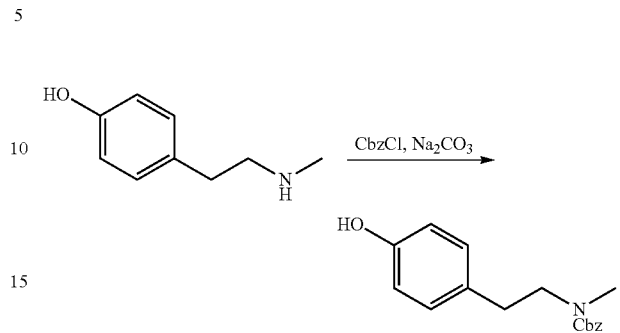

To a solution of 4-(2-(methylamino)ethyl)phenol hydrochloride (2.0 g, 13.22 mmol) in THF (30 mL) and water (10 mL) was added Na$_2$CO$_3$ (4.2 g, 39.6 mmol) and CbzCl (2.48 g, 14.54 mmol) at 0° C. The reaction mixture was stirred at room temperature overnight. TLC showed the reaction completed. The reaction was diluted with water and extracted with ethyl acetate. The organic layer was washed with water and brine, dried over sodium sulfate and concentrated in vacuo. The crude product was purified by column chromatography (EtOAc:Hexane=1:5) to afford the title compound as white solid (1.1 g, 29%).

Example 209

Benzyl 4-(2-(pyrrolidin-1-yl)ethoxy)phenethyl(methyl)carbamate

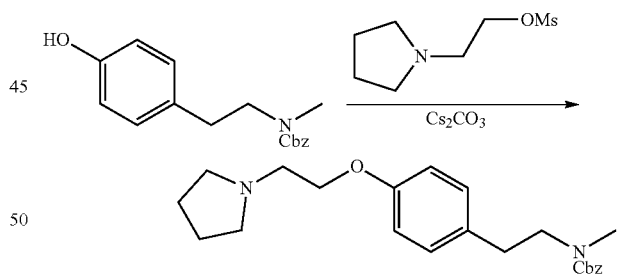

To a solution of benzyl 4-hydroxyphenethyl(methyl)carbamate (300 mg, 1.05 mmol) in MeCN (20 mL) was added cesium carbonate (1.02 g, 3.15 mmol) and 2-(pyrrolidin-1-yl)ethyl methanesulfonate (304 mg, 1.57 mmol). The reaction mixture was stirred at 70° C. overnight. TLC showed the reaction completed. The reaction mixture was quenched with water and extracted with EtOAc. The organic layer was washed with water and brine, dried over sodium sulfate and concentrated in vacuo. The crude product was purified by column chromatography (EtOAc:MeOH=20:1) to afford the title compound as white solid (110 mg, 35% yield).

Example 210

N-Methyl-2-(4-(2-(pyrrolidin-1-yl)ethoxy)phenyl)ethanamine

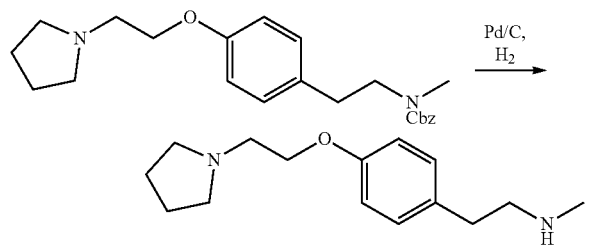

To a solution of benzyl 4-(2-(pyrrolidin-1-yl)ethoxy)phenethyl(methyl)carbamate (105 mg, 0.27 mmol) in MeOH (10 mL) was added Pd/C (10%). The reaction mixture was stirred under H2 at 50° C. for 2 h. TLC showed the reaction completed. The reaction mixture was filtered through diatomite. The filtrate was concentrated in vacuo to afford the title compound as colorless oil (61 mg, 89% yield), which was used for the next step directly.

Example 211

N5-(4-(2-(Pyrrolidin-1-yl)ethoxy)phenethyl)-2-(furan-2-yl)-N5-methyl-[1,2,4]triazolo[1,5-a][1,3,5]triazine-5,7-diamine

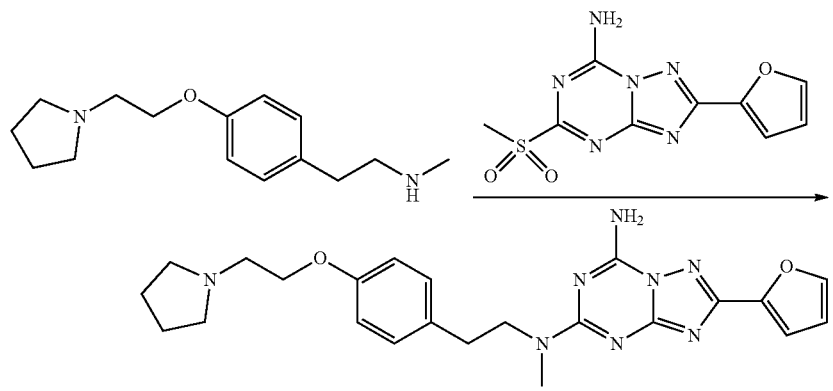

The reaction was carried out as in Example 5 to afford the title compound as yellow solid (48.8 mg, 50.8% yield). ¹H NMR (500 MHz, DMSO-d6): 8.09-8.21 (m, 2H), 7.87 (s, 1H), 7.20 (t, 2H), 7.05 (d, 1H), 6.69 (t, 2H), 6.68 (s, 1H), 4.12 (dr, 2H), 3.74-3.75 (m, 2H), 3.32-3.47 (m, 2H), 3.04 (d, 3H), 2.81-2.82 (m, 6H), 1.77 (m, 4H).

Example 212

(R)-Benzyl 4-(2-(3-(dimethylamino)pyrrolidin-1-yl)ethoxy)phenethylcarbamate

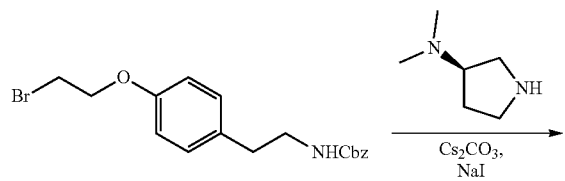

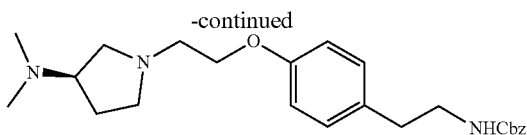

To a solution of benzyl 4-(2-bromoethoxy)phenethylcarbamate (95 mg, 0.25 mmol) in MeCN (15 mL) was added cesium carbonate (163 mg, 0.50 mmol) and (R)-N,N-dimethylpyrrolidin-3-amine hydrochloride (57 mg, 0.50 mmol). The reaction mixture was stirred at 70° C. overnight. TLC showed the reaction completed. The reaction mixture was quenched with water and extracted with ethyl acetate. The organic layer was washed with water and brine, dried over sodium sulfate and concentrated in vacuo. The crude product was purified by column chromatography (EtOAc:Hexane=1:3) to afford the title compound as white solid (70 mg, 68.6%).

Example 213

(R)-1-(2-(4-(2-Aminoethyl)phenoxy)ethyl)-N,N-dimethylpyrrolidin-3-amine

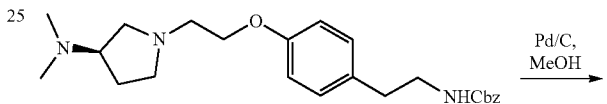

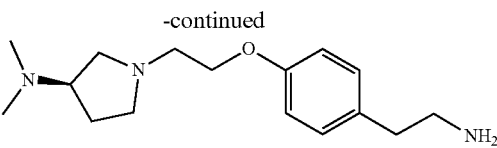

To a solution of benzyl 4-(2-(3-(dimethylamino)pyrrolidin-1-yl)ethoxy)phenethyl-carbamate (70 mg, 0.17 mmol) in MeOH (20 mL) was added Pd/C (10%). The reaction mixture was stirred under H2 at 40° C. for 2 h. TLC showed the reaction completed. The reaction mixture was filtered through diatomite. The filtrate was concentrated in vacuo to afford the title compound as white solid, which was used for the next step directly.

Example 214

N5-((R)-4-(2-(3-(Dimethylamino)pyrrolidin-1-yl)ethoxy)phenethyl)-2-(furan-2-yl)-[1,2,4]triazolo[1,5-a][1,3,5]triazine-5,7-diamine

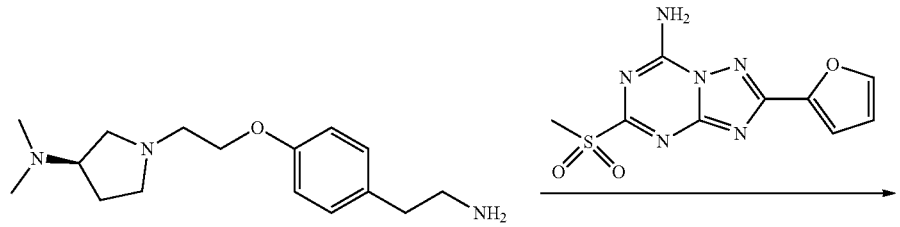

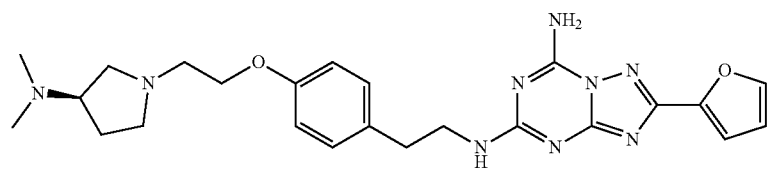

The reaction was carried out as in Example 5 to afford the title compound as yellow solid (30 mg, 62.9% yield). $^1$H NMR (500 MHz, DMSO-d6) δ: 8.03-8.24 (m, 2H), 7.87 (s, 1H), 7.49-7.58 (m, 1H), 7.15 (d, 2H), 7.06 (s, 1H), 6.86 (d, 2H), 6.68 (m, 1H), 4.01 (s, 2H), 3.42-3.44 (m, 2H), 2.65-2.90 (m, 9H), 2.42-2.58 (m, 2H), 2.18 (s, 6H), 1.81-1.90 (m, 1H), 1.63-1.64 (m, 1H).

Example 215 tert-Butyl 4-(2-(2-(2-(2-(2-methoxyethoxy)ethoxy)ethoxy)ethylamino)phenethyl-carbamate

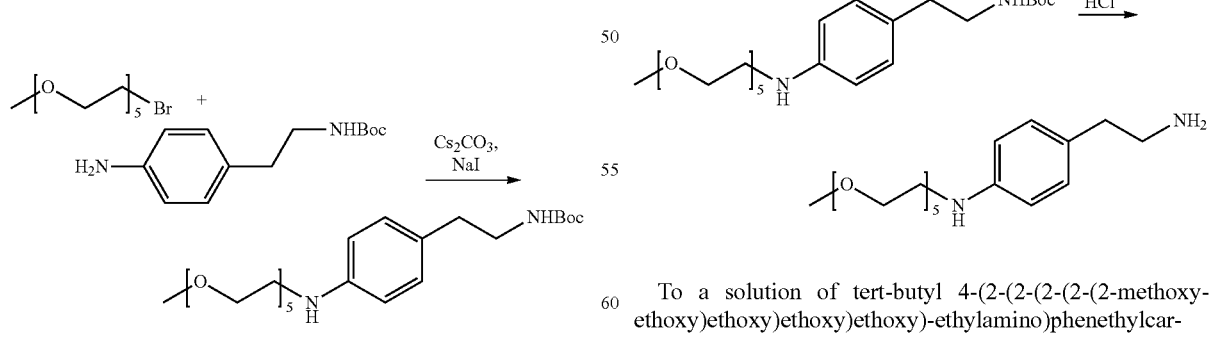

To a solution of 1-bromo-2-(2-(2-(2-(2-methoxyethoxy)ethoxy)ethoxy)ethane (400 mg, 1.27 mmol) in DMF (15 mL) was added tert-butyl 4-aminophenethylcarbamate (451 mg, 1.91 mmol), cesium carbonate (828 mg, 2.54 mmol) and NaI. The reaction mixture was stirred 110° C. for 2 h. The organic layer was washed with water and brine, dried over sodium sulfate and concentrated in vacuo. The crude product was purified by column chromatography (EtOAc:Hexane=1:1) to afford the title compound as colorless oil (110 mg, 18.6% yield). $^1$H NMR (500 MHz, CDCl$_3$) δ: 6.88 (d, 2H), 6.80 (t, 1H), 6.50 (d, 2H), 5.33 (t, 1H), 3.49-3.54 (m, 18H), 3.40-3.42 (m, 2H), 3.23 (s, 3H), 3.12-3.16 (m, 2H), 3.00-3.04 (m, 2H), 1.36 (s, 9H).

Example 216

4-(2-Aminoethyl)-N-(2-(2-(2-(2-(2-methoxyethoxy)ethoxy)ethoxy)ethyl)-benzenamine

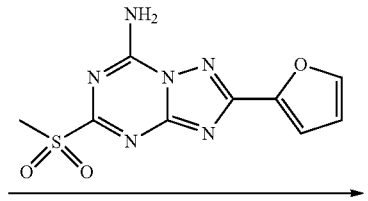

To a solution of tert-butyl 4-(2-(2-(2-(2-(2-methoxyethoxy)ethoxy)ethoxy)ethoxy)-ethylamino)phenethylcarbamate (110 mg, 0.24 mmol) in 1,4-dioxane (4 mL) was added 4N HCL/dioxane (4 mL). The reaction mixture was stirred at room temperature overnight. TLC showed the reaction completed. The excess HCl and 1,4-dioxane were removed. The crude product was used for the next step directly.

Example 217

N5-(4-(2-(2-(2-(2-(2-Methoxyethoxy)ethoxy)ethoxy)ethoxy)ethylamino)phenethyl)-2-(furan-2-yl)-[1,2,4]triazolo[1,5-a][1,3,5]triazine-5,7-diamine

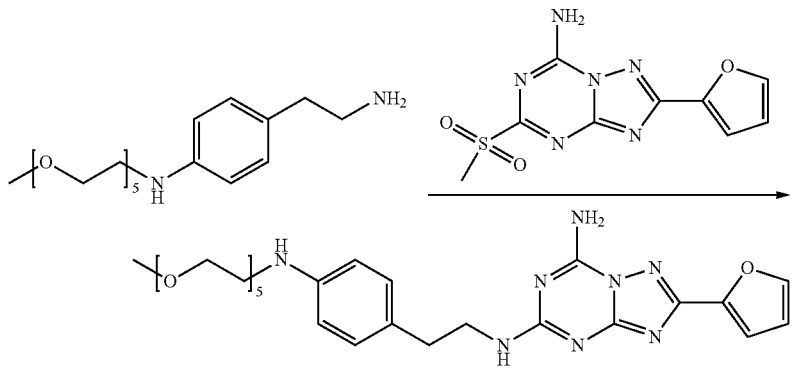

The reaction was carried out as in Example 5 to afford the title compound as yellow oil (40 mg, 30% yield). $^1$H NMR (500 MHz, DMSO-d6): 8.09-8.21 (m, 2H), 7.86 (s, 1H), 7.38-7.48 (m, 1H), 7.25 (d, 1H), 6.96 (d, 2H), 6.67 (s, 1H), 6.53 (d, 2H), 5.31 (t, 1H), 3.49-3.55 (m, 16H), 3.37-3.42 (m, 4H), 3.22 (s, 3H), 3.13-3.17 (m, 2H), 2.66-2.69 (m, 2H).

Example 218 tert-Butyl 4-(2-(diethylamino)ethoxy)phenethylcarbamate

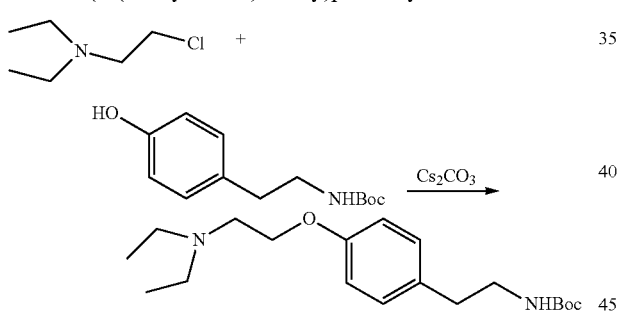

A mixture of 2-chloro-N,N-diethylethanamine (344 mg, 2 mmol), tert-butyl 4-hydroxyphenethylcarbamate (475 mg, 2 mmol) and cesium carbonate (1.30 g, 4 mmol) in acetone (10 mL) was stirred at 60° C. for 4 h. TLC showed the reaction completed. The reaction mixture was filtered. The filtrate was concentrated and purified by column chromatography to afford the title compound as yellow oil (300 mg, 44.58% yield). $^1$H NMR (500 MHz, DMSO-d6) δ: 7.08 (d, J=8.5 Hz, 2H), 6.83 (d, J=8.6 Hz, 3H), 3.96 (t, J=6.2 Hz, 2H), 3.08 (dd, J=14.0, 6.5 Hz, 2H), 2.74 (t, J=6.0 Hz, 2H), 2.64-2.57 (m, 2H), 2.53 (dd, J=14.2, 7.2 Hz, 4H), 1.36 (s, 9H), 0.96 (t, J=7.1 Hz, 6H).

Example 219

2-(4-(2-Aminoethyl)phenoxy)-N,N-diethylethanamine

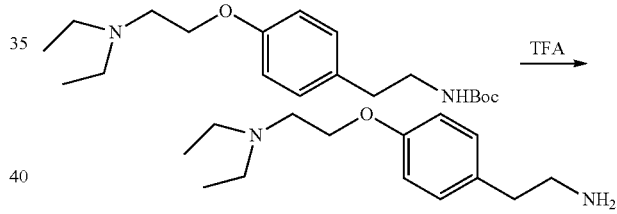

To a stirred mixture of tert-butyl 4-(2-(diethylamino)ethoxy)phenethylcarbamate (300 mg, 0.89 mmol) in DCM (5 mL) was added TFA (2 mL) at room temperature. After stirring overnight, TLC showed the reaction completed. The reaction mixture was concentrated in vacuo to afford the crude product, which was used for the next step directly.

Example 220

N5-(4-(2-(Diethylamino)ethoxy)phenethyl)-2-(furan-2-yl)-[1,2,4]triazolo[1,5-a][1,3,5]triazine-5,7-diamine

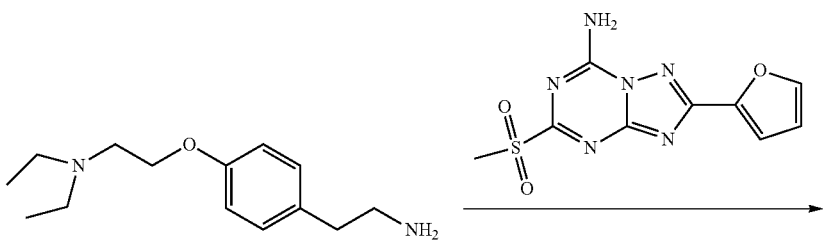

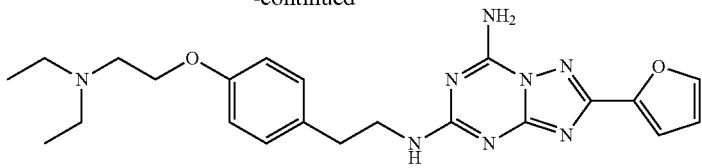

The reaction was carried out as in Example 5 to afford the title compound as white solid (73.3 mg, 18.89% yield). ¹H NMR (500 MHz, DMSO-d6) δ: 8.12 (s, 2H), 7.86 (s, 1H), 7.47 (d, J=39.9 Hz, 1H), 7.15 (d, J=7.2 Hz, 2H), 7.05 (d, J=2.8 Hz, 1H), 6.85 (d, J=7.7 Hz, 2H), 6.67 (s, 1H), 3.98 (s, 2H), 3.45 (s, 2H), 2.77 (d, J=6.8 Hz, 4H), 2.55 (s, 4H), 0.97 (s, 6H); LC-MS (m/z): 437.31 [M+H]⁺

Example 221 tert-Butyl 4-(3-morpholinopropanamido)phenethylcarbamate

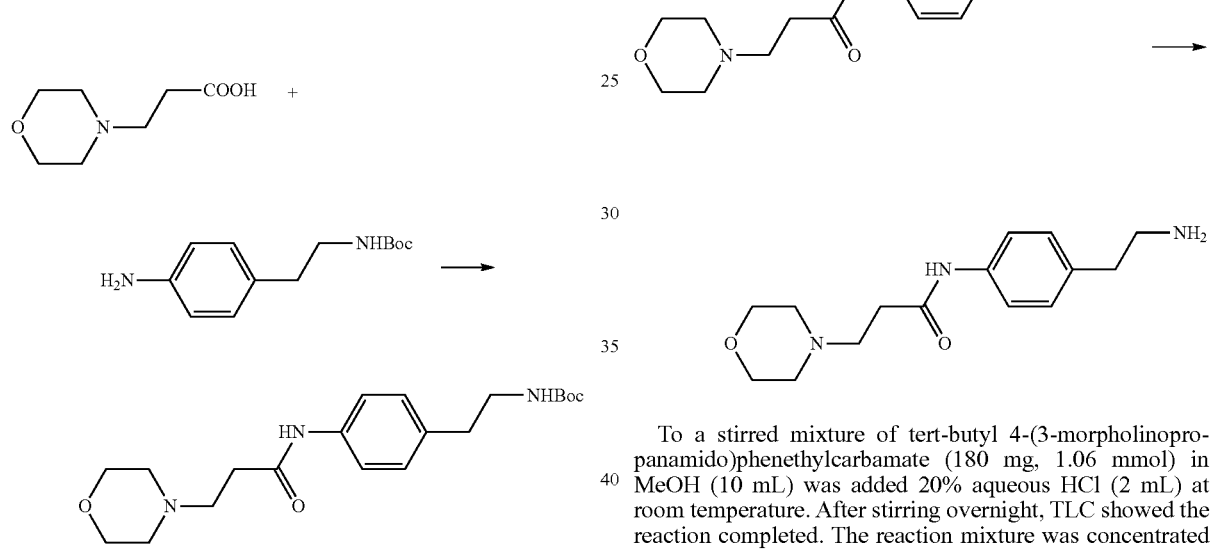

A mixture of 3-morpholinopropanoic acid (196 mg, 1 mmol), HATU (456 mg, 1.20 mmol) and DIPEA (323 mg, 5.88 mmol) in DCM (10 mL) was stirred at room temperature for 0.5 h. Then tert-butyl 4-aminophenethylcarbamate (236 mg, 1 mmol) was added and the reaction was stirred at room temperature overnight. TLC showed the reaction completed. The reaction mixture was concentrated and purified by column chromatography to afford the title compound as yellow solid (185 mg, 47.68% yield). ¹H NMR (500 MHz, DMSO-d6) δ: 9.95 (s, 1H), 7.48 (d, J=8.4 Hz, 2H), 7.10 (d, J=8.4 Hz, 2H), 6.83 (d, J=5.0 Hz, 1H), 3.58 (s, 4H), 3.09 (dd, J=14.2, 6.5 Hz, 2H), 2.67-2.55 (m, 4H), 2.47 (s, 4H), 1.36 (s, 9H), 1.28-1.22 (m, 2H).

Example 222

N-(4-(2-Aminoethyl)phenyl)-3-morpholinopropanamide

To a stirred mixture of tert-butyl 4-(3-morpholinopropanamido)phenethylcarbamate (180 mg, 1.06 mmol) in MeOH (10 mL) was added 20% aqueous HCl (2 mL) at room temperature. After stirring overnight, TLC showed the reaction completed. The reaction mixture was concentrated in vacuo to afford the crude product, which was used for the next step directly (The amide group was most likely hydrolyzed in certain degree. That is most likely why the following reaction gave two products).

Example 223

N5-(4-Aminophenethyl)-2-(furan-2-yl)-[1,2,4]triazolo[1,5-a][1,3,5]triazine-5,7-diamine and N-(4-(2-((7-Amino-2-(furan-2-yl)-[1,2,4]triazolo[1,5-a][1,3,5]triazin-5-yl)amino)ethyl)-phenyl)-3-morpholinopropanamide

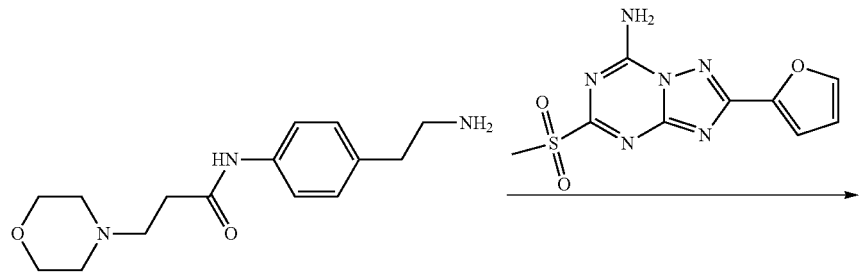

-continued

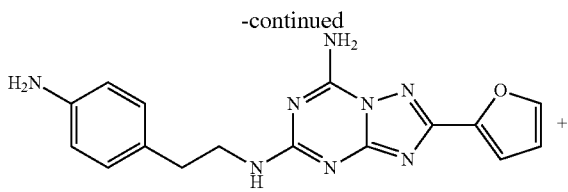

+

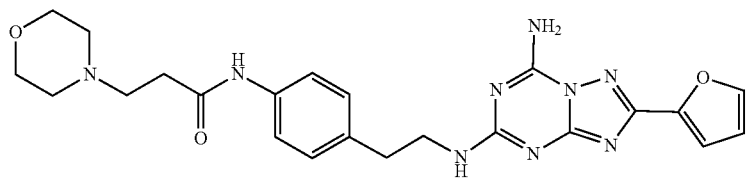

The reaction was carried out as in Example 5 to afford N5-(4-aminophenethyl)-2-(furan-2-yl)-[1,2,4]triazolo[1,5-a][1,3,5]triazine-5,7-diamine (14.6 mg, 9.24% yield) and N-(4-(2-((7-amino-2-(furan-2-yl)-[1,2,4]triazolo[1,5-a][1,3,5]triazin-5-yl)amino)ethyl)phenyl)-3-morpholinopropanamide (72.1 mg, 32.12% yield).

N5-(4-Aminophenethyl)-2-(furan-2-yl)-[1,2,4]triazolo[1,5-a][1,3,5]triazine-5,7-diamine. $^1$H NMR (500 MHz, DMSO-d6) δ: 8.15 (s, 2H), 7.87 (s, 1H), 7.42 (dd, J=26.1, 20.8 Hz, 1H), 7.06 (d, J=3.2 Hz, 1H), 6.90 (d, J=7.7 Hz, 2H), 6.68 (s, 1H), 6.51 (d, J=7.9 Hz, 2H), 4.88 (s, 2H), 3.44-3.36 (m, 2H), 2.74-2.61 (m, 2H); LC-MS (m/z): 337.15[M+H]$^+$ N-(4-(2-((7-Amino-2-(furan-2-yl)-[1,2,4]triazolo[1,5-a][1,3,5]triazin-5-yl)amino)ethyl)phenyl)-3-morpholinopropanamide. $^1$H NMR (500 MHz, DMSO-d6) δ: 9.97 (s, 1H), 8.18 (s, 2H), 7.87 (s, 1H), 7.63-7.41 (m, 3H), 7.18 (t, J=8.0 Hz, 2H), 7.06 (d, J=3.3 Hz, 1H), 6.68 (d, J=1.5 Hz, 1H), 3.64-3.54 (m, 4H), 3.46 (dd, J=13.7, 6.5 Hz, 2H), 2.80 (t, J=7.4 Hz, 2H), 2.62 (s, 2H), 2.45 (dd, J=20.2, 13.2 Hz, 6H); LC-MS (m/2z): 239.75[M+H]$^+$ Example 224 tert-Butyl 4-(3-(pyrrolidin-1-yl)propanamido)phenethylcarbamate

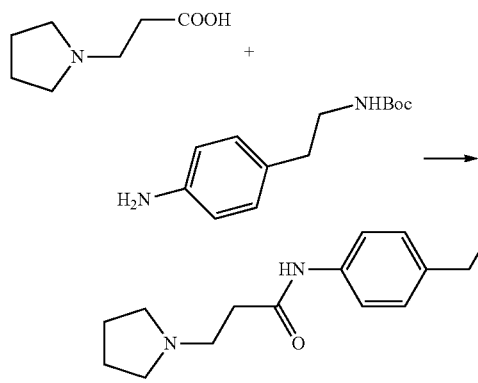

A mixture of 3-(pyrrolidin-1-yl)propanoic acid (143 mg, 1 mmol), T3P (1.27 g, 2 mmol), DIPEA (323 mg, 2.5 mmol) and tert-butyl 4-aminophenethylcarbamate (236 mg, 1 mmol) in DMF (10 mL) was stirred at room temperature overnight. TLC showed the reaction completed. The reaction mixture was concentrated and purified by column chromatography to afford the title compound as yellow solid (300 mg, 83.1% yield). $^1$H NMR (500 MHz, DMSO-d6) δ: 11.24 (s, 1H), 7.56 (d, J=8.3 Hz, 2H), 7.07 (d, J=8.4 Hz, 2H), 6.82 (dd, J=9.8, 4.9 Hz, 1H), 3.27 (d, J=6.7 Hz, 2H), 3.09 (d, J=7.7 Hz, 2H), 2.89 (s, 2H), 2.65-2.58 (m, 2H), 1.87 (s, 4H), 1.49 (d, J=3.5 Hz, 4H), 1.36 (d, J=2.2 Hz, 9H).

Example 225

N-(4-(2-Aminoethyl)phenyl)-3-(pyrrolidin-1-yl)propanamide

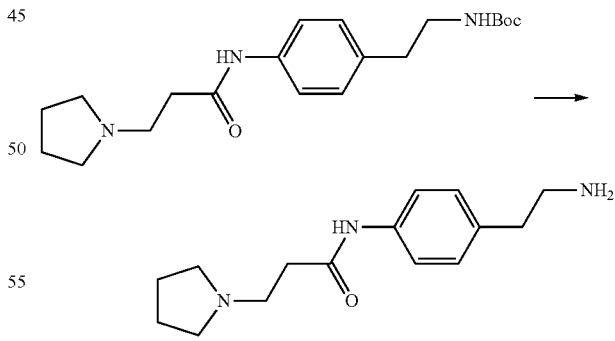

To a stirred mixture of tert-butyl 4-(3-(pyrrolidin-1-yl)propanamido)phenethylcarbamate (300 mg, 0.83 mmol) in MeOH (10 mL) was added 20% aqueous HCl (2 mL) at room temperature. After stirring overnight, TLC showed the reaction completed. The reaction mixture was concentrated in vacuo to afford the crude product, which was used for the next step directly.

Example 226

N-(4-(2-((7-Amino-2-(furan-2-yl)-[1,2,4]triazolo[1,5-a][1,3,5]triazin-5-yl)amino)ethyl)-phenyl)-3-(pyrrolidin-1-yl)propanamide

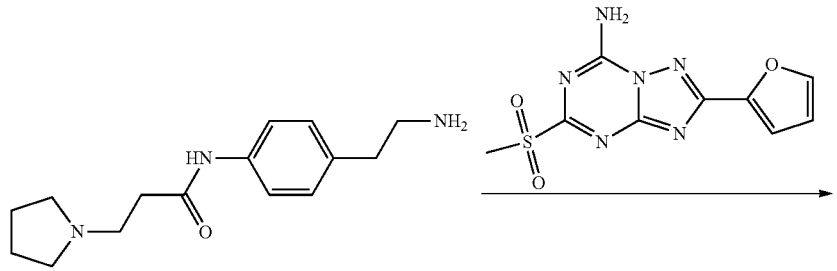

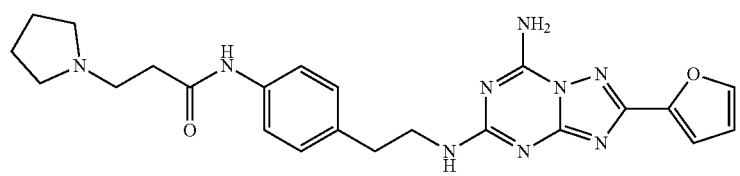

The reaction was carried out as in example 5 to afford the title compound as white solid (22.3 mg, 5.8% yield). $^1$H NMR (500 MHz, DMSO-d6) δ: 10.02 (s, 1H), 8.17 (s, 2H), 7.87 (s, 1H), 7.49 (t, J=14.5 Hz, 3H), 7.17 (d, J=7.1 Hz, 2H), 7.06 (s, 1H), 6.68 (s, 1H), 3.46 (s, 2H), 3.17 (s, 2H), 2.80 (s, 4H), 2.57 (s, 4H), 1.71 (s, 4H).

Example 227 tert-Butyl 4-(3-(4-methylpiperazin-1-yl)propanamido) phenethyl carbamate

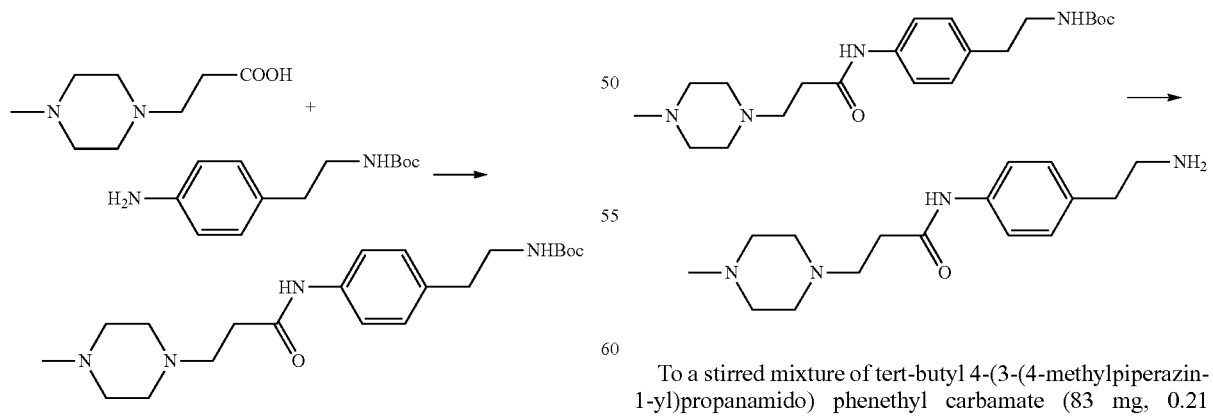

A mixture of 3-(4-methylpiperazin-1-yl)propanoic acid (172 mg, 1 mmol), HATU (456 mg, 1.2 mmol), DIPEA (323 mg, 2.5 mmol) and tert-butyl 4-aminophenethylcarbamate (236 mg, 1 mmol) in DCM (10 mL) was stirred at room temperature overnight. TLC showed the reaction completed. The reaction mixture was concentrated and purified by column chromatography to afford the title compound as yellow solid (90 mg, 23.0% yield). $^1$H NMR (500 MHz, DMSO-d6) δ: 10.01 (s, 1H), 7.48 (d, J=8.4 Hz, 2H), 7.10 (d, J=8.4 Hz, 2H), 6.84 (dd, J=13.1, 6.9 Hz, 1H), 3.10 (dd, J=14.1, 6.4 Hz, 2H), 2.64 (dd, J=24.9, 17.1 Hz, 6H), 2.45 (dd, J=15.8, 8.8 Hz, 8H), 2.20 (d, J=12.1 Hz, 3H), 1.37 (d, J=1.6 Hz, 9H).

Example 228

N-(4-(2-Aminoethyl)phenyl)-3-(4-methylpiperazin-1-yl)propanamide

To a stirred mixture of tert-butyl 4-(3-(4-methylpiperazin-1-yl)propanamido) phenethyl carbamate (83 mg, 0.21 mmol) in MeOH (5 mL) was added 20% aqueous HCl (1 mL) at room temperature. After stirring overnight, TLC showed the reaction completed. The reaction mixture was concentrated in vacuo to afford the crude product, which was used for the next step directly.

Example 229

N-(4-(2-((7-Amino-2-(furan-2-yl)-[1,2,4]triazolo[1,5-a][1,3,5]triazin-5-yl)amino)ethyl)-phenyl)-3-(4-methylpiperazin-1-yl)propanamide

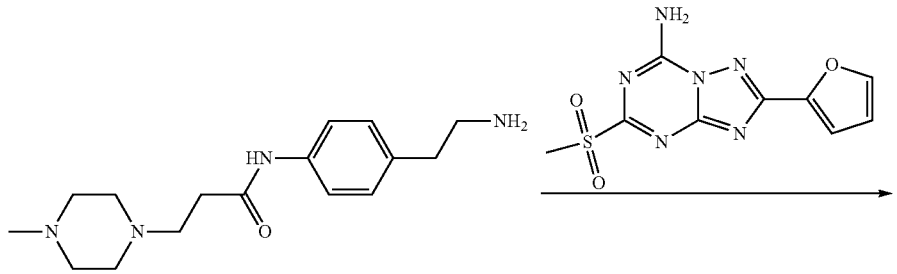

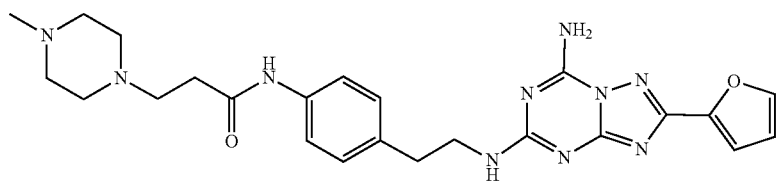

The reaction was carried out as in Example 5 to afford the title compound as white solid (17.3 mg, 16.8% yield). $^1$H NMR (500 MHz, DMSO-d6) δ: 10.02 (s, 1H), 8.31 (d, J=128.4 Hz, 2H), 7.87 (s, 1H), 7.49 (t, J=11.2 Hz, 3H), 7.18 (d, J=7.5 Hz, 2H), 7.06 (s, 1H), 6.68 (s, 1H), 4.11 (s, 1H), 3.45 (s, 4H), 3.18 (s, 3H), 2.80 (s, 2H), 2.63 (s, 2H), 2.45 (s, 5H), 2.22 (s, 2H); LC-MS (m/z): 491.27 [M+H]$^+$

Example 230

2-(4,4-Difluoropiperidin-1-yl)ethyl methanesulfonate

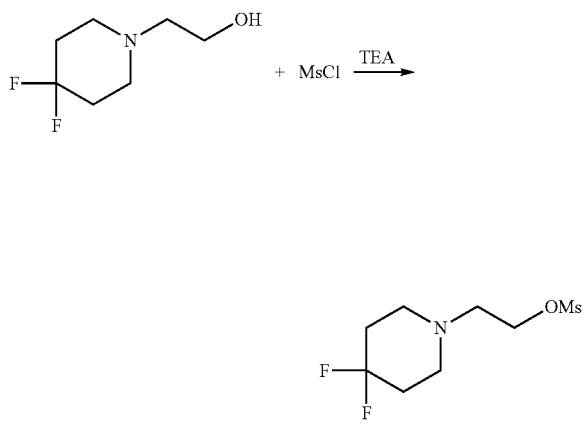

To a stirred mixture of 2-(4,4-difluoropiperidin-1-yl)ethanol (400 mg, 2.42 mmol) and TEA (490 mg, 4.84 mmol) in DCM (20 mL) was added MsCl (414 mg, 3.63 mmol) at room temperature. After stirring for 1 h, TLC showed the reaction completed. The reaction mixture was quenched with water (50 mL) and extracted with DCM (15 mL×3). The organic layer was washed with water and brine, dried over sodium sulfate and concentrated in vacuo to afford the crude product.

Example 231 tert-Butyl 4-(2-(4,4-difluoropiperidin-1-yl)ethoxy)phenethylcarbamate

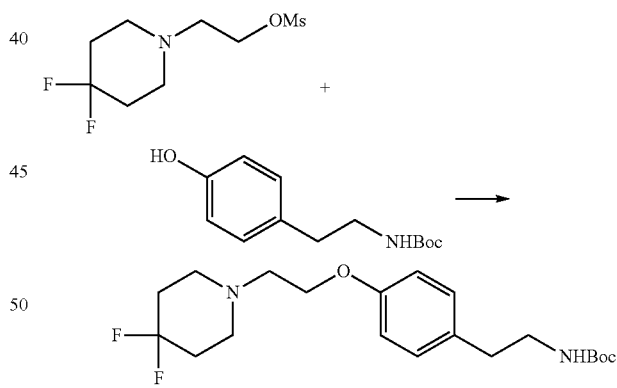

A mixture of 2-(4,4-difluoropiperidin-1-yl)ethyl methanesulfonate (588 mg, 2.42 mmol), tert-butyl 4-hydroxyphenethylcarbamate (530 g, 1.94 mmol) and cesium carbonate (2.36 g, 4.08 mmol) in acetone (20 mL) was stirred at 60° C. overnight. TLC showed the reaction completed. The reaction mixture was filtered. The filtrate was concentrated and purified by column chromatography to afford the title compound as yellow oil (471 mg, 50.7% yield). $^1$H NMR (500 MHz, DMSO-d6) δ: 7.09 (t, J=7.2 Hz, 2H), 6.84 (dd, J=9.8, 7.1 Hz, 3H), 4.04 (dd, J=9.3, 3.3 Hz, 2H), 3.08 (dd, J=14.1, 6.4 Hz, 2H), 2.76 (t, J=5.7 Hz, 2H), 2.61 (dd, J=9.8, 4.5 Hz, 6H), 1.99-1.90 (m, 4H), 1.37 (s, 9H).

Example 232

2-(4-(2-(4,4-Difluoropiperidin-1-yl)ethoxy)phenyl)ethanamine

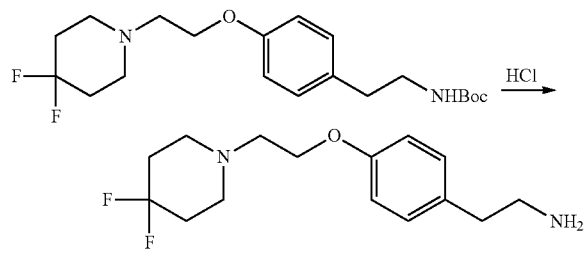

To a stirred mixture of tert-butyl 4-(2-(4,4-difluoropiperidin-1-yl)ethoxy)phenethyl-carbamate (200 mg, 0.52 mmol) in dioxane (10 mL) was added 4N HCl in dioxane (2 mL) at room temperature. After stirring overnight, TLC showed the reaction completed. The reaction mixture was concentrated in vacuo to afford the crude product, which was used for the next step directly.

Example 233

N5-(4-(2-(4,4-Difluoropiperidin-1-yl)ethoxy)phenethyl)-2-(furan-2-yl)-[1,2,4]triazolo[1,5-a][1,3,5]triazine-5,7-diamine

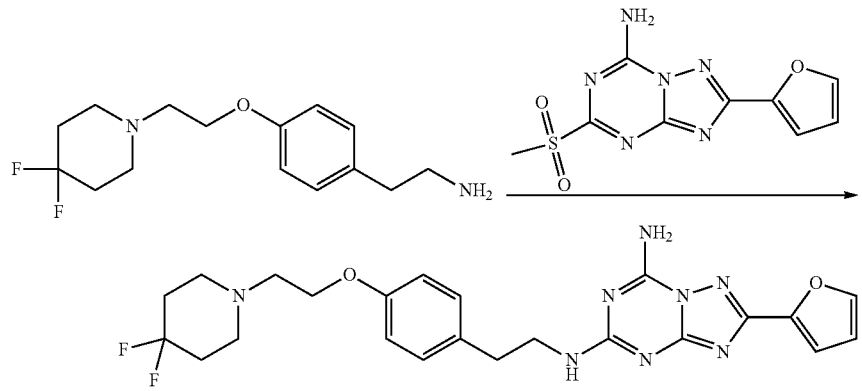

The reaction was carried out as in Example 5 to afford the title compound as white solid (72.1 mg, 28.7% yield). $^1$H NMR (500 MHz, DMSO-d6) δ: 8.32 (d, J=122.7 Hz, 2H), 7.87 (s, 1H), 7.58-7.44 (m, 1H), 7.16 (t, J=7.1 Hz, 2H), 7.06 (d, J=3.3 Hz, 1H), 6.87 (d, J=8.5 Hz, 2H), 6.68 (dd, J=3.3, 1.7 Hz, 1H), 4.04 (t, J=5.7 Hz, 2H), 3.44 (dd, J=13.7, 6.9 Hz, 2H), 2.80-2.74 (m, 4H), 2.61 (s, 4H), 1.95 (ddd, J=19.8, 13.9, 5.6 Hz, 4H); LC-MS (m/z): 485.20 [M+H]$^+$

Example 234

2-(3-Fluoropiperidin-1-yl)ethanol

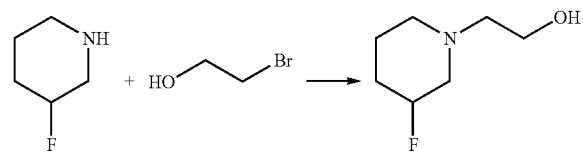

To a stirred mixture of 3-fluoropiperidine (1.0 g, 7.16 mmol) and potassium carbonate (4.95 g, 35.8 mmol) in MeCN (30 mL) was added 2-bromoethanol (2.68 g, 21.49 mmol) at room temperature. Then the mixture was stirred at 50° C. overnight. TLC showed the reaction completed. The reaction mixture was filtered. The filtrate was concentrated and purified by column chromatography to afford the title compound as yellow oil (980 mg, 93.3% yield). $^1$H NMR (500 MHz, DMSO-d6) δ: 4.65-4.51 (m, 1H), 4.40 (s, 1H), 3.48 (dd, J=10.3, 5.9 Hz, 2H), 2.83-2.70 (m, 1H), 2.49-2.37 (m, 3H), 2.37-2.28 (m, 1H), 2.23 (dd, J=13.9, 5.6 Hz, 1H), 1.82 (ddd, J=15.7, 8.1, 4.1 Hz, 1H), 1.68 (tdd, J=10.0, 6.7, 3.5 Hz, 1H), 1.54-1.36 (m, 2H).

Example 235

2-(3-Fluoropiperidin-1-yl)ethyl methanesulfonate

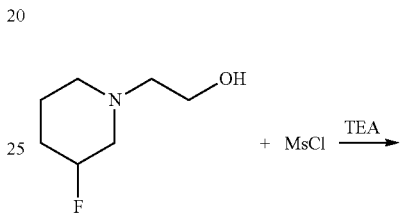

-continued

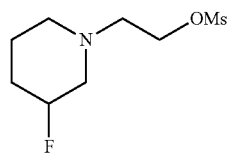

To a stirred mixture of 2-(3-fluoropiperidin-1-yl)ethanol (500 mg, 3.42 mmol) and TEA (692 mg, 6.84 mmol) in DCM (20 mL) was added MsCl (585 mg, 5.13 mmol) at room temperature. Then the mixture was stirred at room temperature for 1 h. TLC showed the reaction completed. The reaction mixture was quenched with water (50 mL) and extracted with DCM (15 mL×3). The organic layer was washed with water and brine, dried over sodium sulfate and concentrated in vacuo to afford the crude product, which was used for the next step directly.

Example 236 tert-Butyl 4-(2-(3-fluoropiperidin-1-yl)ethoxy)phenethylcarbamate

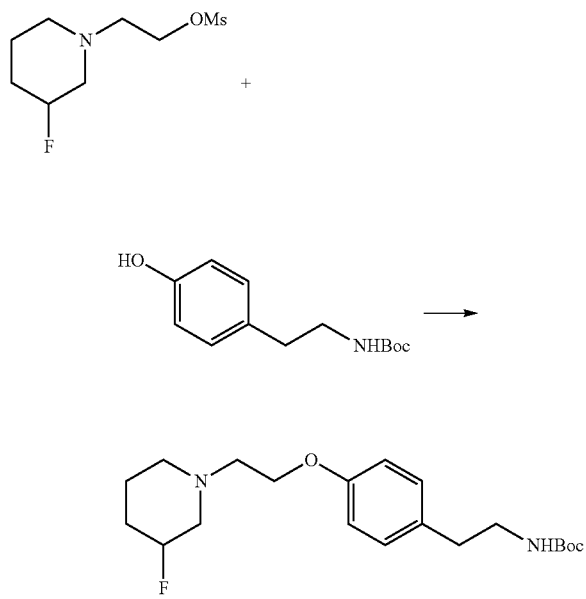

A mixture of 2-(3-fluoropiperidin-1-yl)ethyl methanesulfonate (770 mg, 3.42 mmol), tert-butyl 4-hydroxyphenethylcarbamate (742 mg, 2.73 mmol) and cesium carbonate (3.34 g, 10.26 mmol) in acetone (20 mL) was stirred at 50° C. overnight. TLC showed the reaction completed. The reaction mixture was filtered. The filtrate was concentrated and purified by column chromatography to afford the title compound as yellow oil (360 mg, 28.8% yield). $^1$H NMR (500 MHz, DMSO-d6) δ: 7.08 (d, J=8.5 Hz, 2H), 6.84 (d, J=8.4 Hz, 3H), 4.61 (dt, J=7.2, 3.0 Hz, 1H), 4.03 (t, J=5.8 Hz, 2H), 3.08 (dd, J=14.1, 6.4 Hz, 2H), 2.82 (dd, J=16.0, 11.6 Hz, 1H), 2.71 (dt, J=8.8, 6.6 Hz, 2H), 2.65-2.57 (m, 2H), 2.43 (dt, J=11.0, 7.3 Hz, 1H), 2.34 (d, J=2.8 Hz, 1H), 1.87-1.65 (m, 2H), 1.54-1.40 (m, 3H), 1.35 (d, J=13.1 Hz, 9H).

Example 237

2-(4-(2-(3-Fluoropiperidin-1-yl)ethoxy)phenyl)ethanamine

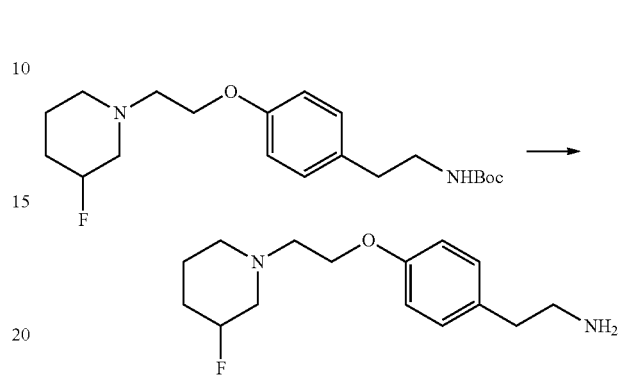

To a stirred mixture of tert-butyl 4-(2-(3-fluoropiperidin-1-yl)ethoxy)phenethyl-carbamate (360 mg, 1 mmol) in dioxane (10 mL) was added 4N HCl in dioxane (2 mL) at room temperature. After stirring overnight, TLC showed the reaction completed. The reaction mixture was concentrated in vacuo to afford the crude product, which was used for the next step directly.

Example 238

N5-(4-(2-(3-Fluoropiperidin-1-yl)ethoxy)phenethyl)-2-(furan-2-yl)-[1,2,4]triazolo[1,5-a][1,3,5]triazine-5,7-diamine

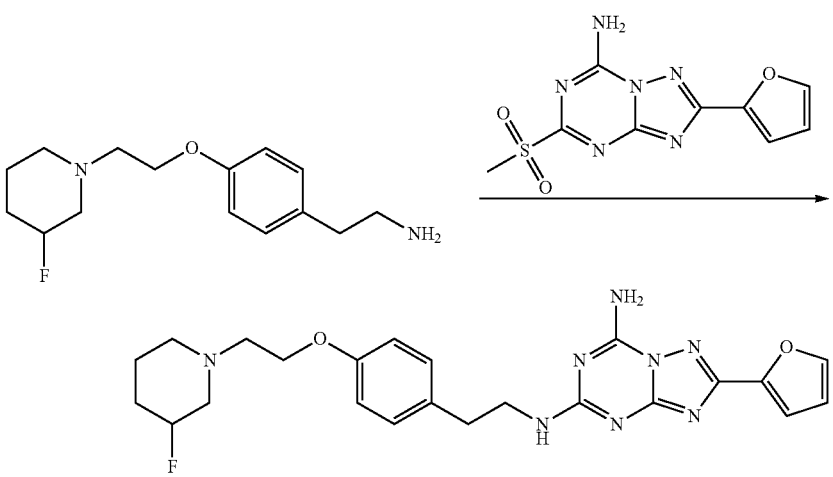

The reaction was carried out as in Example 5 to afford the title compound as white solid (135.1 mg, 29% yield). $^1$H NMR (500 MHz, DMSO-d6) δ: 8.31 (d, J=127.3 Hz, 2H), 7.91-7.85 (m, 1H), 7.55-7.43 (m, 1H), 7.15 (d, J=8.3 Hz, 2H), 7.06 (d, J=3.3 Hz, 1H), 6.87 (d, J=8.5 Hz, 2H), 6.68 (dd, J=3.2, 1.7 Hz, 1H), 4.71-4.52 (m, 1H), 4.03 (t, J=5.8 Hz, 2H), 3.50-3.41 (m, 2H), 2.88-2.69 (m, 5H), 2.51 (s, 1H), 2.44 (dt, J=11.0, 7.3 Hz, 1H), 2.33 (t, J=8.4 Hz, 1H), 1.74 (dddd, J=13.3, 10.2, 7.7, 3.8 Hz, 2H), 1.52-1.40 (m, 2H).

Example 239 tert-Butyl 4-(1-methylpiperidine-4-carboxamido)phenethylcarbamate

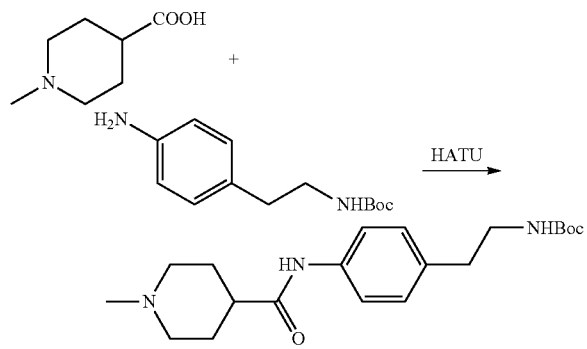

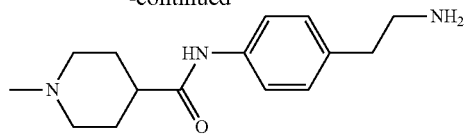

A mixture of 1-methylpiperidine-4-carboxylic acid (500 mg, 3.49 mmol), HATU (1.59 g, 4.18 mmol) and DIPEA (1.13 g, 8.73 mmol) in DCM (20 mL) was stirred at room temperature for 0.5 h. Then tert-butyl 4-aminophenethylcarbamate (825 mg, 3.49 mmol) was added and the reaction was stirred at room temperature overnight. TLC showed the reaction completed. The reaction mixture was concentrated and purified by column chromatography to afford the title compound as white solid (170 mg, 13.5% yield). $^1$H NMR (500 MHz, DMSO-d6) δ: 9.75 (s, 1H), 7.49 (d, J=8.4 Hz, 2H), 7.08 (d, J=8.4 Hz, 2H), 6.82 (t, J=5.3 Hz, 1H), 3.14-3.04 (m, 2H), 2.80 (d, J=11.4 Hz, 2H), 2.62 (t, J=7.5 Hz, 2H), 2.23 (ddd, J=15.5, 7.8, 4.1 Hz, 1H), 2.15 (s, 3H), 1.91-1.79 (m, 2H), 1.66 (ddd, J=17.6, 15.5, 6.7 Hz, 4H), 1.36 (s, 9H).

Example 240

N-(4-(2-Aminoethyl)phenyl)-1-methylpiperidine-4-carboxamide

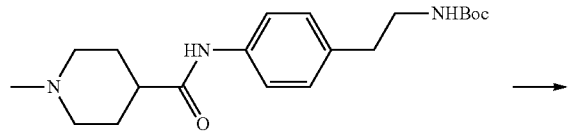

To a stirred mixture of tert-butyl 4-(1-methylpiperidine-4-carboxamido)phenethyl-carbamate (170 mg, 0.47 mmol) in dioxane (6 mL) was added 4N HCl in dioxane (1.5 mL) at room temperature. The reaction mixture was stirred at room temperature overnight. TLC showed the reaction completed. The reaction mixture was concentrated in vacuo to afford the crude product, which was used for the next step directly.

Example 241

N-(4-(2-((7-Amino-2-(furan-2-yl)-[1,2,4]triazolo[1,5-a][1,3,5]triazin-5-yl)amino)ethyl)-phenyl)-1-methylpiperidine-4-carboxamide

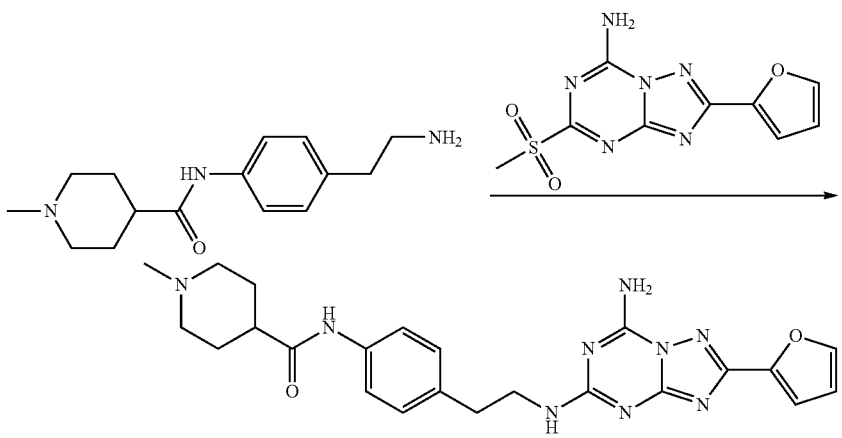

The reaction was carried out as in example 5 to afford the title compound as white solid (117.6 mg, 53.9% yield). $^1$H NMR (500 MHz, DMSO-d6) δ: 9.79 (s, 1H), 8.28 (d, J=151.1 Hz, 2H), 7.86 (s, 1H), 7.57-7.39 (m, 3H), 7.16 (d, J=8.0 Hz, 2H), 7.06 (d, J=3.2 Hz, 1H), 6.67 (s, 1H), 3.45 (d, J=6.4 Hz, 2H), 2.89-2.74 (m, 4H), 2.32-2.24 (m, 1H), 2.20 (s, 3H), 1.95 (t, J=10.8 Hz, 2H), 1.77-1.61 (m, 4H).

Example 242

2-(2-Fluoroethoxy)ethyl 4-methylbenzenesulfonate

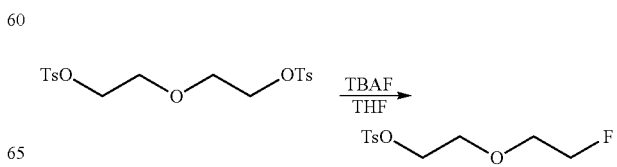

A mixture of oxybis(ethane-2,1-diyl) bis(4-methylbenzenesulfonate) (2.0 g, 4.8 mmol), TBAF (9.6 mL, 9.6 mmol) in THF (20 mL) was stirred at 80° C. for 2 h. TLC showed the reaction completed. The reaction mixture was concentrated and purified by column chromatography to afford the title compound as white oil (520 mg, 41.3% yield). $^1$H NMR (500 MHz, DMSO-d6) δ: 7.79 (d, J=8.3 Hz, 2H), 7.48 (d, J=8.1 Hz, 2H), 4.55-4.38 (m, 2H), 4.13 (dd, J=5.1, 3.6 Hz, 2H), 3.63-3.59 (m, 3H), 3.57-3.53 (m, 1H), 2.42 (s, 3H).

Example 243 tert-Butyl 4-(2-(2-fluoroethoxy)ethoxy)phenethylcarbamate

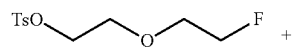

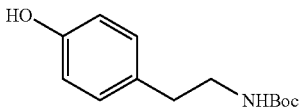

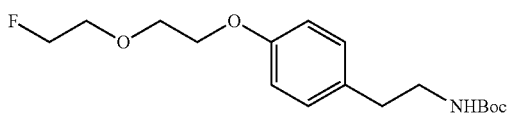

A mixture of 2-(2-fluoroethoxy)ethyl 4-methylbenzenesulfonate (262 mg, 1 mmol), tert-butyl 4-hydroxyphenethylcarbamate (217 g, 0.8 mmol) and cesium carbonate (977 mg, 3 mmol) in acetone (10 mL) was stirred at 50° C. for 4 h. TLC showed the reaction completed. The reaction mixture was filtered. The filtrate was concentrated and purified by column chromatography to afford the title compound as white solid (160 mg, 46.6% yield). $^1$H NMR (500 MHz, DMSO-d6) δ: 7.09 (d, J=8.5 Hz, 2H), 6.84 (dd, J=13.4, 7.0 Hz, 3H), 4.63-4.44 (m, 2H), 4.06 (dd, J=5.4, 3.9 Hz, 2H), 3.81-3.64 (m, 4H), 3.06 (s, 2H), 2.66-2.56 (m, 2H), 1.36 (s, 9H).

Example 244

2-(4-(2-(2-Fluoroethoxy)ethoxy)phenyl)ethanamine

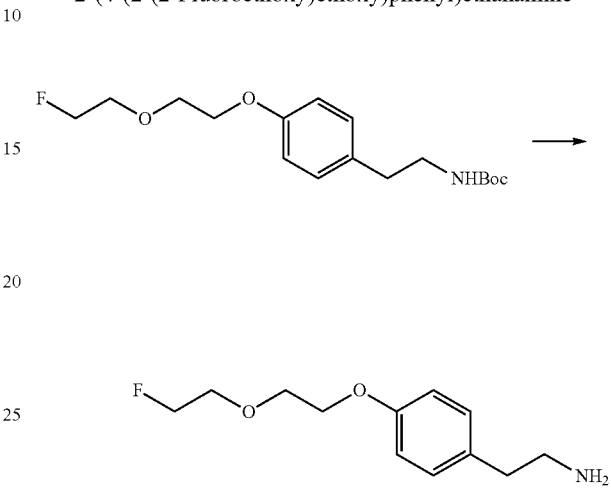

To a stirred mixture of tert-butyl 4-(2-(2-fluoroethoxy)ethoxy)phenethylcarbamate (160 mg, 0.46 mmol) in dioxane (8 mL) was added 4N HCl in dioxane (2 mL) at room temperature. The reaction mixture was stirred at room temperature overnight. TLC showed the reaction completed. The reaction mixture was concentrated in vacuo to afford the crude product, which was used for the next step directly.

Example 245

N5-(4-(2-(2-Fluoroethoxy)ethoxy)phenethyl)-2-(furan-2-yl)-[1,2,4]triazolo[1,5-a][1,3,5]triazine-5,7-diamine

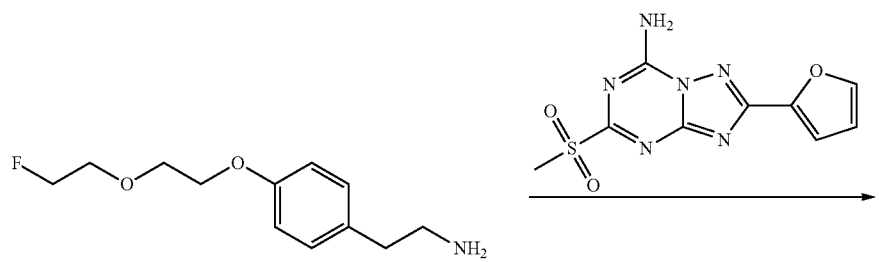

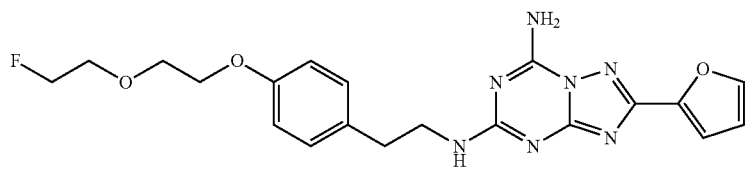

The reaction was carried out as in Example 5 to afford the title compound as white solid (82.0 mg, 41.8% yield). ¹H NMR (500 MHz, DMSO-d6) δ: 8.16 (s, 2H), 7.87 (s, 1H), 7.47 (dd, J=27.6, 22.0 Hz, 1H), 7.16 (d, J=8.2 Hz, 2H), 7.06 (d, J=3.3 Hz, 1H), 6.88 (d, J=8.4 Hz, 2H), 6.68 (d, J=1.4 Hz, 1H), 4.62-4.46 (m, 2H), 4.12-4.02 (m, 2H), 3.73 (ddd, J=31.2, 8.8, 4.3 Hz, 4H), 3.45 (dd, J=13.4, 6.7 Hz, 2H), 2.79 (t, J=7.3 Hz, 2H).

Example 246 tert-Butyl 4-((2-methoxyethyl)amino)phenethylcarbamate

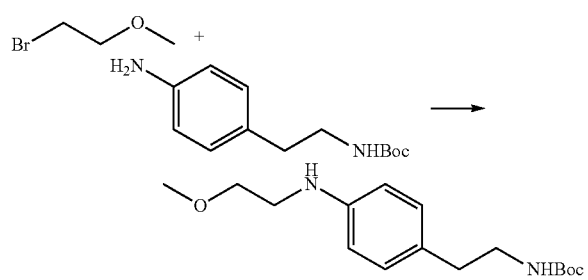

To a stirred mixture of tert-butyl 4-aminophenethylcarbamate (7.01 g, 30 mmol) and cesium carbonate (19.5 g, 60 mmol) in DMF (100 mL) was added 1-bromo-2-methoxyethane (2.92 mg, 21 mmol) in DMF (30 mL) slowly. Then the mixture was stirred at 110° C. for 2 h. TLC showed the reaction completed. The reaction mixture was filtered. The filtrate was concentrated, diluted with water (100 mL) and extracted with EA (50 mL×3). The organic layer was washed with water and brine, dried over sodium sulfate and concentrated in vacuo. The crude product was purified by column chromatography to afford the title compound as yellow oil (1.92 g, 21.7% yield). ¹H NMR (500 MHz, DMSO-d6) δ: 6.89 (d, J=8.3 Hz, 2H), 6.79 (t, J=5.1 Hz, 1H), 6.49 (dd, J=30.0, 8.4 Hz, 2H), 5.34 (t, J=5.7 Hz, 1H), 3.46 (q, J=6.0 Hz, 2H), 3.29-3.25 (m, 3H), 3.15 (q, J=5.8 Hz, 2H), 3.03 (dd, J=14.3, 6.6 Hz, 2H), 2.54-2.51 (m, 2H), 1.37 (s, 9H).

Example 247

4-(2-Aminoethyl)-N-(2-methoxyethyl)aniline

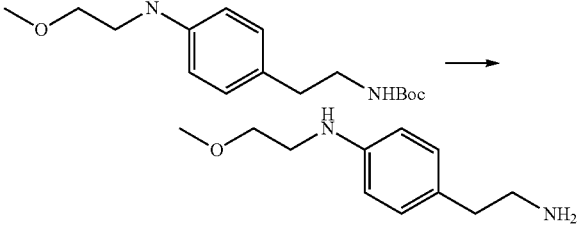

To a stirred mixture of tert-butyl 4-((2-methoxyethyl)amino)phenethylcarbamate (1.92 g, 6.5 mmol) in dioxane (10 mL) was added 4N HCl in dioxane (10 mL) at room temperature. The reaction mixture was stirred at room temperature overnight. TLC showed the reaction completed. The reaction mixture was concentrated in vacuo to afford the crude product, which was used for the next step directly.

Example 248

2-(Furan-2-yl)-N5-(4-((2-methoxyethyl)amino)phenethyl)-[1,2,4]triazolo[1,5-a][1,3,5]triazine-5,7-diamine

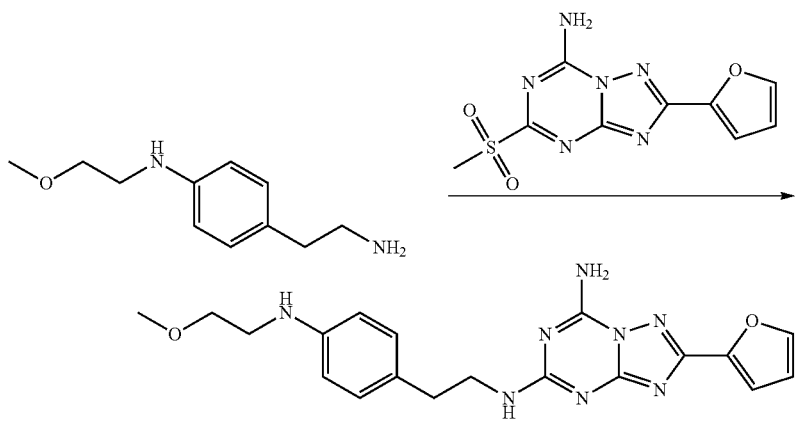

The reaction was carried out as in Example 5 to afford the title compound as white solid (1.19 g, 46.5% yield). ¹H NMR (500 MHz, DMSO-d6) δ: 8.27 (d, J=136.2 Hz, 2H), 7.87 (s, 1H), 7.42 (dd, J=26.5, 21.0 Hz, 1H), 7.06 (d, J=3.4 Hz, 1H), 6.96 (d, J=8.2 Hz, 2H), 6.68 (d, J=1.6 Hz, 1H), 6.54 (d, J=8.3 Hz, 2H), 5.35 (t, J=5.7 Hz, 1H), 3.47 (t, J=5.8 Hz, 2H), 3.40 (dd, J=14.2, 6.4 Hz, 2H), 3.28 (s, 3H), 3.19-3.12 (m, 2H), 2.73-2.65 (m, 2H); LC-MS (m/z): 395.3 [M+H]⁺

Example 249 tert-Butyl 4-(4-methylpiperazin-1-yl)phenethylcarbamate

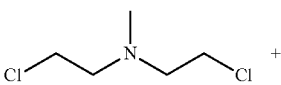

147

-continued

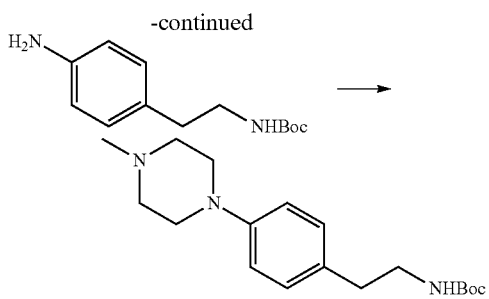

A mixture of 2-chloro-N-(2-chloroethyl)-N-methylethanamine (385 mg, 2 mmol), tert-butyl 4-aminophenethylcarbamate (473 mg, 2 mmol) and potassium carbonate (553 mg, 4 mmol) in DMF (10 mL) was stirred at 110° C. overnight. TLC showed the reaction completed. The reaction mixture was filtered. The filtrate was concentrated and purified by column chromatography to afford the title compound as yellow oil (67 mg, 10.5% yield). $^1$H NMR (500 MHz, DMSO-d6) δ: 7.02 (d, J=8.5 Hz, 2H), 6.83 (dd, J=14.2, 7.7 Hz, 3H), 3.12-3.00 (m, 6H), 2.60-2.54 (m, 2H), 2.47-2.40 (m, 4H), 2.21 (s, 3H), 1.36 (s, 9H).

Example 250

2-(4-(4-Methylpiperazin-1-yl)phenyl)ethanamine

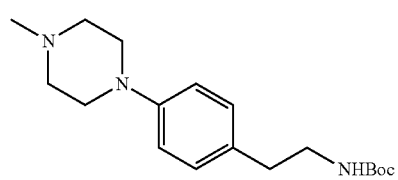

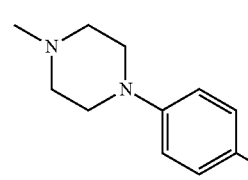

148

To a stirred mixture of tert-butyl 4-(4-methylpiperazin-1-yl)phenethylcarbamate (67 mg, 0.21 mmol) in dioxane (5 mL) was added 4N HCl in dioxane (3 mL) at room temperature. The reaction mixture was stirred at room temperature overnight. TLC showed the reaction completed. The reaction mixture was concentrated in vacuo to afford the crude product, which was used for the next step directly.

Example 251

2-(Furan-2-yl)-N5-(4-(4-methylpiperazin-1-yl)phenethyl)-[1,2,4]triazolo[1,5-a][1,3,5]triazine-5,7-diamine

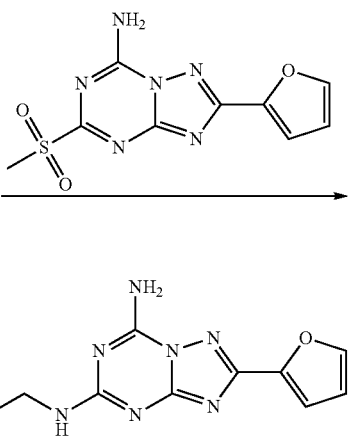

The reaction was carried out as in Example 5 to afford the title compound as white solid (14.8 mg, 16.8% yield). $^1$H NMR (500 MHz, DMSO-d6) δ: 8.20 (s, 2H), 7.87 (s, 1H), 7.50 (d, J=34.4 Hz, 1H), 7.09 (d, J=38.5 Hz, 3H), 6.91 (s, 2H), 6.68 (s, 1H), 3.43 (s, 3H), 3.28-3.17 (m, 3H), 2.96 (s, 4H), 2.76 (s, 2H), 2.57 (s, 3H); LC-MS (m/z): 420.3[M+H]$^+$ Example 252 tert-Butyl 4-((2-(dimethylamino)ethyl)amino)phenethylcarbamate

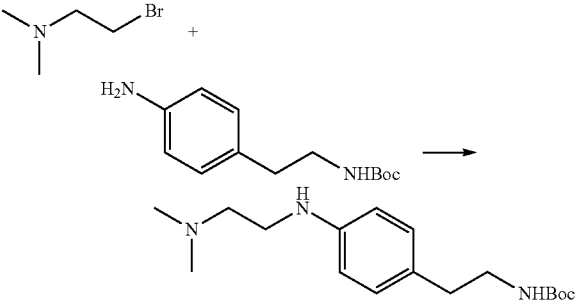

A mixture of 2-bromo-N,N-dimethylethanamine (349 mg, 1.5 mmol), tert-butyl 4-aminophenethylcarbamate (709 mg, 3 mmol) and DIPEA (39 mg, 0.3 mmol) in DMF (5 mL) was stirred at 100° C. overnight. TLC showed the reaction completed. The reaction mixture was concentrated and purified by column chromatography to afford the title compound as yellow oil (200 mg, 43.4% yield). $^1$H NMR (500 MHz, DMSO-d6) δ: 6.95 (d, J=8.2 Hz, 2H), 6.85 (t, J=5.6 Hz, 1H), 6.58 (d, J=8.3 Hz, 2H), 3.37 (d, J=6.3 Hz, 2H), 3.21 (t, J=6.3 Hz, 2H), 3.03 (dd, J=14.7, 6.2 Hz, 2H), 2.81 (s, 6H), 2.57-2.52 (m, 2H), 1.37 (s, 10H).

Example 253

N1-(4-(2-Aminoethyl)phenyl)-N2,N2-dimethyl-ethane-1,2-diamine

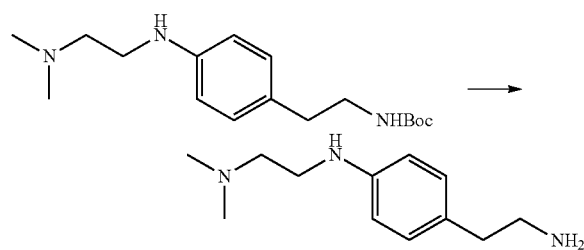

To a stirred mixture of tert-butyl 4-((2-(dimethylamino)ethyl)amino)phenethylcarbamate (200 mg, 0.65 mmol) in dioxane (10 mL) was added 4N HCl in dioxane (4 mL) at room temperature. The reaction mixture was stirred at room temperature for 4 h. TLC showed the reaction completed. The reaction mixture was concentrated in vacuo to afford the crude product, which was used for the next step directly.

Example 254

N5-(4-((2-(Dimethylamino)ethyl)amino)phenethyl)-2-(furan-2-yl)-[1,2,4]triazolo[1,5-a][1,3,5]triazine-5,7-diamine

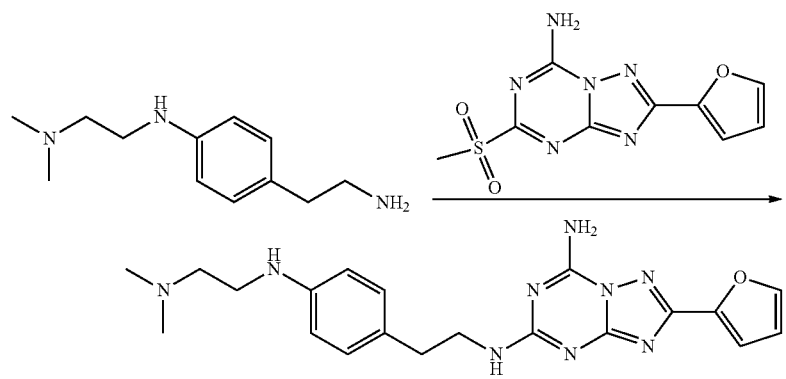

The reaction was carried out as in Example 5 to afford the title compound as white solid (106.2 mg, 40.2% yield). $^1$H NMR (500 MHz, DMSO-d6) δ: 8.19 (s, 2H), 7.87 (s, 1H), 7.46 (dd, J=26.0, 20.6 Hz, 1H), 7.06 (d, J=2.9 Hz, 1H), 6.96 (d, J=7.5 Hz, 2H), 6.68 (s, 1H), 6.53 (d, J=7.8 Hz, 2H), 5.19 (s, 1H), 3.44-3.37 (m, 2H), 3.06 (s, 2H), 2.71-2.63 (m, 2H), 2.43 (t, J=6.3 Hz, 2H), 2.18 (s, 6H).

Example 255

Methyl 2-(4-fluoropiperidin-1-yl)acetate

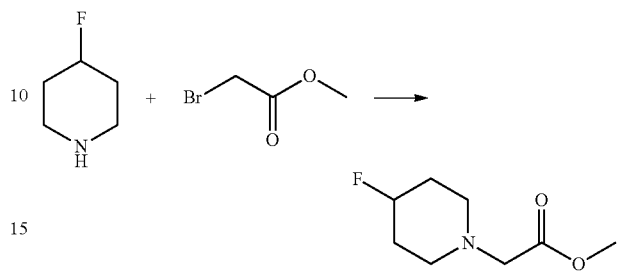

A mixture of 4-fluoropiperidine (279 mg, 2 mmol), methyl 2-bromoacetate (306 mg, 2 mmol) and potassium carbonate (829 mg, 6 mmol) in MeCN (10 mL) was stirred at 50° C. overnight. TLC showed the reaction completed. The reaction mixture was filtered. The filtrate was concentrated and purified by column chromatography to afford the title compound as yellow oil (260 mg, 74.3% yield). $^1$H NMR (500 MHz, DMSO-d6) δ: 4.66 (dtd, J=48.9, 7.1, 3.6 Hz, 1H), 3.60 (s, 3H), 3.23 (s, 2H), 2.61 (dd, J=11.5, 7.4 Hz, 2H), 2.43 (ddd, J=11.2, 7.4, 3.8 Hz, 2H), 1.89-1.75 (m, 2H), 1.73-1.63 (m, 2H).

Example 256

2-(4-Fluoropiperidin-1-yl)acetic acid

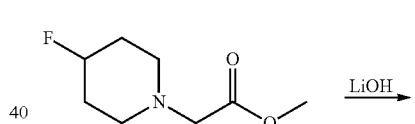

-continued

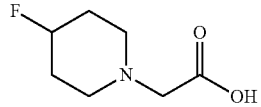

A mixture of methyl 2-(4-fluoropiperidin-1-yl)acetate (260 mg, 1.48 mmol) and LiOH (178 mg, 7.42 mmol) in methanol (9 mL) and water (1 mL) was stirred at room temperature overnight. TLC showed the reaction completed. The reaction mixture was concentrated in vacuo to afford the crude product, which was used for the next step directly.

Example 257 tert-Butyl 4-(2-(4-fluoropiperidin-1-yl)acetamido)phenethylcarbamate

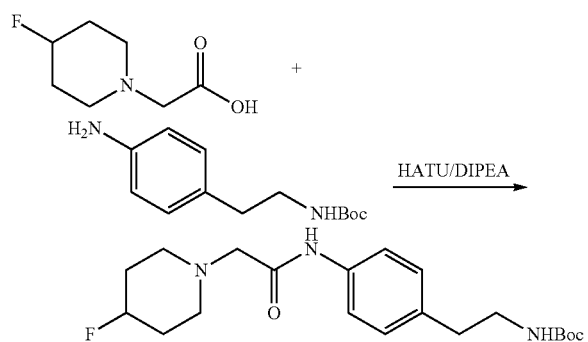

A mixture of 2-(4-fluoropiperidin-1-yl)acetic acid (239 mg, 1.48 mmol), HATU (619 mg, 1.63 mmol) and DIPEA (524 mg, 4.44 mmol) in DCM (10 mL) and DMF (10 mL) was stirred at room temperature for 0.5 h. Then tert-butyl 4-aminophenethylcarbamate (350 mg, 1.48 mmol) was added and the reaction was stirred at room temperature overnight. TLC showed the reaction completed. The reaction mixture was concentrated and purified by column chromatography to afford the title compound as yellow solid (400 mg, 71.3% yield). $^1$H NMR (500 MHz, DMSO-d6) δ: 10.38 (s, 1H), 7.50 (d, J=8.3 Hz, 2H), 7.18 (t, J=8.5 Hz, 2H), 6.87 (d, J=5.5 Hz, 1H), 4.92 (d, J=52.6 Hz, 1H), 3.95 (dd, J=34.1, 9.3 Hz, 1H), 3.11 (dd, J=13.9, 6.5 Hz, 5H), 2.81 (d, J=79.7 Hz, 1H), 2.65 (t, J=7.4 Hz, 2H), 2.20-1.99 (m, 4H), 1.91 (s, 1H), 1.36 (s, 10H).

Example 258

N-(4-(2-Aminoethyl)phenyl)-2-(4-fluoropiperidin-1-yl)acetamide

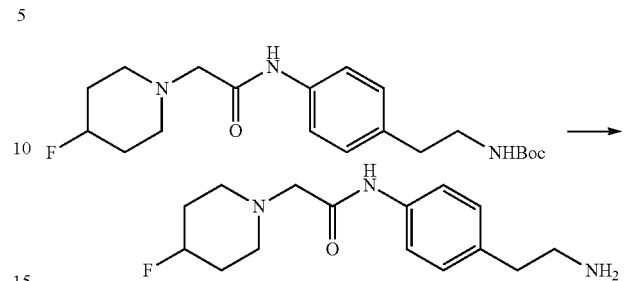

To a stirred mixture of tert-butyl 4-(2-(4-fluoropiperidin-1-yl)acetamido)phenethyl-carbamate (200 mg, 0.53 mmol) in dioxane (10 mL) was added 4N HCl in dioxane (3 mL) at room temperature. The reaction mixture was stirred at room temperature for 4 h. TLC showed the reaction completed. The reaction mixture was concentrated in vacuo to afford the crude product, which was used for the next step directly.

Example 259

N-(4-(2-((7-Amino-2-(furan-2-yl)-[1,2,4]triazolo[1,5-a][1,3,5]triazin-5-yl)amino)ethyl)-phenyl)-2-(4-fluoropiperidin-1-yl)acetamide

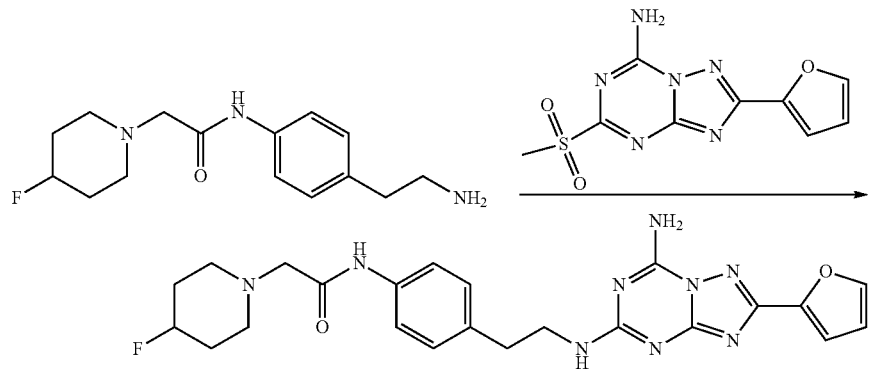

The reaction was carried out as in Example 5 to afford the title compound as white solid (58.7 mg, 23.3% yield). $^1$H NMR (500 MHz, DMSO-d6) δ: 9.62 (s, 1H), 8.27 (d, J=149.5 Hz, 2H), 7.86 (s, 1H), 7.60-7.41 (m, 3H), 7.19 (d, J=8.2 Hz, 2H), 7.05 (dd, J=3.4, 0.7 Hz, 1H), 6.67 (d, J=1.5 Hz, 1H), 4.81-4.60 (m, 1H), 3.46 (dd, J=13.4, 6.6 Hz, 2H), 3.11 (s, 2H), 2.81 (t, J=7.4 Hz, 2H), 2.64 (s, 2H), 2.47 (d, J=11.2 Hz, 2H), 1.96-1.85 (m, 2H), 1.79 (ddd, J=9.6, 8.6, 5.6 Hz, 2H).

Example 260 tert-Butyl 4-(bis(2-methoxyethyl)amino)phenethylcarbamate

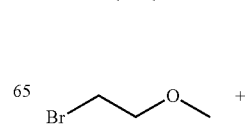

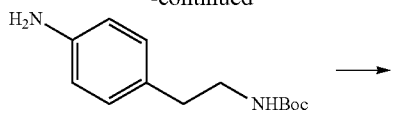

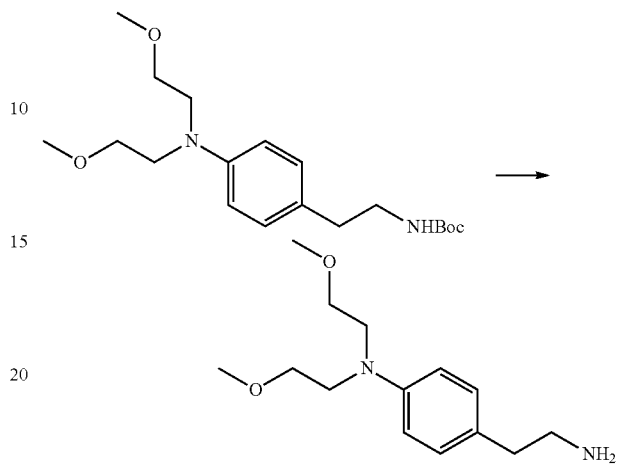

Example 261

4-(2-Aminoethyl)-N,N-bis(2-methoxyethyl)aniline

A mixture of 1-bromo-2-methoxyethane (1.39 g, 10 mmol), tert-butyl 4-aminophenethylcarbamate (473 mg, 2 mmol), potassium carbonate (1.1 g, 8 mmol) and NaI (150 mg, 1 mmol) in DMF (15 mL) was stirred at 120° C. for 2 days. TLC showed the reaction completed. The reaction mixture was filtered. The filtrate was concentrated and purified by column chromatography to afford the title compound as yellow oil (150 mg, 4.3% yield).

To a stirred mixture of tert-butyl 4-(bis(2-methoxyethyl)amino)phenethylcarbamate (150 mg, 0.43 mmol) in dioxane (6 mL) was added 4N HCl in dioxane (2 mL) at room temperature. The reaction mixture was stirred at room temperature for 4 h. TLC showed the reaction completed. The reaction mixture was concentrated in vacuo to afford the crude product, which was used for the next step directly.

Example 262

N5-(4-(Bis(2-methoxyethyl)amino)phenethyl)-2-(furan-2-yl)-[1,2,4]triazolo[1,5-a][1,3,5]triazine-5,7-diamine

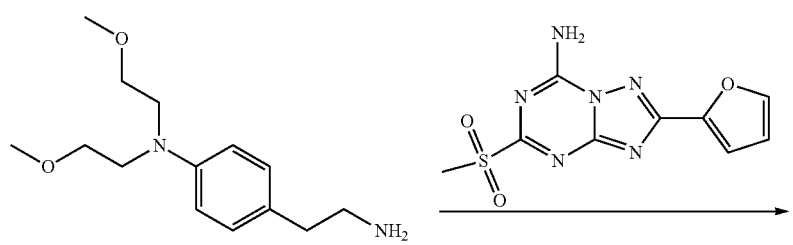

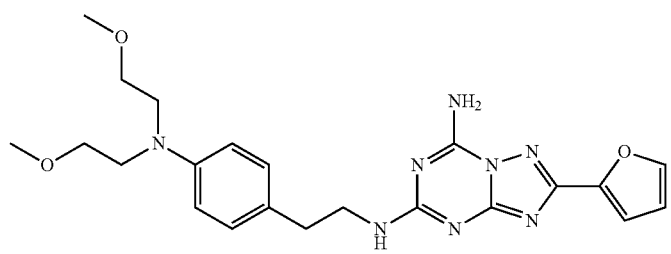

The reaction was carried out as in Example 5 to afford the title compound as white solid (16.9 mg, 8.7% yield). $^1$H NMR (500 MHz, DMSO-d6) δ: 8.30 (d, J=121.9 Hz, 2H), 7.87 (s, 1H), 7.46 (dd, J=25.6, 20.3 Hz, 1H), 7.04 (dd, J=14.7, 5.7 Hz, 3H), 6.69-6.60 (m, 3H), 3.46 (dd, J=7.0, 4.0 Hz, 10H), 3.25 (s, 6H), 2.73-2.67 (m, 2H); LC-MS (m/z): 453.2 [M+H]$^+$ Example 263 tert-Butyl 4-(2-(pyrrolidin-1-yl)acetamido)phenethylcarbamate

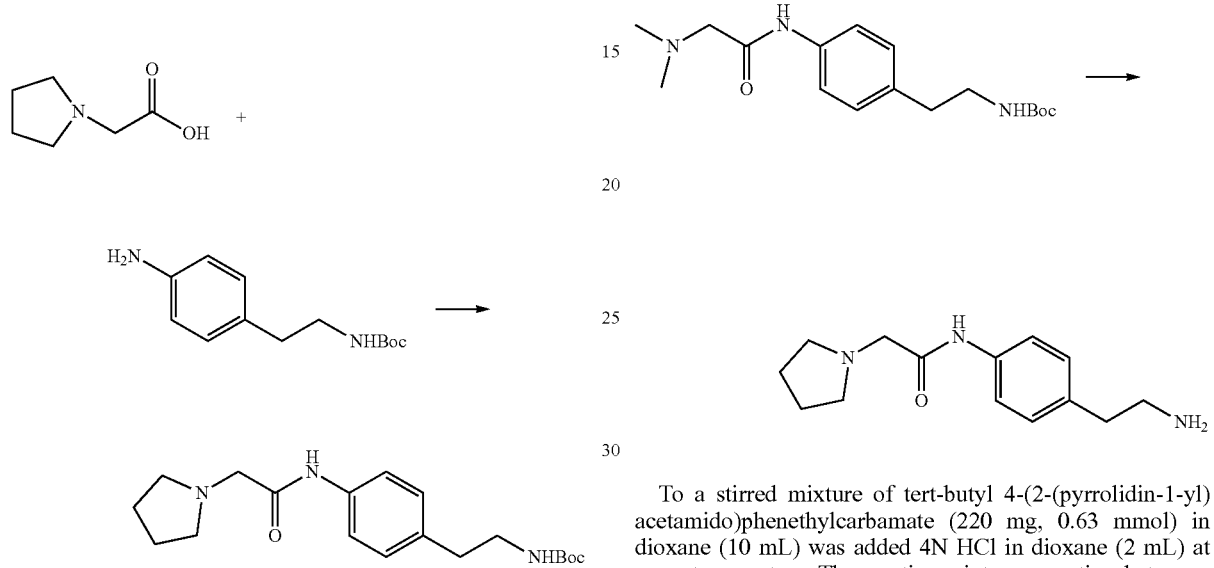

A mixture of 2-(pyrrolidin-1-yl)acetic acid (194 mg, 1.5 mmol), HATU (627 mg, 1.65 mmol) and DIPEA (582 mg, 4.5 mmol) in DCM (10 mL) was stirred at room temperature for 0.5 h. Then tert-butyl 4-aminophenethylcarbamate (354 mg, 1.5 mmol) was added and the reaction was stirred at room temperature overnight. TLC showed the reaction completed. The reaction mixture was concentrated and purified by column chromatography to afford the title compound as yellow solid (220 mg, 42.3% yield). $^1$H NMR (500 MHz, DMSO-d6) δ: 9.74 (s, 1H), 7.53 (d, J=8.3 Hz, 2H), 7.12 (d, J=8.3 Hz, 2H), 6.86 (t, J=5.3 Hz, 1H), 3.37 (s, 2H), 3.10 (dd, J=13.9, 6.5 Hz, 2H), 2.70 (d, J=3.3 Hz, 4H), 2.66-2.60 (m, 2H), 1.78 (dd, J=6.1, 3.0 Hz, 4H), 1.37 (s, 9H).

Example 264

N-(4-(2-Aminoethyl)phenyl)-2-(pyrrolidin-1-yl)acetamide

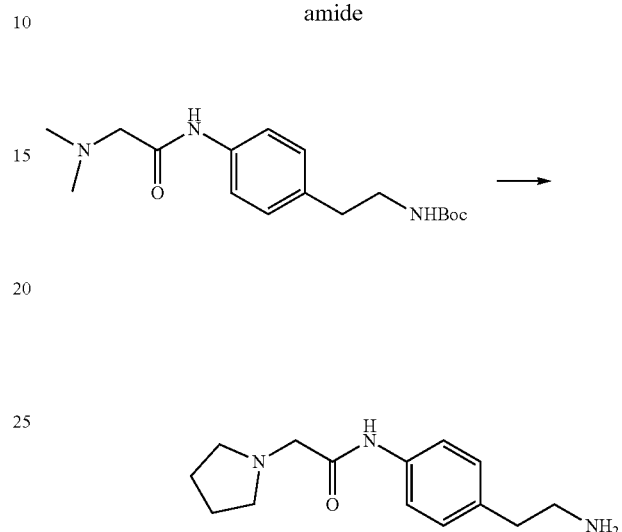

To a stirred mixture of tert-butyl 4-(2-(pyrrolidin-1-yl)acetamido)phenethylcarbamate (220 mg, 0.63 mmol) in dioxane (10 mL) was added 4N HCl in dioxane (2 mL) at room temperature. The reaction mixture was stirred at room temperature for 4 h. TLC showed the reaction completed. The reaction mixture was concentrated in vacuo to afford the crude product, which was used for the next step directly.

Example 265

N-(4-(2-((7-Amino-2-(furan-2-yl)-[1,2,4]triazolo[1,5-a][1,3,5]triazin-5-yl)amino)ethyl)-phenyl)-2-(pyrrolidin-1-yl)acetamide

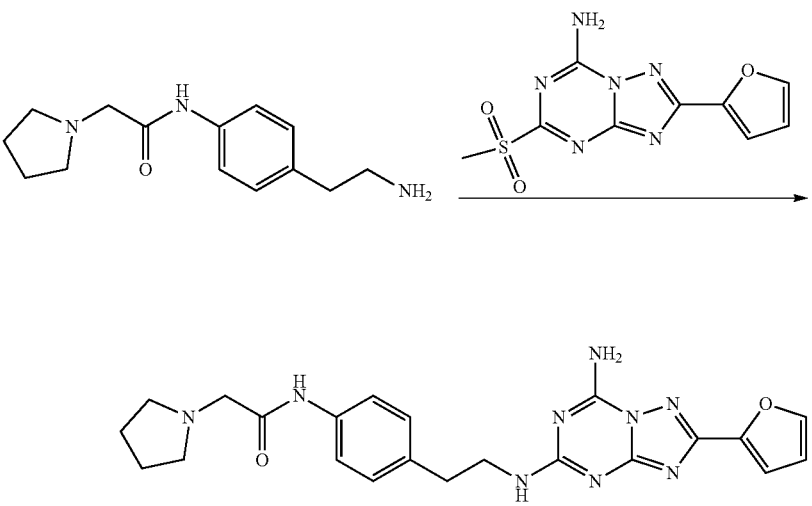

The reaction was carried out as in Example 5 to afford the title compound as white solid (47.3 mg, 16.8% yield). $^1$H NMR (500 MHz, DMSO-d6) δ: 9.60 (s, 1H), 8.27 (d, J=148.6 Hz, 2H), 7.86 (s, 1H), 7.62-7.40 (m, 3H), 7.18 (d, J=8.1 Hz, 2H), 7.05 (d, J=3.3 Hz, 1H), 6.67 (s, 1H), 3.46 (dd, J=13.1, 6.7 Hz, 2H), 3.22 (s, 2H), 2.81 (t, J=7.4 Hz, 2H), 2.59 (s, 4H), 1.74 (dt, J=6.4, 3.1 Hz, 4H).

Example 266

Methyl 2-(4,4-difluoropiperidin-1-yl)acetate

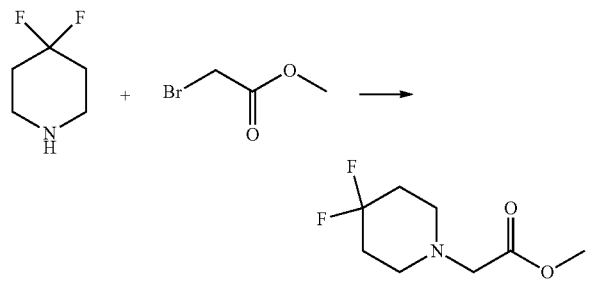

A mixture of 4,4-difluoropiperidine (315 mg, 2 mmol), methyl 2-bromoacetate (306 mg, 2 mmol) and potassium carbonate (829 mg, 6 mmol) in MeCN (10 mL) was stirred at 50° C. overnight. TLC showed the reaction completed. The reaction mixture was filtered. The filtrate was concentrated and purified by column chromatography to afford the title compound as yellow oil (320 mg, 82.9% yield). $^1$H NMR (500 MHz, DMSO-d6) δ: 3.62 (s, 3H), 3.34 (s, 2H), 2.68-2.63 (m, 4H), 1.94 (ddd, J=14.1, 13.0, 5.8 Hz, 4H).

Example 267

2-(4,4-Difluoropiperidin-1-yl)acetic acid

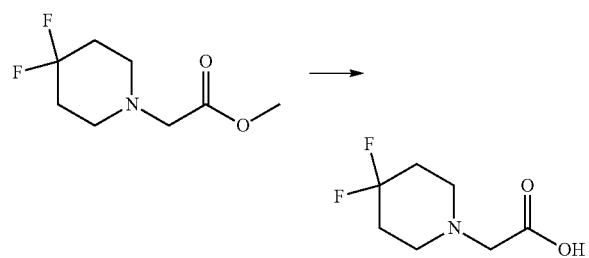

A mixture of methyl 2-(4,4-difluoropiperidin-1-yl)acetate (300 mg, 1.55 mmol) and LiOH (186 mg, 7.75 mmol) in MeOH (9 mL) and H$_2$O (1 mL) was stirred at room temperature overnight. TLC showed the reaction completed. The reaction mixture was concentrated in vacuo to afford the crude product, which was used for the next step directly.

Example 268 tert-Butyl 4-(2-(4,4-difluoropiperidin-1-yl)acetamido)phenethylcarbamate

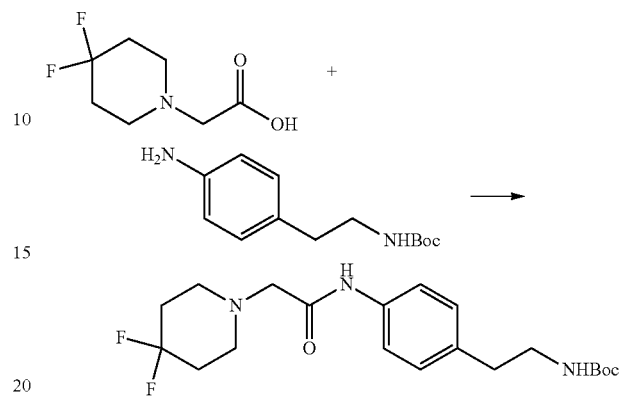

A mixture of 2-(4,4-difluoropiperidin-1-yl)acetic acid (277 mg, 1.55 mmol), HATU (648 mg, 1.71 mmol) and DIPEA (601 mg, 4.65 mmol) in DMF (10 mL) was stirred at room temperature for 0.5 h. Then tert-butyl 4-aminophenethylcarbamate (366 mg, 1.55 mmol) was added and the reaction was stirred at room temperature overnight. TLC showed the reaction completed. The reaction mixture was concentrated and purified by column chromatography to afford the title compound as yellow solid (70 mg, 11.4% yield).

Example 269

N-(4-(2-Aminoethyl)phenyl)-2-(4,4-difluoropiperidin-1-yl)acetamide

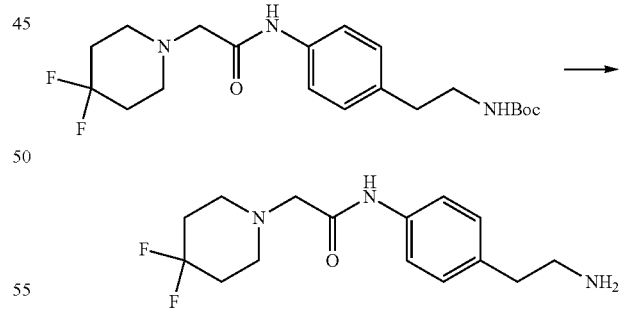

To a stirred mixture of tert-butyl 4-(2-(4,4-difluoropiperidin-1-yl)acetamido)phenethyl-carbamate (65 mg, 0.16 mmol) in dioxane (5 mL) was added 4N HCl in dioxane (2 mL) at room temperature. The reaction mixture was stirred at room temperature overnight. TLC showed the reaction completed. The reaction mixture was concentrated in vacuo to afford the crude product, which was used for the next step directly.

Example 270

N-(4-(2-((7-Amino-2-(furan-2-yl)-[1,2,4]triazolo[1,5-a][1,3,5]triazin-5-yl)amino)ethyl)-phenyl)-2-(4,4-difluoropiperidin-1-yl)acetamide

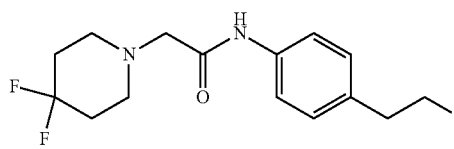
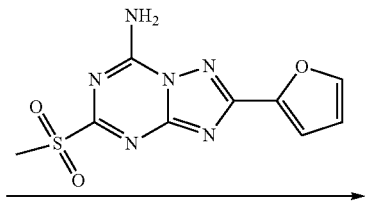
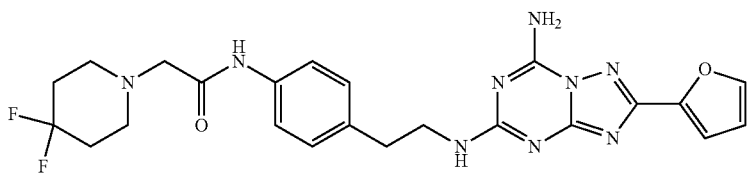

The reaction was carried out as in Example 5 to afford the title compound as white solid (13.3 mg, 16.7% yield). ¹H NMR (500 MHz, DMSO-d6) δ: 9.60 (s, 1H), 8.27 (d, J=148.6 Hz, 2H), 7.86 (s, 1H), 7.62-7.40 (m, 3H), 7.18 (d, J=8.1 Hz, 2H), 7.05 (d, J=3.3 Hz, 1H), 6.67 (s, 1H), 3.46 (dd, J=13.1, 6.7 Hz, 2H), 3.22 (s, 2H), 2.81 (t, J=7.4 Hz, 2H), 2.59 (s, 4H), 1.74 (dt, J=6.4, 3.1 Hz, 4H).

Example 271 tert-Butyl 4-(isonicotinamido)phenethylcarbamate

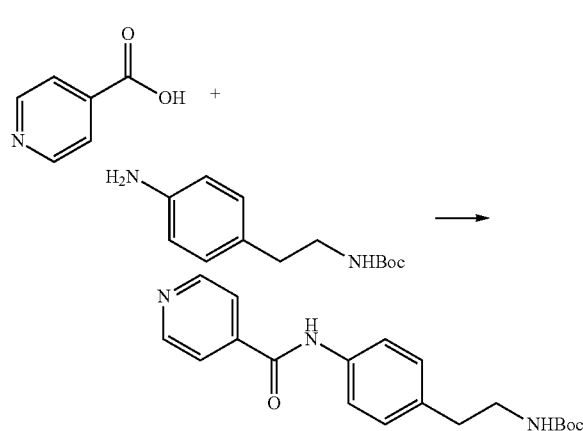

A mixture of isonicotinic acid (246 mg, 2 mmol), HATU (837 mg, 2.2 mmol) and DIPEA (775 mg, 6 mmol) in DCM (10 mL) was stirred at room temperature for 0.5 h. Then tert-butyl 4-aminophenethylcarbamate (378 mg, 1.6 mmol) was added and the reaction was stirred at room temperature overnight. TLC showed the reaction completed. The reaction mixture was concentrated and purified by column chromatography to afford the title compound as yellow solid (300 mg, 43.9% yield). ¹H NMR (500 MHz, DMSO-d6) δ: 10.45 (s, 1H), 8.79 (dd, J=4.5, 1.5 Hz, 2H), 7.86 (dd, J=4.5, 1.4 Hz, 2H), 7.68 (d, J=8.3 Hz, 2H), 7.20 (d, J=8.4 Hz, 2H), 6.90 (t, J=5.4 Hz, 1H), 3.13 (dd, J=13.9, 6.5 Hz, 2H), 2.68 (t, J=7.5 Hz, 2H), 1.38 (s, 9H).

Example 272

N-(4-(2-Aminoethyl)phenyl)isonicotinamide

To a stirred mixture of tert-butyl 4-(isonicotinamido)phenethylcarbamate (300 mg, 0.88 mmol) in dioxane (10 mL) was added 4N HCl in dioxane (5 mL) at room temperature. The reaction mixture was stirred at room temperature for 4 h. TLC showed the reaction completed. The reaction mixture was concentrated in vacuo to afford the crude product, which was used for the next step directly.

Example 273

N-(4-(2-((7-Amino-2-(furan-2-yl)-[1,2,4]triazolo[1,5-a][1,3,5]triazin-5-yl)amino)ethyl)-phenyl)isonicotinamide

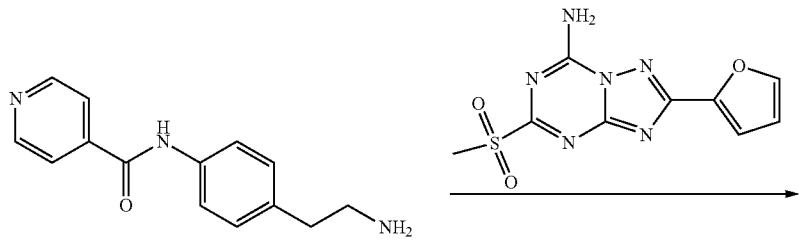

temperature overnight. TLC showed the reaction completed. The reaction mixture was concentrated and purified by column chromatography to afford the title compound as yellow solid (400 mg, 56.3% yield). $^1$H NMR (500 MHz, DMSO-d6) δ: 10.20 (s, 1H), 8.53-8.45 (m, 2H), 7.53-7.46

The reaction was carried out as in Example 5 to afford the title compound as white solid (13.3 mg, 3.4% yield). $^1$H NMR (500 MHz, DMSO-d6) δ: 10.44 (s, 1H), 8.79 (s, 2H), 8.28 (d, J=145.0 Hz, 2H), 7.86 (s, 3H), 7.70 (d, J=7.1 Hz, 2H), 7.52 (d, J=43.1 Hz, 1H), 7.27 (s, 2H), 7.06 (s, 1H), 6.68 (s, 1H), 3.51 (s, 2H), 2.86 (s, 2H).

Example 274 tert-Butyl 4-(2-(pyridin-4-yl)acetamido)phenethylcarbamate

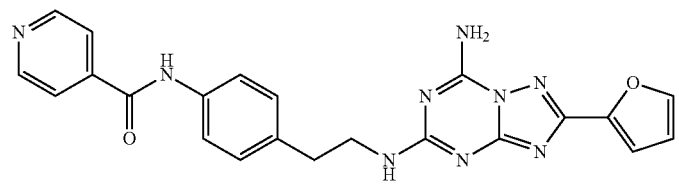

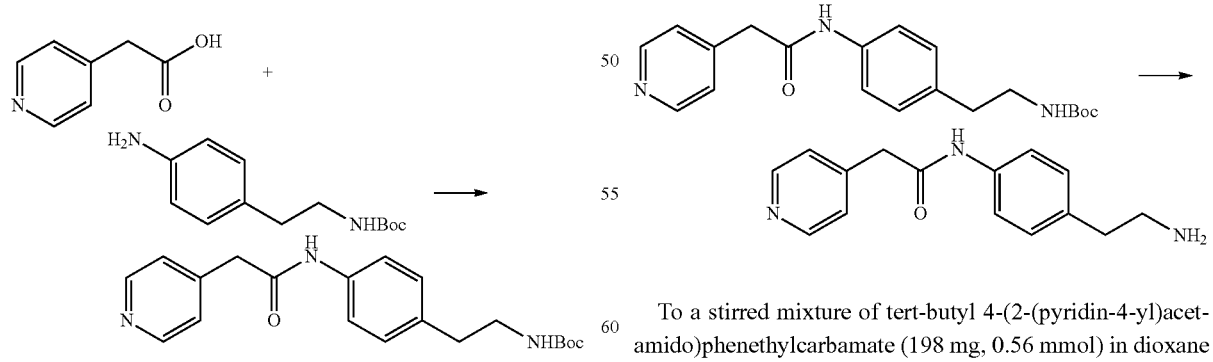

A mixture of 2-(pyridin-4-yl)acetic acid (347 mg, 2 mmol), HATU (837 mg, 2.2 mmol) and DIPEA (775 mg, 6 mmol) in DCM (10 mL) was stirred at room temperature for 0.5 h. Then tert-butyl 4-aminophenethylcarbamate (378 mg, 1.6 mmol) was added and the reaction was stirred at room temperature overnight. TLC showed the reaction completed. The reaction mixture was concentrated and purified by column chromatography to afford the title compound as yellow solid (400 mg, 56.3% yield). (m, 2H), 7.35 (d, J=5.9 Hz, 2H), 7.12 (d, J=8.4 Hz, 2H), 6.86 (s, 1H), 3.69 (s, 2H), 3.14-3.02 (m, 2H), 2.69-2.58 (m, 2H), 1.36 (s, 9H).

Example 275

N-(4-(2-Aminoethyl)phenyl)-2-(pyridin-4-yl)acetamide

To a stirred mixture of tert-butyl 4-(2-(pyridin-4-yl)acetamido)phenethylcarbamate (198 mg, 0.56 mmol) in dioxane (10 mL) was added 4N HCl in dioxane (2 mL) at room temperature. The reaction mixture was stirred at room temperature overnight. TLC showed the reaction completed. The reaction mixture was concentrated in vacuo to afford the crude product, which was used for the next step directly.

Example 276

N-(4-(2-((7-Amino-2-(furan-2-yl)-[1,2,4]triazolo[1,5-a][1,3,5]triazin-5-yl)amino)ethyl)-phenyl)-2-(pyridin-4-yl)acetamide

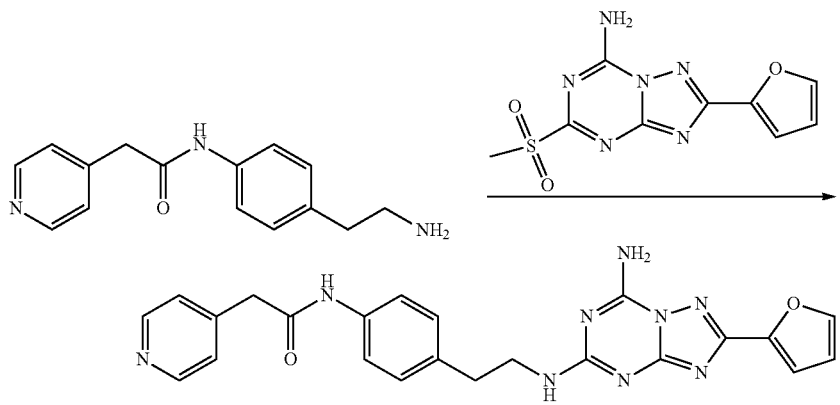

The reaction was carried out as in Example 5 to afford the title compound as white solid (9.7 mg, 8.2% yield). $^1$H NMR (500 MHz, DMSO-d6) δ: 10.22 (s, 1H), 8.55 (d, J=4.7 Hz, 2H), 8.16 (s, 2H), 7.87 (s, 1H), 7.56-7.41 (m, 5H), 7.19 (d, J=7.6 Hz, 2H), 7.06 (s, 1H), 6.68 (s, 1H), 3.74 (s, 2H), 3.46 (d, J=6.1 Hz, 2H), 2.80 (d, J=7.0 Hz, 2H).

Example 277

N-(4-(2-((7-Amino-2-(furan-2-yl)-[1,2,4]triazolo[1,5-a][1,3,5]triazin-5-yl)amino)ethyl)-phenyl)-2-(pyridin-3-yl)acetamide

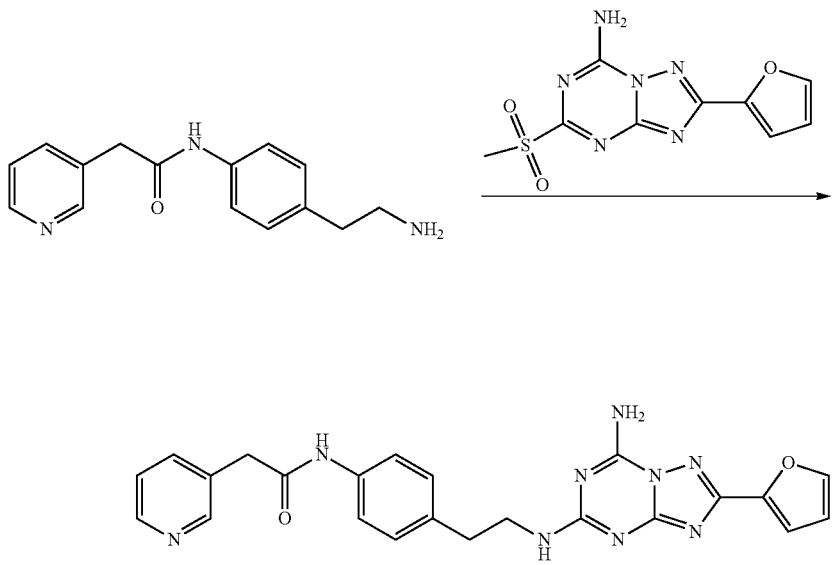

The title compound was prepared in a similar way as the title compound in Example 276. $^1$H NMR (500 MHz, DMSO-d6) δ: 10.22 (s, 1H), 8.52 (dd, J=18.5, 14.9 Hz, 2H), 8.19 (s, 2H), 7.89-7.81 (m, 2H), 7.58-7.39 (m, 4H), 7.20 (t, J=8.0 Hz, 2H), 7.06 (d, J=3.2 Hz, 1H), 6.68 (d, J=1.5 Hz, 1H), 3.73 (s, 2H), 3.48-3.44 (m, 2H), 2.80 (t, J=7.4 Hz, 2H).

Example 278

N-(4-(2-((7-Amino-2-(furan-2-yl)-[1,2,4]triazolo[1,5-a][1,3,5]triazin-5-yl)amino)ethyl)-phenyl)nicotinamide

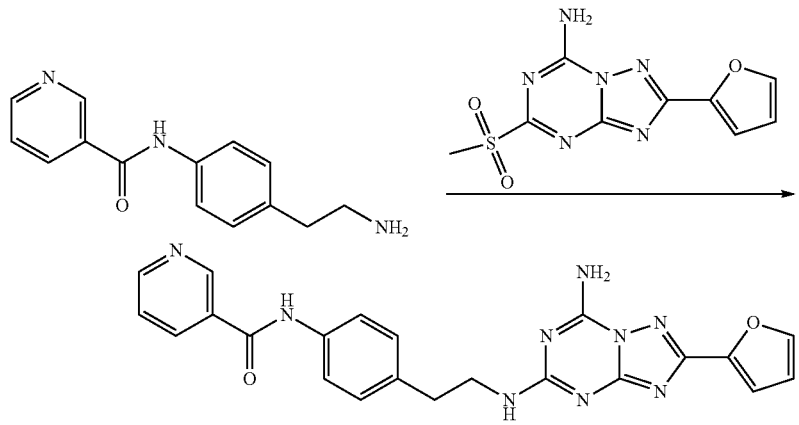

The title compound was prepared in a similar way as the title compound in Example 273. ¹H NMR (500 MHz, DMSO-d6) δ: 10.44 (s, 1H), 9.12 (s, 1H), 8.78 (d, J=4.5 Hz, 1H), 8.41 (t, J=57.2 Hz, 3H), 7.89 (s, 1H), 7.75-7.51 (m, 4H), 7.27 (t, J=8.2 Hz, 2H), 7.08 (s, 1H), 6.69 (s, 1H), 3.52 (s, 2H), 2.89-2.79 (m, 2H).

Example 279

(R)-(1-(Pyridin-3-ylmethyl)pyrrolidin-3-yl)methanol

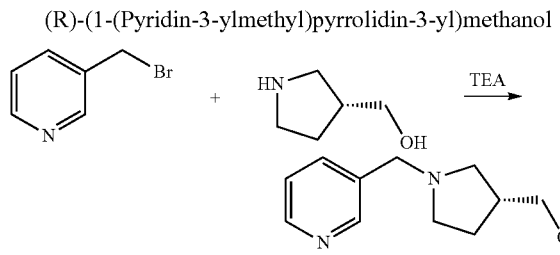

A mixture of 3-(bromomethyl)pyridine (506 mg, 2 mmol), (R)-pyrrolidin-3-ylmethanol (202 mg, 2 mmol) and TEA (607 mg, 6 mmol) in DCM (15 mL) was stirred at room temperature for 1.5 h. TLC showed the reaction completed. The reaction mixture was concentrated in vacuo to afford the crude product, which was used for the next step directly.

Example 280

(R)-(1-(Pyridin-3-ylmethyl)pyrrolidin-3-yl)methyl methanesulfonate

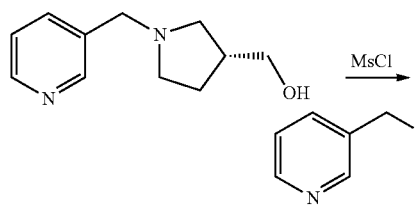

To a stirred mixture of (R)-(1-(pyridin-3-ylmethyl)pyrrolidin-3-yl)methanol (385 mg, 2 mmol) in DCM (15 mL) was added MsCl (251 mg, 2.2 mmol) at room temperature. The reaction mixture was stirred at room temperature for 2 h. TLC showed the reaction completed. The reaction mixture was concentrated in vacuo to afford the crude product, which was used for the next step directly.

Example 281

(R)-tert-Butyl 4-((1-(pyridin-3-ylmethyl)pyrrolidin-3-yl)methoxy)phenethylcarbamate A mixture of (R)-(1-(pyridin-3-ylmethyl)pyrrolidin-3-yl)methyl methanesulfonate (310 mg, 1.15 mmol), tert-butyl 4-hydroxyphenethylcarbamate (218 g, 0.82 mmol) and cesium carbonate (1.12 g, 3.45 mmol) in acetone (10 mL) was stirred at 50° C. overnight. TLC showed the reaction completed. The reaction mixture was filtered. The filtrate was concentrated and purified by column chromatography to afford the title compound as white solid (120 mg, 25.4% yield).

Example 282

(R)-2-(4-((1-(Pyridin-3-ylmethyl)pyrrolidin-3-yl)methoxy)phenyl)ethanamine

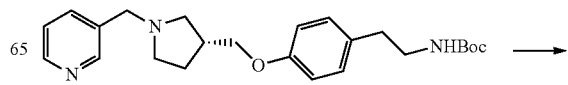

167

-continued

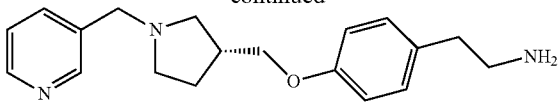

To a stirred mixture of (R)-tert-butyl 4-((1-(pyridin-3-ylmethyl)pyrrolidin-3-yl)methoxy)phenethylcarbamate (100 mg, 0.24 mmol) in dioxane (4 mL) was added 4N HCl in dioxane (2 mL) at room temperature. The reaction mixture was stirred at room temperature for 4 h. TLC showed the reaction completed. The reaction mixture was concentrated in vacuo to afford the crude product, which was used for the next step directly.

Example 283

(S)-2-(Furan-2-yl)-N5-(4-((1-(pyridin-3-ylmethyl)pyrrolidin-3-yl)methoxy)phenethyl)-[1,2,4]triazolo[1,5-a][1,3,5]triazine-5,7-diamine

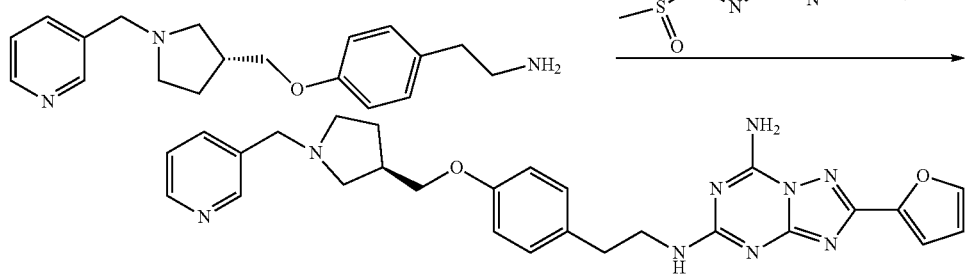

The reaction was carried out as in example 5 to afford the title compound as white solid (37.4 mg, 30.7% yield). $^1$H NMR (500 MHz, DMSO-d6) δ: 8.53 (s, 1H), 8.47 (d, J=4.3 Hz, 1H), 8.16 (s, 2H), 7.87 (s, 1H), 7.75 (d, J=7.5 Hz, 1H), 7.46 (dd, J=25.2, 19.8 Hz, 1H), 7.36 (dd, J=7.6, 4.9 Hz, 1H), 7.14 (d, J=8.0 Hz, 2H), 7.06 (d, J=3.3 Hz, 1H), 6.85 (d, J=8.2 Hz, 2H), 6.68 (s, 1H), 3.87-3.81 (m, 2H), 3.69 (s, 2H), 3.49-3.41 (m, 4H), 2.81-2.74 (m, 2H), 2.71-2.54 (m, 4H), 2.44 (s, 1H); LC-MS (m/z): 512.2 [M+H]$^+$ Example 284

2-(Furan-2-yl)-N5-(4-(2-(methyl(pyridin-3-ylmethyl)amino)ethoxy)phenethyl)-[1,2,4]triazolo[1,5-a][1,3,5]triazine-5,7-diamine

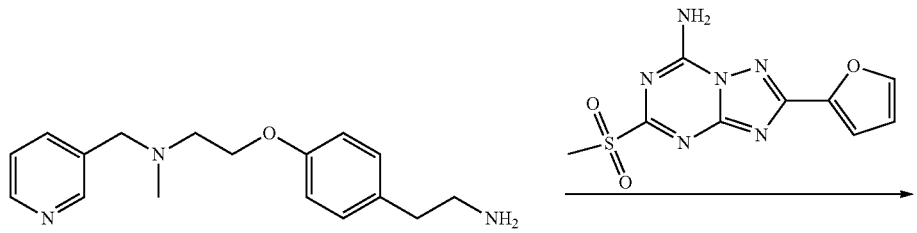

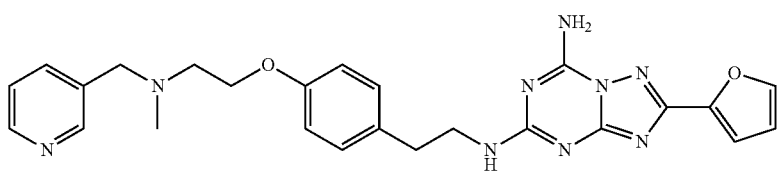

The title compound was prepared in a similar way as the title compound in Example 283. ¹H NMR (500 MHz, DMSO-d6) δ: 8.50 (s, 1H), 8.46 (d, J=3.5 Hz, 1H), 8.20 (s, 2H), 7.87 (s, 1H), 7.72 (d, J=7.8 Hz, 1H), 7.56-7.44 (m, 1H), 7.35 (dd, J=7.7, 4.8 Hz, 1H), 7.16 (t, J=7.3 Hz, 2H), 7.06 (d, J=3.3 Hz, 1H), 6.87 (d, J=8.5 Hz, 2H), 6.68 (dd, J=3.2, 1.7 Hz, 1H), 4.07 (t, J=5.8 Hz, 2H), 3.60 (s, 2H), 3.47-3.42 (m, 2H), 2.76 (dt, J=11.6, 6.8 Hz, 4H), 2.23 (s, 3H); LC-MS (m/z): 486.2[M+H]⁺

Example 285

N-(4-(2-((7-Amino-2-(furan-2-yl)-[1,2,4]triazolo[1,5-a][1,3,5]triazin-5-yl)amino)ethyl)-phenyl)-4-methyltetrahydro-2H-pyran-4-carboxamide

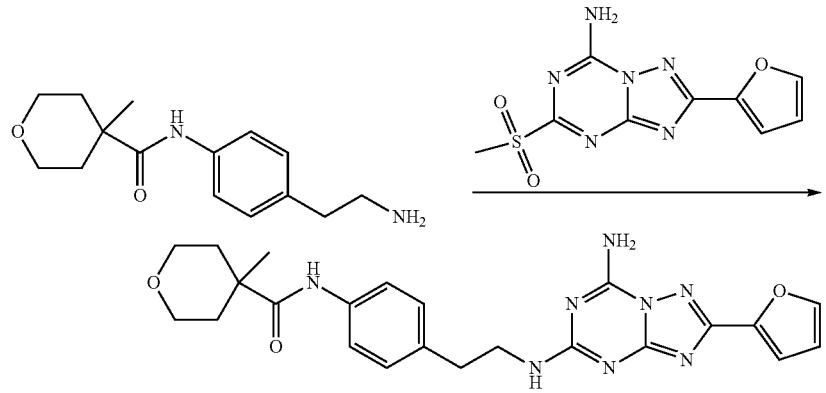

The title compound was prepared in a similar way as the title compound in Example 278. ¹H NMR (500 MHz, DMSO-d6) δ: 9.27 (s, 1H), 8.34 (d, J=125.5 Hz, 2H), 7.87 (s, 1H), 7.63-7.44 (m, 3H), 7.18 (t, J=7.9 Hz, 2H), 7.06 (d, J=3.3 Hz, 1H), 6.76-6.60 (m, 1H), 3.67 (dt, J=8.9, 4.1 Hz, 2H), 3.44 (dd, J=14.6, 5.6 Hz, 4H), 2.87-2.72 (m, 2H), 2.08 (d, J=14.0 Hz, 2H), 1.47 (ddd, J=13.2, 9.2, 3.7 Hz, 2H), 1.25 (s, 3H); LC-MS (m/z): 463.2 [M+H]⁺

Example 286

2-(Furan-2-yl)-N5-(4-(2-(4-methyl-1,4-diazepan-1-yl)ethoxy)phenethyl)-[1,2,4]triazolo[1,5-a][1,3,5]triazine-5,7-diamine

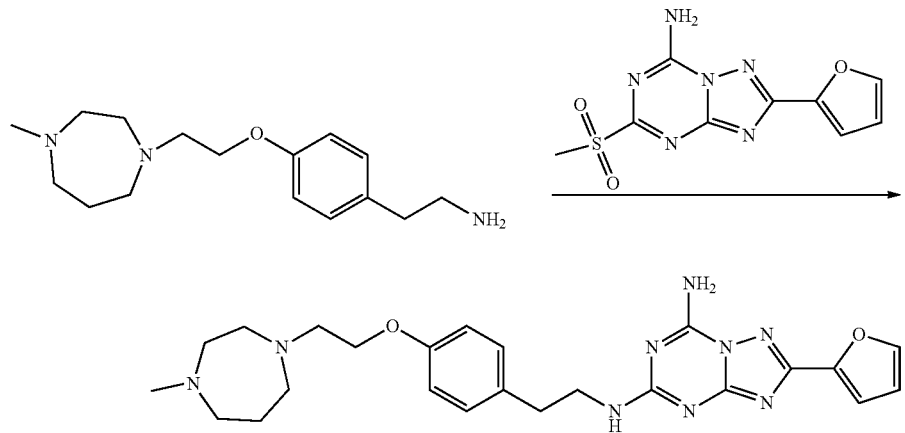

The title compound was prepared in a similar way as the title compound in Example 204. $^1$H NMR (500 MHz, DMSO-d6) δ: 8.25 (t, J=93.1 Hz, 2H), 7.88 (s, 1H), 7.53 (d, J=37.2 Hz, 1H), 7.16 (d, J=7.3 Hz, 2H), 7.06 (s, 1H), 6.87 (d, J=7.4 Hz, 2H), 6.68 (s, 1H), 4.01 (d, J=5.5 Hz, 2H), 3.44 (d, J=6.5 Hz, 2H), 2.89-2.73 (m, 12H), 2.42 (s, 3H), 1.78 (s, 2H); LC-MS (m/z): 478.2 [M+H]$^+$ Example 287

N5-(4-(2-(7,8-Dihydro-1,6-naphthyridin-6(5H)-yl)ethoxy)phenethyl)-2-(furan-2-yl)-[1,2,4]triazolo[1,5-a][1,3,5]triazine-5,7-diamine

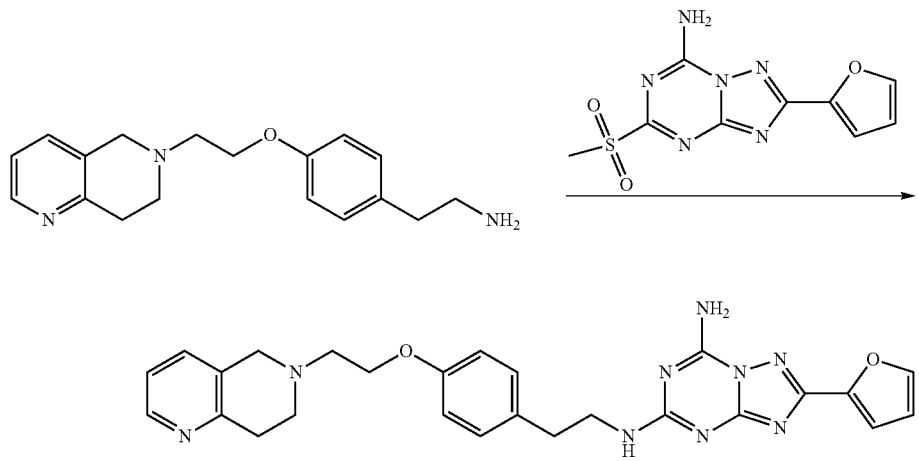

The title compound was prepared in a similar way as the title compound in Example 204. $^1$H NMR (500 MHz, DMSO-d6) δ: 8.25 (dd, J=83.8, 36.3 Hz, 3H), 7.88 (s, 1H), 7.58 (t, J=5.4 Hz, 1H), 7.52-7.44 (m, 2H), 7.16 (dt, J=7.6, 5.8 Hz, 3H), 7.06 (d, J=3.2 Hz, 1H), 6.91 (d, J=8.4 Hz, 2H), 6.68 (dd, J=3.3, 1.8 Hz, 1H), 4.14 (t, J=5.4 Hz, 2H), 3.70 (s, 2H), 3.47-3.41 (m, 2H), 2.89 (s, 6H), 2.81-2.75 (m, 2H); LC-MS (m/2z): 249.8 [M+H]$^+$ Example 288

2-(Furan-2-yl)-N5-(4-((2-(pyrrolidin-1-yl)ethyl)amino)phenethyl)-[1,2,4]triazolo[1,5-a][1,3,5]triazine-5,7-diamine

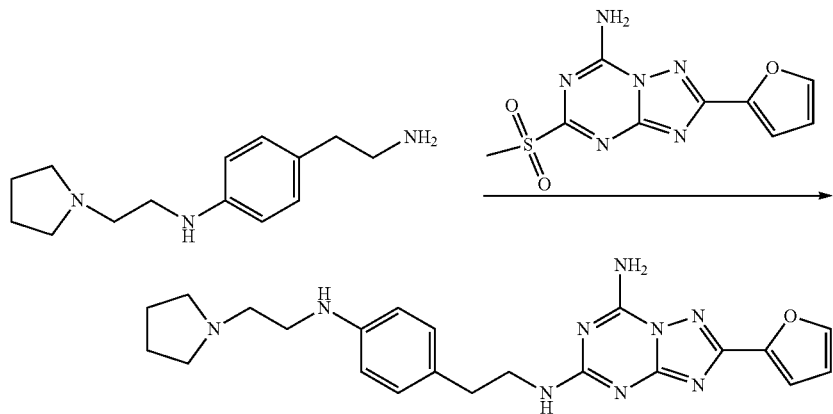

The title compound was prepared in a similar way as the title compound in Example 254. ¹H NMR (500 MHz, DMSO-d6) δ: 8.29 (d, J=126.7 Hz, 2H), 7.87 (s, 1H), 7.43 (dd, J=25.2, 19.8 Hz, 1H), 7.05 (d, J=3.2 Hz, 1H), 6.96 (d, J=8.1 Hz, 2H), 6.67 (d, J=1.5 Hz, 1H), 6.53 (d, J=8.1 Hz, 2H), 5.27 (s, 1H), 3.43-3.37 (m, 2H), 3.10 (s, 2H), 2.67 (dd, J=19.8, 12.6 Hz, 4H), 2.51 (s, 4H), 1.70 (s, 4H); LC-MS (m/z): 434.3 [M+H]⁺

Example 289

N5-(4-(2,5,8,11-Tetraoxatridecan-13-ylamino)phenethyl)-2-(furan-2-yl)-[1,2,4]triazolo[1,5-a][1,3,5]triazine-5,7-diamine

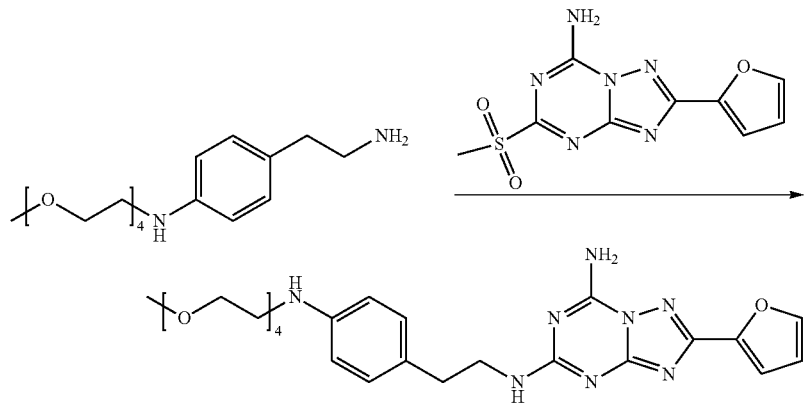

The title compound was prepared in a similar way as the title compound in Example 217. ¹H NMR (500 MHz, DMSO-d6) δ: 8.15 (s, 2H), 7.87 (s, 1H), 7.45 (d, J=42.0 Hz, 1H), 7.01 (dd, J=46.8, 5.1 Hz, 3H), 6.68 (s, 1H), 6.54 (d, J=7.6 Hz, 2H), 5.33 (s, 1H), 3.54 (dd, J=15.4, 9.2 Hz, 12H), 3.44-3.39 (m, 4H), 3.23 (s, 3H), 3.16 (s, 2H), 2.68 (d, J=6.7 Hz, 2H); LC-MS (m/z): 527.3 [M+H]⁺

Example 290 tert-Butyl 4-((3-((tetrahydro-2H-pyran-2-yl)oxy)propyl)amino)phenethylcarbamate

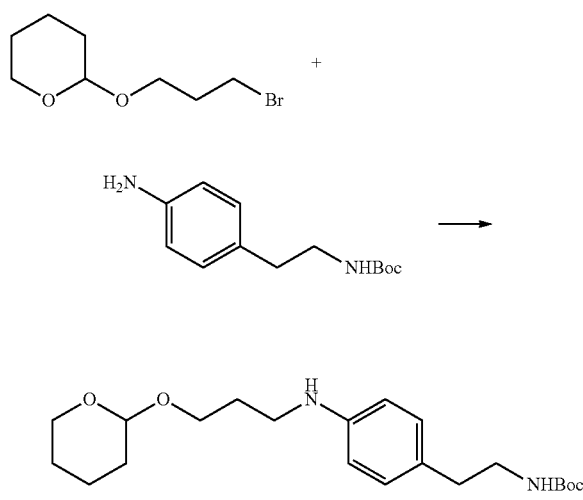

A mixture of 2-(3-bromopropoxy)tetrahydro-2H-pyran (669 mg, 3 mmol), tert-butyl 4-aminophenethylcarbamate (709 mg, 3 mmol) and cesium carbonate (2.9 g, 9 mmol) in DMF (20 mL) was stirred at 110° C. for 2 h. TLC showed the reaction completed. The reaction mixture was filtered. The filtrate was concentrated and purified by column chromatography to afford the title compound as yellow oil (180 mg, 15.9% yield). ¹H NMR (500 MHz, DMSO-d6) δ: 6.94 (d, J=8.3 Hz, 2H), 6.84 (t, J=5.4 Hz, 1H), 6.54 (d, J=8.4 Hz, 2H), 5.42 (t, J=5.6 Hz, 1H), 4.61 (t, J=3.4 Hz, 1H), 3.79 (tt, J=12.6, 4.8 Hz, 2H), 3.49 (dt, J=9.4, 6.2 Hz, 2H), 3.16-3.02 (m, 4H), 2.58 (d, J=8.0 Hz, 2H), 1.87-1.64 (m, 4H), 1.57-1.47 (m, 4H), 1.41 (d, J=15.5 Hz, 9H).

Example 291

3-((4-(2-Aminoethyl)phenyl)amino)propan-1-ol

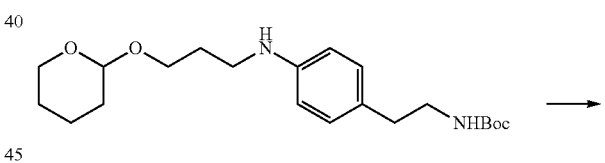

To a stirred mixture of tert-butyl 4-((3-((tetrahydro-2H-pyran-2-yl)oxy)propyl)amino)phenethylcarbamate (240 mg, 0.63 mmol) in dioxane (6 mL) was added 4N HCl in dioxane (3 mL) at room temperature. The reaction mixture was stirred at room temperature overnight. TLC showed the reaction completed. The reaction mixture was concentrated in vacuo to afford the crude product, which was used for the next step directly.

Example 292

3-((4-(2-((7-Amino-2-(furan-2-yl)-[1,2,4]triazolo[1,5-a][1,3,5]triazin-5-yl)amino)ethyl)-phenyl)amino)propan-1-ol

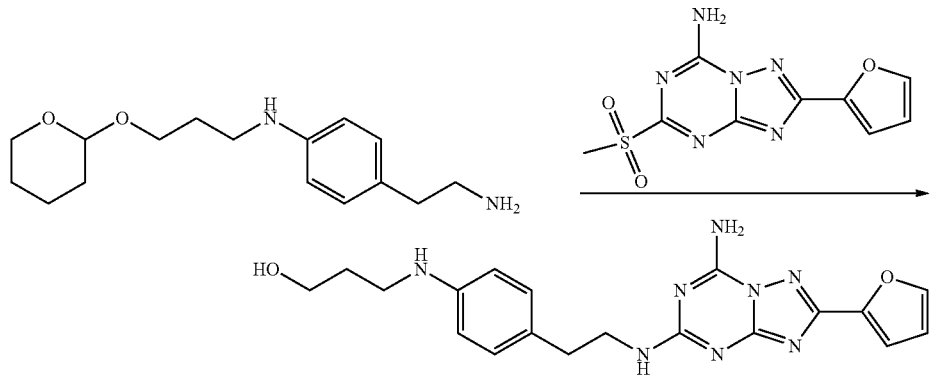

The reaction was carried out as in Example 5 to afford the title compound as white solid (36.9 mg, 14.9% yield). $^1$H NMR (500 MHz, DMSO-d6) δ: 8.28 (d, J=142.3 Hz, 2H), 7.87 (s, 1H), 7.53-7.34 (m, 1H), 7.06 (d, J=3.1 Hz, 1H), 6.96 (d, J=7.9 Hz, 2H), 6.68 (s, 1H), 6.50 (d, J=8.0 Hz, 2H), 5.33 (s, 1H), 4.45 (t, J=4.9 Hz, 1H), 3.50 (dd, J=11.0, 5.8 Hz, 2H), 3.44-3.37 (m, 2H), 3.03 (t, J=6.7 Hz, 2H), 2.72-2.63 (m, 2H), 1.74-1.63 (m, 2H).

Example 293

2-((4-(2-((7-Amino-2-(furan-2-yl)-[1,2,4]triazolo[1,5-a][1,3,5]triazin-5-yl)amino)ethyl)-phenyl)amino)ethanol

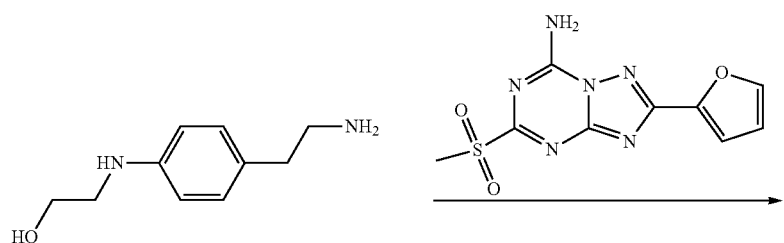

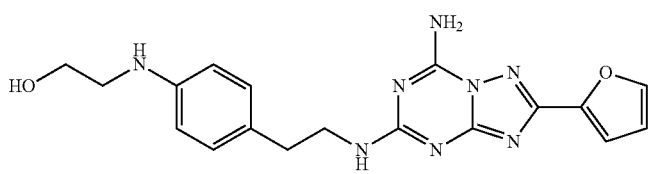

The title compound was prepared in a similar way as the title compound in Example 292. $^1$H NMR (500 MHz, DMSO-d6) δ: 8.28 (d, J=130.6 Hz, 2H), 7.87 (s, 1H), 7.42 (dd, J=26.7, 21.2 Hz, 1H), 7.08-7.03 (m, 1H), 6.96 (d, J=8.2 Hz, 2H), 6.68 (d, J=1.6 Hz, 1H), 6.53 (d, J=8.2 Hz, 2H), 5.30 (s, 1H), 4.65 (t, J=5.4 Hz, 1H), 3.54 (q, J=5.8 Hz, 2H), 3.40 (dd, J=13.9, 6.5 Hz, 2H), 3.06 (t, J=5.9 Hz, 2H), 2.73-2.64 (m, 2H).

Example 294

5-(Pyridin-2-yl)-1H-1,2,4-triazol-3-amine

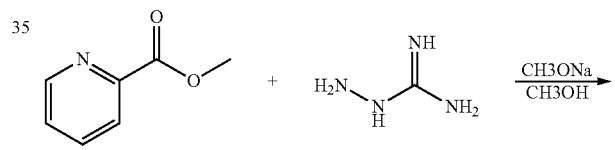

-continued

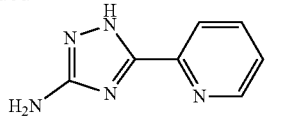

To a stirred mixture of CH₃ONa (31.49 g, 583 mmol) and hydrazinecarboximidamide (64.5 g, 583 mmol) in MeOH (450 mL) was added methyl picolinate (40 g, 292 mmol) in MeOH (120 mL) at 0° C. slowly. The reaction mixture was stirred at 75° C. overnight. TLC showed the reaction completed. The reaction mixture was filtered. The filtrate was concentrated afford the crude product. Then 150 mL of H₂O was added and the pH was adjusted to pH 5 with 36% hydrochloric acid. The precipitate formed was filtered to afford the title compound as white solid (21 g, 55.3% yield). ¹H NMR (500 MHz, DMSO-d6) δ: 8.70-8.48 (m, 1H), 8.06-7.82 (m, 2H), 7.41 (ddd, J=7.2, 4.8, 1.4 Hz, 1H).

Example 295

5-(Methylthio)-2-(pyridin-2-yl)-[1,2,4]triazolo[1,5-a][1,3,5]triazin-7-amine

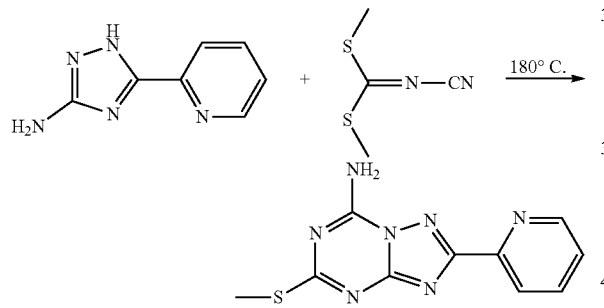

A mixture of 5-(pyridin-2-yl)-1H-1,2,4-triazol-3-amine (5.0 g, 31 mmol) and dimethyl cyanocarbonimidodithioate (4.5 g, 31 mmol) was stirred at 180° C. for 1 h. TLC showed the reaction completed. The residue was purified by column chromatography to afford the title compound as white solid (4.0 g, 50.0% yield). ¹H NMR (500 MHz, DMSO-d6) δ: 8.95 (d, J=57.3 Hz, 2H), 8.74 (d, J=4.3 Hz, 1H), 8.22 (d, J=7.8 Hz, 1H), 8.01 (td, J=7.7, 1.7 Hz, 1H), 7.55 (dd, J=6.6, 4.8 Hz, 1H), 2.54 (s, 3H).

Example 296

5-Methylsulfonyl-2-(1-oxidopyridin-1-ium-2-yl)-[1,2,4]triazolo[1,5-a][1,3,5]triazin-7-amine

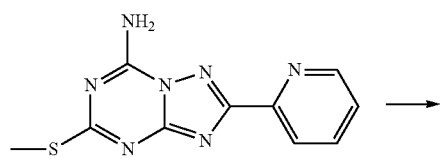

-continued

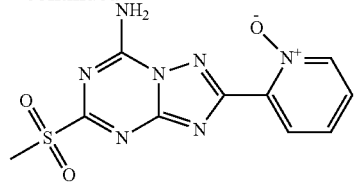

To a stirred mixture of 5-(methylthio)-2-(pyridin-2-yl)-[1,2,4]triazolo[1,5-a][1,3,5]triazin-7-amine (4.0 g, 15.4 mmol) in DCM (240 mL) was added m-CPBA (12.5 g, 61.6 mmol) in DCM (120 mL) at 0° C. The reaction mixture was stirred at room temperature overnight. TLC showed the reaction completed. The reaction mixture was concentrated in vacuo to afford the crude product. Then EtOH (80 mL) was added and the mixture was stirred at room temperature 1 h. The precipitate was filtered to afford the title compound as white solid (4.36 g, 92.2% yield). ¹H NMR (500 MHz, DMSO-d6) δ: 8.95 (d, J=57.3 Hz, 2H), 8.74 (d, J=4.3 Hz, 1H), 8.22 (d, J=7.8 Hz, 1H), 8.01 (td, J=7.7, 1.7 Hz, 1H), 7.55 (dd, J=6.6, 4.8 Hz, 1H), 2.54 (s, 3H); LC-MS (m/z): 308.1 [M+H]⁺

Example 297 tert-Butyl 4-(oxetan-3-ylamino)phenethylcarbamate

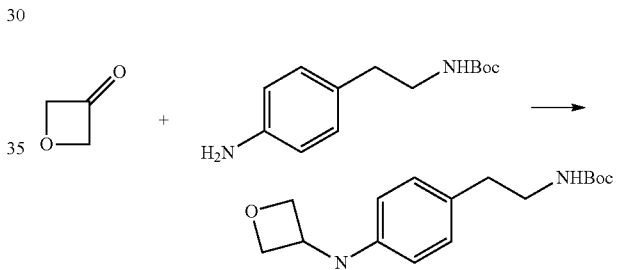

To a stirred mixture of oxetan-3-one (216 mg, 3.00 mol), zinc chloride (818 mg, 6.00 mmol) and tert-butyl 4-aminophenethylcarbamate (472 mg, 2.00 mmol) in methanol (10 mL) was added sodium cyanoborohydride (628 mg, 10.00 mmol). After stirring at room temperature for 15 h, the reaction mixture was concentrated. The residue was dissolved in dichloromethane (100 mL) and washed with water. The organic layer was dried with anhydrous sodium sulfate, concentrated and purified by column chromatography to afford the title compound as white solid (380 mg, 64.8% yield). ¹H NMR (500 MHz, DMSO-d6) δ: 6.90 (d, 2H), 6.78 (t, 1H), 6.39 (d, 2H), 6.15 (d, 1H), 4.82 (t, 2H), 4.48 (m, 1H), 4.38 (t, 2H), 3.02 (q, 2H), 2.53 (t, 2H), 1.37 (s, 9H).

Example 298

N-(4-(2-Aminoethyl)phenyl)oxetan-3-amine

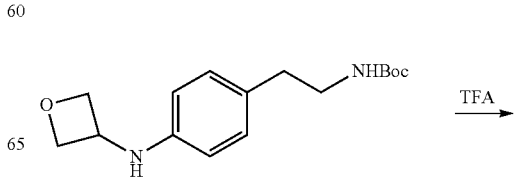

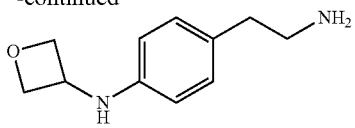

To a stirred solution of tert-butyl 4-(oxetan-3-ylamino) phenethylcarbamate (120 mg, 0.41 mol) in 1,4-dioxane (3 ml) was added TFA (1 mL). After stirring at 35° C. for 3 hours, the reaction mixture was concentrated in vacuo to afford the title compound as yellow oil, which was used for the next step directly.

Example 299

2-(Furan-2-yl)-N5-(4-(oxetan-3-ylamino)phenethyl)-[1,2,4]triazolo[1,5-a][1,3,5]triazine-5,7-diamine

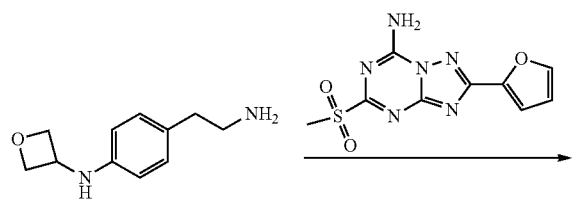

The reaction was carried out as in Example 5 to afford the title compound as white solid (50 mg, 43.9% yield). $^1$H NMR (500 MHz, DMSO-d6) δ: 8.05-8.49 (d, 2H), 7.87 (s, 1H), 7.41 (d, 1H), 7.05 (d, 1H), 6.98 (d, 2H), 6.68 (s, 1H), 6.42 (d, 2H), 6.17 (d, 1H), 4.82 (t, 2H), 4.48 (m, 1H), 4.38 (t, 2H), 3.40 (t, 2H), 2.69 (t, 2H); LCMS m/z [M+H]$^+$: 393.2

Example 300

N5-[2-[4-(oxetan-3-ylamino)phenyl]ethyl]-2-(1-oxidopyridin-1-ium-2-yl)-[1,2,4]triazolo[1,5-a][1,3,5]triazine-5,7-diamine

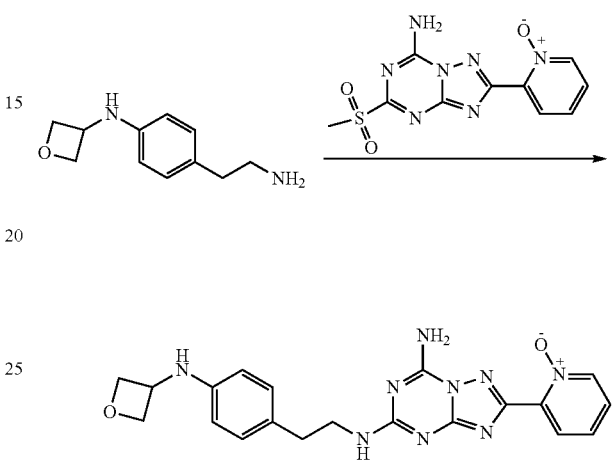

The reaction was carried out as in Example 5 afford the title compound as white solid (54.6 mg, 13.0% yield). $^1$H NMR (500 MHz, DMSO-d6) δ: 8.55-8.09 (m, 3H), 7.84 (dd, J=19.9, 6.7 Hz, 1H), 7.56-7.40 (m, 3H), 6.98 (d, J=8.0 Hz, 2H), 6.42 (d, J=8.2 Hz, 2H), 6.18 (d, J=6.5 Hz, 1H), 4.82 (t, J=6.4 Hz, 2H), 4.49 (dd, J=12.8, 6.4 Hz, 1H), 4.39 (t, J=6.0 Hz, 2H), 3.44-3.40 (m, 2H), 2.73-2.66 (m, 2H); LC-MS (m/z): 420.3[M+H]$^+$ Example 301

N5-[2-[4-(2-methoxyethylamino)phenyl]ethyl]-2-(1-oxidopyridin-1-ium-2-yl)-[1,2,4]triazolo[1,5-a][1,3,5]triazine-5,7-diamine

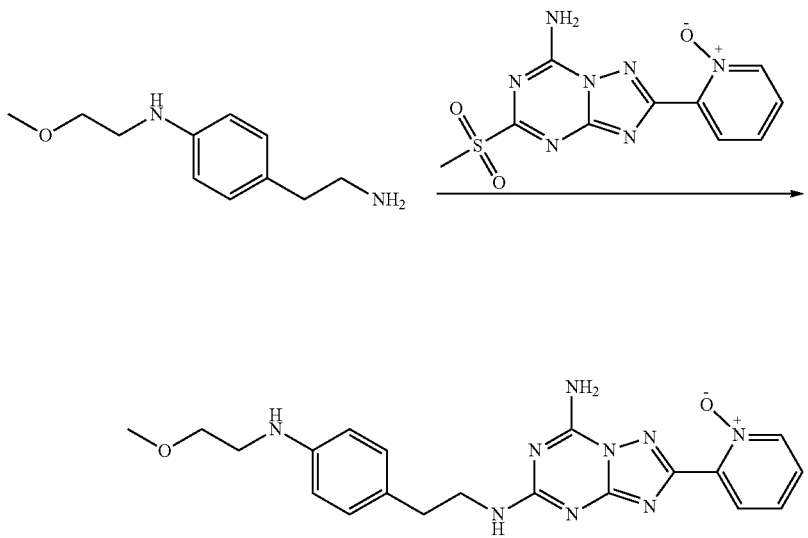

The reaction was carried out as in Example 5 to afford the title compound as yellow solid (151.6 mg, 36.0% yield). ¹H NMR (500 MHz, DMSO-d6) δ: 8.66-7.90 (m, 3H), 7.90-7.78 (m, 1H), 7.62-7.39 (m, 2H), 7.07-6.90 (m, 2H), 6.55 (t, J=8.3 Hz, 2H), 5.41 (tt, J=14.9, 7.5 Hz, 1H), 3.47 (t, J=5.7 Hz, 2H), 3.42 (dd, J=13.4, 7.5 Hz, 2H), 3.27 (s, 3H), 3.07-2.88 (m, 2H), 2.75-2.64 (m, 2H); LC-MS (m/z): 422.3 [M+H]⁺

Example 302

2-(Furan-2-yl)-N5-(2-(pyridin-2-yl)ethyl)-[1,2,4]triazolo[1,5-a][1,3,5]triazine-5,7-diamine

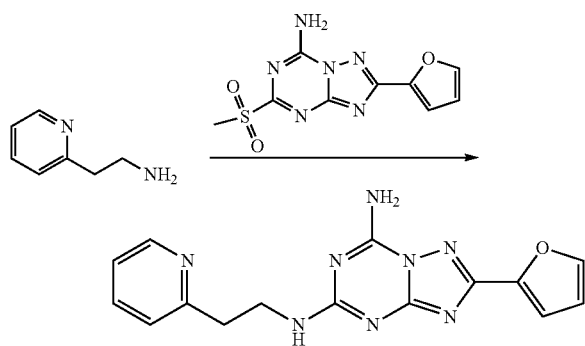

The reaction was carried out as in Example 5 to afford the title compound (361 mg, 74.4% yield). ¹H NMR (500 MHz, DMSO-d6) δ: 8.51 (s, 1H), 8.04-8.40 (d, 2H), 7.87 (s, 1H), 7.72 (q, 1H), 7.47-7.54 (d, 1H), 7.29 (d, 1H), 7.21 (t, 1H), 7.06 (s, 1H), 6.67 (s, 1H), 3.63 (t, 2H), 3.02 (t, 2H).

Example 303

N-(2-((4-(2-((7-Amino-2-(furan-2-yl)-[1,2,4]triazolo[1,5-a][1,3,5]triazin-5-yl)amino)ethyl)-phenyl)amino)ethyl)acetamide The title compound was prepared in a similar way as the title compound in Example 165. ¹H NMR (500 MHz, DMSO-d6) δ: 8.30 (d, J=127.1 Hz, 2H), 7.93 (s, 1H), 7.87 (s, 1H), 7.43 (dd, J=26.9, 21.3 Hz, 1H), 7.06 (d, J=3.2 Hz, 1H), 6.97 (d, J=7.8 Hz, 2H), 6.68 (s, 1H), 6.53 (d, J=8.1 Hz, 2H), 5.45 (s, 1H), 3.44-3.37 (m, 2H), 3.19 (dd, J=12.5, 6.3 Hz, 2H), 3.05 (s, 2H), 2.74-2.64 (m, 2H), 1.81 (s, 3H); LC-MS (m/z): 422.2 [M+H]⁺

Example 304

2-(Furan-2-yl)-N5-(4-phenoxyphenethyl)-[1,2,4]triazolo[1,5-a][1,3,5]triazine-5,7-diamine

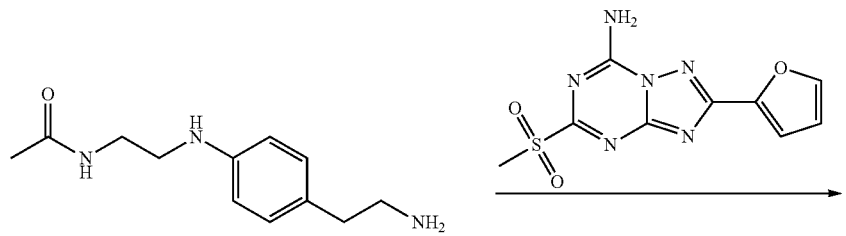

The reaction was carried out as in Example 42 to afford the title compound as white solid (420 mg, 67.7% yield). ¹H NMR (500 MHz, DMSO-d6) δ: 8.05-8.49 (d, 2H), 7.87 (s, 1H), 7.56 (d, 1H), 7.37 (t, 2H), 7.27 (t, 2H), 7.10 (t, 1H), 7.05 (d, 1H), 6.67 (d, 1H), 3.50 (q, 2H), 2.84 (t, 2H).

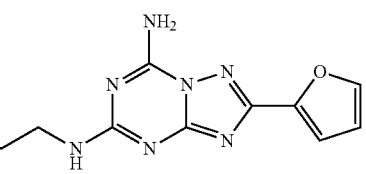

Example 305

2-(Furan-2-yl)-N5-(4-(trifluoromethoxy)phenethyl)-[1,2,4]triazolo[1,5-a][1,3,5]triazine-5,7-diamine

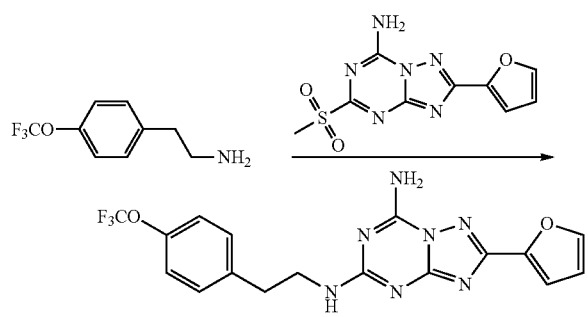

The reaction was carried out as in Example 42 to afford the title compound as white solid (143 mg, 17.0% yield). $^1$H NMR (500 MHz, DMSO-d6) δ: 8.05-8.49 (d, 2H), 7.86 (s, 1H), 7.56 (d, 1H), 7.37 (d, 2H), 7.27 (d, 2H), 7.05 (d, 1H), 6.67 (d, 1H), 3.50 (q, 2H), 2.89 (t, 2H).

Example 306

N5-(4-((Dimethylamino)methyl)phenethyl)-2-(furan-2-yl)-[1,2,4]triazolo[1,5-a][1,3,5]triazine-5,7-diamine

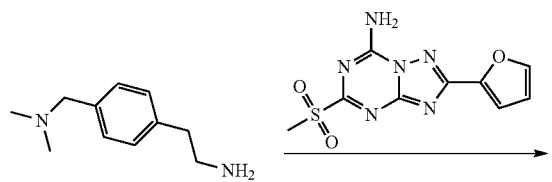

The reaction was carried out as in Example 42 to afford the title compound as white solid (81 mg, 14.3% yield). $^1$H NMR (500 MHz, DMSO-d6) δ: 8.05-8.49 (d, 2H), 7.86 (s, 1H), 7.54 (d, 1H), 7.24 (d, 2H), 7.05 (d, 1H), 6.67 (d, 1H), 3.50 (q, 2H), 2.86 (t, 2H), 2.23 (s, 6H).

Example 307

N5-(4-(Dimethylamino)phenethyl)-2-(furan-2-yl)-[1,2,4]triazolo[1,5-a][1,3,5]triazine-5,7-diamine

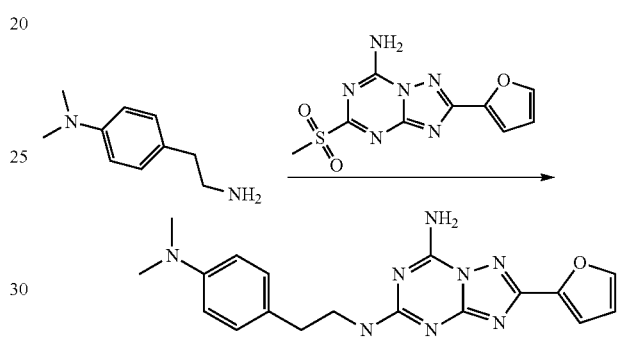

The reaction was carried out as in Example 42 to afford the title compound as white solid (90 mg, 24.7% yield). $^1$H NMR (500 MHz, DMSO-d6) δ: 8.05-8.49 (d, 2H), 7.86 (s, 1H), 7.41 (d, 1H), 7.05 (q, 3H), 6.67 (q, 3H), 3.42 (q, 2H), 2.84 (s, 6H), 2.72 (t, 2H).

Example 308

2-(Furan-2-yl)-N5-(4-(2-(4-(2,2,2-trifluoroethyl)piperazin-1-yl)ethoxy)phenethyl)-[1,2,4]triazolo[1,5-a][1,3,5]triazine-5,7-diamine

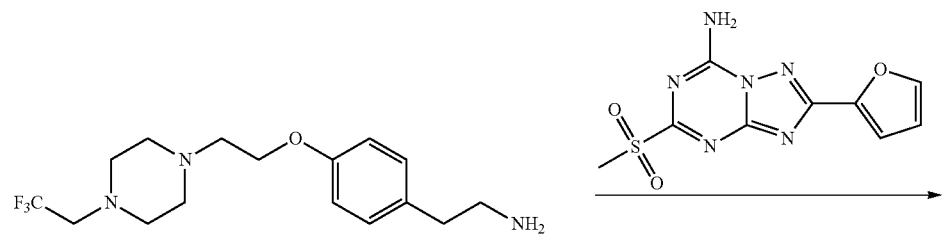

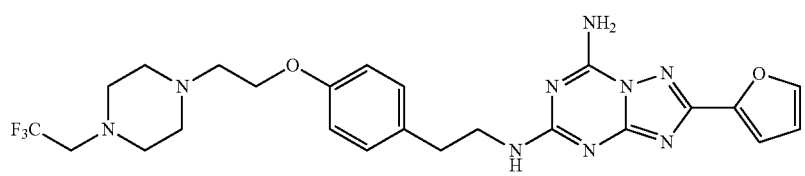

The title compound was prepared in a similar way as the title compound in Example 9. $^1$H NMR (500 MHz, DMSO-d6) δ: 8.05-8.49 (d, 2H), 7.87 (s, 1H), 7.46 (d, 1H), 7.17 (d, 2H), 7.05 (d, 1H), 6.85 (d, 2H), 6.68 (q, 1H), 4.02 (t, 2H), 3.45 (q, 2H), 3.12 (q, 2H), 2.78 (q, 2H), 2.66 (t, 2H), 2.60 (s, 4H), 2.48 (m, 4H); LCMS m/z [M+H]$^+$: 532.3

Example 309

(R)-N5-(4-(2-(3-Fluoropyrrolidin-1-yl)ethoxy)phenethyl)-2-(furan-2-yl)-[1,2,4]triazolo[1,5-a][1,3,5]triazine-5,7-diamine

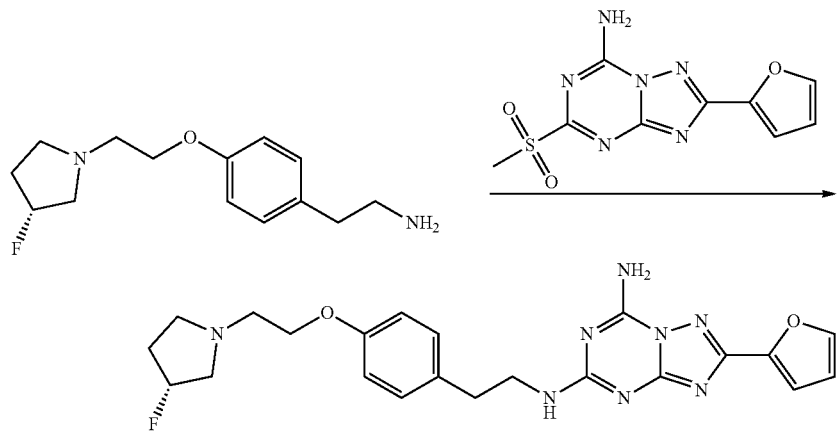

The title compound was prepared in a similar way as the title compound in Example 9. $^1$H NMR (500 MHz, DMSO-d6) δ: 8.05-8.49 (d, 2H), 7.87 (s, 1H), 7.46 (d, 1H), 7.17 (d, 2H), 7.05 (d, 1H), 6.86 (d, 2H), 6.67 (s, 1H), 5.10 (d, 1H), 4.03 (t, 2H), 3.45 (q, 2H), 2.78 (m, 7H), 2.40 (m, 1H), 2.12 (m, 1H), 1.85 (m, 1H); LCMS m/z [M+H]$^+$: 453.2

Example 310

N5-(4-(2-(4-Fluoropiperidin-1-yl)ethoxy)phenethyl)-2-(furan-2-yl)-[1,2,4]triazolo[1,5-a][1,3,5]triazine-5,7-diamine

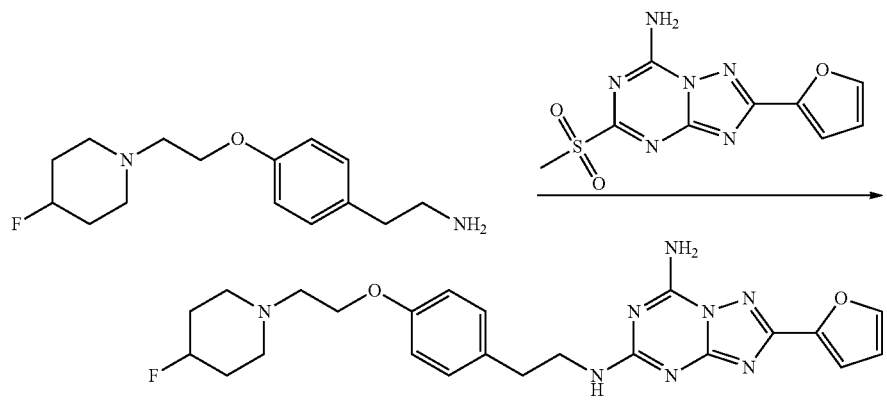

The title compound was prepared in a similar way as the title compound in Example 9. $^1$H NMR (500 MHz, DMSO-d6) δ: 8.05-8.49 (d, 2H), 7.87 (s, 1H), 7.46 (d, 1H), 7.17 (d, 2H), 7.05 (d, 1H), 6.85 (d, 2H), 6.68 (q, 1H), 4.67 (d, 1H), 4.02 (s, 2H), 2.77 (q, 2H), 2.67 (m, 4H), 2.38 (s, 2H), 1.85 (m, 2H), 1.71 (m, 2H); LCMS m/z [M+H]$^+$: 467.2

Example 311

2-(Furan-2-yl)-N5-(4-(2-(piperidin-1-yl)ethoxy)
phenethyl)-[1,2,4]triazolo[1,5-a][1,3,5]triazine-5,7-
diamine

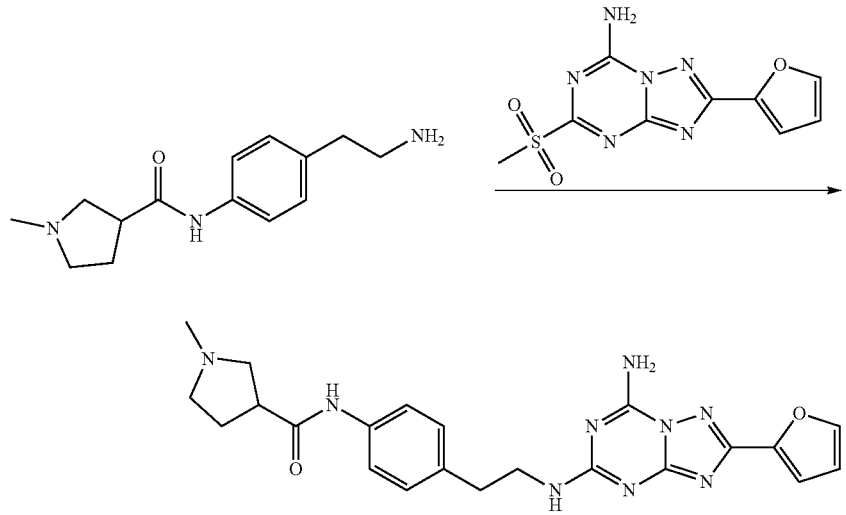

The title compound was prepared in a similar way as the title compound in Example 278. $^1$H NMR (500 MHz, DMSO-d6) δ: 9.85 (s, 1H), 8.05-8.49 (d, 2H), 7.87 (s, 1H), 7.50 (d, 2H), 7.45 (t, 1H), 7.19 (d, 2H), 7.06 (d, 1H), 6.67 (d, 1H), 3.45 (q, 2H), 3.07 (s, 1H), 2.89 (s, 1H), 2.78 (q, 2H), 2.68 (s, 1H), 2.56 (s, 1H), 2.46 (s, 1H), 2.30 (s, 3H), 1.99 (s, 2H).

Example 312

(S)-N5-(4-(2-(3-Fluoropyrrolidin-1-yl)ethoxy)phen-
ethyl)-2-(furan-2-yl)-[1,2,4]triazolo[1,5-a][1,3,5]
triazine-5,7-diamine

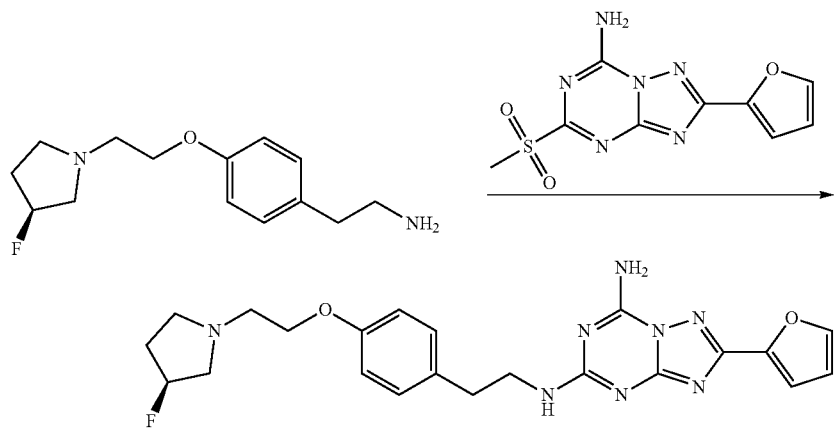

The title compound was prepared in a similar way as the title compound in Example 9. $^1$H NMR (500 MHz, DMSO-d6) δ: 8.05-8.49 (d, 2H), 7.87 (s, 1H), 7.46 (d, 1H), 7.17 (d, 2H), 7.05 (d, 1H), 6.86 (d, 2H), 6.67 (s, 1H), 5.10 (d, 1H), 4.03 (t, 2H), 3.45 (q, 2H), 2.78 (m, 7H), 2.37 (m, 1H), 2.12 (m, 1H), 1.85 (m, 1H).

Example 313

N-(4-(2-((7-Amino-2-(furan-2-yl)-[1,2,4]triazolo[1,5-a][1,3,5]triazin-5-yl)amino)ethyl)-phenyl)-3-(azetidin-1-yl)propanamide

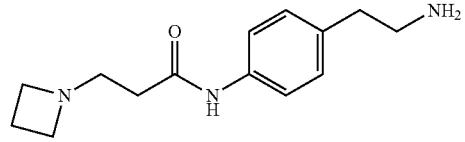
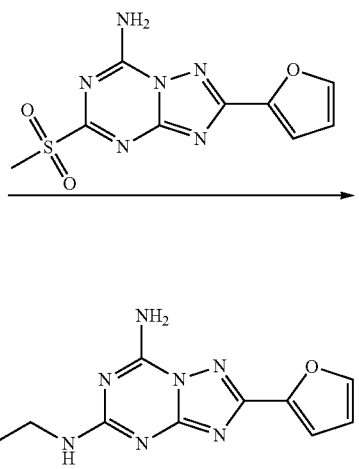
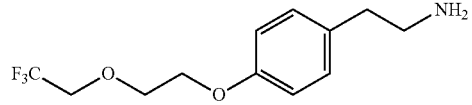

The title compound was prepared in a similar way as the title compound in Example 278. $^1$H NMR (500 MHz, DMSO-d6) δ: 9.91 (s, 1H), 8.05-8.49 (d, 2H), 7.87 (s, 1H), 7.49 (d, 2H), 7.43 (t, 1H), 7.17 (d, 2H), 7.05 (d, 1H), 6.67 (s, 1H), 3.44 (q, 2H), 3.11 (t, 4H), 2.79 (t, 2H), 2.62 (t, 2H), 2.26 (t, 2H), 1.93 (t, 2H).

Example 314

2-(Furan-2-yl)-N5-(4-(2-(2,2,2-trifluoroethoxy)ethoxy)phenethyl)-[1,2,4]triazolo[1,5-a][1,3,5]triazine-5,7-diamine

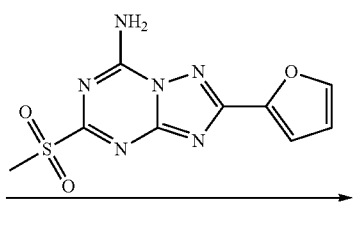
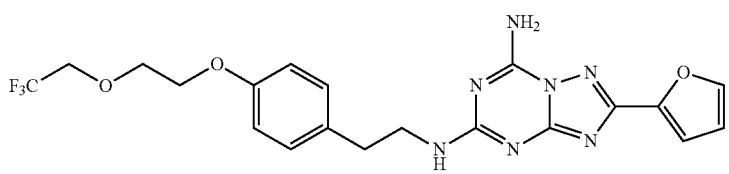

The title compound was prepared in a similar way as the title compound in Example 74. $^1$H NMR (500 MHz, DMSO-d6) δ: 8.05-8.49 (d, 2H), 7.87 (s, 1H), 7.46 (d, 1H), 7.17 (d, 2H), 7.05 (d, 1H), 6.85 (d, 2H), 6.68 (s, 1H), 4.15 (q, 2H), 4.09 (t, 2H), 3.91 (t, 2H), 3.45 (q, 4H), 2.79 (t, 2H); LCMS m/z [M+H]$^+$: 464.1

Example 315 tert-Butyl 4-morpholinophenethylcarbamate

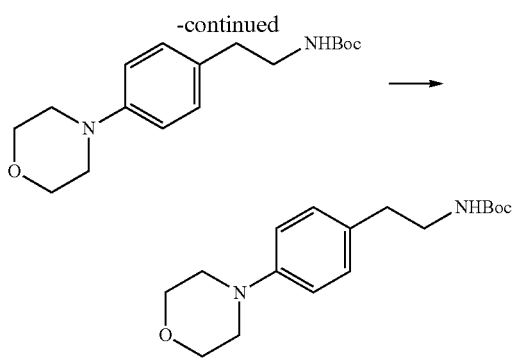

A mixture of tert-butyl 4-aminophenethylcarbamate (473 mg, 2.00 mol), potassium carbonate (0.83 g, 6.00 mmol) and 1-bromo-2-(2-bromoethoxy)ethane (464 mg, 2.00 mmol) in acetonitrile (25 mL) was stirred at 80° C. for 15 h. The reaction mixture was filtrated. The filtrate was concentrated and purified by column chromatography to afford the title compound as white solid (230 mg, 37.5% yield). $^1$H NMR (500 MHz, DMSO-d6) δ: 7.05 (d, 2H), 6.85 (d, 2H), 6.82 (t, 1H), 3.72 (t, 4H), 3.05 (m, 6H), 2.58 (t, 2H), 1.37 (s, 9H).

Example 316

2-(4-Morpholinophenyl)ethanamine

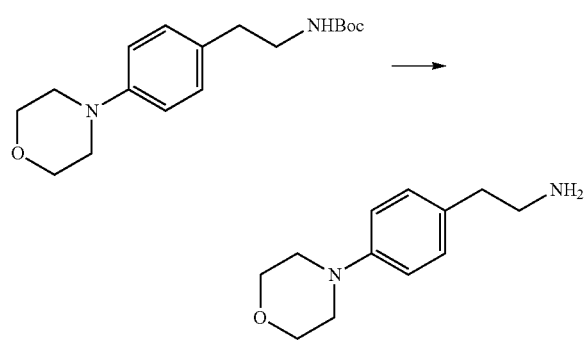

To a stirred solution of tert-butyl 4-morpholinopheneth-ylcarbamate (220 mg, 0.72 mol) in 1,4-dioxane (3 ml) was added 4M HCl in 1,4-dioxane (1 mL). After stirring at 35° C. for 3 hours, the reaction mixture was concentrated in vacuo to afford the title compound as colorless oil, which was used for the next step directly.

Example 317

2-(Furan-2-yl)-N5-(4-((2-morpholinoethyl)amino)phenethyl)-[1,2,4]triazolo[1,5-a][1,3,5]triazine-5,7-diamine

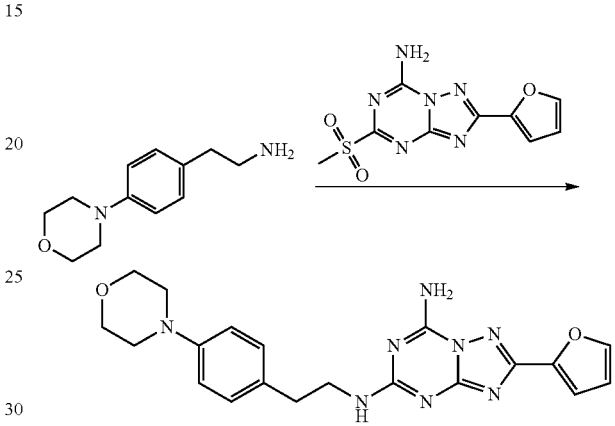

The reaction was carried out as in Example 5 to afford the title compound as white solid (120 mg, 37.1% yield). $^1$H NMR (500 MHz, DMSO-d6) δ: 8.05-8.49 (d, 2H), 7.87 (s, 1H), 7.46 (d, 1H), 7.10 (d, 2H), 7.05 (d, 1H), 6.85 (d, 2H), 6.68 (s, 1H), 3.72 (t, 4H), 3.43 (q, 2H), 3.04 (t, 4H), 2.74 (t, 2H).

Example 318

2-(Furan-2-yl)-N5-(4-((2-morpholinoethyl)amino)phenethyl)-[1,2,4]triazolo[1,5-a][1,3,5]triazine-5,7-diamine

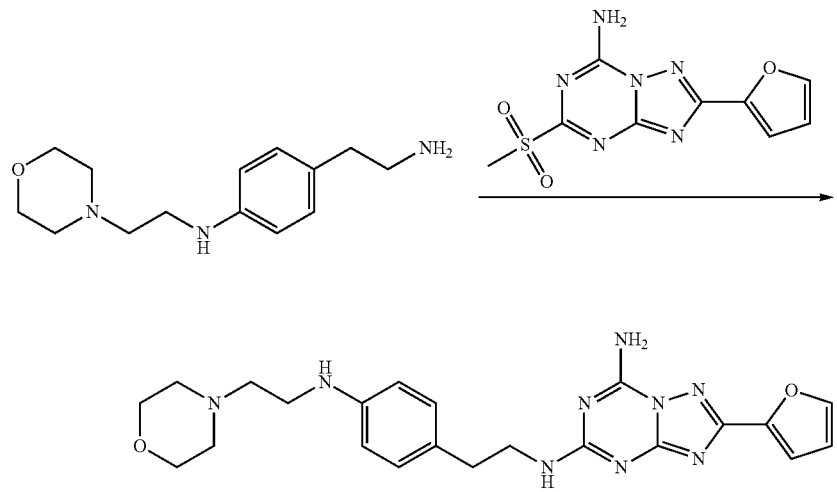

The title compound was prepared in a similar way as the title compound in Example 165. ¹H NMR (500 MHz, DMSO-d6) δ: 8.05-8.49 (d, 2H), 7.87 (s, 1H), 7.42 (d, 1H), 7.05 (d, 1H), 6.95 (d, 2H), 6.68 (m, 1H), 6.51 (d, 2H), 5.21 (t, 1H), 3.58 (t, 4H), 3.39 (q, 2H), 3.09 (q, 2H), 2.67 (t, 2H), 2.47 (t, 2H), 2.39 (s, 4H).

Example 319

N-(4-(2-((7-Amino-2-(furan-2-yl)-[1,2,4]triazolo[1,5-a][1,3,5]triazin-5-yl)amino)ethyl)-phenyl)-3-(4,4-difluoropiperidin-1-yl)propanamide

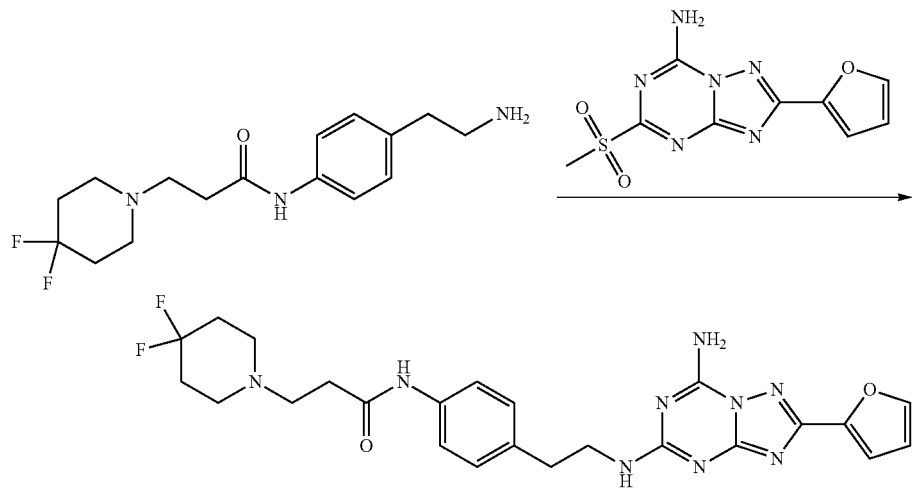

The title compound was prepared in a similar way as the title compound in Example 278. ¹H NMR (500 MHz, DMSO-d6) δ: 9.91 (s, 1H), 8.05-8.49 (d, 2H), 7.87 (s, 1H), 7.50 (d, 2H), 7.43 (t, 1H), 7.17 (d, 2H), 7.05 (d, 1H), 6.67 (s, 1H), 3.44 (t, 2H), 3.11 (t, 4H), 2.79 (t, 2H), 2.70 (t, 2H), 2.53 (m, 4H), 2.46 (t, 2H), 1.93 (m, 4H); LCMS m/z [M+H]⁺: 512.2

Example 320

N-(4-(2-((7-Amino-2-(furan-2-yl)-[1,2,4]triazolo[1,5-a][1,3,5]triazin-5-yl)amino)ethyl)-phenyl)-2-morpholinoacetamide

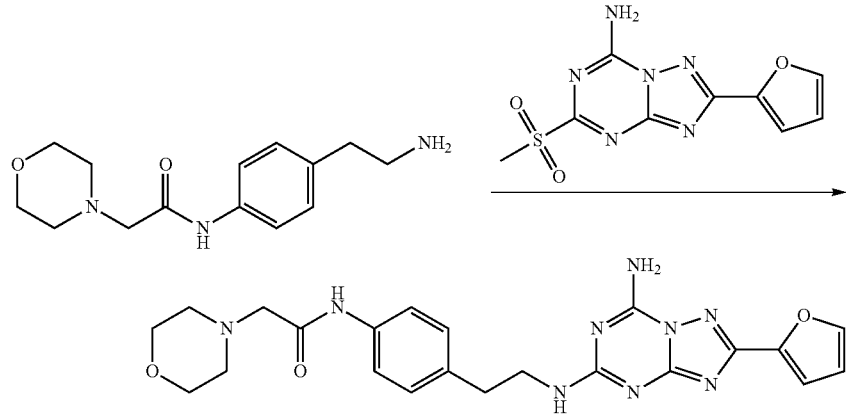

The title compound was prepared in a similar way as the title compound in Example 278. ¹H NMR (500 MHz, DMSO-d6) δ: 9.65 (s, 1H), 8.05-8.49 (d, 2H), 7.87 (s, 1H), 7.53 (d, 2H), 7.46 (t, 1H), 7.19 (d, 2H), 7.05 (d, 1H), 6.67 (s, 1H), 3.63 (t, 4H), 3.47 (q, 2H), 3.10 (s, 2H), 2.81 (t, 2H), 2.49 (m, 2H); LCMS m/z [M+H]⁺: 464.2

Example 321

N-(4-(2-((7-Amino-2-(furan-2-yl)-[1,2,4]triazolo[1,5-a][1,3,5]triazin-5-yl)amino)ethyl)-phenyl)-2-(4-methylpiperazin-1-yl)acetamide

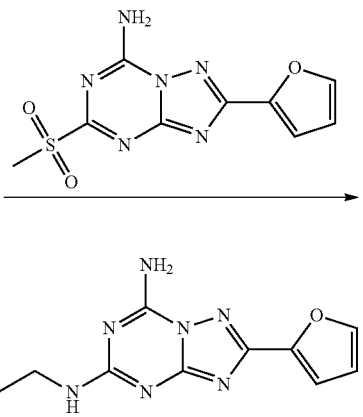

The title compound was prepared in a similar way as the title compound in Example 278. ¹H NMR (500 MHz, DMSO-d6) δ: 9.61 (s, 1H), 8.05-8.49 (d, 2H), 7.87 (s, 1H), 7.53 (d, 2H), 7.46 (t, 1H), 7.19 (d, 2H), 7.05 (d, 1H), 6.67 (s, 1H), 3.47 (q, 2H), 3.17 (d, 2H), 3.11 (s, 2H), 2.81 (t, 2H), 2.53 (m, 6H), 2.27 (s, 3H); LCMS m/z [M+H]⁺: 477.2

Example 322

N-(4-(2-((7-Amino-2-(furan-2-yl)-[1,2,4]triazolo[1,5-a][1,3,5]triazin-5-yl)amino)ethyl)-phenyl)-3-(4-fluoropiperidin-1-yl)propanamide

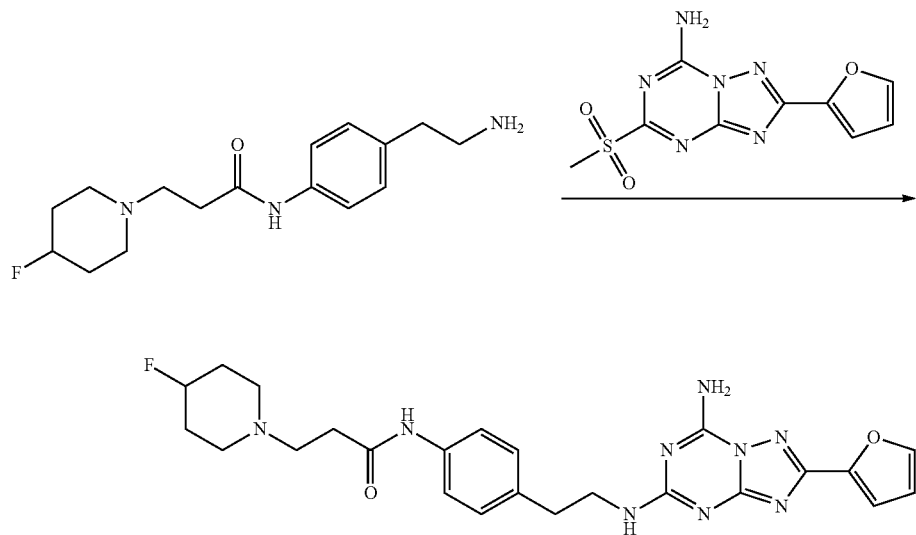

The title compound was prepared in a similar way as the title compound in Example 278. ¹H NMR (500 MHz, DMSO-d6) δ: 9.99 (s, 1H), 8.05-8.49 (d, 2H), 7.87 (s, 1H), 7.50 (d, 2H), 7.43 (t, 1H), 7.17 (d, 2H), 7.05 (d, 1H), 6.67 (s, 1H), 4.74 (d, 1H), 3.45 (d, 2H), 2.79 (t, 2H), 2.70 (t, 2H), 2.64 (m, 4H), 2.36 (m, 4H), 1.72 (m, 4H); LCMS m/z [M+H]⁺: 494.2

Example 323

N-(4-(2-((7-Amino-2-(furan-2-yl)-[1,2,4]triazolo[1,5-a][1,3,5]triazin-5-yl)amino)ethyl)-phenyl)picolinamide

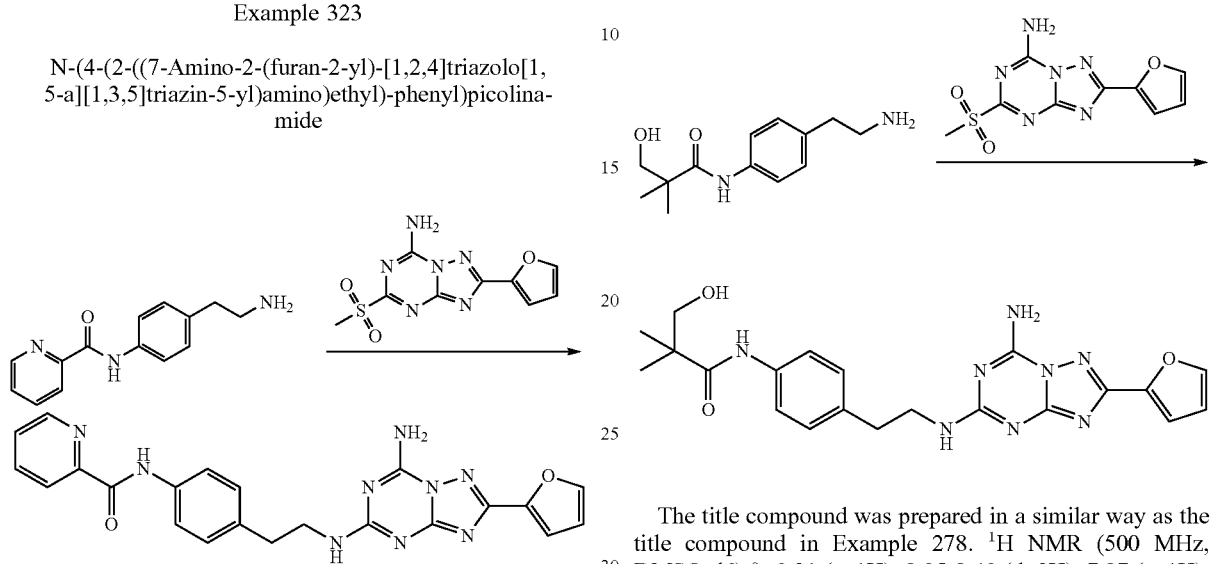

The title compound was prepared in a similar way as the title compound in Example 278. ¹H NMR (500 MHz, DMSO-d6) δ: 10.58 (s, 1H), 8.74 (s, 1H), 8.05-8.49 (d, 2H), 8.15 (d, 2H), 8.07 (t, 1H), 7.87 (s, 1H), 7.83 (d, 2H), 7.68 (t, 1H), 7.49 (d, 1H), 7.27 (t, 1H), 7.06 (d, 1H), 6.68 (s, 1H), 3.50 (q, 2H), 2.85 (q, 2H); LCMS m/z [M+H]⁺: 442.1

Example 324

N-(4-(2-((7-Amino-2-(furan-2-yl)-[1,2,4]triazolo[1,5-a][1,3,5]triazin-5-yl)amino)ethyl)-phenyl)pivalamide

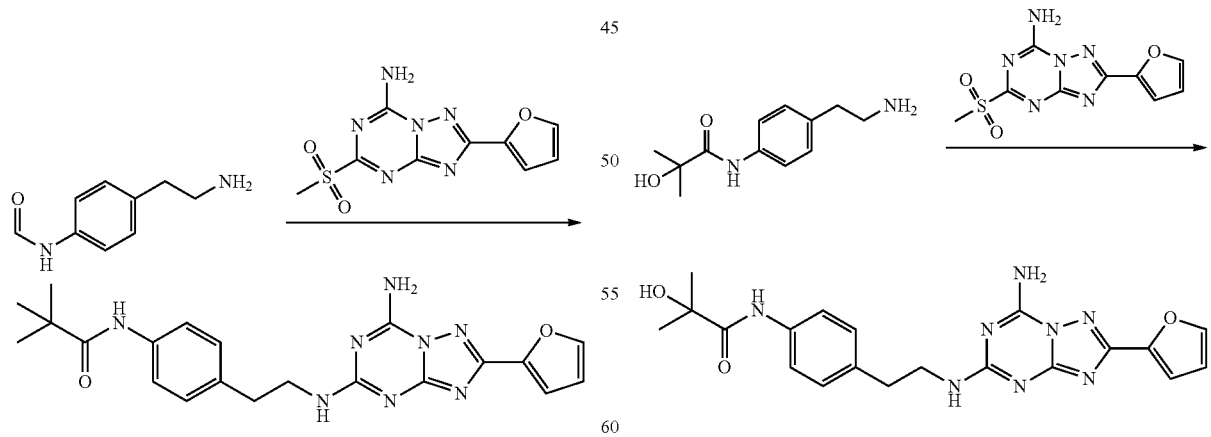

The title compound was prepared in a similar way as the title compound in Example 278. ¹H NMR (500 MHz, DMSO-d6) δ: 9.14 (s, 1H), 8.05-8.49 (d, 2H), 7.53 (d, 2H), 7.49 (t, 1H), 7.17 (d, 2H), 7.05 (d, 1H), 6.67 (s, 1H), 3.46 (q, 2H), 2.81 (t, 2H), 1.25 (s, 9H); LCMS m/z [M+H]⁺: 421.2

Example 325

N-(4-(2-((7-Amino-2-(furan-2-yl)-[1,2,4]triazolo[1,5-a][1,3,5]triazin-5-yl)amino)ethyl)-phenyl)-3-hydroxy-2,2-dimethylpropanamide

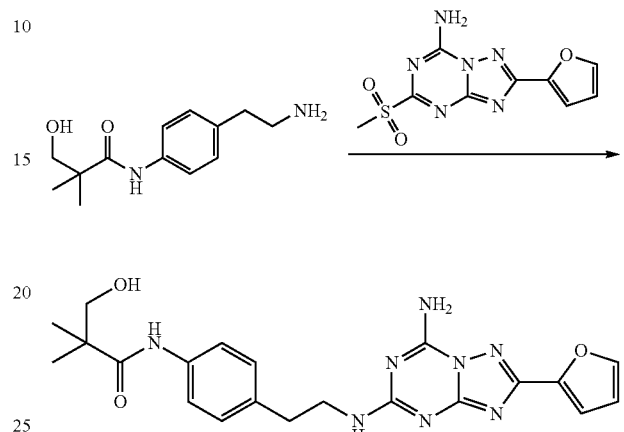

The title compound was prepared in a similar way as the title compound in Example 278. ¹H NMR (500 MHz, DMSO-d6) δ: 9.21 (s, 1H), 8.05-8.49 (d, 2H), 7.87 (s, 1H), 7.53 (d, 2H), 7.49 (t, 1H), 7.17 (d, 2H), 7.05 (d, 1H), 6.68 (q, 1H), 5.12 (t, 1H), 3.48 (m, 4H), 2.79 (t, 2H), 1.13 (s, 6H); LCMS m/z [M+H]⁺: 437.2

Example 326

N-(4-(2-((7-Amino-2-(furan-2-yl)-[1,2,4]triazolo[1,5-a][1,3,5]triazin-5-yl)amino)ethyl)-phenyl)-2-hydroxy-2-methylpropanamide

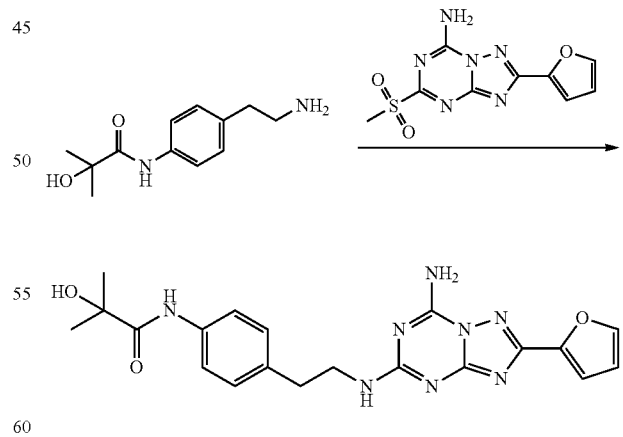

The title compound was prepared in a similar way as the title compound in Example 278. ¹H NMR (500 MHz, DMSO-d6) δ: 9.49 (s, 1H), 8.05-8.49 (d, 2H), 7.87 (s, 1H), 7.64 (d, 2H), 7.49 (t, 1H), 7.17 (t, 2H), 7.05 (d, 1H), 6.68 (s, 1H), 5.74 (s, 1H), 3.45 (m, 2H), 2.79 (t, 2H), 1.34 (s, 6H); LCMS m/z [M+H]⁺: 423.2

Example 327

2-(Furan-2-yl)-N5-(4-((2-(2-(2-methoxyethoxy)ethoxy)ethyl)amino)phenethyl)-[1,2,4]triazolo[1,5-a][1,3,5]triazine-5,7-diamine

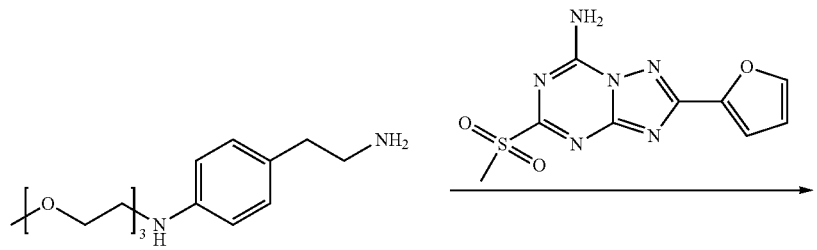

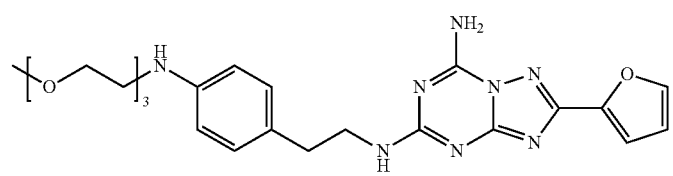

The title compound was prepared in a similar way as the title compound in Example 217. ¹H NMR (500 MHz, DMSO-d6) δ: 8.05-8.49 (d, 2H), 7.41 (d, 1H), 7.05 (d, 1H), 6.95 (d, 2H), 6.68 (d, 1H), 6.53 (d, 2H), 5.33 (s, 1H), 3.53 (m, 6H), 3.40 (m, 4H), 3.24 (s, 3H), 3.15 (q, 2H); LCMS m/z [M+H]⁺: 483.2

Example 328

2-(Furan-2-yl)-N5-(4-((1-methoxypropan-2-yl)amino)phenethyl)-[1,2,4]triazolo[1,5-a][1,3,5]triazine-5,7-diamine

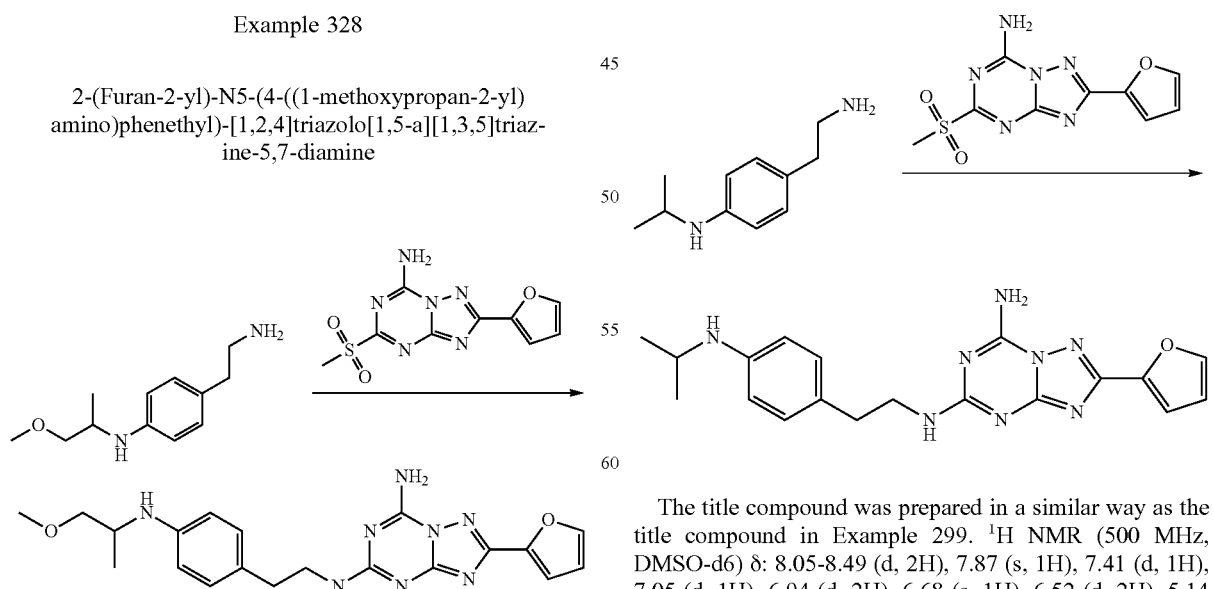

The title compound was prepared in a similar way as the title compound in Example 299. ¹H NMR (500 MHz, DMSO-d6) δ: 8.05-8.49 (d, 2H), 7.87 (s, 1H), 7.41 (d, 1H), 7.05 (d, 1H), 6.94 (d, 2H), 6.68 (s, 1H), 6.52 (d, 2H), 5.14 (d, 1H), 3.54 (m, 1H), 3.40 (s, 3H), 3.19 (q, 1H), 2.67 (t, 2H), 1.09 (d, 3H). LCMS m/z [M+H]⁺: 409.2

Example 329

2-(Furan-2-yl)-N5-(4-(isopropylamino)phenethyl)-[1,2,4]triazolo[1,5-a][1,3,5]triazine-5,7-diamine The title compound was prepared in a similar way as the title compound in Example 299. ¹H NMR (500 MHz, DMSO-d6) δ: 8.05-8.49 (d, 2H), 7.87 (s, 1H), 7.41 (d, 1H), 7.05 (d, 1H), 6.94 (d, 2H), 6.68 (s, 1H), 6.52 (d, 2H), 5.14 (d, 1H), 3.49 (m, 1H), 3.40 (m, 2H), 2.67 (t, 2H), 1.09 (d, 6H); LCMS m/z [M+H]⁺: 379.2

Example 330

2-(Furan-2-yl)-N5-(4-(propylamino)phenethyl)-[1,2,4]triazolo[1,5-a][1,3,5]triazine-5,7-diamine

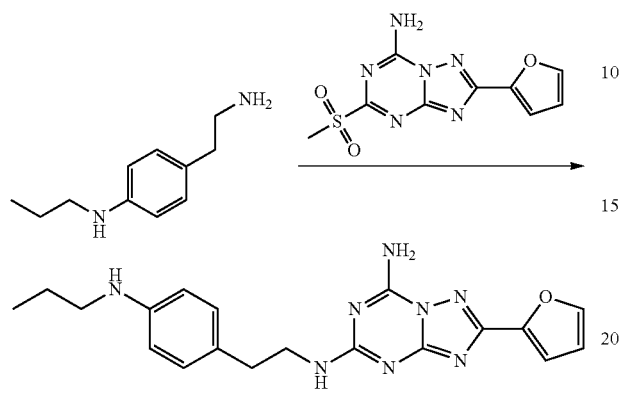

The title compound was prepared in a similar way as the title compound in Example 299. ¹H NMR (500 MHz, DMSO-d6) δ: 8.05-8.49 (d, 2H), 7.91 (s, 1H), 7.46 (d, 1H), 7.11 (d, 1H), 6.99 (d, 2H), 6.73 (s, 1H), 6.55 (d, 2H), 5.43 (t, 1H), 3.46 (m, 2H), 2.98 (q, 2H), 2.46 (t, 2H), 1.59 (q, 2H), 1.00 (t, 3H); LCMS m/z [M+H]⁺: 379.2

Example 331

N5-(4-((2-Ethoxyethyl)amino)phenethyl)-2-(furan-2-yl)-[1,2,4]triazolo[1,5-a][1,3,5]triazine-5,7-diamine

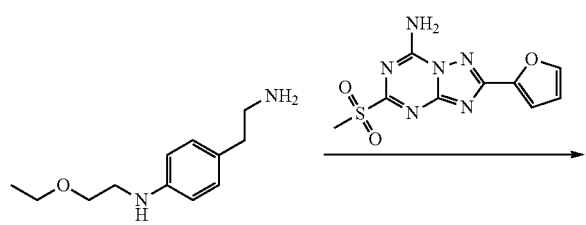

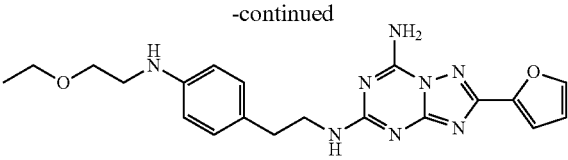

The title compound was prepared in a similar way as the title compound in Example 165. ¹H NMR (500 MHz, DMSO-d6) δ: 8.05-8.49 (d, 2H), 7.93 (s, 1H), 7.49 (d, 1H), 7.11 (d, 1H), 6.99 (d, 2H), 6.73 (s, 1H), 6.59 (d, 2H), 5.40 (t, 1H), 3.56 (t, 2H), 3.50 (q, 2H), 3.44 (m, 2H), 3.20 (q, 2H), 2.72 (t, 2H), 1.18 (t, 3H); LCMS m/z [M+H]⁺: 409.2

Example 332

2-(Furan-2-yl)-N5-(4-((3-methoxypropyl)amino)phenethyl)-[1,2,4]triazolo[1,5-a][1,3,5]triazine-5,7-diamine

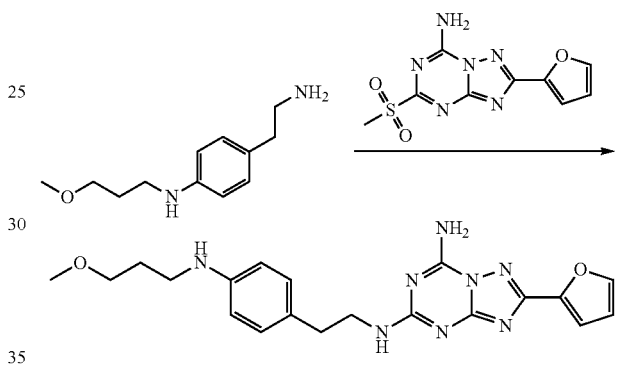

The reaction was carried out as in Example 5 to afford the title compound as white solid (60 mg, 43.3% yield). ¹H NMR (500 MHz, DMSO-d6) δ: 8.05-8.49 (d, 2H), 7.87 (s, 1H), 7.42 (d, 1H), 7.06 (d, 1H), 6.96 (d, 2H), 6.68 (s, 1H), 6.50 (d, 2H), 5.38 (t, 1H), 3.41 (q, 4H), 3.23 (s, 3H), 3.01 (q, 2H), 2.68 (t, 2H), 1.75 (t, 2H); LCMS m/z [M+H]⁺: 409.2

Example 333

2-(Furan-2-yl)-N5-(4-((2-(2,2,2-trifluoroethoxy)ethyl)amino)phenethyl)-[1,2,4]triazolo[1,5-a][1,3,5]triazine-5,7-diamine

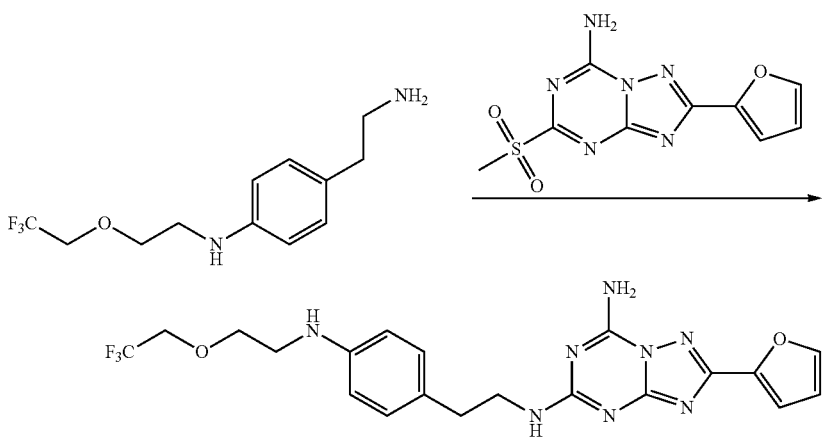

The title compound was prepared in a similar way as the title compound in Example 165. ¹H NMR (500 MHz, DMSO-d6) δ: 8.05-8.49 (d, 2H), 7.87 (s, 1H), 7.41 (d, 1H), 7.06 (d, 1H), 6.96 (d, 2H), 6.68 (q, 1H), 6.56 (d, 2H), 5.45 (s, 1H), 4.08 (q, 2H), 3.72 (t, 2H), 3.40 (q, 2H), 3.20 (d, 2H), 2.68 (t, 2H); LCMS m/z [M+H]⁺: 463.2

Example 334

2-(Furan-2-yl)-N5-(4-((2,2,2-trifluoroethyl)amino)phenethyl)-[1,2,4]triazolo[1,5-a][1,3,5]triazine-5,7-diamine

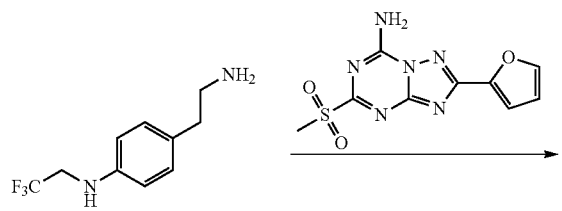

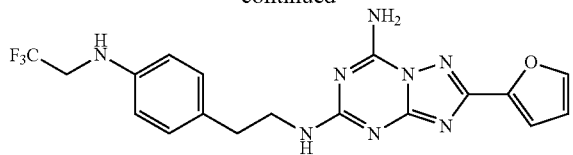

The title compound was prepared in a similar way as the title compound in Example 299. ¹H NMR (500 MHz, DMSO-d6) δ: 8.05-8.49 (d, 2H), 7.81 (s, 1H), 7.41 (d, 1H), 7.05 (d, 1H), 6.98 (d, 2H), 6.68 (d, 3H), 6.04 (t, 1H), 6.17 (d, 1H), 3.87 (m, 2H), 3.41 (q, 2H), 2.70 (t, 2H). LCMS m/z [M+H]⁺: 419.2

Example 335

2-(Furan-2-yl)-N5-(4-((pyridin-2-ylmethyl)amino)phenethyl)-[1,2,4]triazolo[1,5-a][1,3,5]triazine-5,7-diamine

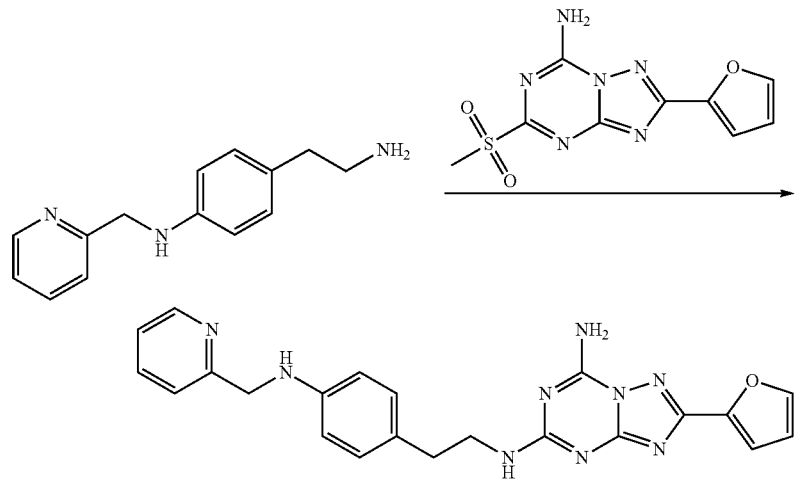

The title compound was prepared in a similar way as the title compound in Example 165. ¹H NMR (500 MHz, DMSO-d6) δ: 8.51 (d, 1H), 8.05-8.49 (d, 2H), 7.86 (s, 1H), 7.74 (dt, 1H), 7.40 (d, 1H), 7.36 (d, 1H), 7.23 (t, 1H), 7.05 (d, 1H), 6.93 (d, 2H), 6.67 (t, 1H), 6.51 (d, 2H), 6.18 (s, 1H), 4.33 (s, 2H), 3.38 (q, 2H), 2.66 (t, 2H). LCMS m/z [M+H]⁺: 428.2

Example 336

2-(Furan-2-yl)-N5-(4-((2-(pyridin-2-yl)ethyl)amino)phenethyl)-[1,2,4]triazolo[1,5-a][1,3,5]triazine-5,7-diamine

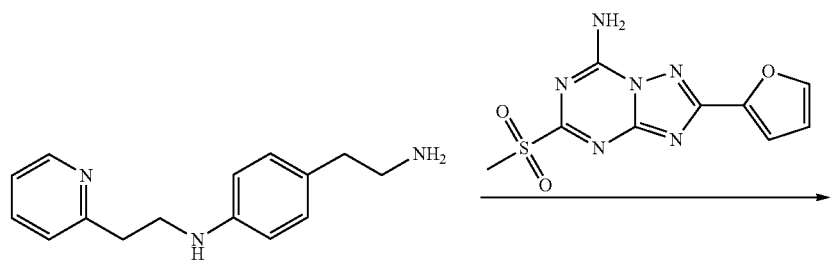

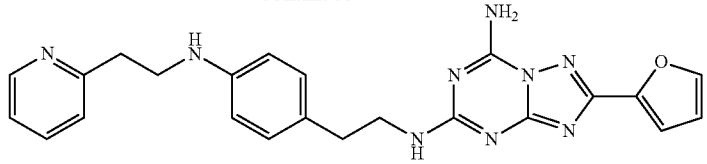

To a stirred solution of 4-(2-aminoethyl)-N-(2-(pyridin-2-yl)ethyl)aniline (142 mg, 0.59 mmol) and 2-(furan-2-yl)-5-(methylsulfonyl)-[1,2,4]triazolo[1,5-a][1,3,5]triazin-7-amine (132 mg, 0.47 mmol) in MeCN (5 mL) was added TEA to adjust pH to 8. After stirring at room temperature for 15 h, the precipitated solid was collected and dried to afford the title compound as yellow solid (110 mg, 53.1% yield).

$^1$H NMR (500 MHz, DMSO-d6) δ: 8.51 (d, 1H), 8.05-8.49 (d, 2H), 7.86 (s, 1H), 7.71 (dt, 1H), 7.40 (d, 1H), 7.30 (d, 1H), 7.23 (dt, 1H), 7.05 (d, 1H), 6.96 (d, 2H), 6.67 (t, 1H), 6.54 (d, 2H), 5.51 (t, 1H), 3.42 (m, 4H), 2.97 (t, 2H), 2.69 (t, 2H).

Example 337

5-(Methylsulfonyl)-2-phenyl-[1,2,4]triazolo[1,5-a][1,3,5]triazin-7-amine

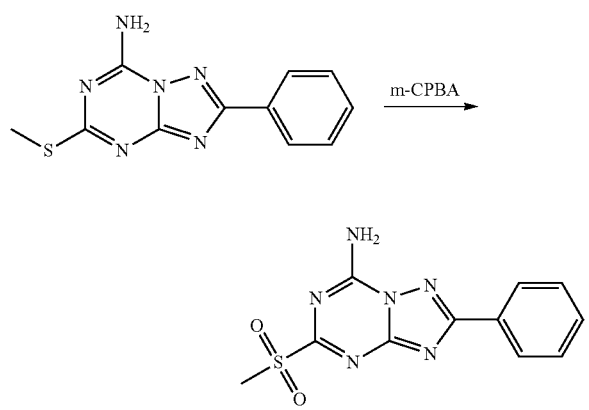 [SMILES: CSc1nc(N)n2nc(-c3ccccc3)nc2n1 ; CS(=O)(=O)c1nc(N)n2nc(-c3ccccc3)nc2n1]

The title compound was prepared in a similar way as the title compound in Example 4. $^1$H NMR (500 MHz, DMSO-d6) δ: 9.83 (s, 1H), 9.39 (s, 1H), 8.32-8.16 (m, 2H), 7.66-7.54 (m, 3H), 3.38 (s, 3H).

Example 338

N5-(4-((2-Methoxyethyl)amino)phenethyl)-2-phenyl-[1,2,4]triazolo[1,5-a][1,3,5]triazine-5,7-diamine

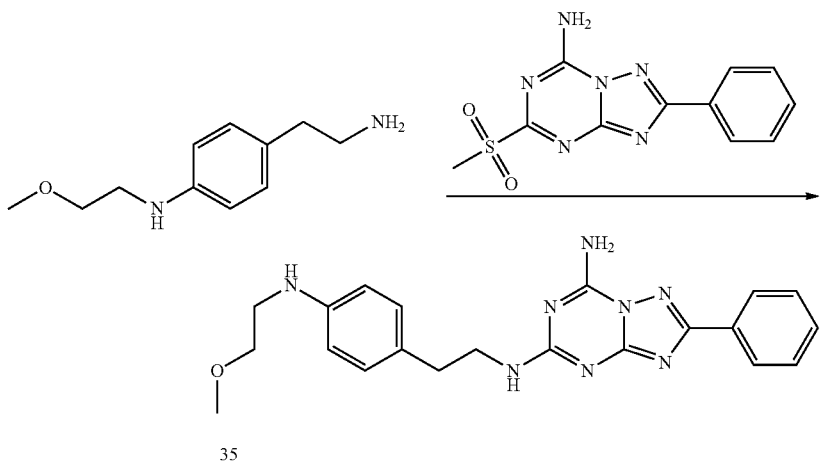

The title compound was prepared in a similar way as the title compound in Example 248. $^1$H NMR (500 MHz, DMSO-d6) δ: 8.44-8.12 (m, 4H), 7.61-7.47 (m, 3H), 7.40 (dd, J=21.4, 15.8 Hz, 1H), 6.97 (d, J=8.3 Hz, 2H), 6.55 (d, J=8.3 Hz, 2H), 5.36 (s, 1H), 3.47 (t, J=5.8 Hz, 2H), 3.42 (dd, J=13.6, 7.1 Hz, 2H), 3.27 (s, 3H), 3.16 (d, J=3.2 Hz, 2H), 2.75-2.64 (m, 2H).

Example 339

N5-(4-(Oxetan-3-ylamino)phenethyl)-2-phenyl-[1,2,4]triazolo[1,5-a][1,3,5]triazine-5,7-diamine The title compound was prepared in a similar way as the title compound in Example 299. LC-MS m/z [M+H]$^+$: 403;

¹H NMR (500 MHz, DMSO-d6) δ: 8.43-8.11 (m, 4H), 7.60-7.49 (m, 3H), 7.40 (dd, J=20.3, 14.8 Hz, 1H), 6.99 (d, J=8.2 Hz, 2H), 6.43 (d, J=8.2 Hz, 2H), 6.18 (d, J=6.5 Hz, 1H), 4.82 (t, J=6.4 Hz, 2H), 4.57-4.43 (m, 1H), 4.39 (t, J=6.0 Hz, 2H), 3.42 (dd, J=13.5, 6.5 Hz, 2H), 2.80-2.65 (m, 2H).

Example 340

2-(3-Fluorophenyl)-5-(methylsulfonyl)-[1,2,4]triazolo[1,5-a][1,3,5]triazin-7-amine

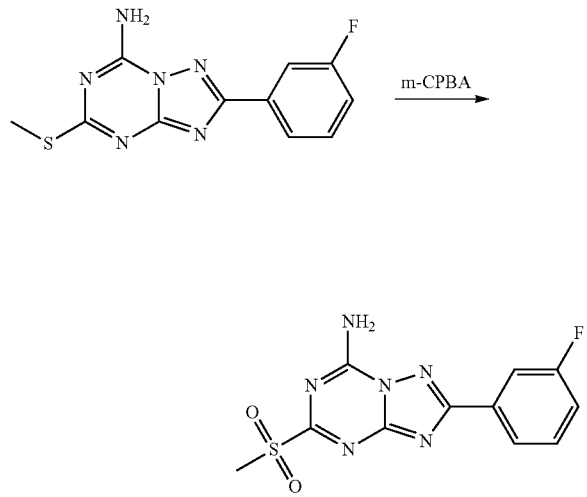

The title compound was prepared in a similar way as the title compound in Example 4. ¹H NMR (500 MHz, DMSO-d6) δ: 9.87 (s, 1H), 9.41 (s, 1H), 8.04 (d, 1H), 7.91 (d, 1H), 7.65 (q, 1H), 7.43 (dt, 1H), 3.38 (s, 3H).

Example 341

2-(3-Fluorophenyl)-N5-(4-(oxetan-3-ylamino)phenethyl)-[1,2,4]triazolo[1,5-a][1,3,5]triazine-5,7-diamine

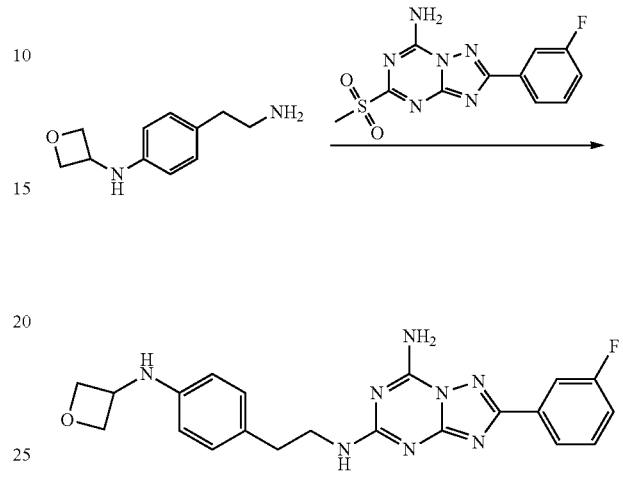

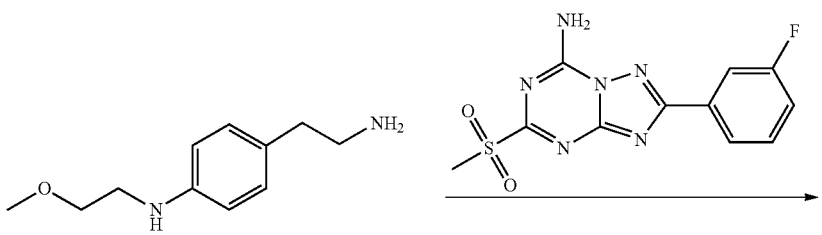

The title compound was prepared in a similar way as the title compound in Example 299. ¹H NMR (500 MHz, DMSO-d6) δ: 8.05-8.49 (m, 2H), 7.94 (d, 1H), 7.81 (d, 1H), 7.56 (q, 1H), 7.42 (d, 1H), 7.34 (dt, 1H), 6.98 (d, 2H), 6.41 (d, 2H), 6.16 (d, 1H), 4.82 (t, 2H), 4.49 (q, 1H), 4.38 (t, 2H), 3.42 (q, 2H), 2.70 (t, 2H); LCMS m/z [M/2+H]⁺: 421.3

Example 342

2-(3-Fluorophenyl)-N5-(4-((2-methoxyethyl)amino)phenethyl)-[1,2,4]triazolo[1,5-a][1,3,5]triazine-5,7-diamine

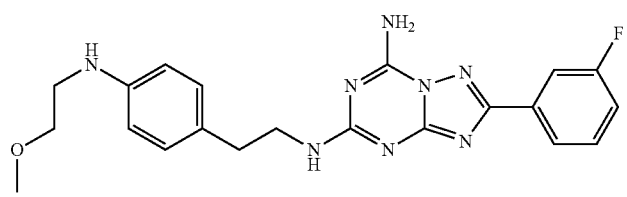

The title compound was prepared in a similar way as the title compound in Example 248. ¹H NMR (500 MHz, DMSO-d6) δ: 8.05-8.49 (m, 2H), 7.95 (d, 1H), 7.81 (d, 1H), 7.56 (q, 1H), 7.42 (d, 1H), 7.34 (t, 1H), 6.96 (d, 2H), 6.53 (d, 2H), 5.35 (t, 1H), 3.47 (t, 2H), 3.42 (q, 2H), 3.27 (s, 3H), 3.16 (q, 2H), 2.70 (t, 2H).

Example 343

2-((4-(2-((7-Amino-2-(furan-2-yl)-[1,2,4]triazolo[1,5-a][1,3,5]triazin-5-yl)amino)ethyl)-phenyl)amino)acetamide

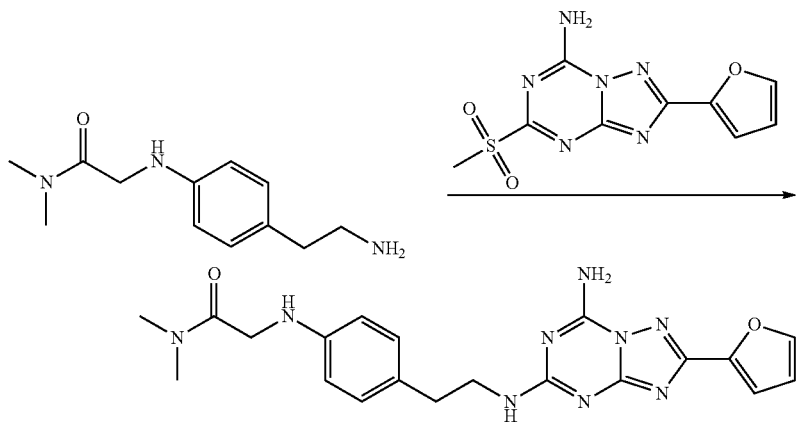

The title compound was prepared in a similar way as the title compound in Example 165. ¹H NMR (500 MHz, DMSO-d6) δ: 8.16 (s, 2H), 7.87 (s, 1H), 7.45 (d, J=46.8 Hz, 1H), 7.02 (dd, J=40.7, 5.1 Hz, 3H), 6.72-6.55 (m, 3H), 5.34 (s, 1H), 3.85 (s, 2H), 3.40 (s, 2H), 3.01 (s, 3H), 2.87 (s, 3H), 2.69 (d, J=6.8 Hz, 2H); LC-MS (m/z): 422.3 [M+H]⁺

Example 344

2-((4-(2-((7-Amino-2-(furan-2-yl)-[1,2,4]triazolo[1,5-a][1,3,5]triazin-5-yl)amino)ethyl)-phenyl)amino)acetamide

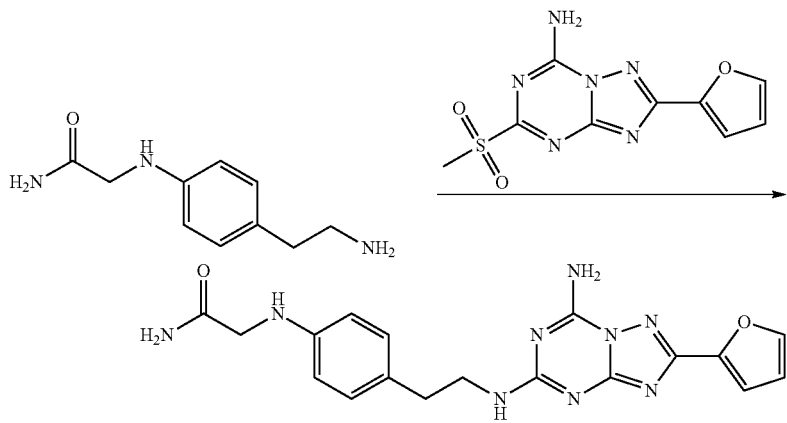

The title compound was prepared in a similar way as the title compound in Example 165. ¹H NMR (500 MHz, DMSO-d6) δ: 8.29 (d, J=131.3 Hz, 2H), 7.87 (s, 1H), 7.43 (dd, J=29.7, 24.3 Hz, 1H), 7.30 (s, 1H), 7.12-7.04 (m, 2H), 6.99 (d, J=8.0 Hz, 2H), 6.68 (d, J=1.4 Hz, 1H), 6.49 (d, J=8.2 Hz, 2H), 5.71 (t, J=5.7 Hz, 1H), 3.55 (d, J=5.8 Hz, 2H), 3.41 (s, 2H), 2.74-2.65 (m, 2H); LC-MS (m/z): 394.3 [M+H]⁺

Example 345

2-((4-(2-((7-Amino-2-(furan-2-yl)-[1,2,4]triazolo[1,5-a][1,3,5]triazin-5-yl)amino)ethyl)-phenyl)amino)-N-methylacetamide

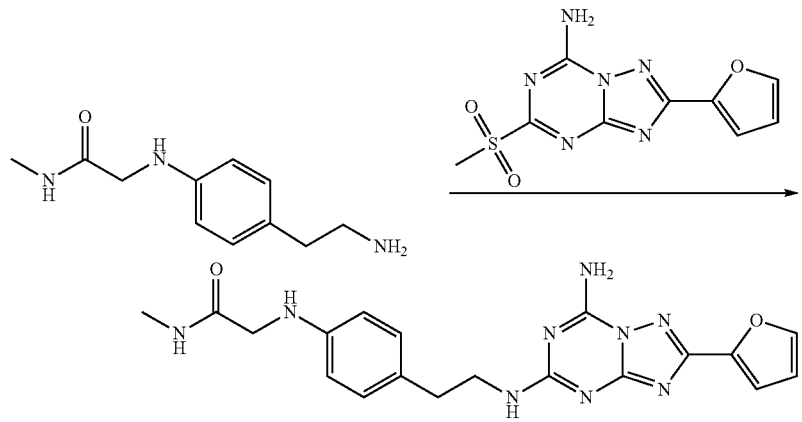

The title compound was prepared in a similar way as the title compound in Example 165. $^1$H NMR (500 MHz, DMSO-d6) δ: 8.29 (d, J=130.6 Hz, 2H), 7.87 (s, 1H), 7.78 (d, J=4.6 Hz, 1H), 7.52-7.38 (m, 1H), 7.06 (d, J=2.9 Hz, 1H), 6.99 (d, J=8.1 Hz, 2H), 6.70-6.65 (m, 1H), 6.48 (d, J=8.3 Hz, 2H), 5.81 (t, J=5.7 Hz, 1H), 3.57 (d, J=5.8 Hz, 2H), 3.40 (dd, J=13.8, 6.9 Hz, 2H), 2.73-2.65 (m, 2H), 2.60 (d, J=4.7 Hz, 3H); LC-MS (m/z): 408.3 [M+H]$^+$

Example 346

2-((4-(2-((7-Amino-2-(furan-2-yl)-[1,2,4]triazolo[1,5-a][1,3,5]triazin-5-yl)amino)ethyl)-phenyl)amino)acetonitrile

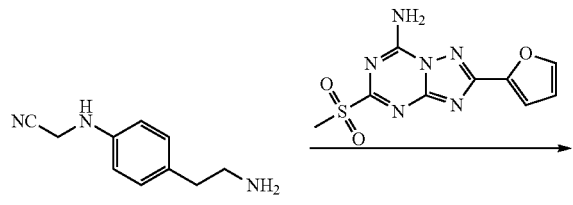

-continued

The title compound was prepared in a similar way as the title compound in Example 165. $^1$H NMR (500 MHz, DMSO-d6) δ: 8.30 (d, J=127.7 Hz, 2H), 7.87 (s, 1H), 7.46 (dd, J=31.1, 25.5 Hz, 1H), 7.11-7.05 (m, 3H), 6.67 (d, J=8.3 Hz, 3H), 6.10 (t, J=6.8 Hz, 1H), 4.23 (d, J=6.9 Hz, 2H), 3.43 (dd, J=13.8, 6.8 Hz, 2H), 2.77-2.69 (m, 2H); LC-MS (m/z): 376.3 [M+H]$^+$

Example 347

N5-(4-(1,3-dimethoxypropan-2-ylamino)phenethyl)-2-(furan-2-yl)-[1,2,4]triazolo[1,5-a][1,3,5]triazine-5,7-diamine

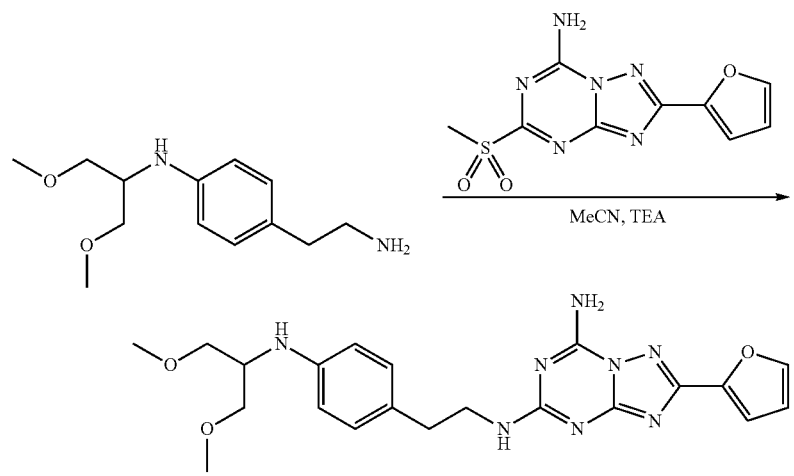

The title compound was prepared in a similar way as the title compound in Example 174. $^1$H NMR (500 MHz, DMSO-d6): 8.18-8.47 (m, 2H), 7.86 (s, 1H), 7.41-7.53 (m, 1H), 7.05 (d, 1H), 6.94 (d, 2H), 6.67 (dr, 1H), 6.66 (d, 2H), 5.19 (d, 1H), 3.57-3.64 (m, 1H), 3.36-3.41 (m, 6H), 3.25 (s, 6H), 2.64-2.69 (m, 2H).

The above exemplary embodiments are used as illustrations of the invention. These embodiments are not intended to limit the scope of the invention. In fact, the invention is intended to cover all alternatives, modifications, and equivalents of these embodiments. It should not be understood that the present invention is only limited to the illustrated examples.

Biological Activities of the A2A Receptor Antagonists

The antagonistic activities of the triazolotriazine derivatives of the present invention were measured in a functional cAMP production assay. The assay consists of NECA stimulation of cAMP production and its inhibition by A2AR antagonists in A2AR-expressing HEK293 cells (hADORA2A-HEK293). All cells were cultured in complete medium at 37° C. in 5% $CO_2$. The cells were detached with pancreatin and collected at 200 g for 5 min. After resuspending the cells in fresh complete medium, the cell viability is counted using the trypan blue exclusion method. The cAMP production assay was conducted only when cell viability was greater than 95%. After the cells were diluted with Hank's buffered saline solution containing HEPES (5 mM), BSA stabilizer (0.1%) and 20 Rolipram (10 µM), cells were loaded into white opaque 384-well plates (~500 cells/well, 10 µl/well) and incubated with test compound at a suitable concentration range (11 concentrations) for 20 min at room temperature. Then the A2A receptor agonist NECA (final concentration=$EC_{80}$, which was determined in the same experiment slightly earlier) was added to the sample and the mixture was incubated again for 30 min at 37° C. The amount of cAMP production was determined using Eu-cAMP tracer and Ulight-anti-cAMP by measuring the ratio of the TR-FRET emission at 665 nm and fluorescent emission at 615 nm. The inhibition rate (%) was calculated according to the following formula. The $IC_{50}$ values were calculated from concentration-inhibition (%) curves after log transformation.

$$\% \text{ Inhibition} = \left(1 - \frac{\text{Ratio}_{665mm/615mmhigh} - \text{Ratio}_{665mm/615mmcmpd}}{\text{Ratio}_{665mm/615mmhigh} - \text{Ratio}_{665mm/615mmlow}}\right) \times 100\%$$

Table (2) shows representative antagonistic activities of the triazolotriazine derivatives of the present invention.

TABLE 2

The Potency of A2AR antagonists

| Compounds | A2AR Potency (nM) |
|---|---|
| Example 13 | 18.00 |
| Example 16 | 24.00 |
| Example 19 | 29.00 |
| Example 26 | 8.00 |
| Example 29 | 7.00 |
| Example 32 | 8.00 |
| Example 36 | 11.00 |
| Example 40 | 11.00 |
| Example 42 | 128.80 |
| Example 44 | 63.81 |
| Example 51 | 25.37 |
| Example 54 | 19.18 |
| Example 57 | 7.00 |
| Example 60 | 10.00 |
| Example 65 | 21.50 |
| Example 70 | 19.00 |
| Example 74 | 32.30 |
| Example 78 | 31.30 |
| Example 82 | 9.00 |
| Example 86 | 14.30 |
| Example 90 | 10.90 |
| Example 94 | 16.00 |
| Example 98 | 48.47 |
| Example 102 | 19.00 |
| Example 109 | 55.00 |
| Example 113 | 15.00 |
| Example 117 | 38.00 |
| Example 121 | 14.10 |
| Example 124 | 8.40 |
| Example 142 | 8.09 |
| Example 154 | 25.34 |
| Example 162 | 17.53 |
| Example 165 | 6.77 |
| Example 174 | 3.83 |
| Example 207 | 8.96 |
| Example 214 | 35.20 |
| Example 226 | 19.98 |
| Example 229 | 25.32 |
| Example 241 | 11.19 |
| Example 245 | 10.05 |
| Example 248 | 10.57 |
| Example 254 | 19.62 |
| Example 262 | 1.62 |
| Example 276 | 17.55 |
| Example 283 | 43.20 |
| Example 284 | 32.31 |
| Example 285 | 9.24 |
| Example 286 | 32.98 |
| Example 299 | 7.07 |
| Example 302 | 12.67 |
| Example 306 | 162.84 |
| Example 309 | 30.45 |
| Example 313 | 13.80 |
| Example 314 | 15.37 |
| Example 317 | 3.01 |
| Example 318 | 11.05 |
| Example 320 | 11.50 |
| Example 321 | 40.68 |
| Example 324 | 10.80 |
| Example 325 | 11.86 |
| Example 326 | 10.65 |
| Example 331 | 3.52 |
| Example 347 | 4.88 |
| ZM241385 | 9.00 |

The invention claimed is:
1. A compound of formula (1):

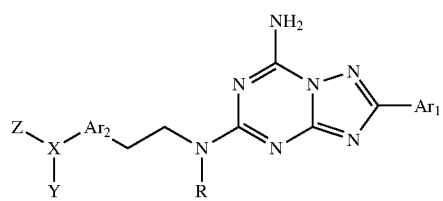

Formula 1 wherein:
R is hydrogen;
$Ar_1$ is 2-furanyl;
$Ar_2$ is phenyl;
X is nitrogen; and Y and Z are each independently hydrogen, or oxetanyl ring that is optionally substituted with methoxy, ethoxy, trifluoromethoxy, or trifluoroethoxy; Y and Z are not simultaneously hydrogen; Or Y and Z are joined to form a morpholinyl ring, or a pharmaceutically acceptable solvate or salt thereof.

2. A compound selected from:

N-(4-(2-((7-Amino-2-(furan-2-yl)-[1,2,4]triazolo[1,5-a][1,3,5]triazin-5-yl)amino)ethyl)-phenyl)-3-morpholinopropanamide;

N-(4-(2-((7-Amino-2-(furan-2-yl)-[1,2,4]triazolo[1,5-a][1,3,5]triazin-5-yl)amino)ethyl)-phenyl)-2-morpholinoacetamide;

N-(4-(2-((7-Amino-2-(furan-2-yl)-[1,2,4]triazolo[1,5-a][1,3,5]triazin-5-yl)amino)ethyl)-phenyl)-4-methyltetrahydro-2H-pyran-4-carboxamide;

2-(Furan-2-yl)-N5-(4-((2-morpholinoethyl)amino)phenethyl)-[1,2,4]triazolo[1,5-a][1,3,5]triazine-5,7-diamine;

2-(Furan-2-yl)-N5-(4-((tetrahydro-2H-pyran-4-yl)amino)phenethyl)-[1,2,4]triazolo[1,5-a][1,3,5]triazine-5,7-diamine;

2-(Furan-2-yl)-N5-(4-((tetrahydrofuran-3-yl)amino)phenethyl)-[1,2,4]triazolo[1,5-a][1,3,5]triazine-5,7-diamine;

2-(Furan-2-yl)-N5-(4-(4-methylpiperazin-1-yl)phenethyl)-[1,2,4]triazolo[1,5-a][1,3,5]triazine-5,7-diamine;

2-(Furan-2-yl)-N5-(4-(oxetan-3-ylamino)phenethyl)-[1,2,4]triazolo[1,5-a][1,3,5]triazine-5,7-diamine;

2-(Furan-2-yl)-N5-(4-(oxetan-3-ylmethyl)phenethyl)-[1,2,4]triazolo[1,5-a][1,3,5]triazine-5,7-diamine.

* * * * *